United States Patent
Swinnen et al.

(10) Patent No.: US 9,403,835 B2
(45) Date of Patent: Aug. 2, 2016

(54) TETRAAZA-CYCLOPENTA[A]INDENYL AND THEIR USE AS POSITIVE ALLOSTERIC MODULATORS

(71) Applicant: Merck Patent GmbH, Darmstadt (DE)

(72) Inventors: Dominique Swinnen, Braine L'Alleud (BE); Cyril Montagne, Saint-Genis-Pouilly (FR); Vincent Pomel, Groisy (FR); Anna Quattropani, Rolle (CH); Jerome Molette, Prevessin Moens (FR); Patrick Gerber, Etoy (CH)

(73) Assignee: Ares Trading S.A., Aubonne (CH)

( * ) Notice: Subject to any disclaimer, the term of this patent is extended or adjusted under 35 U.S.C. 154(b) by 58 days.

(21) Appl. No.: 14/366,901

(22) PCT Filed: Nov. 30, 2012

(86) PCT No.: PCT/EP2012/004968
§ 371 (c)(1),
(2) Date: Jun. 19, 2014

(87) PCT Pub. No.: WO2013/091773
PCT Pub. Date: Jun. 27, 2013

(65) Prior Publication Data
US 2015/0018343 A1 Jan. 15, 2015

Related U.S. Application Data

(60) Provisional application No. 61/657,978, filed on Jun. 11, 2012, provisional application No. 61/578,931, filed on Dec. 22, 2011.

(30) Foreign Application Priority Data

Dec. 22, 2011 (EP) .................................... 11195214
Jun. 11, 2012 (EP) .................................... 12171415

(51) Int. Cl.
| | | |
|---|---|---|
| *A61K 31/519* | (2006.01) | |
| *C07D 487/14* | (2006.01) | |
| *C07D 471/14* | (2006.01) | |
| *C07D 519/00* | (2006.01) | |
| *A61K 31/5513* | (2006.01) | |

(52) U.S. Cl.
CPC ............ *C07D 487/14* (2013.01); *A61K 31/519* (2013.01); *A61K 31/5513* (2013.01); *C07D 471/14* (2013.01); *C07D 519/00* (2013.01)

(58) Field of Classification Search
CPC ........................... A61K 31/519; C07D 487/14
See application file for complete search history.

(56) References Cited

FOREIGN PATENT DOCUMENTS

| WO | 02076987 A1 | 10/2002 | |
|---|---|---|---|
| WO | 2008060488 A1 | 5/2008 | |
| WO | 2011137049 A1 | 11/2011 | |
| WO | WO 2011/137049 | * 11/2011 | ............. A01N 43/42 |

OTHER PUBLICATIONS

West, Anthony R., Solid State Chemistry and Its Applications, Wiley, New York, 1988, 358.*
Bridges et al., Looking Ahead: The Antipsychotic Potential of Muscarinic Allosteric Modulation, Drug News & Perspectives, 2010, 23(4):229-240.
Conn et al., Subtype-selective allosteric modulators of muscarinic receptors for the treatment of CNS disorders, Trends in Pharmacological Sciences, 2009, 30(3):148-155.
Digby et al., Allosteric activators of muscarinic receptors as novel approaches for treatment of CNS disorders, Mol Biosystems, 2010, 6:1345-1354.
Eglen et al, Therapeutic opportunities from muscarinic receptor research, TRENDS in Pharmacological Sciences, 2001, 22(8):409-414.
Fisher, Abraham, Therapeutic Strategies in Alzheimer's Disease: M1 Muscarinic Agonists, Jpn J Pharmacol, 2000, 84:101-112.
Greene Theodora W. and Wuts Peter G. M., "Protective Groups in Organic Synthesis", Wiley Interscience, 3rd Edition 1999.
Higuchi T. and Stella V. "Pro-drugs as Novel Delivery Systems", vol. 14 of the A.C.S. Symposium Series, American Chemical Society, 1975.
Houben-Weyl, Methoden der organischen Chemie [Methods of Organic Chemistry], Georg-Thieme-Verlag, Stuttgart.
Jakubik et al., Allosteric Modulation of Muscarinic Acetylcholine Receptors, Pharmaceuticals, 2010, 3:2838-2860.
Kocienski, Phillip J., "Protecting Groups", Georg Thieme Verlag Stuttgart, New York, 1994.
Lazareno et al, Allosteric Interactions of Staurosporine and Other Indolocarbazoles with N-[methyl-3H] Scopolamine and Acetylcholine at Muscarinic Receptor Subtypes: Identification of a Second Allosteric Site, Mol Pharmacol, 2000, 58:194-207.
Lazareno et al, Analogs of WIN 62,577 Define a Second Allosteric Site on Muscarinic Receptors, Mol Pharmacol, 2002, 62:1492-1505.
Patrick, G., An Introduction to Medicinal Chemistry, Fifth Edition, Chapter 13: Drug design: optimizing target interactions, 1995, pp. 215-247.

(Continued)

*Primary Examiner* — Erich A Leeser
(74) *Attorney, Agent, or Firm* — Dwight D. Kim; EMD Serono Research and Development Institute

(57) ABSTRACT

The present invention provides compounds of Formula (I) as M1 receptor positive allosteric modulators for the treatment of diseases mediated by the muscarinic M1 mediator.

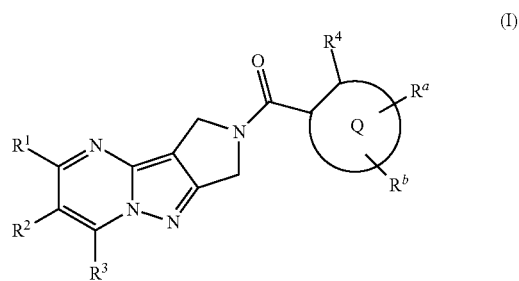

19 Claims, No Drawings

(56) References Cited

OTHER PUBLICATIONS

Schwartz et al., Allosteric enhancers, allosteric agonists and ago-allosteric modulators: where do they bind and how do they act? Trends in Pharmacological Sciences, 2007, 28(8):366-373.

Shi et al., Design and synthesis of 1,4,5,6-tetrahydropyrrolo[3,4-c]pyrazoles and pyrazolo[3,4-b]pyridines for Aurora-A kinase inhibitors, Biorg. Med. Chem. Lett, 2010, 20:4273-4278.

Spalding et al, Discovery of an Ectopic Activation Site on the M1 Muscarinic Receptor, Mol Pharmacol, 2002, 61(6): 1297-1302.

Tyle, Praveen, Iontophoretic Devices for Drug Delivery, Pharmaceutical Research, 1986, 3(6):318-326.

Yoshida et al., Study of biodegradable copoly (L-lactic acid/glycolic acid) formulations with controlled release of Z-100 for application in radiation therapy, Int. J. Pharm., 1995, 115:61-67.

International Search Report, dated Mar. 13, 2013.

* cited by examiner

TETRAAZA-CYCLOPENTA[A]INDENYL AND THEIR USE AS POSITIVE ALLOSTERIC MODULATORS

RELATED APPLICATIONS

This application is a U.S. national stage application of PCT international application PCT/EP2012/004968, filed on Nov. 30, 2012, which claims the benefit of U.S. provisional Application No. 61/657,978, filed on Jun. 11, 2012, European Application Number 12171415.8, filed on Jun. 11, 2012, U.S. Provisional Application No. 61/578,931, filed on Dec. 22, 2011, and European Application Number 11195214.9, filed on Dec. 22, 2011. The entire contents of the aforementioned applications are hereby incorporated by reference.

The invention is directed to a class of tetraaza-cyclopenta[a]indenyl compounds, their salts, pharmaceutical compositions comprising them and their use in therapy of the human body. In particular, the invention is directed to a class of tetraaza-cyclopenta[a]indenyl compounds, which are muscarinic M1 receptor positive allosteric modulators, and hence are useful in the treatment of Alzheimer's disease, schizophrenia and other diseases mediated by the muscarinic M1 receptor.

BACKGROUND OF THE INVENTION

Alzheimer's disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

The cholinergic pathway is involved in a variety of Central Nervous System (CNS) functions like information processing, attention, learning and memory, nociception, regulation of sleep-wake cycles, motor control. Agents that regulate cholinergic transmission are used to treat various CNS disorders including chronic and neuropathic pain, sleep disorders, epilepsy, schizophrenia, Alzheimer's disease, Parkinson's disease, and other movement disorders and memory disorders (Jeffrey Conn et al. Trends in Pharmacological Sciences Vol 30, N° 30, p 148, 2009, Gregory Digby et al. Mol Biosystems 2010, 6, 1345-1354).

Activation of muscarinic receptors is a way to counteract cholinergic hypofunction. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions like cardiovascular functions, renal and gastrointestinal functions. The muscarinic M1 receptor, which is prevalent in the cerebral cortex, hippocampus and striatum, has been found to have a major role in cognitive processing and in the pathophysiology of Alzheimer's disease (Eglen et al, TRENDS in Pharmacological Sciences, 2001, 22:8, 409-414).

M1 agonists have the potential to treat the underlying disease mechanism of Alzheimer's disease. The cholinergic hypothesis of Alzheimer's disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective aAPPs fragment, thereby preventing the formation of the Aβ peptide. Thus, M1 agonists may alter APP processing and enhance aAPPs secretion (Fisher, Jpn J Pharmacol, 2000, 84:101-112).

Non selective muscarinic ligands which have been developed and studied for Alzheimer's disease have produced side effects, such as sweating, nausea and diarrhea (Spalding et al, Mol Pharmacol, 2002, 61:6, 1297-1302).

The muscarinic receptors are known to contain one or more allosteric sites, which may alter the affinity with which muscarinic ligands bind to the primary binding or orthosteric sites (S. Lazareno et al, Mol Pharmacol, 2002, 62:6, 1491-1505; S. Lazareno et al, Mol Pharmacol, 2000, 58, 194-207).

Positive allosteric modulation has several advantages in the treatment of CNS disorders. In particular, it mimics neurotransmission under physiological conditions, with greater subtype selectivity. Also, the maximum effect reached by an allosteric modulator is not exceeded by increasing the dose (Jan Jakubik, Pharmaceuticals, 2010, 3, 2838).

Furthermore, the antipsychotic potential of M1 allosteric modulation provides a promising way of treating schizophrenia, dementia, and related disorders like hallucination, delusions, paranoia and other disorganized behaviors (Thomas Bridge et al. Drug news & perspectives 2010, 23, 229).

Thus the compounds of the present invention, which are muscarinic M1 receptor positive allosteric modulators, are useful in the treatment of CNS disorders including Alzheimer's disease, Parkinson's disease, schizophrenia, and other diseases mediated by the muscarinic M1 receptor like movement disorders and memory disorders, chronic and neuropathic pain, sleep disorders, epilepsy.

The present invention also provides a method of synthesis of the compounds of Formula (I) as well as pharmaceutical formulations containing them.

More particularly the compounds of the present invention are compounds of Formula (I)

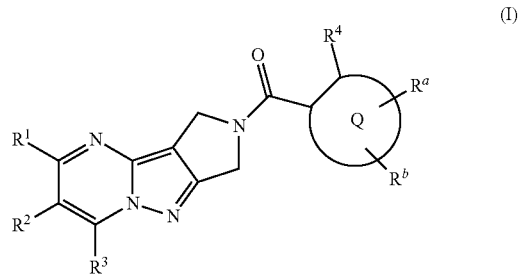

Wherein $R^1$, $R^2$, $R^3$ are independently from each other selected from H, linear or branched $C_1$-$C_6$-alkyl, linear or branched $C_1$-$C_6$-alkoxy, Hal, or hydroxyl;

$R^a$, $R^b$ are independently from each other selected from H, Hal, hydroxyl or A;

Q denotes a 6-membered aromatic group or a 5-6-membered heteroaromatic group having 1 to 4 heteroatoms independently selected from N, O and S.

$R^4$ denotes G, OG, $OCHF_2$, $OCF_2CHF_2$, SG, $NR^5G$, —COOG, or OCOG;

$R^5$ denotes H or a linear or branched alkyl having 1 to 6 carbon atoms.

G denotes —$CH_3$, —$CF_3$, —$CH_2$-A, Het, Cyc, Ar, —$CH_2$-Het, —$CH_2$-Cyc, —$CH_2$—Ar, Hal, hydroxyl;

Hal denotes F, Cl, Br or I, preferably F, Cl or Br;
A is a linear or branched carbon chain having 1 to 6 carbon atoms, wherein 1 to 3 non adjacent —CH$_2$-groups may be independently from each other replaced by a group selected from O, NR$^5$, S, SO, SO$_2$, CO, and wherein 1 to 5 hydrogen atoms may be independently from each other replaced by Het, Cyc, Ar, or Hal;
Het denotes a saturated, unsaturated or aromatic ring, being monocyclic or bicyclic or fused-bicyclic and having 3- to 8-members and containing 1 to 4 heteroatoms independently selected from N, NR$^5$, O, S, CO, SO or SO$_2$, which may be substituted by 1 to 3 substituents independently selected from A, Hal, OH and Het$^1$;
Het$^1$ denotes a 4, 5 or 6 membered carbocyclic ring wherein 1 or 2 carbon atom are replaced by Oxygen atoms.
Ar denotes a 6-membered carbocyclic aromatic ring or a fused or non fused byclic aromatic ring, and optionally substituted by 1 to 3 substituents independently selected from A or Hal;
Cyc denotes a saturated or unsaturated carbocyclic ring having from 3 to 8 carbon atoms and optionally substituted by 1 to 3 substituents independently selected from A or Hal;
as well as pharmaceutically acceptable salts, isomers and tautomers thereof.

In a specific embodiment, R$^1$ and R$^3$ denote a linear or branched C$_1$-C$_6$-alkyl.

In another specific embodiment R$^2$ is an Halogen, preferably chlorine.

In another specific embodiment, R$^4$ denotes G or OG,

In another specific embodiment G denotes —CH$_2$-A,

In another specific embodiment, A is a linear or branched carbon chain having 1 to 6 carbon atoms, wherein 1-CH$_2$— group may be replaced by NR$^5$.

In another embodiment, Ar denotes a 6-membered carboxylic aromatic ring optionally substituted by A or Hal.

In a specific embodiment, the compounds of the present invention are compounds of Formula (I) wherein
Q is a phenyl ring;
R$^a$, R$^b$ are independently selected from H, Hal, Hydroxy, or a linear or branched alkyl group having 1 to 6 carbon atoms and wherein 1 to 3 hydrogen atoms may be replaced by Hal;
R$^4$ is G or OG;

In another specific embodiment, the present invention provides compounds of Formula (I) and related Formulae wherein Q bears R$^4$ and the rest of the molecule on two adjacent atoms.

In another embodiment, the present invention provides compounds of Formula (I')

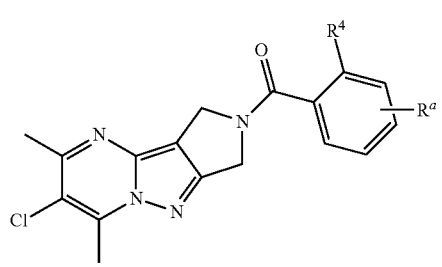

(I')

Wherein R$^4$ and R$^a$ are as above defined.

In another specific embodiment, the group

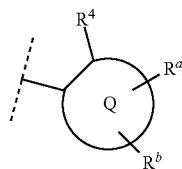

is selected from one of the following groups

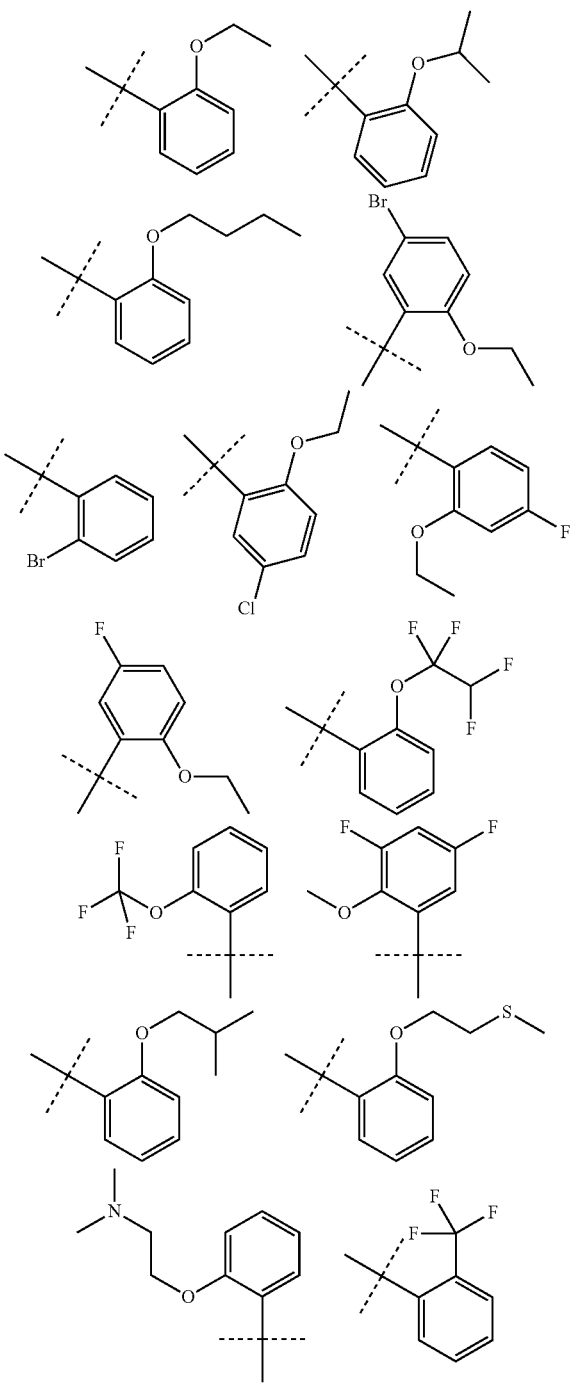

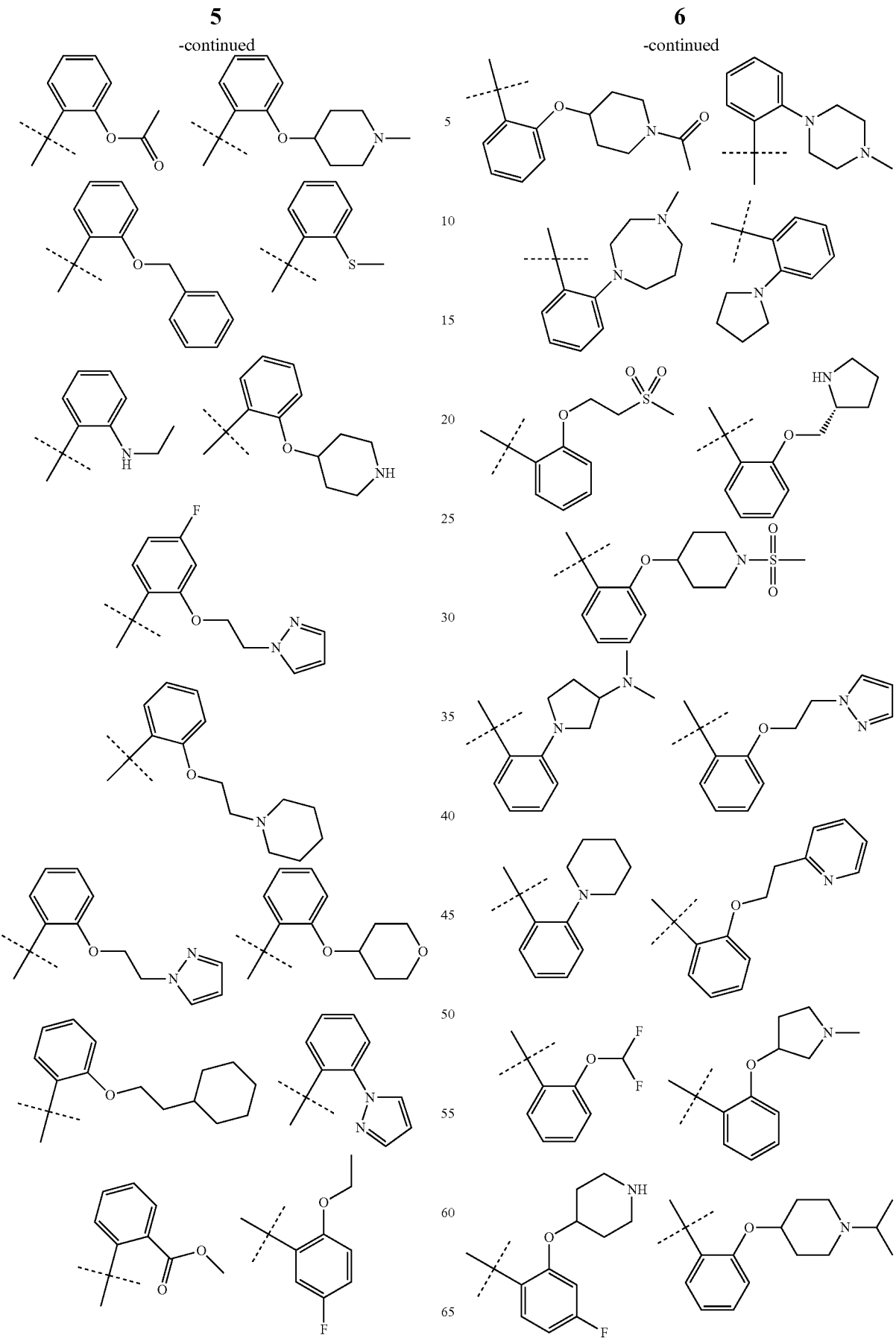

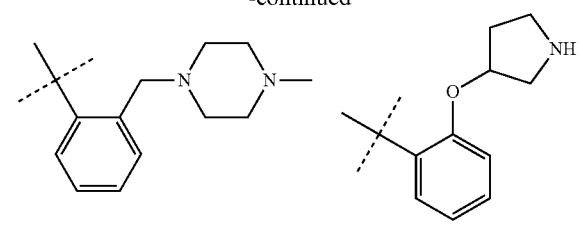
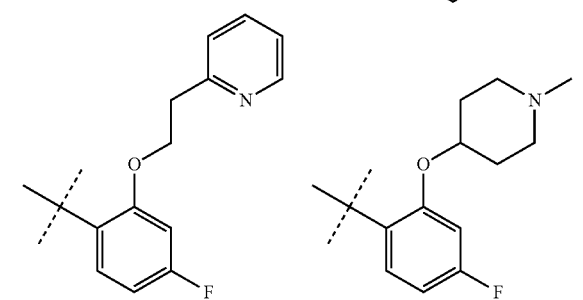
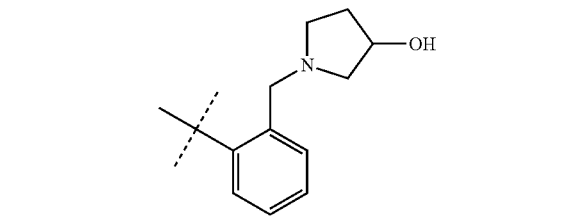
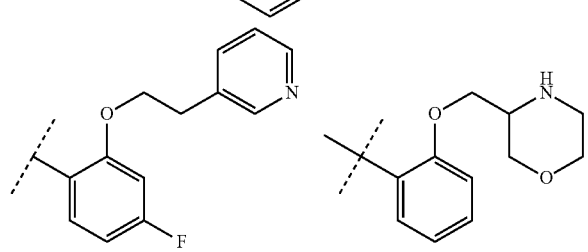
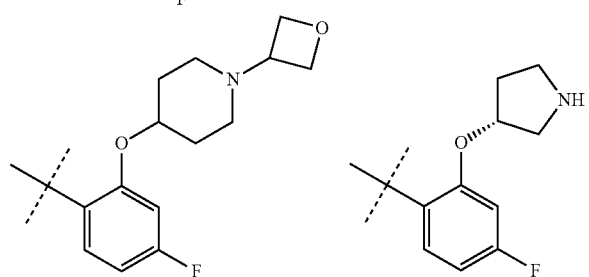
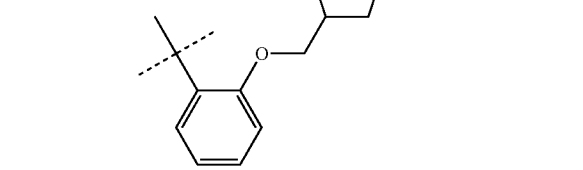
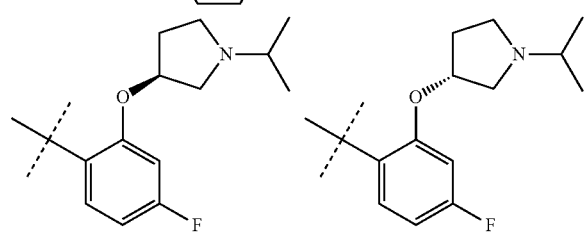
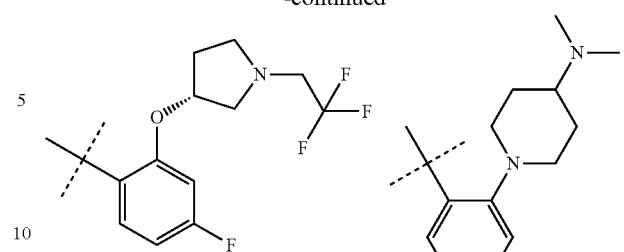
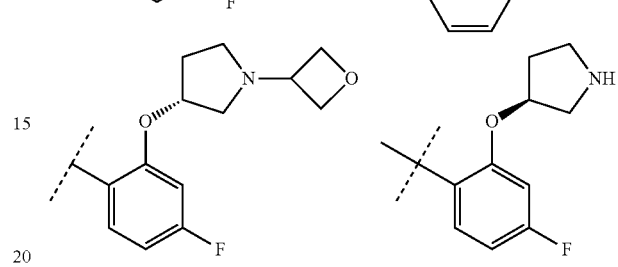
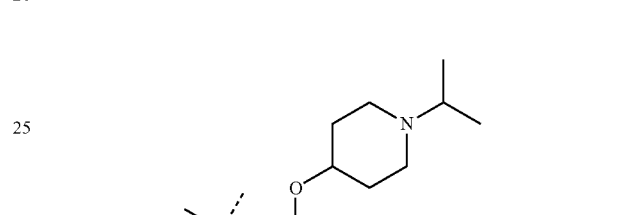
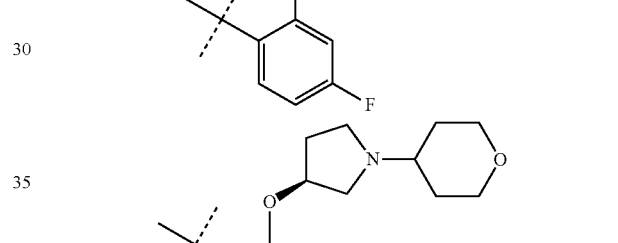
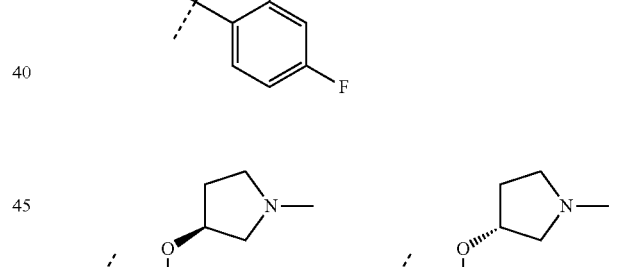
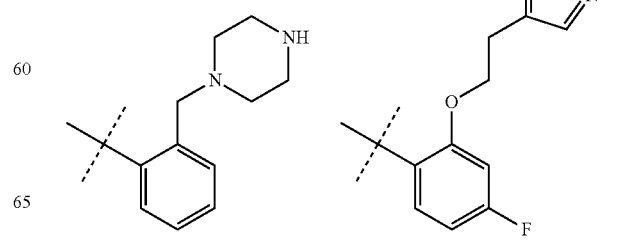

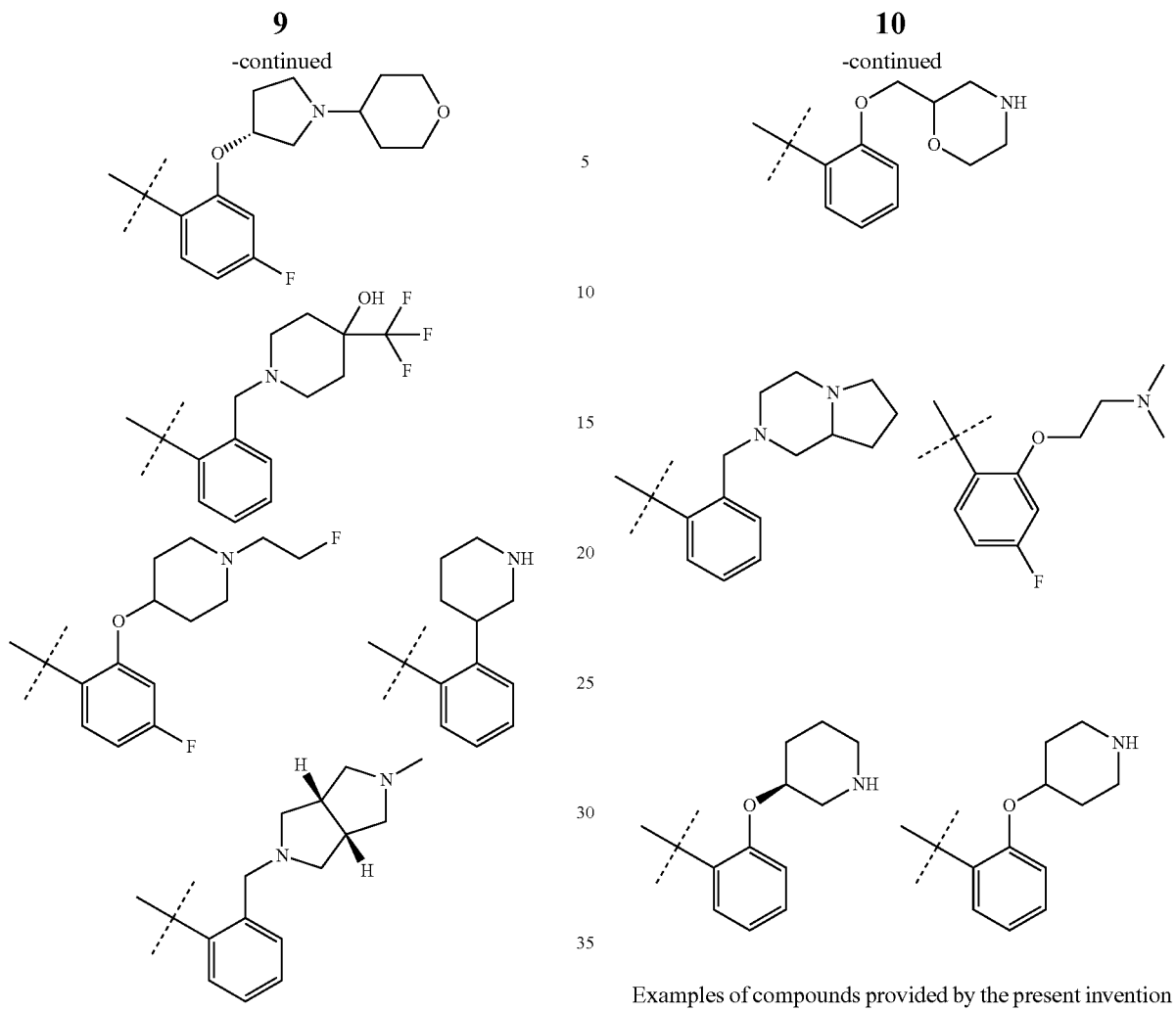
Examples of compounds provided by the present invention are the following:
| Ex | Structures |
|---|---|
| 1 | 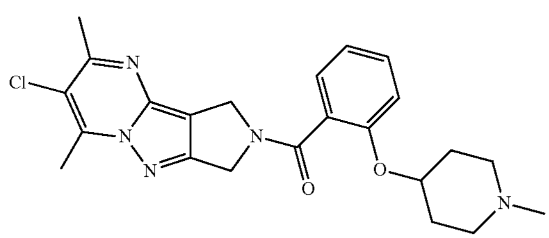 [SMILES: Cc1nc2c3c(nn2c(C)c1Cl)CN(C(=O)c1ccccc1OC1CCN(C)CC1)C3] |
| 2 | 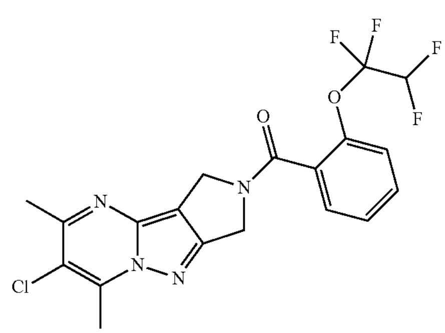 [SMILES: Cc1nc2c3c(nn2c(C)c1Cl)CN(C(=O)c1ccccc1OC(F)(F)C(F)F)C3] |

-continued
| Ex | Structures |
|---|---|
| 3 | 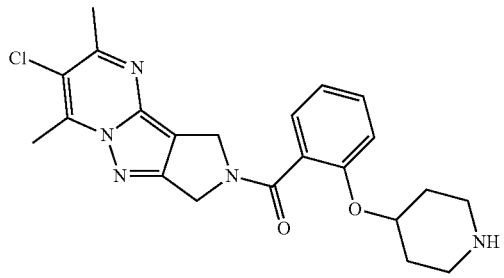 [SMILES: Cc1nc2c3c(nn2c(C)c1Cl)CN(C(=O)c1ccccc1OC1CCNCC1)C3] |
| 4 | 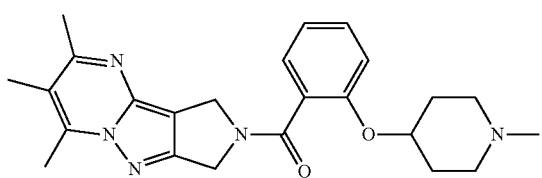 |
| 5 | 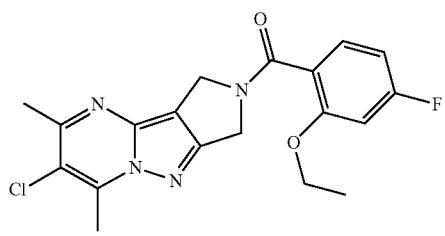 [SMILES: CCOc1cc(F)ccc1C(=O)N1Cc2nn3c(C)c(Cl)c(C)nc3c2C1] |
| 6 | 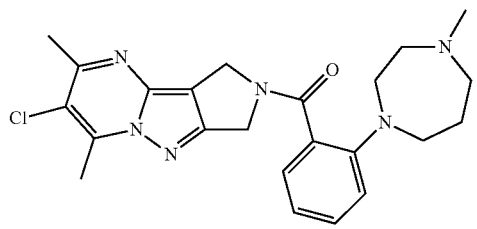 [SMILES: Cc1nc2c3c(nn2c(C)c1Cl)CN(C(=O)c1ccccc1N1CCCN(C)CC1)C3] |
| 7 | 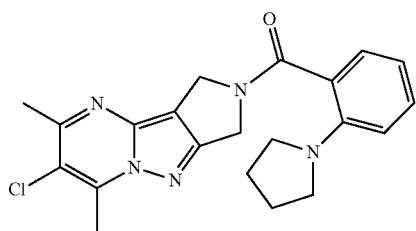 [SMILES: Cc1nc2c3c(nn2c(C)c1Cl)CN(C(=O)c1ccccc1N1CCCC1)C3] |
| 8 | 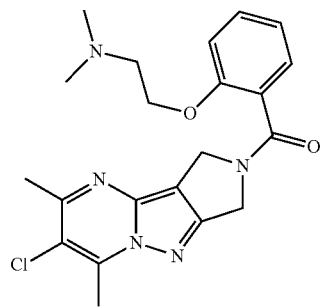 [SMILES: Cc1nc2c3c(nn2c(C)c1Cl)CN(C(=O)c1ccccc1OCCN(C)C)C3] |

-continued
| Ex | Structures |
|---|---|
| 9 | 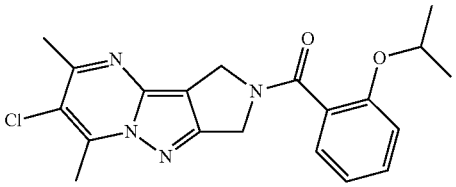 [SMILES: Cc1nc2c3c(nn2c(C)c1Cl)CN(C(=O)c1ccccc1OC(C)C)C3] |
| 10 | 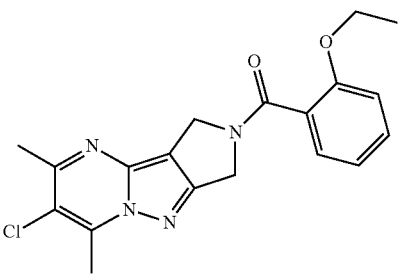 [SMILES: CCOc1ccccc1C(=O)N1Cc2nn3c(C)c(Cl)c(C)nc3c2C1] |
| 11 | 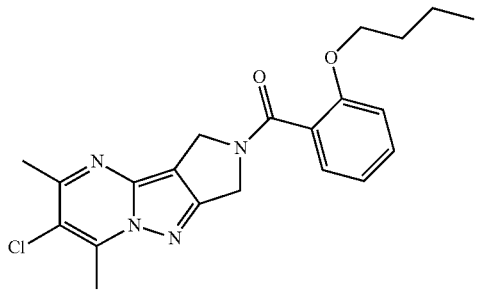 [SMILES: CCCCOc1ccccc1C(=O)N1Cc2nn3c(C)c(Cl)c(C)nc3c2C1] |
| 12 | 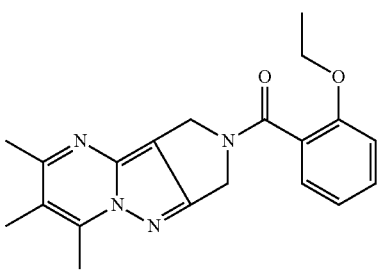 [SMILES: CCOc1ccccc1C(=O)N1Cc2nn3c(C)c(C)c(C)nc3c2C1] |
| 13 | 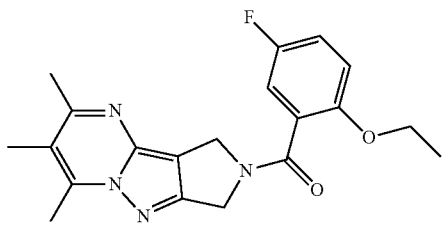 [SMILES: CCOc1ccc(F)cc1C(=O)N1Cc2nn3c(C)c(C)c(C)nc3c2C1] |
| 14 | 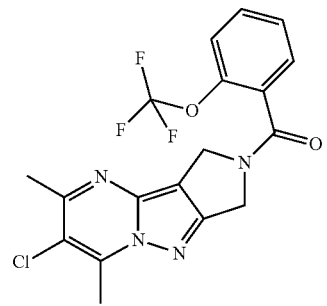 |

-continued
| Ex | Structures |
|---|---|
| 15 | 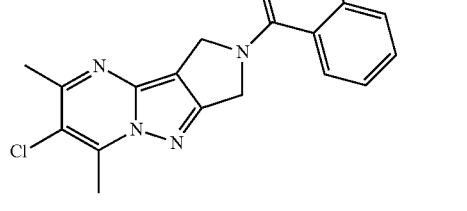 |
| 16 | 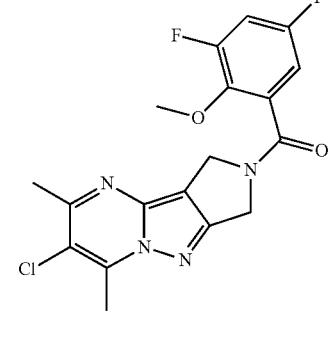 |
| 17 | 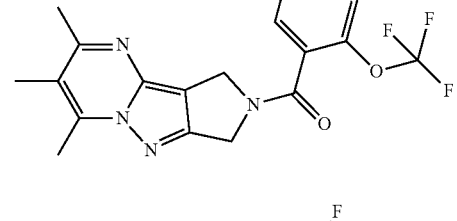 |
| 18 | 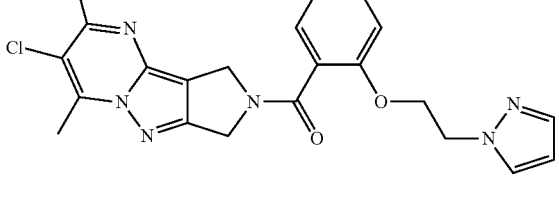 |
| 19 | 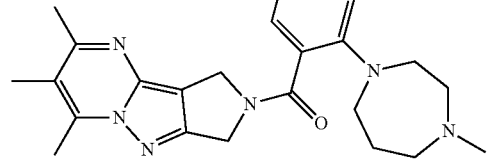 |

-continued
| Ex | Structures |
|---|---|
| 20 | 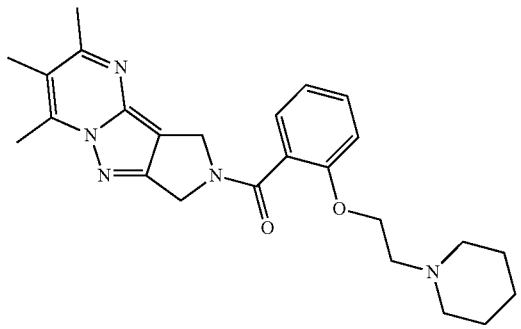 [SMILES: Cc1nc2c3c(nn2c(C)c1C)CN(C(=O)c1ccccc1OCCN1CCCCC1)C3] |
| 21 | 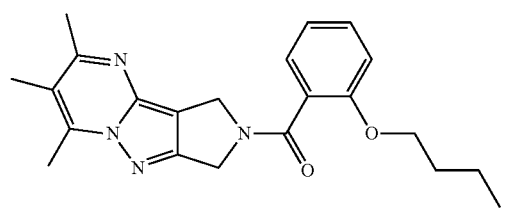 [SMILES: CCCCOc1ccccc1C(=O)N1Cc2nn3c(C)c(C)c(C)nc3c2C1] |
| 22 | 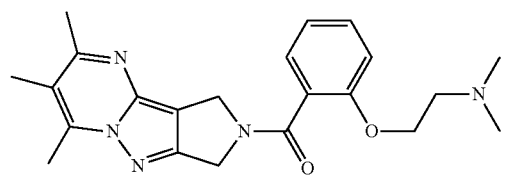 |
| 23 | 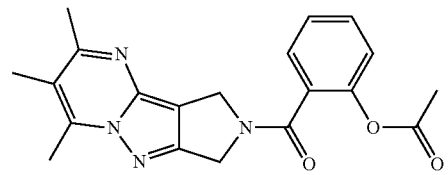 [SMILES: CC(=O)Oc1ccccc1C(=O)N1Cc2nn3c(C)c(C)c(C)nc3c2C1] |
| 24 | 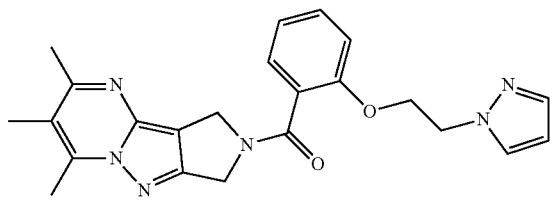 [SMILES: Cc1nc2c3c(nn2c(C)c1C)CN(C(=O)c1ccccc1OCCn1cccn1)C3] |
| 25 | 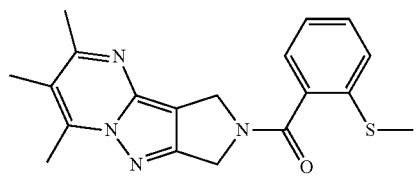 |
| 26 | 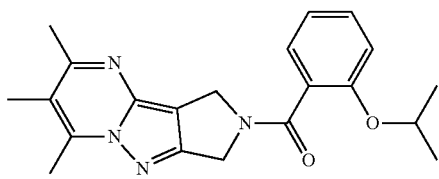 [SMILES: Cc1nc2c3c(nn2c(C)c1C)CN(C(=O)c1ccccc1OC(C)C)C3] |

-continued
| Ex | Structures |
|---|---|
| 27 | 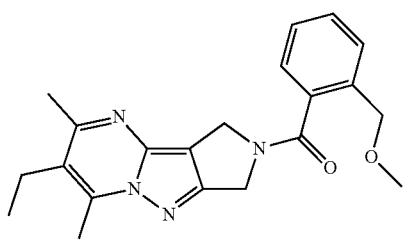 [SMILES: CCc1c(C)nc2c3c(nn2c1C)CN(C(=O)c1ccccc1COC)C3] |
| 28 | 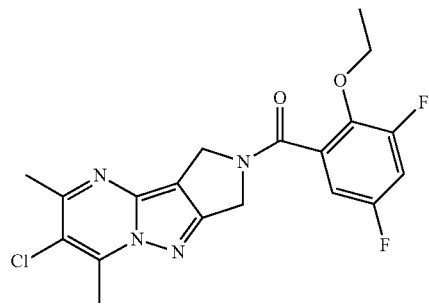 [SMILES: CCOc1c(F)cc(F)cc1C(=O)N1Cc2nn3c(C)c(Cl)c(C)nc3c2C1] |
| 29 | 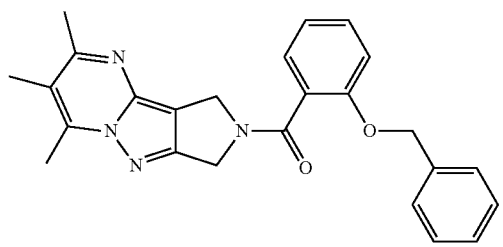 [SMILES: Cc1nc2c3c(nn2c(C)c1C)CN(C(=O)c1ccccc1OCc1ccccc1)C3] |
| 30 | 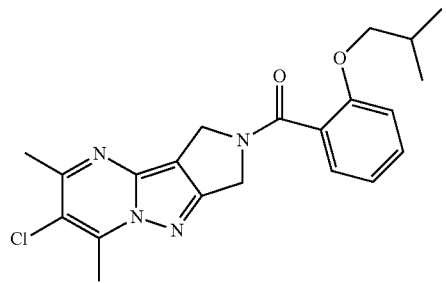 [SMILES: Cc1nc2c3c(nn2c(C)c1Cl)CN(C(=O)c1ccccc1OCC(C)C)C3] |
| 31 | 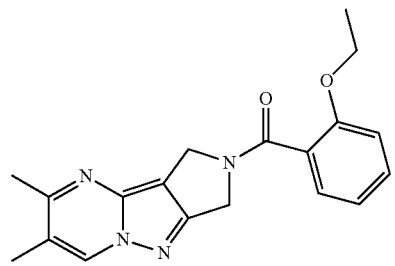 [SMILES: CCOc1ccccc1C(=O)N1Cc2nn3cc(C)c(C)nc3c2C1] |
| 32 | 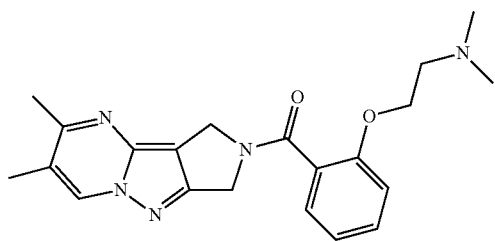 |

-continued
| Ex | Structures |
|---|---|
| 33 | 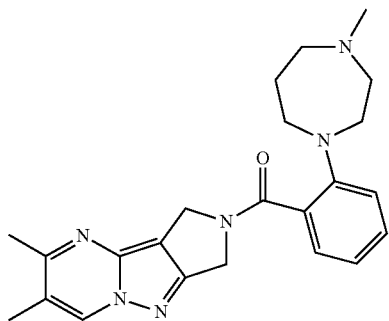 [SMILES: Cc1cn2nc3c(c2nc1C)CN(C(=O)c1ccccc1N1CCCN(C)CC1)C3] |
| 34 | 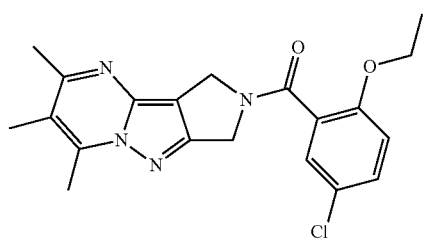 [SMILES: CCOc1ccc(Cl)cc1C(=O)N1Cc2nn3c(C)c(C)c(C)nc3c2C1] |
| 35 | 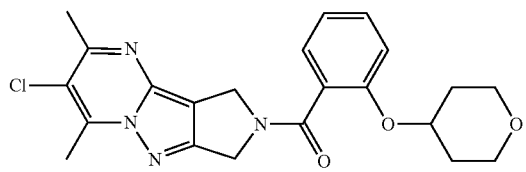 [SMILES: Cc1nc2c3c(nn2c(C)c1Cl)CN(C(=O)c1ccccc1OC1CCOCC1)C3] |
| 36 | 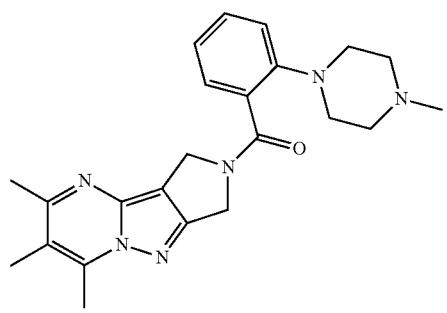 |
| 37 | 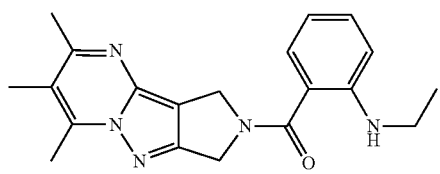 [SMILES: CCNc1ccccc1C(=O)N1Cc2nn3c(C)c(C)c(C)nc3c2C1] |
| 38 | 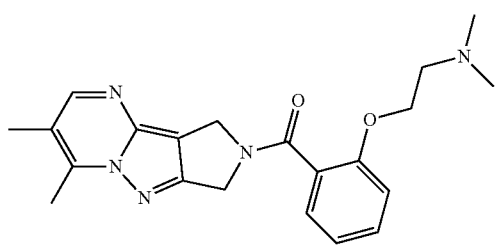 |

-continued
| Ex | Structures |
|---|---|
| 39 | 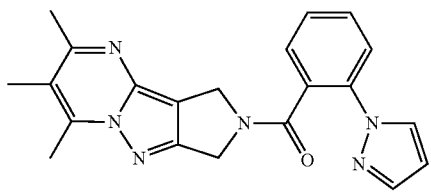 [SMILES: Cc1nc2c3c(nn2c(C)c1C)CN(C(=O)c1ccccc1-n1cccn1)C3] |
| 40 | 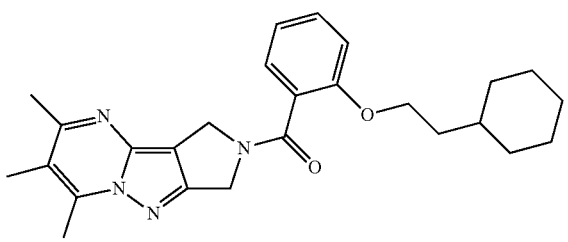 [SMILES: Cc1nc2c3c(nn2c(C)c1C)CN(C(=O)c1ccccc1OCCC1CCCCC1)C3] |
| 41 | 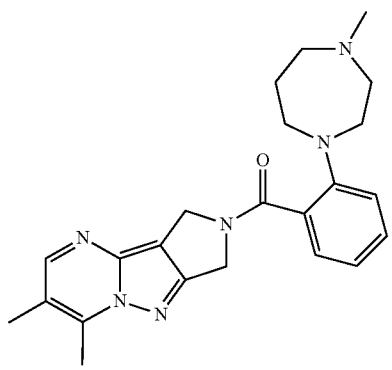 [SMILES: Cc1cnc2c3c(nn2c1C)CN(C(=O)c1ccccc1N1CCCN(C)CC1)C3] |
| 42 | 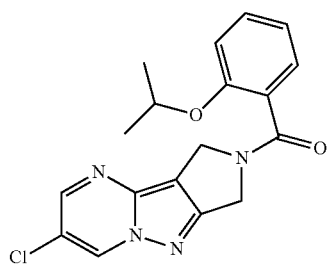 [SMILES: CC(C)Oc1ccccc1C(=O)N1Cc2nn3cc(Cl)cnc3c2C1] |
| 43 | 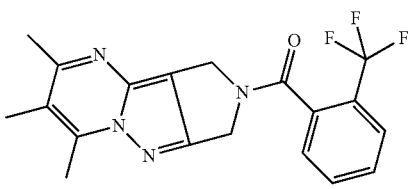 [SMILES: Cc1nc2c3c(nn2c(C)c1C)CN(C(=O)c1ccccc1C(F)(F)F)C3] |
| 44 | 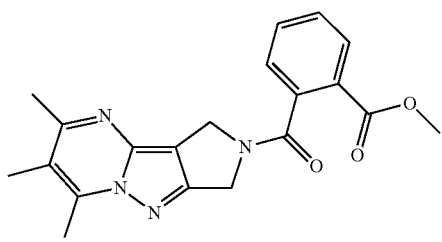 |

-continued
| Ex | Structures |
|---|---|
| 45 | 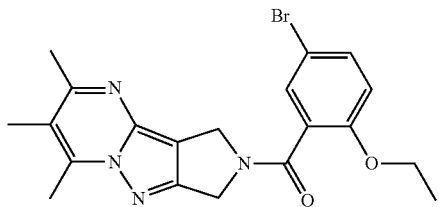 [SMILES: CCOc1ccc(Br)cc1C(=O)N1Cc2nn3c(C)c(C)c(C)nc3c2C1] |
| 46 | 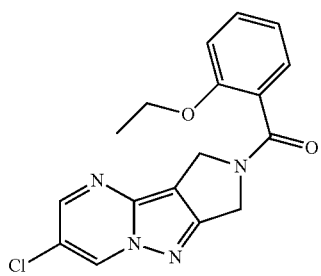 |
| 47 | 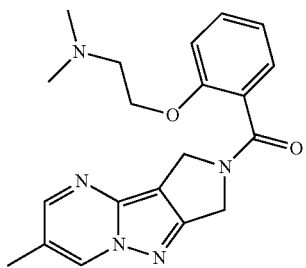 [SMILES: Cc1cnc2c3c(nn2c1)CN(C(=O)c1ccccc1OCCN(C)C)C3] |
| 48 | 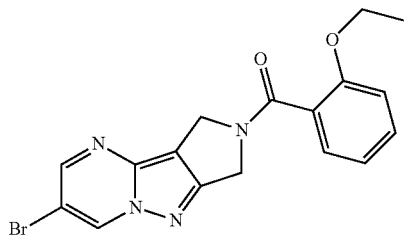 [SMILES: CCOc1ccccc1C(=O)N1Cc2nn3cc(Br)cnc3c2C1] |
| 49 | 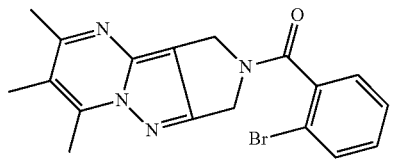 [SMILES: Cc1nc2c3c(nn2c(C)c1C)CN(C(=O)c1ccccc1Br)C3] |
| 50 | 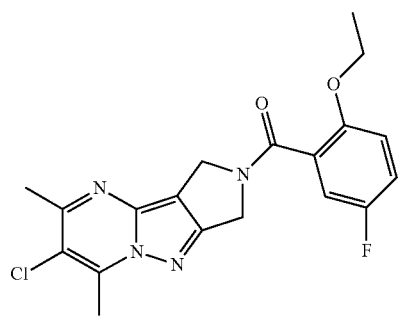 [SMILES: CCOc1ccc(F)cc1C(=O)N1Cc2nn3c(C)c(Cl)c(C)nc3c2C1] |

| Ex | Structures |
|---|---|
| 51 | 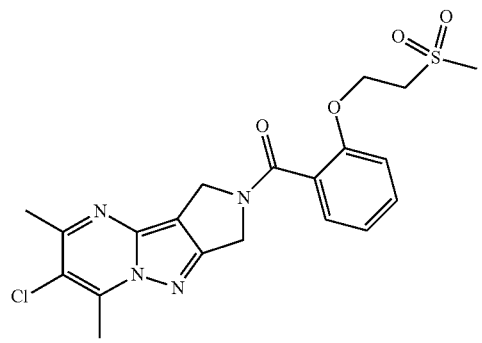 |
| 52 | 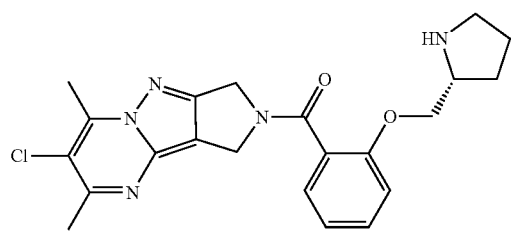 [SMILES: Cc1nc2c3c(nn2c(C)c1Cl)CN(C(=O)c1ccccc1OC[C@H]1CCCN1)C3] |
| 53 | 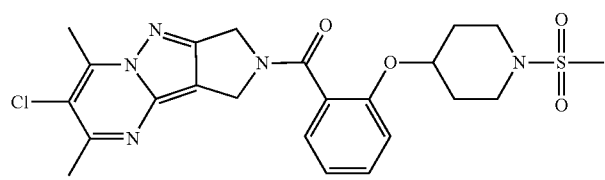 [SMILES: Cc1nc2c3c(nn2c(C)c1Cl)CN(C(=O)c1ccccc1OC1CCN(S(C)(=O)=O)CC1)C3] |
| 54 | 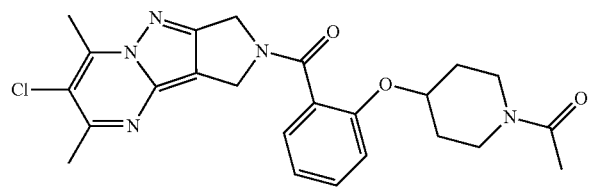 [SMILES: CC(=O)N1CCC(Oc2ccccc2C(=O)N2Cc3nn4c(C)c(Cl)c(C)nc4c3C2)CC1] |
| 55 | 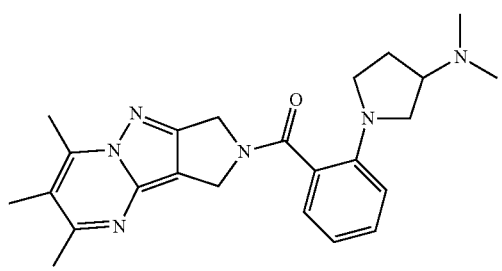 |
| 56 | 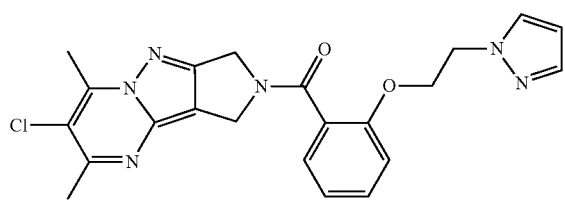 [SMILES: Cc1nc2c3c(nn2c(C)c1Cl)CN(C(=O)c1ccccc1OCCn1cccn1)C3] |

-continued
| Ex | Structures |
|---|---|
| 57 | 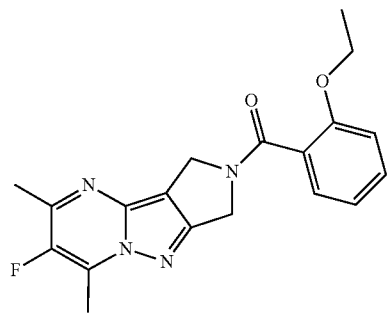 [SMILES: CCOc1ccccc1C(=O)N1Cc2nn3c(C)c(F)c(C)nc3c2C1] |
| 58 | 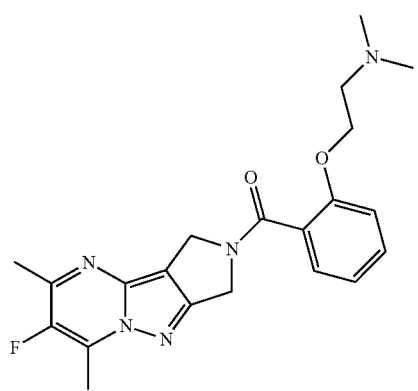 |
| 59 | 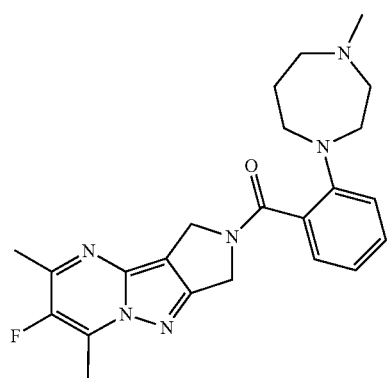 [SMILES: Cc1nc2c3c(nn2c(C)c1F)CN(C(=O)c1ccccc1N1CCCN(C)CC1)C3] |
| 60 | 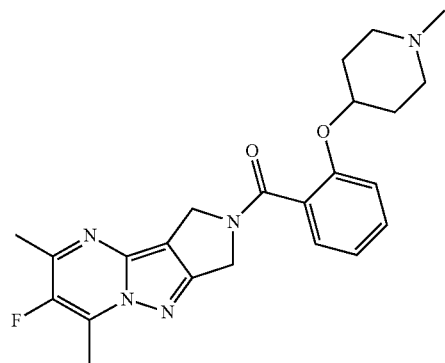 |

-continued
| Ex | Structures |
|---|---|
| 61 | 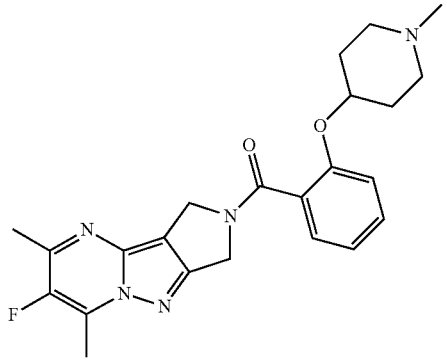 |
| 62 | 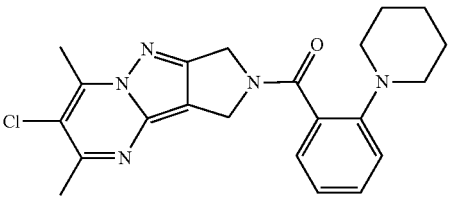 [SMILES: Cc1nc2c3c(nn2c(C)c1Cl)CN(C(=O)c1ccccc1N1CCCCC1)C3] |
| 63 | 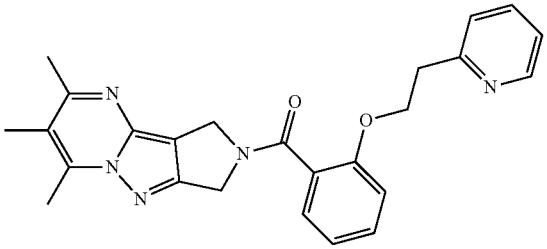 [SMILES: Cc1nc2c3c(nn2c(C)c1C)CN(C(=O)c1ccccc1OCCc1ccccn1)C3] |
| 64 | 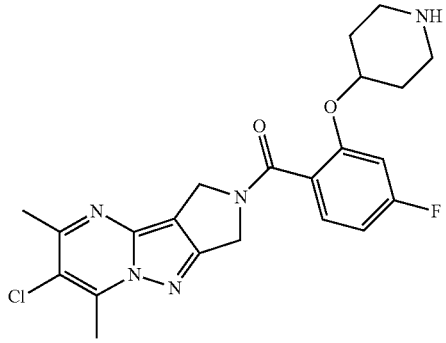 [SMILES: Cc1nc2c3c(nn2c(C)c1Cl)CN(C(=O)c1ccc(F)cc1OC1CCNCC1)C3] |
| 65 | 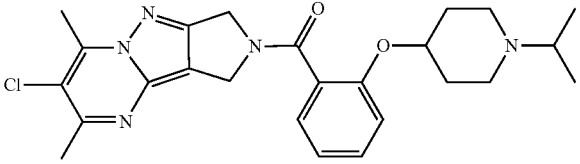 [SMILES: Cc1nc2c3c(nn2c(C)c1Cl)CN(C(=O)c1ccccc1OC1CCN(C(C)C)CC1)C3] |
| 66 | 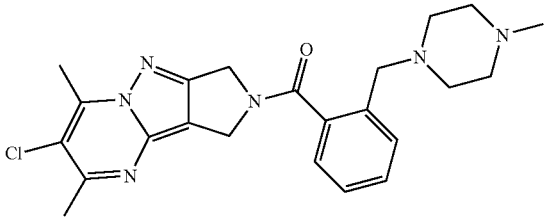 [SMILES: Cc1nc2c3c(nn2c(C)c1Cl)CN(C(=O)c1ccccc1CN1CCN(C)CC1)C3] |

| Ex | Structures |
|---|---|
| 67 | 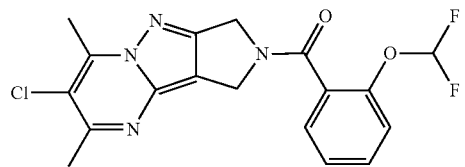 [SMILES: Cc1nc2c3c(nn2c(C)c1Cl)CN(C(=O)c1ccccc1OC(F)F)C3] |
| 68 | 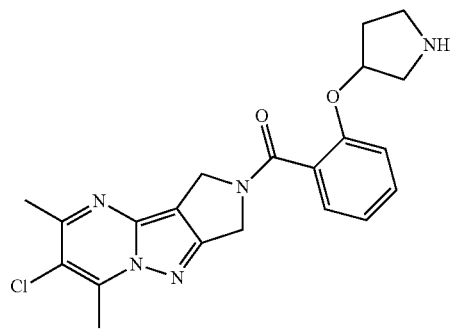 [SMILES: Cc1nc2c3c(nn2c(C)c1Cl)CN(C(=O)c1ccccc1OC1CCNC1)C3] |
| 69 | 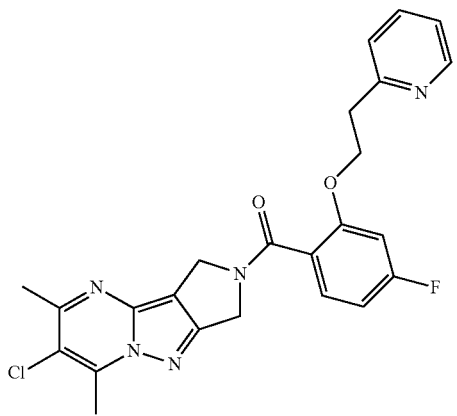 [SMILES: Cc1nc2c3c(nn2c(C)c1Cl)CN(C(=O)c1ccc(F)cc1OCCc1ccccn1)C3] |
| 70 | 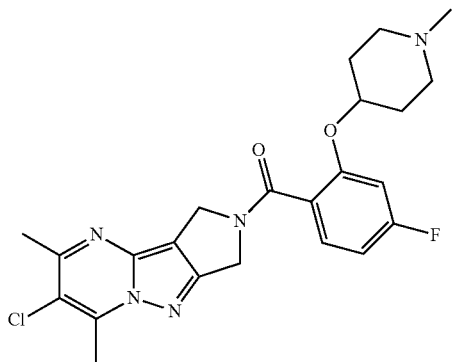 |

| Ex | Structures |
|---|---|
| 71 | 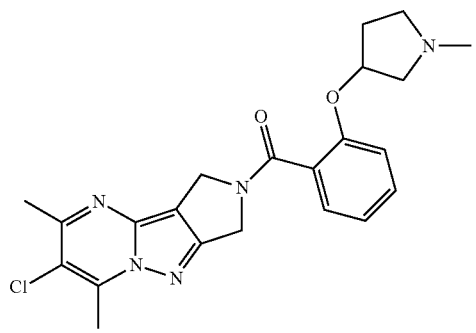 |
| 72 | 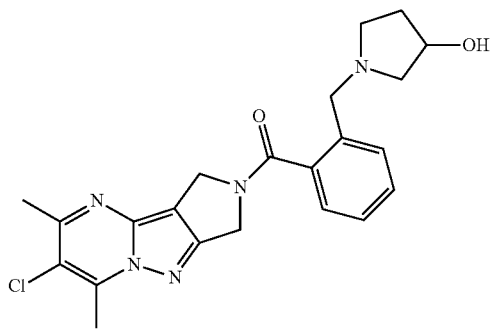 [SMILES: Cc1nc2c3c(nn2c(C)c1Cl)CN(C(=O)c1ccccc1CN1CCC(O)C1)C3] |
| 73 | 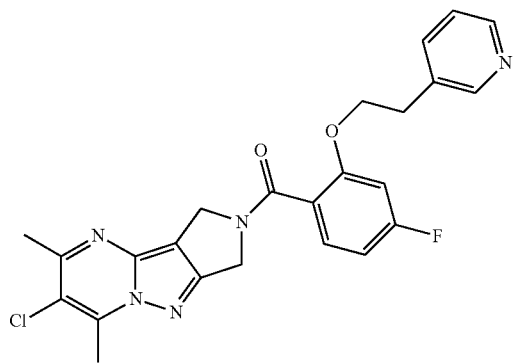 [SMILES: Cc1nc2c3c(nn2c(C)c1Cl)CN(C(=O)c1ccc(F)cc1OCCc1cccnc1)C3] |
| 74 | 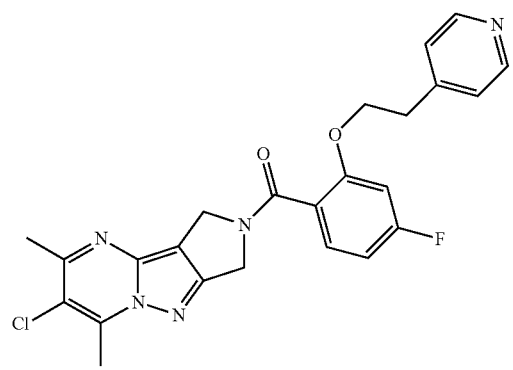 [SMILES: Cc1nc2c3c(nn2c(C)c1Cl)CN(C(=O)c1ccc(F)cc1OCCc1ccncc1)C3] |

| Ex | Structures |
|---|---|
| 75 | 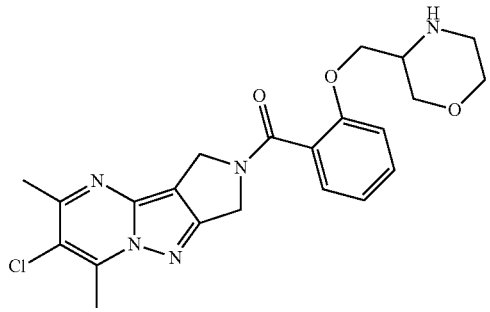 [SMILES: Cc1nc2c3c(nn2c(C)c1Cl)CN(C(=O)c1ccccc1OCC1COCCN1)C3] |
| 76 | 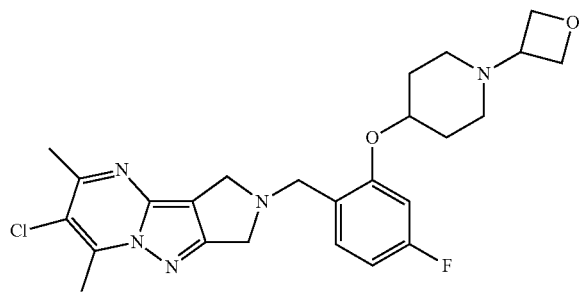 [SMILES: Cc1nc2c3c(nn2c(C)c1Cl)CN(Cc1ccc(F)cc1OC1CCN(C2COC2)CC1)C3] |
| 77 | 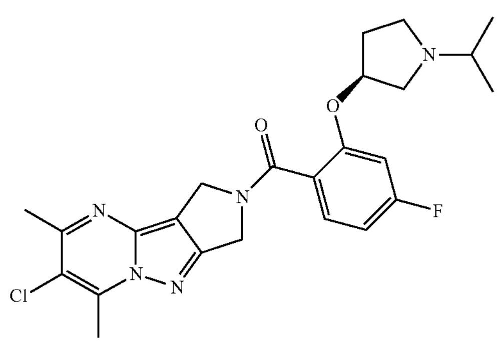 [SMILES: Cc1nc2c3c(nn2c(C)c1Cl)CN(C(=O)c1ccc(F)cc1O[C@H]1CCN(C(C)C)C1)C3] |
| 78 | 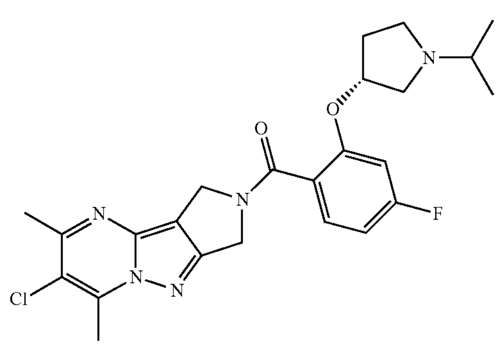 [SMILES: Cc1nc2c3c(nn2c(C)c1Cl)CN(C(=O)c1ccc(F)cc1O[C@@H]1CCN(C(C)C)C1)C3] |

-continued
| Ex | Structures |
|---|---|
| 79 | 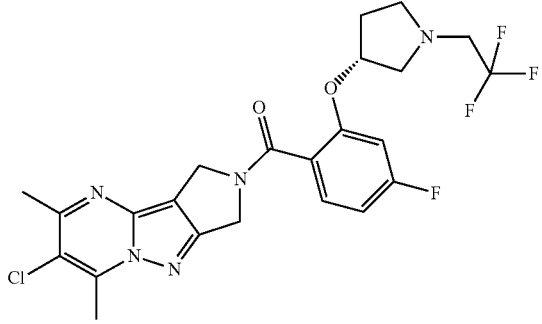 [SMILES: Cc1nc2c3c(nn2c(C)c1Cl)CN(C(=O)c1ccc(F)cc1O[C@@H]1CCN(CC(F)(F)F)C1)C3] |
| 80 | 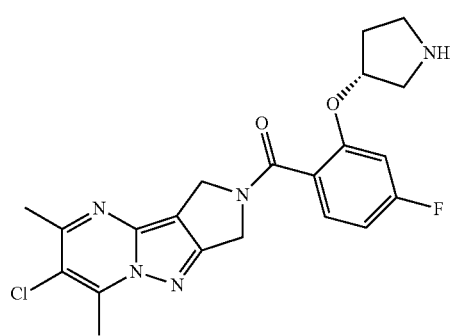 [SMILES: Cc1nc2c3c(nn2c(C)c1Cl)CN(C(=O)c1ccc(F)cc1O[C@@H]1CCNC1)C3] |
| 81 | 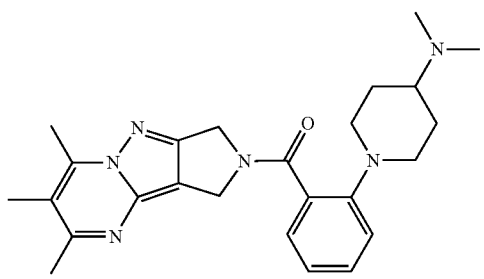 |
| 82 | 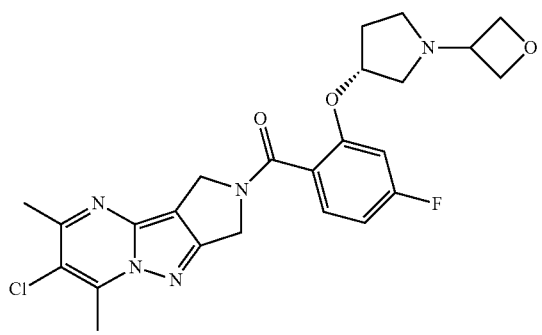 [SMILES: Cc1nc2c3c(nn2c(C)c1Cl)CN(C(=O)c1ccc(F)cc1O[C@@H]1CCN(C2COC2)C1)C3] |
| 83 | 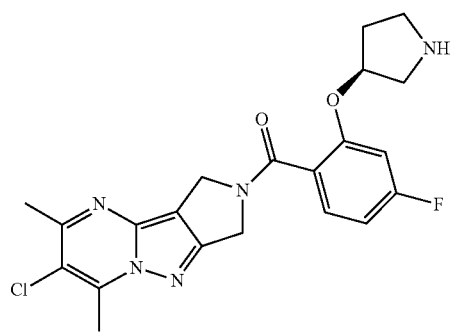 [SMILES: Cc1nc2c3c(nn2c(C)c1Cl)CN(C(=O)c1ccc(F)cc1O[C@H]1CCNC1)C3] |

| Ex | Structures |
|---|---|
| 84 | 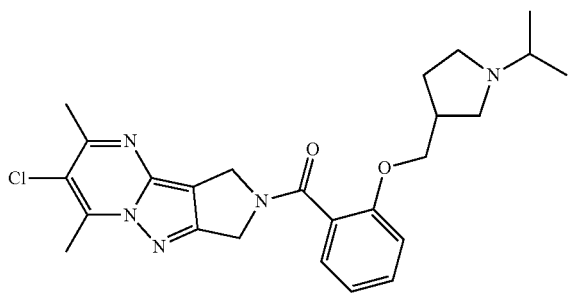 [SMILES: Cc1nc2c3c(nn2c(C)c1Cl)CN(C(=O)c1ccccc1OCC1CCN(C(C)C)C1)C3] |
| 85 | 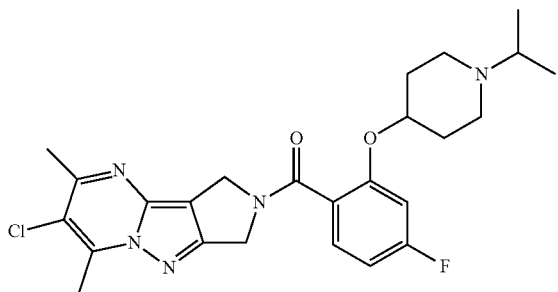 [SMILES: Cc1nc2c3c(nn2c(C)c1Cl)CN(C(=O)c1ccc(F)cc1OC1CCN(C(C)C)CC1)C3] |
| 86 | 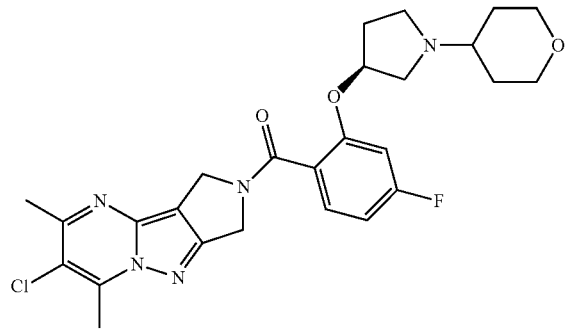 [SMILES: Cc1nc2c3c(nn2c(C)c1Cl)CN(C(=O)c1ccc(F)cc1O[C@H]1CCN(C2CCOCC2)C1)C3] |
| 87 | 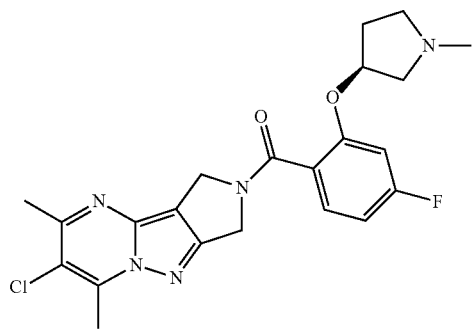 |

| Ex | Structures |
|---|---|
| 88 | 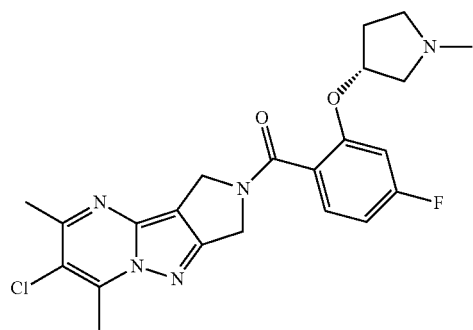 |
| 89 | 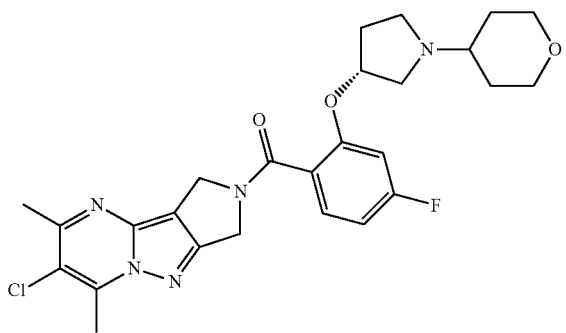 [SMILES: Cc1nc2c3c(nn2c(C)c1Cl)CN(C(=O)c1ccc(F)cc1O[C@@H]1CCN(C2CCOCC2)C1)C3] |
| 90 | 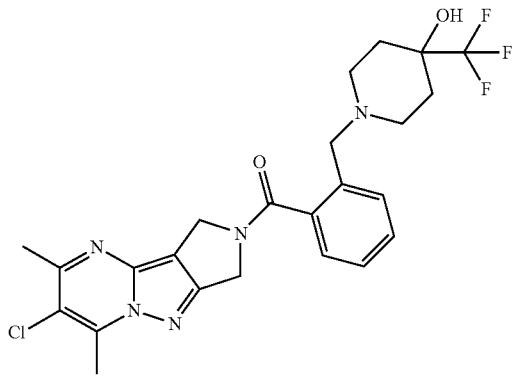 [SMILES: Cc1nc2c3c(nn2c(C)c1Cl)CN(C(=O)c1ccccc1CN1CCC(O)(C(F)(F)F)CC1)C3] |
| 91 | 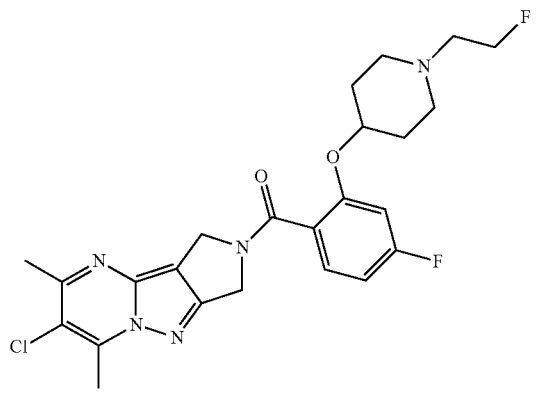 [SMILES: Cc1nc2c3c(nn2c(C)c1Cl)CN(C(=O)c1ccc(F)cc1OC1CCN(CCF)CC1)C3] |

-continued
| Ex | Structures |
|---|---|
| 92 | 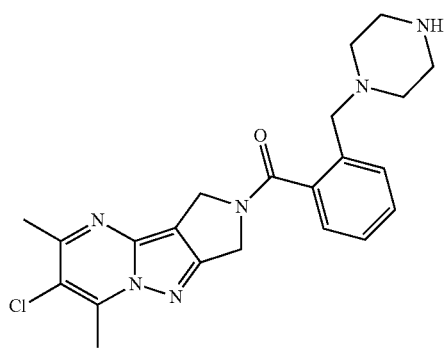 [SMILES: Cc1nc2c3c(nn2c(C)c1Cl)CN(C(=O)c1ccccc1CN1CCNCC1)C3] |
| 93 | 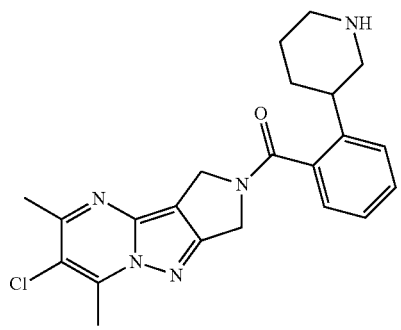 [SMILES: Cc1nc2c3c(nn2c(C)c1Cl)CN(C(=O)c1ccccc1C1CCCNC1)C3] |
| 94 | 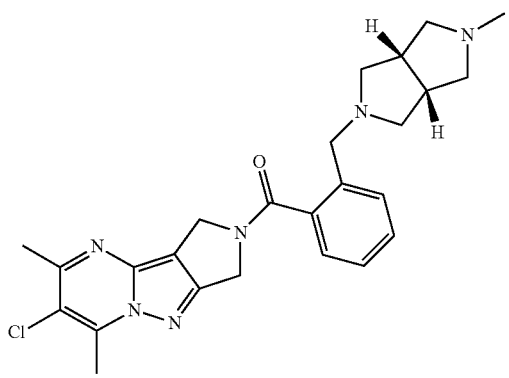 |
| 95 | 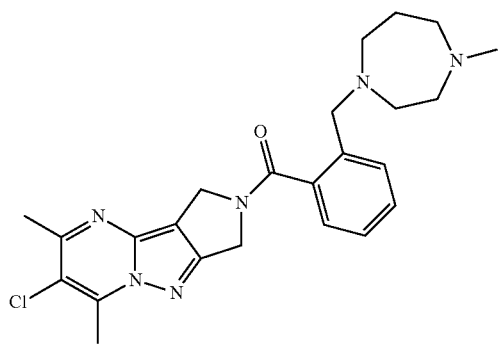 |

| Ex | Structures |
|---|---|
| 96 | 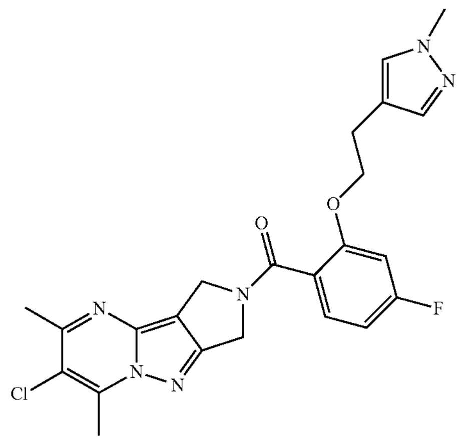 [SMILES: Cc1nc2c3c(nn2c(C)c1Cl)CN(C(=O)c1ccc(F)cc1OCCc1cnn(C)c1)C3] |
| 97 | 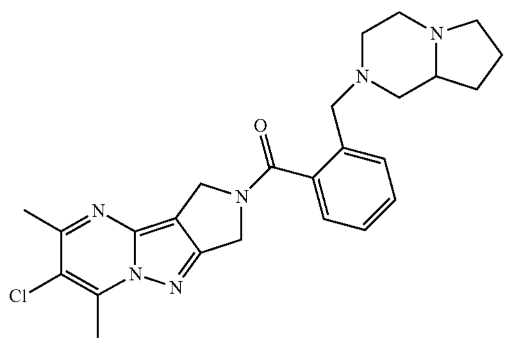 [SMILES: Cc1nc2c3c(nn2c(C)c1Cl)CN(C(=O)c1ccccc1CN1CCN2CCCC2C1)C3] |
| 98 | 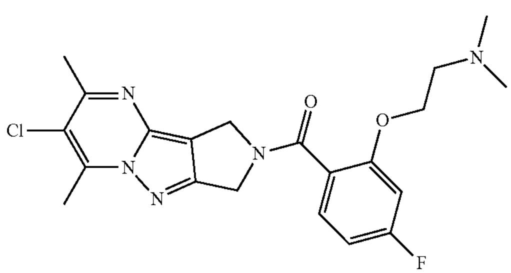 [SMILES: Cc1nc2c3c(nn2c(C)c1Cl)CN(C(=O)c1ccc(F)cc1OCCN(C)C)C3] |
| 99 | 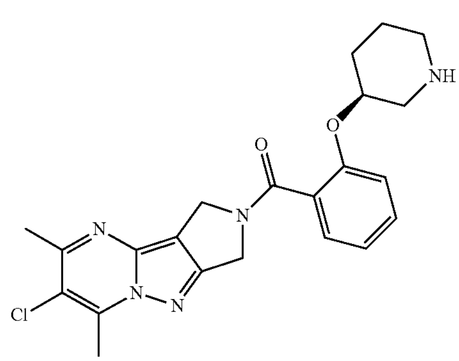 [SMILES: Cc1nc2c3c(nn2c(C)c1Cl)CN(C(=O)c1ccccc1O[C@H]1CCCNC1)C3] |

| Ex | Structures |
|---|---|
| 100 | 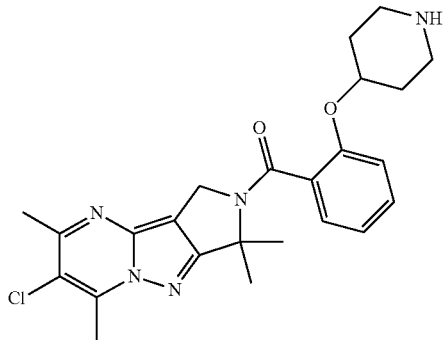 [SMILES: Cc1nc2c3c(nn2c(C)c1Cl)C(C)(C)N(C(=O)c1ccccc1OC1CCNCC1)C3] |
| 101 | 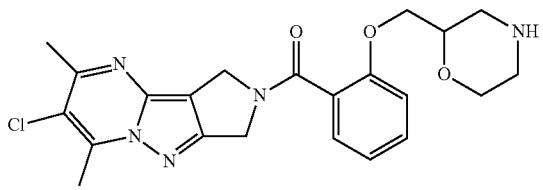 [SMILES: Cc1nc2c3c(nn2c(C)c1Cl)CN(C(=O)c1ccccc1OCC1CNCCO1)C3] |

The following abbreviations refer to the abbreviations used below:

ACN (acetonitrile), AcOH (acetic acid), aq. (aqueous), dba (dibenzylideneacetone), DBAD (di-tert-butylazodicarboxylate), DCC (dicyclohexylcarbodiimide), DCM (dichloromethane), DEAD (diethylazodicarboxylate), DIAD (diisopropylazodicarboxylate), DIC (diisopropylcarbodiimide), DIEA (di-isopropyl ethylamine), DMSO (dimethyl sulfoxide), DMF (N,N-dimethylformamide), DMP (Dess-Martin periodinane: acetic acid 1,1-diacetoxy-3-oxo-1λ5-ioda-2-oxa-indan-1-yl ester), EA (ethyl acetate), EDC (1-ethyl-3-(3-dimethylaminopropyl)carbodiimide hydrochloride), eq. (equivalent), EtOH (ethanol), g (gram), HATU (2-(1H-7-azabenzotriazol-1-yl)-1,1,3,3-tetramethyl uronium hexafluorophosphate methanaminium), cHex (cyclohexane), HPLC (high performance liquid chromatography), LG (leaving group), MeOH (methanol), MHz (Megahertz), MIBK (methyl isobutyl ketone), min (minute), mL (milliliter), mmol (millimole), MS (mass spectrometry), MTBE (tert-butyl methyl ether), MW (microwave), NMR (nuclear magnetic resonance), ppm (part per million), sat. (saturated), SFC (supercritical fluid chromatography), T3P (2,4,6-Tripropyl-[1,3,5,2,4,6]trioxatriphosphinane 2,4,6-trioxide), TEA (triethylamine), TFA (trifluoroacetic acid), THF (tetrahydrofurane), UV (ultraviolet).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituent of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

A "leaving group" denotes a chemical moiety which can be removed or replaced by another chemical group.

Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N hydroxysuccinimide.

Depending on the nature of $R^1$, $R^2$, $R^3$, $R^4$, $R^a$, $R^b$, and Q, different synthetic strategies may be selected for the synthesis of compounds of Formula (I). In the process illustrated in the following schemes, $R^1$, $R^2$, $R^3$, $R^4$, $R^a$, $R^b$, and Q are as above defined in the description unless otherwise mentioned.

Generally, tetraaza-cyclopenta[a]indenyl compounds of Formula (I) wherein $R^1$, $R^2$, $R^3$, $R^4$, $R^a$, $R^b$, and Q are defined as above can be prepared following the synthetic pathway described in the general scheme 1.

51

General scheme 1

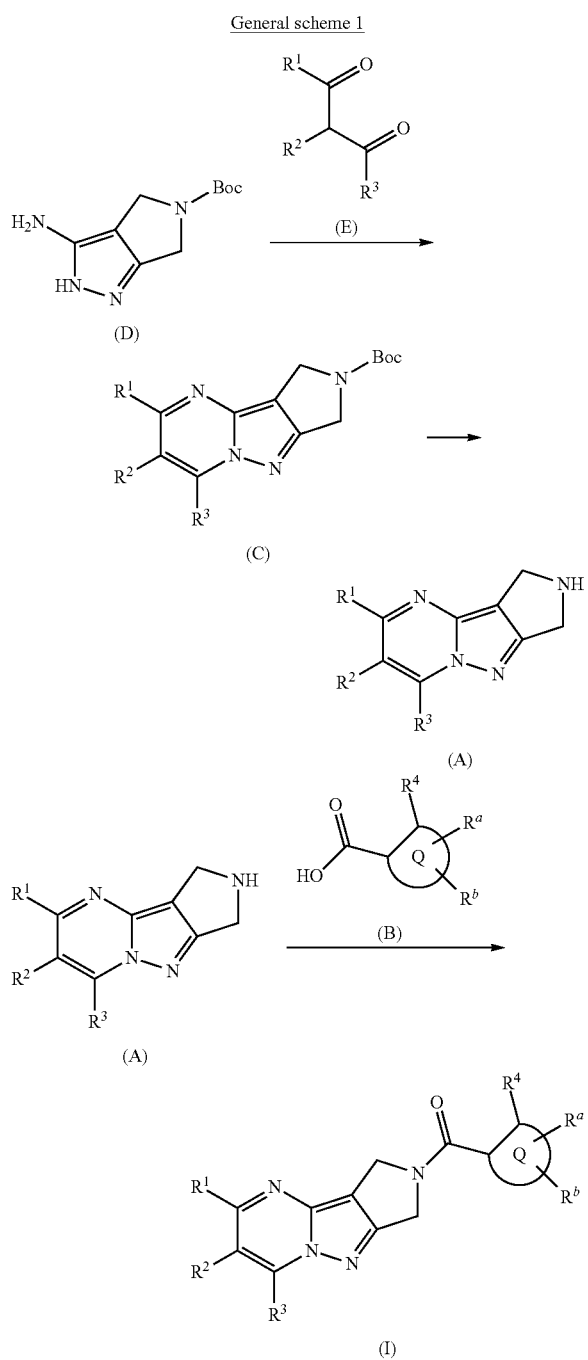

According to a preferred synthetic pathway, compounds of Formula (I) wherein $R^1$, $R^2$, $R^3$, $R^4$, $R^a$, $R^b$, and Q are as above defined, may be prepared by reaction between an amine of Formula (A) and a carboxylic acid of Formula (B) following usual conditions for the formation of an amide starting from a carboxylic acid and an amine by using coupling agents such as EDC, HATU, DCC, DIC or via the formation of an acid chloride or an activated ester. Preferred conditions consist in the treatment of compounds of Formula (A) wherein $R^1$, $R^2$ and $R^3$ are as above defined with HATU or EDC followed by the addition of the amine of Formula (B) wherein $R^4$, $R^a$, $R^b$, and Q are as above defined, in the presence of a base such as TEA or DIEA in a suitable solvent such as DMF or DCM at room temperature.

52

Compounds of Formula (A) wherein $R^1$, $R^2$ and $R^3$ are as above defined may be prepared from the corresponding Boc protected amines of Formula (C), by treatment with an acid such TFA in DCM or HCl in dioxane or HCl in AcOH.

Compounds of Formula (C) wherein $R^1$, $R^2$ and $R^3$ areas above defined may be prepared by reacting compounds of Formula (D) and compounds of Formula (E) in a suitable solvent such as AcOH at a temperature ranging from 25° C. to 75° C., for 30 minutes to 48 hours.

Compound of Formula (D) may be prepared as described in Bioorg. Med. Chem. Lett. 2010, 20(14), 4273-4278.

Alternatively, compounds of general Formula (I) wherein $R^1$, $R^2$, $R^3$, $R^a$, $R^b$, and Q are as above defined and $R^4$ is OG, may be prepared as depicted in general scheme 2.

General scheme 2

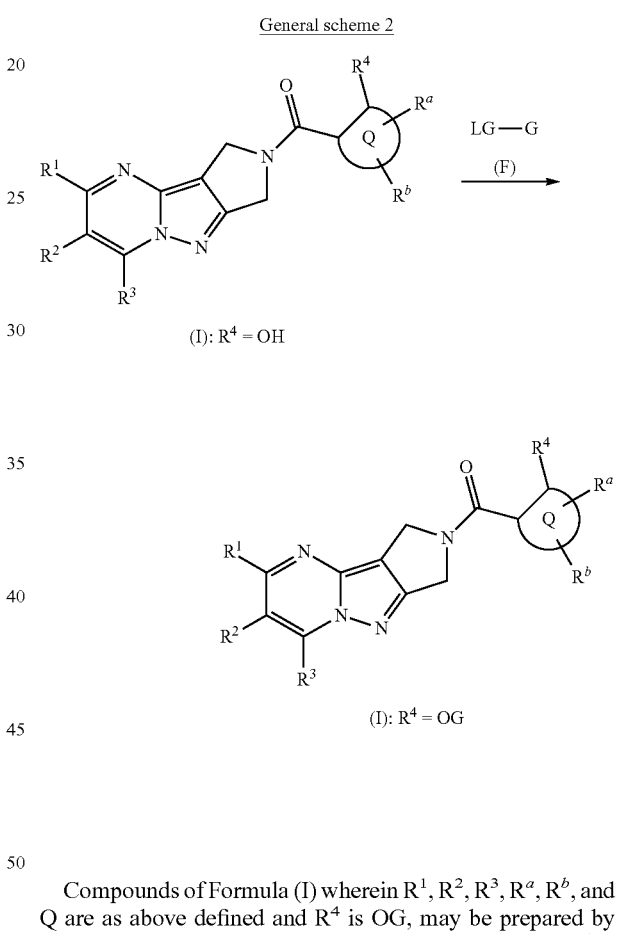

Compounds of Formula (I) wherein $R^1$, $R^2$, $R^3$, $R^a$, $R^b$, and Q are as above defined and $R^4$ is OG, may be prepared by reaction between a compound of Formula (I) wherein $R^4$ is OH and a compound of Formula (F) wherein LG is a leaving group, preferably selected from Hal or an activated ester, in the presence of a base such as $K_2CO_3$, $Cs_2CO_3$, $Na_2CO_3$, NaH, in a solvent such as DMF, DMA, THF, 1,4-dioxane, acetone, ACN at a temperature ranging from 20° C. to 200° C. for few minutes to several hours. Preferred conditions consist in the treatment compound of Formula (I) wherein $R^4$ is OH by a compound of Formula (F) in the presence of $K_2CO_3$, in a solvent such as DMF at a temperature of about 150° C. using microwave heating for 10 minutes to 1 hour.

Compounds of Formula (B) wherein $R^a$, $R^b$, and Q are as above defined and $R^4$ is OG may be prepared according to general scheme 3.

General scheme 3

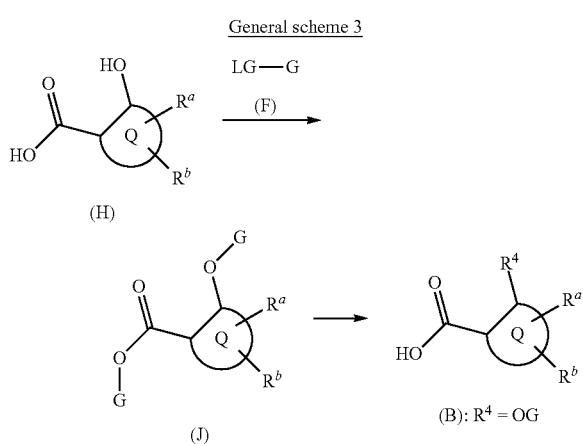

Compounds of Formula (B) wherein $R^4$ is OG may be prepared by saponification of esters of Formula (J) wherein $R^a$, $R^b$, G and Q are as above defined, using LiOH, NaOH or KOH in water, water/THF, water/THF/ethanol or water/1,4-dioxane, at temperatures between 0 and 100° C. Furthermore, ester can be hydrolyzed, for example, using acetic acid, TFA or HCl.

Compounds of Formula (J) wherein $R^a$, $R^b$, G and Q are as above defined may be prepared by reacting compounds of Formula (H) with compounds of Formula (F) in the presence of a base such as $K_2CO_3$, $Cs_2CO_3$, $Na_2CO_3$, NaH, in a solvent such as DMF, DMA, THF, 1,4-dioxane, acetone, ACN or mixtures thereof at a temperature ranging from 20° C. to 200° C. for few minutes to several hours.

Alternatively, compounds of general Formula (I) wherein $R^1$, $R^2$, $R^3$, $R^a$, $R^b$, and Q are as above defined and $R^4$ is OG, may be prepared as depicted in general scheme 4.

General scheme 4

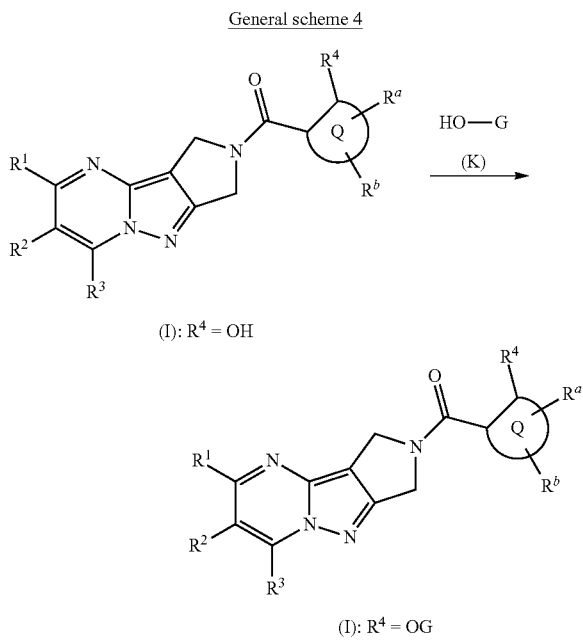

Compounds of Formula (I) wherein $R^1$, $R^2$, $R^3$, $R^a$, $R^b$, and Q are as above defined and $R^4$ is OG, may be prepared by a Mitsunobu type reaction between a compound of Formula (I) wherein $R^4$ is OH and an alcohol of Formula (K), in the presence of a phosphine such as triphenylphosphine or tributylphosphine and an azodicarboxylate such as DEAD, DIAD, DBAD in a solvent such as THF, 1,4-dioxane, at a temperature ranging from 20° C. to 100° C. for few minutes to several hours. Preferred conditions consist in the treatment compound of Formula (I) wherein $R^4$ is OH by an alcohol of Formula (K) in the presence of tributylphosphine and DBAD in a solvent such as 1,4-dioxane or THF at a temperature between 0° C. to 40° C. for several hours.

Compounds of this invention can be isolated in association with solvent molecules by crystallization from an appropriate solvent or by evaporation of an appropriate solvent. The pharmaceutically acceptable anionic salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of the compounds of Formula (I), which contain an acidic center, may be prepared in a conventional manner. For example, a solution of the free acid may be treated with a suitable base, either neat or in a suitable solution, and the resulting salt isolated either by filtration or by evaporation under vacuum of the reaction solvent. In some cases, salts can be prepared by mixing a solution of the acid with a solution of an alkali or earth alkali salt (such as sodium ethylhexanoate, magnesium oleate), employing a solvent in which the desired alkali or earth alkali salt of the compounds of formula (I) precipitates, or can be otherwise isolated by concentration and addition of a non-solvent.

Both types of salts may be formed or interconverted using ion-exchange resin techniques.

Depending on the conditions used, the reaction times are generally between a few minutes and 14 days. The reaction temperature is between about −30° C. and about 140° C., normally between −10° C. and 90° C., in particular between about 0° C. and 70° C.

Compounds of the formula (I) and related formulae can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy-icarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-icarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and aryl-isulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C. Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

The formula (I) and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called pro-drug compounds.

The term "prodrug derivatives" is taken to mean compounds of the formula I which have been modified with, for example, alkyl or acyl groups, sugars or oligopeptides and which are rapidly cleaved in the organism to form the active compounds. Preferably "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14-21 of "Bioreversible Carriers in Drug Design: Theory and Application", edited by E. B. Roche, Pergamon Press: New York (1987). It is intended that these references, and any others cited throughout this specification, are incorporated herein by reference.

These also include biodegradable polymer derivatives of the compounds according to the invention, as described, for example, in Int. J. Pharm. 115, 61-67 (1995).

The formula (I) and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I), and related formulae and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I), and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient.

Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base. Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil. Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a M1 related disorder, comprising administering to said subject an effective amount of a compound of formula (I) and related formulae. The present invention preferably relates to a method, wherein the M1 associated disorder is Alzheimer's disease, Parkinson disease, schizophrenia, movement disorders, memory disorders, chronic neuropathic pain, sleep disorders, epilepsy. Nociception disorder, dementia, hallucination, delusion, paranoia.

EXPERIMENTAL PART

The compounds of invention have been named according to the standards used in the program AutoNom (v1.0.1.1).

The compounds according to formula (I) can be prepared from readily available starting materials by several synthetic approaches, using both solution-phase and solid-phase chemistry protocols or mixed solution and solid phase protocols. Examples of synthetic pathways are described below in the examples.

The commercially available starting materials used in the following experimental description were purchased from Aldrich, Sigma, ACROS or ABCR unless otherwise reported.

$^1$H NMR analyses were carried out using BRUKER NMR, model DPX-300 MHz FT-NMR. Residual signal of deuterated solvent was used as internal reference. Chemical shifts ($\delta$) are reported in ppm in relative to the residual solvent signal ($\delta$=2.50 for $^1$H NMR in DMSO-$d_6$, and 7.26 in CDCl$_3$). s (singlet), d (doublet), t (triplet), q (quadruplet), br (broad), quint (quintuplet). Some compounds in the experimental part exist as mixture of rotamers in different ratios as described in the $^1$H NMR descriptions.

The MS data provided in the examples described below were obtained as followed: Mass spectrum: LC/MS Waters ZMD (ESI). HPLC analyses were obtained as followed using a Waters Xbridge™ C8 50 mm×4.6 mm column at a flow of 2 mL/min; 8 min gradient H$_2$O:CH$_3$CN:TFA from 100:0:0.1% to 0:100:0.05% with UV detection (maxplot).

The SFC purifications were performed with a Prep SFC 100 UV from Thar-Waters.

The mass directed preparative HPLC purifications were performed with a mass directed autopurification Fractionlynx from Waters equipped with a Sunfire Prep C18 OBD column 19×100 mm 5 μm, unless otherwise reported. All purifications were performed with a gradient of ACN/H$_2$O or ACN/H$_2$O/HCOOH (0.1%).

The microwave chemistry was performed on a single mode microwave reactor Emrys™ Optimiser or Initiator™ Sixty from Biotage.

Method A (Amide Formation using HATU):

HATU (1.0-1.2 eq.) was added to a solution of the carboxylic acid (1.0-1.2 eq.) and DIEA (2-4 eq.) in DMF and the reaction mixture was stirred at room temperature for 15 min to 1 hour whereupon the amine (1 eq.) was added. The resulting mixture was stirred at room temperature until completion.

Method B (Amide Formation using EDC):

EDC (1.0-1.2 eq.) was added to a solution of the carboxylic acid (1.0-1.2 eq.) and TEA (2-4 eq.) in DCM and the reaction mixture was stirred at room temperature for 15 min to 1 hour whereupon the amine (1 eq.) was added. The resulting mixture was stirred at room temperature until completion.

Method C (Benzylamine Formation):

Amine (3-10 eq) was added to a solution of benzylhalide (1 eq) in anhydrous DCM (10-20V). The resulting mixture was stirred at RT until completion (usually 3-15 hours). The reaction mixture was diluted with DCM and washed with a basic aqueous solution (usually 1N NaOH) and brine. The organic layer was dried (Na$_2$SO$_4$) and concentrated under vacuum. The crude compound was purified by flash chromatography or crystallization.

Method D (Benzylamine Formation using DIEA):

Amine (2-5 eq) and DIEA (2-5 eq) were added to a solution of benzylhalide (1 eq) in anhydrous DCM (10-20V). The resulting mixture was stirred at RT until completion (usually 3-15 hours). The reaction mixture was diluted with DCM and washed with a basic aqueous solution (usually 1N NaOH) and brine. The organic layer was dried (Na$_2$SO$_4$) and concentrated under vacuum. The crude compound was purified by flash chromatography or crystallization.

Method E (Deprotection of Boc Protected Amine Using HCl in AcOH)

A 32% aqueous solution of HCl (3-5 eq) was added to a solution of the Boc protected amine (1 eq) in AcOH (5-10V). The resulting mixture was stirred at RT until completion (usually 1-24 hours). The reaction mixture was diluted with an aqueous solution of NaOH until pH~14 and extracted several time with DCM. The organic layers were combined, dried (Na$_2$SO$_4$) and concentrated under vacuum. The crude product was purified by flash chromatography or crystallization.

Method F (Amide Formation using T3P)

T3P (1.0-1.2 eq) was added to a mixture of the carboxylic acid (1.0-1.2 eq), the amine (1.0-1.2 eq) and DIEA (2-4 eq) in DCM and the reaction mixture was stirred at room temperature until completion.

Method G (Arylalkylether Formation by Mitsunobu Reaction)

DBAD or DIAD (1.5-2.5 eq) was added to mixture of the phenol (1 eq), the alcohol (1.5-2.5 eq) and tributylphosphine (1.5-2.5 eq) in THF and the reaction mixture was stirred at room temperature until completion.

Preparation of Intermediates

Intermediate A1: 5,6,7-trimethyl-2,3-dihydro-1H-2,4,7a,8-tetraaza-cyclopenta[a]indene hydrochloride

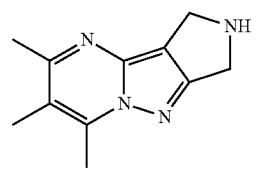

Step 1: 5,6,7-trimethyl-1H,3H-2,4,7a,8-tetraaza-cyclopenta[a]indene-2-carboxylic acid tert-butyl ester A mixture of 3-amino-2,6-dihydro-4H-pyrrolo[3,4-c]pyrazole-5-carboxylic acid tert-butyl ester (2.4 g; 10.7 mmol; 1 eq.) and 3-methyl-2,4-pentanedione (1.75 mL; 15 mmol; 1.4 eq.) in AcOH (25 mL) was stirred at room temperature for 18 hours. The solvent was evaporated in vacuo and the residue partitioned between ethyl acetate and sat. aq. NaHCO$_3$. The organic layer was dried over sodium sulfate and concentrated in vacuo. The residue was triturated in ACN and the precipitate filtered off to afford the title compound (1.7 g, 52%) as a white solid. The mother liquor was concentrated in vacuo and the residue purified by column chromatography (DCM/EtOH, 95/5) to afford the title compound (1.5 g, 46%) as a white solid. $^1$H NMR (DMSO-d$_6$) δ 4.59-4.53 (m, 4H), 3.34 (s, 6H), 2.27 (s, 3H), 1.47 (s, 9H). HPLC (max plot) 96.1%; Rt 3.92 min. UPLC/MS: (MS+) 303.1 ([M+H]$^+$).

Step 2: 5,6,7-trimethyl-2,3-dihydro-1H-2,4,7a,8-tetraaza-cyclopenta[a]indene hydrochloride A 4M solution of HCl in 1,4-dioxane (1.24 mL; 4.96 mmol; 15 eq.) was added to a solution of 5,6,7-trimethyl-1H,3H-2,4,7a,8-tetraaza-cyclopenta[a]indene-2-carboxylic acid tert-butyl ester (100 mg; 0.33 mmol; 1 eq.) in 1,4-dioxane (5 mL) and the resulting mixture was stirred at room temperature for 18 hours. The solvent was evaporated in vacuo and the residue was triturated in 1,4-dioxane. Concentration to dryness afforded the title compound (65 mg, 82%) as a white solid. $^1$H NMR (DMSO-d$_6$) δ 10.40-10.30 (m, 1H), 4.57-4.50 (m, 4H), 2.73 (s, 3H), 2.54 (s, 3H), 2.28 (s, 3H). HPLC (max plot) 100.0%; Rt 1.26 min. UPLC/MS: (MS+) 203.1 ([M+H]$^+$).

Intermediate A2: 6-ethyl-5,7-dimethyl-2,3-dihydro-1H-2,4,7a,8-tetraaza-cyclopenta[a]indene

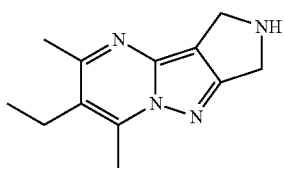 [SMILES: CCc1c(C)nc2c3c(nn2c1C)CNC3]

A mixture of 3-amino-2,6-dihydro-4H-pyrrolo[3,4-c]pyrazole-5-carboxylic acid tert-butyl ester (0.6 g; 2.68 mmol; 1 eq.) and 3-ethyl-2,4-pentanedione (0.36 mL; 2.68 mmol; 1 eq.) in AcOH (8 mL) was stirred at room temperature for 32 hours. Aq. 32% HCl (1.05 mL; 10.7 mmol; 4 eq.) was added and the resulting mixture stirred for a further 16 hours. After concentration in vacuo, the residue was triturated in MTBE and the precipitate filtered off and dried. The solid was taken up in ethyl acetate and washed with 1M aq. NaOH (2×), dried over magnesium sulfate and concentrated in vacuo to afford the title compound (450 mg, 94%) as a beige solid. $^1$H NMR (DMSO-$d_6$) δ 4.05-4.00 (m, 4H), 2.73-2.63 (m, 5H), 2.51 (s, 3H), 1.12 (t, J=7.4 Hz, 3H). UPLC/MS: (MS+) 217.3 ([M+H]$^+$).

Intermediate A3: 6-chloro-5,7-dimethyl-2,3-dihydro-1H-2,4,7a,8-tetraaza-cyclopenta[a]indene hydrochloride

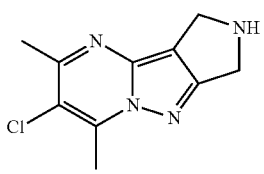

Step 1: 6-chloro-5,7-dimethyl-1H,3H-2,4,7a,8-tetraaza-cyclopenta[a]indene-2-carboxylic acid tea-butyl ester A solution of 3-amino-2,6-dihydro-4H-pyrrolo[3,4-c]pyrazole-5-carboxylic acid tert-butyl ester (1 g; 4.46 mmol; 1 eq.) and 3-chloroacetylacetone (0.71 mL; 6.24 mmol; 1.4 eq.) in AcOH (10 mL) was stirred at room temperature for 18 hours. The reaction was poured into water (100 mL) under vigorous stirring and the precipitate filtered off, washed with water (3×) and dried to afford the title compound (1298 mg, 90%) as an off-white solid. $^1$H NMR (DMSO-$d_6$) δ 4.60-4.52 (m, 4H), 2.81 (br s, 3H), 2.60-2.57 (m, 3H), 1.48 (s, 9H). HPLC (max plot) 98.4%; Rt 3.96 min. UPLC/MS: (MS+) 323 ([M+H]$^+$).

Step 2: 6-chloro-5,7-dimethyl-2,3-dihydro-1H-2,4,7a,8-tetraaza-cyclopenta[a]indene hydrochloride Aq. 32% HCl (1.14 mL; 11.62 mmol; 3 eq.) was added to a suspension of 6-chloro-5,7-dimethyl-1H,3H-2,4,7a,8-tetraaza-cyclopenta[a]indene-2-carboxylic acid tert-butyl ester (1.25 g; 3.87 mmol; 1 eq.) in AcOH (6.25 mL) and the resulting mixture was stirred at room temperature for 2 hours then poured into MTBE (40 mL). The precipitate was filtered off, washed with MTBE (3×) and dried to afford the title compound (1 g, 100%) as an off-white solid. $^1$H NMR (DMSO-$d_6$) δ 10.55 (s, 2H), 4.57-4.52 (m, 4H), 2.83 (s, 3H), 2.61 (s, 3H). HPLC (max plot) 100.0%; Rt 1.38 min. UPLC/MS: (MS+) 222.9 ([M+H]$^+$).

Intermediate A4: 6-chloro-2,3-dihydro-1H-2,4,7a,8-tetraaza-cyclopenta[a]indene hydrochloride

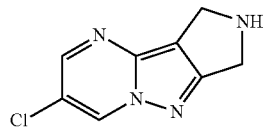 [SMILES: Clc1cnc2c3c(nn2c1)CNC3]

Step 1: 6-chloro-1H,3H-2,4,7a,8-tetraaza-cyclopenta[a]indene-2-carboxylic acid tert-butyl ester A mixture of 3-amino-2,6-dihydro-4H-pyrrolo[3,4-c]pyrazole-5-carboxylic acid tert-butyl ester (2 g; 8.92 mmol; 1 eq.) and 2-chloromalonaldehyde (1.04 g; 9.81 mmol; 1.1 eq.) in AcOH was stirred at room temperature for 18 hours then diluted with water (30 mL). The precipitate was filtered off and purified by column chromatography (DCM/EA, from 95/5 to 80/20) to afford the title compound (1.24 g, 47%) as a white solid. $^1$H NMR (DMSO-$d_6$) δ 9.57 (d, J=2.3 Hz, 1H), 8.59 (d, J=2.3 Hz, 1H), 4.63-4.57 (m, 4H), 1.47 (s, 9H). HPLC (max plot) 99.1%; Rt 3.75 min.

Step 2: 6-chloro-2,3-dihydro-1H-2,4,7a,8-tetraaza-cyclopenta[a]indene hydrochloride Aq. 32% HCl (1.2 mL; 12.2 mmol; 3 eq.) was added to a suspension 6-chloro-1H,3H-2,4,7a,8-tetraaza-cyclopenta[a]indene-2-carboxylic acid tert-butyl ester
(1.2 g; 4.07 mmol; 1 eq.) in AcOH (6 mL) and the resulting mixture was stirred at room temperature for 2 hours then poured dropwise into ACN (40 mL) under vigorous stirring. The precipitate was filtered off, washed with ACN (2×) and dried to afford the title compound (0.85 g, 78%) as a white solid. $^1$H NMR (DMSO) δ 10.49 (s, 2H), 9.65 (d, J=2.3 Hz, 1H), 8.68 (d, J=2.3 Hz, 1H), 4.58 (s, 4H). HPLC (max plot) 100.0%; Rt 3.76 min. UPLC/MS: (MS+) 195 ([M+H]$^+$).

Intermediate A5: 6-methyl-2,3-dihydro-1H-2,4,7a,8-tetraaza-cyclopenta[a]indene hydrochloride

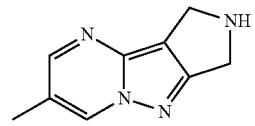

Step 1: 6-methyl-1H,3H-2,4,7a,8-tetraaza-cyclopenta[a]indene-2-carboxylic acid tert-butyl ester A mixture of 3-amino-2,6-dihydro-4H-pyrrolo[3,4-c]pyrazole-5-carboxylic acid tert-butyl ester (5 g; 22.3 mmol; 1 eq.) and 1,1,3,3-tetraethoxy-2-methylpropane (4.32 mL; 22.3 mmol; 1 eq.) in AcOH (50 mL) was stirred at 50° C. for 20 hours then diluted with water (250 mL). The precipitate was filtered off and dried to afford the title compound (3.5 g, 57%) as a pale beige solid. $^1$H NMR (DMSO-$d_6$) δ 8.98-8.95 (m, 1H), 8.43 (d, J=2.1 Hz, 1H), 4.61-4.54 (m, 4H), 2.31 (s, 3H), 1.47 (s, 9H). HPLC (max plot) 99.7%; Rt 3.27 min. UPLC/MS: (MS+) 275.0 ([M+H]+).

Step 2: 6-methyl-2,3-dihydro-1H-2,4,7a,8-tetraaza-cyclopenta[a]indene hydrochloride Aq. 32% HCl (1.61 mL; 16.4 mmol; 3 eq.) was added to a solution of 6-methyl-1H,3H-2,4,7a,8-tetraaza-cyclopenta[a]indene-2-carboxylic acid tert-butyl ester (1.5 g; 5.47 mmol; 1 eq.) in AcOH (7.5 mL) and the resulting mixture was stirred at room temperature for 28 hours then poured dropwise into EtOH (40 mL) under vigorous stirring. The precipitate was filtered off, washed with EtOH then MTBE and dried to afford the title compound (0.75 g, 65%) as a white solid. $^1$H NMR (DMSO-d$_6$) δ 10.50 (s, 2H), 9.06-9.02 (m, 1H), 8.51 (d, J=2.1 Hz, 1H), 4.55-4.52 (m, 4H), 2.33 (s, 3H). HPLC (max plot) 100.0%; Rt 4.36 min.

Intermediate C1: 6,7-dimethyl-1H,3H-2,4,7a,8-tetraaza-cyclopenta[a]indene-2-carboxylic acid tert-butyl ester

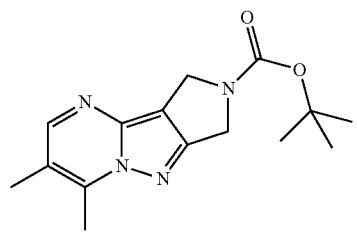 [SMILES: Cc1cnc2c3c(nn2c1C)CN(C(=O)OC(C)(C)C)C3]

A mixture of 3-amino-2,6-dihydro-4H-pyrrolo[3,4-c]pyrazole-5-carboxylic acid tert-butyl ester (1 g; 4.46 mmol; 1 eq.) and (3E)-4-hydroxy-3-methylbut-3-en-2-one (prepared according to J. Het. Chem. 1980, 17(1), 33-37) (0.6 g; 4.91 mmol; 1.1 eq.) in AcOH (5 mL) was stirred at room temperature for 18 hours then concentrated in vacuo. The residue was partitioned between 1M NaOH and DCM, the organic layer was dried over magnesium sulfate and concentrated in vacuo. The resulting oil was triturated in Et$_2$O, the precipitate filtered off and the solution concentrated in vacuo. The residue was purified by SFC (column: Chiralpak IC, eluent 25% MeOH) to afford successively the title compound (140 mg, 11%) as a white solid and Intermediate C2. $^1$H NMR (CDCl$_3$) δ 8.33 (s, 1H), 4.72-4.62 (m, 4H), 2.54 (d, J=3.1 Hz, 3H), 2.29 (d, J=0.7 Hz, 3H), 1.52 (d, J=3.3 Hz, 9H). HPLC (max plot) 87.3%; Rt 3.27 min. UPLC/MS: (MS+) 289.1 ([M+H]+).

Intermediate C2: 5,6-dimethyl-1H,3H-2,4,7a,8-tetraaza-cyclopenta[a]indene-2-carboxylic acid tert-butyl ester

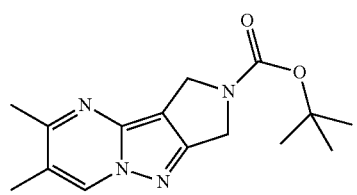 [SMILES: Cc1cn2nc3c(c2nc1C)CN(C(=O)OC(C)(C)C)C3]

Second eluting compound isolated (170 mg, 13%) as a white solid during the preparation of Intermediate C1. $^1$H NMR (CDCl$_3$) δ 8.27 (d, J=3.0 Hz, 1H), 4.75-4.66 (m, 4H), 2.74 (s, 3H), 2.36 (s, 3H), 1.53 (s, 9H). UPLC/MS: (MS+) 289.1 ([M+H]+).

Intermediate A6: 6,7-dimethyl-2,3-dihydro-1H-2,4,7a,8-tetraaza-cyclopenta[a]indene bis hydrochloride

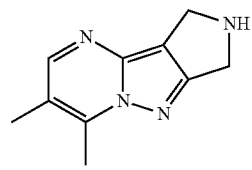

A 4M solution of HCl in 1,4-dioxane (10 mL; 40 mmol; 82.4 eq.) was added to a solution 6,7-dimethyl-1H,3H-2,4,7a,8-tetraaza-cyclopenta[a]indene-2-carboxylic acid tert-butyl ester (140 mg; 0.49 mmol; 1 eq.) in MeOH (2 mL) and the resulting mixture was stirred at room temperature for 18 hours then concentrated in vacuo. The residue was triturated in EtOH and the precipitate filtered off and dried to afford the title compound (78 mg, 62%) as a pale yellow solid. $^1$H NMR (DMSO-d$_6$) δ 10.39 (br s, 2H), 8.91 (d, J=0.9 Hz, 1H), 6.24 (br s, 1H), 4.51-4.48 (m, 4H), 2.49 (s, 3H), 2.26 (s, 3H). HPLC (max plot) 99.9%; Rt 1.03 min. UPLC/MS: (MS+) 189.0 ([M+H]+).

Intermediate A7: 5,6-dimethyl-2,3-dihydro-1H-2,4,7a,8-tetraaza-cyclopenta[a]indene bis hydrochloride

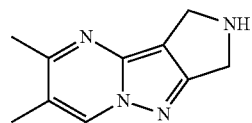

A 4M solution of HCl in 1,4-dioxane (10 mL; 40 mmol; 67.8 eq.) was added to a solution of 5,6-dimethyl-1H,3H-2,4,7a,8-tetraaza-cyclopenta[a]indene-2-carboxylic acid tert-butyl ester (170 mg; 0.59 mmol; 1 eq.) in MeOH (2 mL) and the resulting mixture was stirred at room temperature for 18 hours then concentrated in vacuo. The residue was triturated in EtOH and the precipitate filtered off and dried to afford the title compound (90 mg, 58%) as a pale yellow solid. $^1$H NMR (DMSO-d$_6$) δ 10.41 (br s, 2H), 8.66-8.17 (br s, 1H), 8.45 (s, 1H), 4.57-4.53 (m, 4H), 2.70 (s, 3H), 2.35 (s, 3H). HPLC (max plot) 99.6%; Rt 1.03 min. UPLC/MS: (MS+) 189.0 ([M+H]+).

Intermediate Z1: (2-hydroxy-phenyl)-(5,6,7-trimethyl-1H,3H-2,4,7a,8-tetraaza-cyclopenta[a]inden-2-yl)-methanone

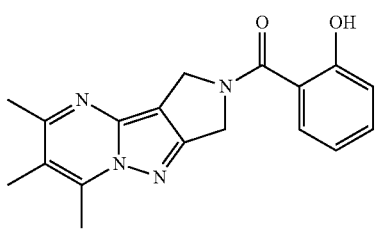 [SMILES: Cc1nc2c3c(nn2c(C)c1C)CN(C(=O)c1ccccc1O)C3]

The title compound was prepared following procedure described in Method B starting Intermediate A1 and salicylic acid. After purification by recrystallization (ACN), the title compound was obtained as a white solid (463 mg, 34%). $^1$H NMR (CDCl$_3$) δ 10.90 (s, 1H), 7.65-7.62 (m, 1H), 7.41-7.35 (m, 1H), 7.04-7.01 (m, 1H), 6.92-6.87 (m, 1H), 5.14-5.09 (m, 4H), 2.77 (s, 3H), 2.56 (s, 3H), 2.31 (s, 3H). HPLC (max plot) 94.4%; Rt 2.44 min. UPLC/MS: (MS+) 323.0 ([M+H]$^+$), (MS+) 321.2 ([M−H]$^−$).

Intermediate A8: 6-bromo-2,3-dihydro-1H-2,4,7a,8-tetraaza-cyclopenta[a]indene hydrochloride

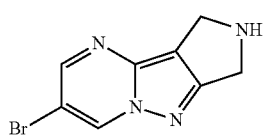

Step 1: 6-bromo-1H,3H-2,4,7a,8-tetraaza-cyclopenta[a]indene-2-carboxylic acid tert-butyl ester A mixture of bromomalonaldehyde (2.02 g; 13.38 mmol; 1 eq.) and 3-amino-2,6-dihydro-4H-pyrrolo[3,4-c]pyrazole-5-carboxylic acid tert-butyl ester (3 g; 13.38 mmol; 1 eq.) in AcOH (21 mL) was stirred at room temperature for 40 minutes. The insoluble material was removed by filtration and the solution diluted with water (60 mL). The precipitate was filtered off, washed with water (3×) and dried. Recrystallization from iPrOH afforded the title compound (2.02 g, 45%) as beige solid. $^1$H NMR (DMSO-d$_6$) δ 9.60 (d, J=2.2 Hz, 1H), 8.60 (d, J=2.2 Hz, 1H), 4.62-4.55 (m, 4H), 1.47 (s, 9H). HPLC (max plot) 99.8%; Rt 3.54 min. UPLC/MS: (MS+) 339.3 and 341.3 ([M+H]$^+$).

Step 2: 6-bromo-2,3-dihydro-1H-2,4,7a,8-tetraaza-cyclopenta[a]indene hydrochloride A 4M solution of HCl in 1,4-dioxane (35 mL; 140 mmol; 23.7 eq.) was added to 6-bromo-1H,3H-2,4,7a,8-tetraaza-cyclopenta[a]indene-2-carboxylic acid tert-butyl ester (2 g; 5.9 mmol; 1 eq.) and the resulting mixture was stirred at room temperature for 18 hours. The precipitate was filtered off, washed with Et$_2$O and dried to afford the title compound (1.56 g, 96%) as beige solid. $^1$H NMR (DMSO-d$_6$) δ 10.61 (br s, 2H), 9.68 (d, J=2.2 Hz, 1H), 8.69 (d, J=2.2 Hz, 1H), 4.56 (s, 4H). UPLC/MS: (MS+) 239.1 and 241.1 ([M+H]$^+$).

Intermediate B1: 2-ethoxy-4-fluoro-benzoic acid

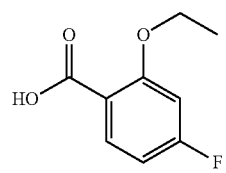

Step 1: 2-ethoxy-4-fluoro-benzoic acid ethyl ester

Iodoethane (2.56 mL; 32.03 mmol; 2.5 eq.) was added to a suspension of 4-fluoro-2-hydroxybenzoic acid (2 g; 12.81 mmol; 1 eq.) and potassium carbonate (5.31 g; 38.43 mmol; 3 eq.) in DMF (20 mL) and the resulting mixture was stirred at 80° C. for 3 hours then partitioned between MTBE (100 mL) and water (100 mL). The organic layer was washed with water then brine, dried over sodium sulfate and concentrated in vacuo to afford the title compound (2.3 g, 85%) as a pale yellow oil. $^1$H NMR (DMSO-d$_6$) δ 7.71 (dd, J=7.0, 8.6 Hz, 1H), 7.03 (dd, J=2.4, 11.7 Hz, 1H), 6.83 (dt, J=2.4, 8.5 Hz, 1H), 4.23 (q, J=7.1 Hz, 2H), 4.09 (q, J=7.0 Hz, 2H), 1.33 (t, J=7.0 Hz, 3H), 1.27 (t, J=7.1 Hz, 3H). HPLC (max plot) 94.3%; Rt 4.04 min. UPLC/MS: (MS+) 213.2 ([M+H]$^+$)

Step 2: 2-ethoxy-4-fluoro-benzoic acid

A 5M solution of sodium hydroxide (6.5 mL; 32.5 mmol; 3 eq.) was added to a solution of 2-ethoxy-4-fluoro-benzoic acid ethyl ester (2.3 g; 10.8 mmol; 1 eq.) in EtOH (46 mL) and the resulting mixture was stirred at 40° C. for 18 hours then concentrated in vacuo. The residue was taken up in water and the pH made acidic with 5M HCl. The precipitate was filtered off, washed with water and dried to afford the title compound (1.8 g, 90%) as a white solid. $^1$H NMR (DMSO-d$_6$) δ 12.56 (s, 1H), 7.71 (dd, J=7.0, 8.6 Hz, 1H), 7.01 (dd, J=2.4, 11.7 Hz, 1H), 6.80 (dt, J=2.4, 8.5 Hz, 1H), 4.09 (q, J=7.0 Hz, 2H), 1.32 (t, J=7.0 Hz, 3H). HPLC (max plot) 99.3%; Rt 2.71 min. UPLC/MS: (MS+) 185.2 ([M+H]$^+$).

Intermediate Z2: (6-chloro-5,7-dimethyl-1H,3H-2,4,7a,8-tetraaza-cyclopenta[a]inden-2-yl)-(4-fluoro-2-hydroxy-phenyl)-methanone

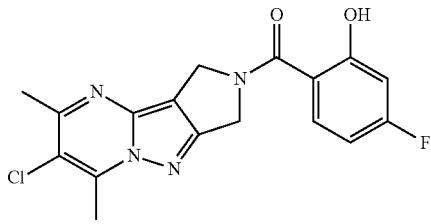 [SMILES: Cc1nc2c3c(nn2c(C)c1Cl)CN(C(=O)c1ccc(F)cc1O)C3]

The title compound was prepared following procedure described in Method A starting from Intermediate A3 and 4-fluoro-2-hydroxybenzoic acid and the compound has precipitated out. After filtration, washing with DMF and drying the title compound was obtained as a white solid (1.14 g, 82%). $^1$H NMR (CDCl$_3$) δ 11.47 (s, 1H), 7.68-7.63 (m, 1H), 6.76-6.71 (m, 1H), 6.69-6.59 (m, 1H), 5.15-5.09 (m, 4H), 2.91 (s, 3H), 2.68 (s, 3H). HPLC (max plot) 91.9%; Rt 3.16 min. UPLC/MS: (MS+) 361.4 ([M+H]$^+$), (MS−) 359.4 V-C.

Intermediate B2: 2-Ethoxy-3,5-difluoro-benzoic acid

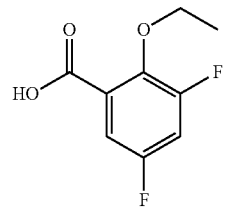

Step 1: 2-ethoxy-3,5-difluoro-benzoic acid ethyl ester

Iodoethane (1.15 mL; 14.36 mmol; 2.5 eq.) was added to a suspension of 3,5-difluoro-2-hydroxybenzoic acid (1 g; 5.74 mmol; 1 eq.) and potassium carbonate (2.38 g; 17.23 mmol; 3 eq.) in DMF (20 mL) and the resulting mixture was stirred at 80° C. for 20 hours then partitioned between MTBE (100 mL) and water (50 mL). The organic layer was washed with water then brine, dried over sodium sulfate and concentrated in vacuo to afford the title compound (1.16 g, 88%) as a colorless liquid. $^1$H NMR (DMSO-d$_6$) δ 7.67-7.58 (m, 1H), 7.38-7.32 (m, 1H), 4.31 (q, J=7.2 Hz, 2H), 4.05 (dq, J=7.0, 0.6 Hz, 2H), 1.35-1.26 (m, 6H). HPLC (max plot) 99.8%; Rt 4.47 min. UPLC/MS: (MS+) 231.2 ([M+H]$^+$).

Step 2: 2-ethoxy-3,5-difluoro-benzoic acid

A 5M solution of sodium hydroxide (3.2 mL; 16 mmol; 3.2 eq.) was added to a solution of 2-ethoxy-3,5-difluoro-benzoic acid ethyl ester (1.16 g; 5.04 mmol; 1 eq.) in EtOH (23 mL) and the resulting mixture was stirred at 40° C. for 18 hours then concentrated in vacuo. The residue was taken up in water and the pH made acidic with 5M HCl. The precipitate was filtered off, washed with water and dried to afford the title compound (1.8 g, 90%) as a white solid. $^1$H NMR (DMSO-d$_6$) δ 13.44 (s, 1H), 7.61-7.52 (m, 1H), 7.35-7.28 (m, 1H), 4.04 (q, J=7.0 Hz, 2H), 1.28 (t, J=7.0 Hz, 3H). HPLC (max plot) 79.5%; Rt 3.13 min.

Intermediate B3: 4-(2-carboxy-phenoxy)-piperidine-1-carboxylic acid tert-butyl ester

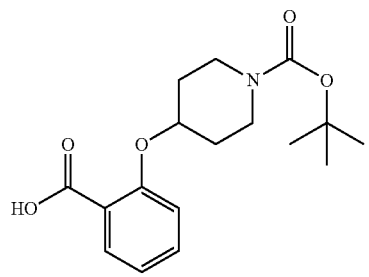 [SMILES: CC(C)(C)OC(=O)N1CCC(Oc2ccccc2C(=O)O)CC1]

Di-tert-butyldicarbonate (2.03 g; 9.31 mmol; 1.2 eq.) was added to a solution of 2-(piperidin-4-yloxy)-benzoic acid hydrochloride (2 g; 7.76 mmol; 1 eq.) and TEA (2.16 mL; 15.5 mmol; 2 eq.) in DCM (20 mL) and the resulting mixture was stirred at room temperature for 16 hours. Water (150 mL) was added and the pH made acidic. The two phases were separated and the aqueous layer extracted with DCM. The combined organic phase was washed with brine, dried over magnesium sulfate and concentrated in vacuo to afford the title compound (1.03 g, 41%) as an off-white solid. $^1$H NMR (DMSO-d$_6$) δ 12.62 (s, 1H), 7.49-7.44 (m, 1H), 7.18 (dd, J=7.7, 1.8 Hz, 1H), 7.18 (d, J=8.2 Hz, 1H), 7.02-6.97 (m, 1H), 4.74-4.67 (m, 1H), 3.55-3.45 (m, 2H), 3.39-3.31 (m, 2H), 1.86-1.77 (m, 2H), 1.67-1.57 (m, 2H), 1.40 (s, 9H). HPLC (max plot) 99.8%; Rt 3.57 min. UPLC/MS: (MS−) 320.4 ([M−H]$^-$).

Intermediate B4: 4-(2-carboxy-5-fluoro-benzyl)-piperazine-1-carboxylic acid tert-butyl ester

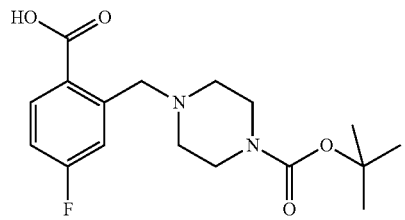 [SMILES: CC(C)(C)OC(=O)N1CCN(Cc2cc(F)ccc2C(=O)O)CC1]

Step 1: 4-(2-bromo-5-fluoro-benzyl)-piperazine-1-carboxylic acid tert-butyl ester A mixture of 2-bromo-5-fluoro-benzaldehyde (3.00 g, 14.8 mmol), piperazine-1-carboxylic acid tert-butyl ester (2.75 g, 14.8 mmol) and sodium triacetoxyborohydride (4.38 g, 20.7 mmol) was prepared in DCE (80 mL) and stirred at RT for 3 hours. The reaction mixture was diluted with DCM (100 mL), and then washed with a mixture of saturated aqueous solution of Na$_2$CO$_3$ (100 mL) and water (50 mL). The aqueous layer was extracted with DCM (100 mL). The organic layers were combined, dried (Na$_2$SO$_4$) and concentrated under vacuum. After purification by filtration through a silica pad (EtOAc), the title compound was obtained as a white powder (5.12 g, 93%). $^1$H NMR (300 MHz, CDCl$_3$) δ 7.48 (dd, J=8.8, 5.3 Hz, 1H), 7.26 (dd, J=9.6, 3.1 Hz, 1H), 6.85 (ddd, J=8.8, 7.8, 3.1 Hz, 1H), 3.56 (s, 2H), 3.49-3.42 (m, 4H), 2.50-2.42 (m, 4H), 1.46 (s, 9H). HPLC (max plot) 94.1%; Rt 2.73 min. UPLC/MS: (MS+) 373.1 and 375.1 ([M+H]$^+$).

Step 2: 4-(2-carboxy-5-fluoro-benzyl)-piperazine-1-carboxylic acid tert-butyl ester A 1.6M solution of butyllithium in hexanes (2.5 mL, 4.0 mmol) was added in three portions over 2 hours into a solution of 4-(2-bromo-5-fluoro-benzyl)-piperazine-1-carboxylic acid tert-butyl ester (500 mg, 1.34 mmol) in anhydrous Et$_2$O cooled at −78° C. After one additional hour at −78° C., an excess of dry ice was added and the cooling bath was removed. The reaction mixture was allowed to warm up to RT and was concentrated under vacuum. The residue was taken up with a saturated aqueous solution of NH$_4$Cl and extracted with EtOAc (3×). The organic layers were combined, dried (Na$_2$SO$_4$) and concentrated under vacuum to give the title compound as a yellow oil (391 mg, 78%), used without further purification. HPLC (max plot) 92.1%; Rt 2.47 min. UPLC/MS: (MS+) 339.3 ([M+H]$^+$), (MS−) 337.4 ([M−H]$^-$).

Intermediate B5: 4-fluoro-2-(1,1,2,2-tetrafluoro-ethoxy)-benzoic acid

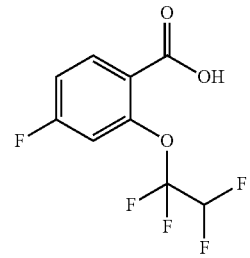 [SMILES: O=C(O)c1ccc(F)cc1OC(F)(F)C(F)F]

Step 1:
4-fluoro-2-(1,1,2,2-tetrafluoro-ethoxy)-benzoic acid methyl ester

A mixture of 4-fluoro-2-hydroxy-benzoic acid methyl ester (1.00 g, 5.88 mmol), 1,2-dibromo-1,1,2,2-tetrafluoro-ethane (3.05 g, 11.76 mmol) and cesium carbonate (2.87 g, 8.82 mmol) was prepared in DMSO (6 mL) and heated at 60° C. for 18 hours. The reaction mixture was diluted with MTBE (100 mL) and washed with water (2×50 mL) and brine (50 mL). The aqueous layers were extracted with MTBE (100 ml). The organic layers were combined, dried ($Na_2SO_4$) and concentrated under vacuum to give 1.85 g of a yellow oil. The oil was taken up with AcOH (6 mL) and heated at 60° C., then zinc powder (1.15 g, 17.6 mmol) was added in four portions over 1 hour. After 1 hour of stirring at 60° C., the reaction mixture was diluted with DCM (50 mL) and the suspension was removed by filtration. The filtrate was washed with water (25 mL) and a 1N aqueous solution of NaOH (25 mL+5N aqueous solution of NaOH to adjust pH=14). The aqueous layers were extracted with DCM (25 mL). The organic layers were combined, dried ($Na_2SO_4$) and concentrated under vacuum. After purification by flash chromatography (silica, heptane/DCM), the title compound was obtained as a colorless oil (917 mg, 58%). $^1$H NMR (300 MHz, DMSO-$d_6$) δ 8.04-7.96 (m, 1H), 7.48-7.38 (m, 2H), 6.80 (tt, J=51.6, 3.5 Hz, 1H), 3.83 (s, 3H). HPLC (max plot) 97.9%; Rt 4.43 min.

Step 2:
4-fluoro-2-(1,1,2,2-tetrafluoro-ethoxy)-benzoic acid

A 5N aqueous solution of NaOH (1.96 mL, 9.82 mmol) was added into a solution of 4-fluoro-2-(1,1,2,2-tetrafluoro-ethoxy)-benzoic acid methyl ester (884 mg, 3.27 mmol) in MeOH (10 mL). The resulting mixture was stirred at RT for 15 hours, then concentrated under vacuum. The residue was taken up with water (20 mL) and acidified until pH=1 with a 1N aqueous solution of HCl. The precipitate was filtered off, washed with water (3×) and dried under vacuum to give the title compound as a white powder (661 mg, 79%). $^1$H NMR (300 MHz, DMSO-$d_6$) δ 13.38 (s, 1H), 8.02-7.93 (m, 1H), 7.43-7.32 (m, 2H), 6.73 (tt, J=51.7, 3.5 Hz, 1H). HPLC (max plot) 96.8%; Rt 3.72 min. UPLC/MS: (MS−) 255.2 ([M−H]$^-$).

Intermediate Z3: Mixture of (2-bromomethyl-phenyl)-(6-chloro-5,7-dimethyl-1H,3H-2,4,7a,8-tetraaza-cyclopenta[a]inden-2-yl)-methanone and (6-chloro-5,7-dimethyl-1H,3H-2,4,7a,8-tetraaza-cyclopenta[a]inden-2-yl)-(2-chloromethyl-phenyl)-methanone

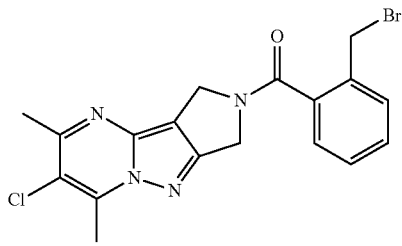

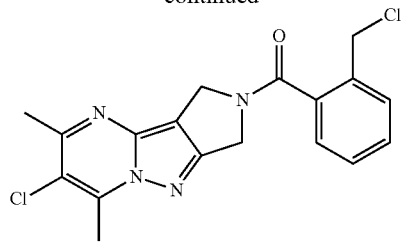

DMF (0.22 mL, 2.84 mmol) and oxalyl chloride (10.7 mL, 124.9 mmol) were added into a suspension of 2-bromomethyl-benzoic acid (Rare Chemicals, 13.43 g, 62.4 mmol) in anhydrous DCM (150 mL). The reaction mixture was stirred at RT for 1 hour (complete dissolution), and then concentrated under vacuum. The residue was taken up with anhydrous DCM and concentrated again to give an oily residue. The acyl chloride was taken up with anhydrous DCM (150 mL) and cooled to 0° C. A suspension of Intermediate A3 (14.7 g, 56.8 mmol) and DIEA (21.2 mL, 124.9 mmol) in DCM (150 mL) was added over 20 minutes. At the end of the addition the reaction was complete. The reaction mixture was diluted with DCM (300 mL) and washed with water (300 mL), a 0.1N aqueous solution of HCl (300 mL), water (300 mL), a 0.1N aqueous solution of NaOH (300 mL) and brine (300 mL). The organic layer was dried ($MgSO_4$) and concentrated under vacuum. ACN was added and the residual DCM was evaporated. The precipitate was filtered off, washed with ACN and dried under vacuum to give a mixture of the title compounds (20.0 g, 84%), used without further purification. (2-bromomethyl-phenyl)-(6-chloro-5,7-dimethyl-1H,3H-2,4,7a,8-tetraaza-cyclopenta[a]inden-2-yl)-methanone: HPLC (max plot) 66%; Rt 3.99 min. UPLC/MS: (MS+) 421.2 and 419.2 ([M+H]$^+$). (6-chloro-5,7-dimethyl-1H,3H-2,4,7a,8-tetraaza-cyclopenta[a]inden-2-yl)-(2-chloromethyl-phenyl)-methanone: HPLC (max plot) 24%; Rt 3.89 min. UPLC/MS: (MS+) 375.3 ([M+H]$^+$).

Intermediate Z5: (2-fluoro-phenyl)-(5,6,7-trimethyl-1H,3H-2,4,7a,8-tetraaza-cyclopenta[a]inden-2-yl)-methanone

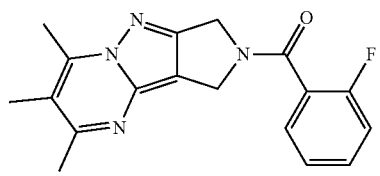 [SMILES: Cc1nc2c3c(nn2c(C)c1C)CN(C(=O)c1ccccc1F)C3]

The title compound was prepared following procedure described in Method B starting from Intermediate A1 and 2-fluorobenzoic acid. Purification by recrystallization from ACN afforded the title compound (372 mg, 55%) as a white solid. HPLC (max plot) 95.9%; Rt 3.51 min. UPLC/MS: (MS+) 345.3 ([M+H]+).

Intermediate A9: 6-fluoro-5,7-dimethyl-2,3-dihydro-1H-2,4,7a,8-tetraaza-cyclopenta[a]indene hydrochloride

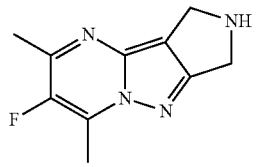

Step 1: 6-fluoro-5,7-dimethyl-1H,3H-2,4,7a,8-tetraaza-cyclopenta[a]indene-2-carboxylic acid tert-butyl ester A solution of 3-amino-2,6-dihydro-4H-pyrrolo[3,4-c]pyrazole-5-carboxylic acid tert-butyl ester (4.3 g; 19.2 mmol; 1 eq.) and 3-fluoropentane-2,4-dione (2.49 g; 21.1 mmol; 1.1 eq.) in AcOH (40 mL) was stirred at room temperature for 18 hours. 3-fluoropentane-2,4-dione (0.45 g; 3.83 mmol; 0.2 eq.) was added and the reaction mixture was stirred for one hour then concentrated in vacuo. The residue was partitioned between EA and 1M NaOH and the aqueous layer extracted with EA. The combined organic phase was dried over magnesium sulfate and concentrated in vacuo. Purification by column chromatography (10 to 40% EA in cyclohexane) afforded the title compound (3 g, 58%) as a white solid. HPLC (max plot) 99.4%; Rt 3.83 min. UPLC/MS: (MS+) 307.2 ([M+H]+).

Step 2: 6-fluoro-5,7-dimethyl-2,3-dihydro-1H-2,4,7a,8-tetraaza-cyclopenta[a]indene hydrochloride To a solution of 6-fluoro-5,7-dimethyl-1H,3H-2,4,7a,8-tetraaza-cyclopenta[a]indene-2-carboxylic acid tert-butyl ester (3.39 g; 11.1 mmol; 1 eq.) in DCM (20 mL) was added 2M HCl (10 mL; 20 mmol; 1.81 eq.) and the resulting mixture was stirred at room temperature for 18 hours than concentrated in vacuo. The residue was triturated in DCM and the precipitate was filtered off to afford the title compound (2 g, 80%) as a white solid. HPLC (max plot) 99.6%; Rt 1.23 min. UPLC/MS: (MS+) 207.1 ([M+H]+).

Intermediate Z6: (6-chloro-5,7-dimethyl-1H,3H-2,4,7a,8-tetraaza-cyclopenta[a]inden-2-yl)-(2-fluoro-phenyl)-methanone

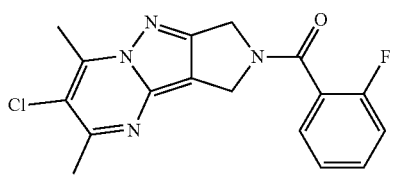 [SMILES: Cc1nc2c3c(nn2c(C)c1Cl)CN(C(=O)c1ccccc1F)C3]

The title compound was prepared following procedure described in Method A starting from 2-fluorobenzoic acid and intermediate A3 and has precipitated out from the reaction mixture. After filtration and drying, the title compound was obtained (2.43 g, 91%) as a white solid. HPLC (max plot) 95.9%; Rt 3.51 min. UPLC/MS: (MS+) 345.3 ([M+H]+).

Intermediate B6: (S)-3-(2-carboxy-phenoxy)-piperidine-1-carboxylic acid tert-butyl ester Chiral

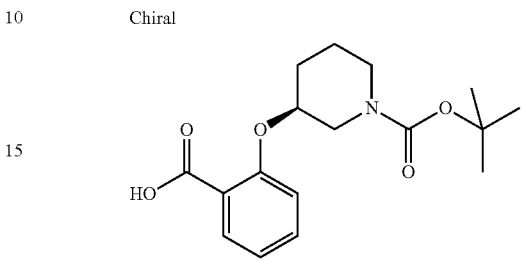

A solution of 2-((S)-piperidin-3-yloxy)-benzonitrile (270 mg; 1.33 mmol; 1 eq.) in 5M NaOH (2 mL) and EtOH (2 mL) was stirred at reflux for 2 days. The reaction mixture was allowed to return to room temperature and di-tert-butyl dicarbonate (2.9 g; 13.35 mmol; 10 eq.) was added portion wise. After 30 min, water was added and the aqueous phase was washed with Et$_2$O (2×). The aqueous phase then acidified and extracted with DCM (3×). The combined organic layer was washed with sat. aq. NH$_4$Cl, dried over magnesium sulfate and concentrated in vacuo to afford the title compound (216 mg, 50%) as a pale yellow oil. HPLC (max plot) 98.2%; Rt 3.76 min. UPLC/MS: (MS−) 320.23 ([M−H]−).

Intermediate B7: 2-(2-carboxy-phenoxymethyl)-morpholine-4-carboxylic acid tert-butyl ester

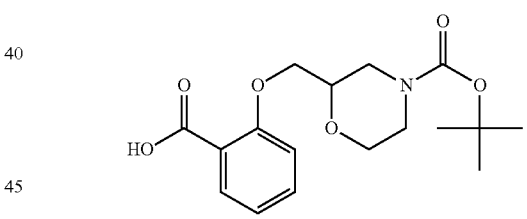

Step 1: tert-butyl 2-(hydroxymethyl)morpholine-4-carboxylate

A mixture of 2-hydroxymethylmorpholine (720 mg; 6.15 mmol; 1 eq.), di-tert-butyl dicarbonate (2.01 g; 9.22 mmol; 1.5 eq.) and 4-(dimethylamino)pyridine (7.5 mg; 0.06 mmol; 0.01 eq.) in DCM (6 mL) was stirred at room temperature for 16 hours then concentrated in vacuo. Purification by column chromatography (0% to 30% EA in heptanes) afforded the title compound (633 mg, 47%) as a colourless oil. $^1$H NMR (300 MHz, CDCl$_3$) δ 4.09-3.73 (m, 3H), 3.73-3.62 (m, 1H), 3.62-3.38 (m, 3H), 3.06-2.83 (m, 1H), 2.83-2.57 (m, 1H), 1.98 (dd, J=6.9, 5.3 Hz, 1H), 1.46 (s, 9H).

Step 2: 2-(2-carboxy-phenoxymethyl)-morpholine-4-carboxylic acid tert-butyl ester A solution of diisopropyl azodicarboxylate (776 µL; 3.94 mmol; 2 eq.) in THF (5 mL) was added to a cold (0° C.)

solution of methyl salicylate (1 g; 6.57 mmol; 1 eq.) and tert-butyl 2-(hydroxymethyl)morpholine-4-carboxylate (641 mg; 2.95 mmol; 1.5 eq.) and triphenylphosphine (1.03 g; 3.94 mmol; 2 eq.) in THF (15 mL) and the reaction mixture was stirred at room temperature for 16 hours then concentrated in vacuo. Purification by column chromatography (EA/heptane) afforded 2-(2-methoxycarbonyl-phenoxymethyl)-morpholine-4-carboxylic acid tert-butyl ester which was dissolved in THF (10 mL) and MeOH (10 mL). 5M NaOH (1.97 mL; 9.86 mmol; 5 eq.) was added and the resulting mixture was stirred at room temperature for 16 hours then concentrated in vacuo. The residue was partitioned between 1M NaOH and DCM and the aqueous layer was washed with DCM. The aqueous phase was made acidic and extracted with DCM (3×). The combined organic phase was dried over magnesium sulfate and concentrated in vacuo to afford the title compound (411 mg, 34%) as an orange oil which was used without further purification. HPLC (max plot) 89.4%; Rt 3.73 min. UPLC/MS: (MS−) 336.1 ([M−H]⁻).

Intermediate B8:
3-(2-carboxy-phenoxy)-azetidine-1-carboxylic acid tert-butyl ester

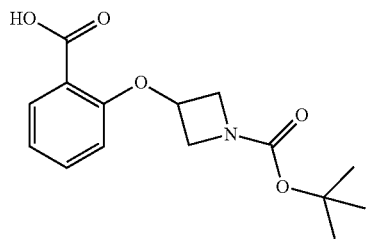 [SMILES: CC(C)(C)OC(=O)N1CC(Oc2ccccc2C(=O)O)C1]

Step 1: 3-(2-formyl-phenoxy)-azetidine-1-carboxylic acid tert-butyl ester

A mixture of 2-fluoro-benzaldehyde (0.85 mL; 8.06 mmol; 1 eq.), 3-hydroxy-azetidine-1-carboxylic acid tert-butyl ester (1.54 g mg; 8.86 mmol; 1.1 eq.) and K₂CO₃ (2.23 g; 16.11 mmol; 2 eq.) in DMF (20 mL) was stirred at 120° C. for 16 hours. 3-Hydroxy-azetidine-1-carboxylic acid tert-butyl ester (279 mg; 1.61 mmol; 0.2 eq.) was added and the reaction mixture was stirred at room temperature for 2 days. The reaction mixture was diluted with DCM, washed with water then brine, dried over magnesium sulfate and concentrated in vacuo. Recrystallization from Et₂O afforded the title compound (1.03 g, 46%) as a yellow solid. HPLC (max plot) 99.4%; Rt 4.07 min.

Step 2:
3-(2-carboxy-phenoxy)-azetidine-1-carboxylic acid tert-butyl ester

A solution of sodium chlorite (1.85 g; 20.43 mmol; 5.5 eq.) and sodium dihydrogenphosphate (1.6 g; 13.37 mmol; 3.6 eq.) in water (10 mL) was added dropwise to a mixture of 2-methyl-2-butene (3.71 mL) and 3-(2-formyl-phenoxy)-azetidine-1-carboxylic acid tert-butyl ester (1.03 g; 3.71 mmol; 1 eq.) in 1,4-dioxane (10 mL). and the reaction mixture was stirred at room temperature for 2 hours. The dioxane was evaporated in vacuo, the mixture diluted with water and the pH made acidic with 0.1M HCl. The precipitate was filtered off, washed with water and dried to afford the title compound (1.02 g, 94%) as a white solid. UPLC/MS: (MS−) 292.4 ([M−H]⁻).

Intermediate B9: 4-(2-carboxy-phenoxy)-3-fluoro-piperidine-1-carboxylic acid tert-butyl ester

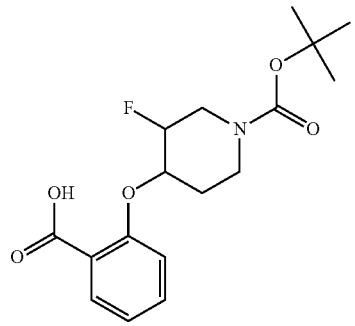 [SMILES: CC(C)(C)OC(=O)N1CCC(Oc2ccccc2C(=O)O)C(F)C1]

Step 1: 3-fluoro-4-(2-formyl-phenoxy)-piperidine-1-carboxylic acid tert-butyl ester NaH (55-65%; 44 mg; 1.09 mmol; 1.2 eq.) was added to a solution of 3-fluoro-4-hydroxy-piperidine-1-carboxylic acid tert-butyl ester (200 mg; 0.91 mmol; 1 eq.) in THF (15 mL) and the resulting mixture was stirred at room temperature for 15 minutes whereupon 2-fluoro-benzaldehyde (113 mg; 0.91 mmol; 1 eq.) was added dropwise. The reaction mixture was stirred at room temperature for 15 hours then at 60° C. for a further 4 hours. NaH (44 mg; 1.09 mmol; 1.2 eq.) was added and the resulting mixture was stirred at 60° C. for 2 hours. The solution was diluted with brine extracted with EA (2×). The combined organic layer was washed with brine, dried over magnesium sulfate and concentrated in vacuo. Purification by column chromatography (DCM then EtOAc) afforded the title compound (196 mg, 66%) as a yellow oil.

¹H NMR (DMSO-d₆) δ 10.38 (s, 1H), 7.74-7.62 (m, 1H), 7.38 (d, J=8.5 Hz, 1H), 7.12 (t, J=7.6 Hz, 1H), 5.08-4.80 (m, 2H), 4.16-3.98 (m, 1H), 3.94-3.78 (m, 1H), 3.42-2.95 (m, 2H), 1.96-1.83 (m, 2H), 1.40 (s, 9H).

Step 2: 4-(2-carboxy-phenoxy)-3-fluoro-piperidine-1-carboxylic acid tea-butyl ester A solution of sodium chlorite (274 mg; 3.03 mmol; 5 eq.) and sodium dihydrogen phosphate (291 mg; 2.42 mmol; 40 eq.) in water (4 mL) was added dropwise to a solution of 2-methyl-but-2-ene (0.5 mL) and 3-fluoro-4-(2-formyl-phenoxy)-piperidine-1-carboxylic acid tert-butyl ester (196 mg; 0.61 mmol; 1 eq.) in 1,4-dioxane (4 mL) and the resulting mixture was stirred a room temperature for 3 hours. The dioxane was evaporated in vacuo and the pH made acidic with 1M HCl. The solution was extracted with ethyl acetate (2×), washed with brine, dried over magnesium sulfate and concentrated in vacuo to afford the title compound (205 mg, 100%) as a yellow oil. UPLC/MS: (MS−) 338.2 ([M−H]⁻).

Intermediate B10:
3-(2-carboxy-phenoxymethyl)-azetidine-1-carboxylic acid tert-butyl ester

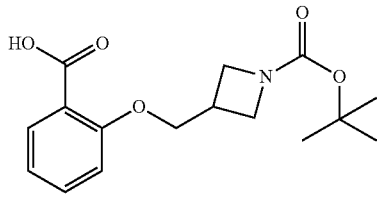 [SMILES: CC(C)(C)OC(=O)N1CC(COc2ccccc2C(=O)O)C1]

Step 1: 3-(2-formyl-phenoxymethyl)-azetidine-1-carboxylic acid tert-butyl ester A mixture of 2-fluoro-benzaldehyde (0.85 mL; 8.06 mmol; 1 eq.), 3-hydroxymethyl-azetidine-1-carboxylic acid tert-butyl ester (1.66 g; 8.86 mmol; 1.1 eq.) and $K_2CO_3$ (2.23 g; 16.11 mmol; 2 eq.) in DMF (20 mL) was stirred at 120° C. for 7 days. The reaction mixture was diluted with sat. aq. $NaHCO_3$ and extracted with DCM (2×). The combined organic layer was washed with brine (2×), dried over magnesium sulfate and concentrated in vacuo. Purification by column chromatography (heptane/EA, 95/5 to 60/40) afforded the title compound (810 mg, 35%) as a white solid. HPLC (max plot) 96.2%; Rt 4.15 min.

Step 2: 3-(2-carboxy-phenoxymethyl)-azetidine-1-carboxylic acid tert-butyl ester A solution of sodium chlorite (1.37 g; 15.10 mmol; 5.5 eq.) and sodium dihydrogenphosphate (1.19 g; 9.89 mmol; 3.6 eq.) in water (8 mL) was added dropwise to a mixture of 2-methyl-2-butene (2.7 mL) and 3-(2-formyl-phenoxymethyl)-azetidine-1-carboxylic acid tert-butyl ester (800 mg; 2.75 mmol; 1 eq.) in 1,4-dioxane (8 mL) and the resulting mixture was stirred at room temperature for 1 hour. The 1,4-dioxane was evaporated in vacuo, water was added and the pH made acidic with 1M HCl. The precipitate was filtered off to afford the title compound (827 mg, 98%) as a white solid. HPLC (max plot) 100%; Rt 3.58 min. UPLC/MS: (MS−) 306.4 ([M−H]−).

Intermediate B11:
4-(2-carboxy-benzylidene)-piperidine-1-carboxylic acid tert-butyl ester

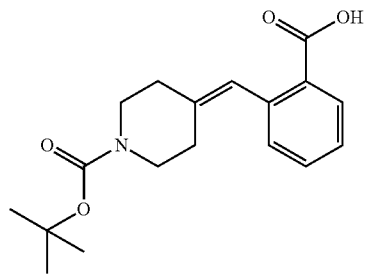 [SMILES: CC(C)(C)OC(=O)N1CCC(=Cc2ccccc2C(=O)O)CC1]

Step 1: 2-(diethoxy-phosphorylmethyl)-benzoic acid methyl ester

A mixture of 2-bromomethyl-benzoic acid methyl ester (5 g; 21.83 mmol; 1 eq.) and phosphorous acid triethyl ester (4.53 mL; 26.19 mmol; 1.2 eq.) was stirred at 150° C. for 16 hours then concentrated in vacuo to afford the title compound (6.54 g, quantitative) a yellow oil. HPLC (max plot) 88.8%; Rt 3.11 min.

Step 2: 4-(2-methoxycarbonyl-benzylidene)-piperidine-1-carboxylic acid tert-butyl ester Sodium hydride (526 mg; 12.05 mmol; 1.2 eq.) was added to a cold (0° C.) solution of 2-(diethoxy-phosphorylmethyl)-benzoic acid methyl ester (3.45 g; 12.05 mmol; 1.2 eq.) and 15-crown-5 (60 μL; 0.30 mmol; 0.03 eq.) in THF (10 mL) and the reaction mixture was stirred at room temperature for 30 min whereupon a solution of 1-boc-piperidin-4-one (2 g; 10.04 mmol; 1 eq.) in THF (10 mL) was added dropwise over 10 min at 0° C. The reaction mixture was stirred at room temperature for 2 days then diluted with water and extracted with EA (2×). The combined organic phase was washed with 1M (NaOH) then brine, dried over magnesium sulfate and concentrated in vacuo. Purification by column chromatography (heptanes/EA, 95/5 to 50/50) afforded the title compound (450 mg, 14%) as a white solid. UPLC/MS: (MS+) 332.3 ([M+H]+).

Step 3: 4-(2-carboxy-benzylidene)-piperidine-1-carboxylic acid tert-butyl ester 1M NaOH (2 mL; 2 mmol; 6.63 eq.) was added to a solution of 4-(2-methoxycarbonyl-benzylidene)-piperidine-1-carboxylic acid tert-butyl ester (100 mg; 0.30 mmol; 1 eq.) in EtOH (2 mL) and the reaction mixture was stirred at room temperature for 16 hours then concentrated in vacuo. The residue was partitioned between DCM and 1M HCl and the two phases separated. The aqueous layer was extracted with DCM and the combined organic layers were dried over magnesium sulfate and concentrated in vacuo to afford the title compound (90 mg, 94%) as a white solid. HPLC (max plot) 98.9%; Rt 4.37 min. UPLC/MS: (MS−) 316.4 ([M−H]−).

Intermediate B12:
2-(1-methyl-piperidin-4-ylidenemethyl)-benzoic acid

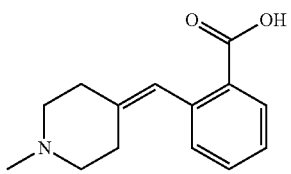 [SMILES: CN1CCC(=Cc2ccccc2C(=O)O)CC1]

Step 1: 2-(1-methyl-piperidin-4-ylidenemethyl)-benzoic acid methyl ester

NaH (55-65%, 231 mg; 5.3 mmol; 1.2 eq.) was added to a cold (0° C.) solution of 2-(diethoxy-phosphorylmethyl)-benzoic acid methyl ester (from Intermediate B11 step 1) (1.52 g; 5.3 mmol; 1.2 eq.) and 15-crown-5 (26 μL; 0.13 mmol; 0.03 eq.) in THF (5 mL) and the reaction mixture was stirred at room temperature for 30 minutes whereupon a solution of 1-methyl-piperidin-4-one (500 mg; 4.42 mmol; 1 eq.) in THF (5 mL) was added dropwise over 10 minutes at 0° C. The resulting mixture was stirred at room temperature for 3.5 hours then concentrated in vacuo. The residue was taken up in water and extracted with EA (2×). The combined organics were washed with 1M NaOH then brine, dried over magnesium sulfate and concentrated in vacuo. Purification by column chromatography (DCM to 10% MeOH in DCM) afforded the title compound (230 mg, 21%) as a yellow oil. UPLC/MS: (MS+) 246.3 ([M+H]+).

Step 2:
2-(1-methyl-piperidin-4-ylidenemethyl)-benzoic acid

1M NaOH (2 mL; 2 mmol; 4.9 eq.) was added to a solution 2-(1-methyl-piperidin-4-ylidenemethyl)-benzoic acid methyl ester (100 mg; 0.41 mmol; 1 eq.) in EtOH (2 mL) and the reaction mixture was stirred at room temperature for 16 hours. The pH was adjusted to 5 with 1M HCl and the solution was concentrated in vacuo to afford the title compound as a white solid which was used without further purification. HPLC (max plot) 99.1%; Rt 1.69 min.

Intermediate A10: 5,7-dimethyl-2,3-dihydro-1H-2,4,7a,8-tetraaza-cyclopenta[a]indene hydrochloride

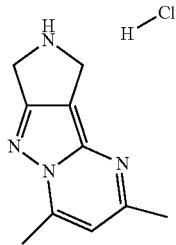

Step 1: 5,7-dimethyl-1H,3H-2,4,7a,8-tetraaza-cyclopenta[a]indene-2-carboxylic acid tert-butyl ester A solution of 3-amino-2,6-dihydro-4H-pyrrolo[3,4-c]pyrazole-5-carboxylic acid tert-butyl ester (700 mg; 3.12 mmol; 1 eq.) and pentane-2,4-dione (0.35 mL; 3.43 mmol; 1.1 eq.) in AcOH (3.1 mL) was stirred at room temperature for 1 hour then poured into sat. aq. NaHCO₃. The precipitate was filtered off and dried to afford the title compound (890 mg, 97%) as a white solid. HPLC (max plot) 98.8%; Rt 3.32 min.

Step 2: 5,7-dimethyl-2,3-dihydro-1H-2,4,7a,8-tetraaza-cyclopenta[a]indene hydrochloride A 4M solution of HCl in 1,4-dioxane (3.34 mL; 91.5 mmol; 29.9 eq.) was added to a solution of 5,7-dimethyl-1H,3H-2,4,7a,8-tetraaza-cyclopenta[a]indene-2-carboxylic acid tert-butyl ester (900 mg; 3.06 mmol; 1 eq.) in 1,4-dioxane (8 mL) and the resulting mixture was stirred at room temperature for 16 hours then concentrated in vacuo to afford the title compound (740 mg, quantitative) as a yellow solid which was used without further purification. UPLC/MS: (MS+) 189.2 ([M+H]±).

Intermediate B13: 3-(2-carboxy-5-fluoro-phenoxy)-azetidine-1-carboxylic acid tert-butyl ester

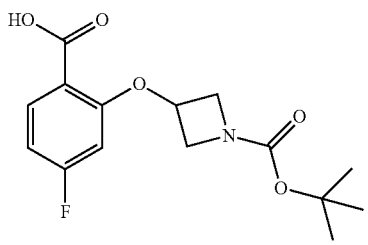

Step 1: 3-(5-fluoro-2-formyl-phenoxy)-azetidine-1-carboxylic acid tert-butyl ester tBuOK (948 mg; 8.44 mmol; 1.2 eq.) was added to a solution of 3-hydroxy-azetidine-1-carboxylic acid tert-butyl ester (1.46 g; 8.44 mmol; 1.2 eq.) in 1,4-dioxane (5 mL) and the solution was stirred at room temperature for 15 minutes whereupon a solution of 2,4-difluoro-benzaldehyde (1 g; 7.04 mmol; 1 eq.) in 1,4-dioxane (5 mL) was added dropwise. The reaction mixture was stirred at room temperature for 5 minutes then diluted with water. The solution was extracted with DCM (2×) and the combined organic phase was dried over magnesium sulfate and concentrated in vacuo. Purification by column chromatography (heptanes/EA) afforded the title compound (705 mg, 34%) as a white solid. ¹H NMR (300 MHz, CDCl₃) δ 10.41 (d, J=0.8 Hz, 1H), 7.93 (dd, J=8.7, 6.8 Hz, 1H), 6.99-6.72 (m, 1H), 6.33 (dd, J=10.2, 2.2 Hz, 1H), 5.07-4.85 (m, 1H), 4.40 (ddd, J=9.9, 6.4, 1.1 Hz, 2H), 4.10 (ddd, J=9.9, 4.0, 1.1 Hz, 2H), 1.48 (s, 9H). HPLC (max plot) 96.4%; Rt 4.22 min.

Step 2: 3-(2-Carboxy-5-fluoro-phenoxy)-azetidine-1-carboxylic acid tert-butyl ester A solution of sodium chlorite (1.19 g; 13.13 mmol; 5.5 eq.) and sodium dihydrogenphosphate (1.03 g; 8.59 mmol; 3.6 eq.) in water (7 mL) was added dropwise to a mixture of 2-methyl-2-butene (2.39 mL) and 3-(5-fluoro-2-formyl-phenoxy)-azetidine-1-carboxylic acid tert-butyl ester (705 mg; 2.39 mmol; 1 eq.) in 1,4-dioxane (7 mL). The reaction mixture was stirred at room temperature for 16 hours and the 1,4-dioxane concentrated in vacuo. The aqueous solution was diluted with water and the pH made acidic with 0.1M HCl. The precipitate was filtered off and dried to afford the title compound (625 mg, 84%) as a white solid. ¹H NMR (CDCl₃) δ 8.17 (dd, J=8.8, 6.7 Hz, 1H), 6.85 (ddd, J=8.9, 7.6, 2.3 Hz, 1H), 6.35 (dd, J=9.9, 2.3 Hz, 1H), 5.25-4.87 (m, 1H), 4.41

Intermediate B14: 4-(2-carboxy-phenyl)-7-trifluoromethyl-[1,4]diazepane-1-carboxylic acid tert-butyl ester

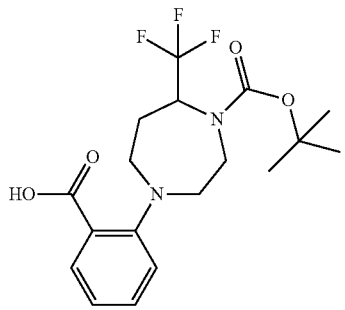 [SMILES: CC(C)(C)OC(=O)N1CCN(c2ccccc2C(=O)O)CCC1C(F)(F)F]

Step 1: 2-(5-trifluoromethyl-[1,4]diazepan-1-yl)-benzaldehyde

A mixture of 5-trifluoromethyl-[1,4]diazepane hydrochloride (1.17 g; 4.83 mmol; 1.2 eq.), sodium carbonate decahydrate (2.13 g; 20.14 mmol; 5 eq.) and 2-fluoro-benzaldehyde (500 mg; 4.03 mmol; 1 eq.) in DMSO (20 mL) and water (20 mL) was stirred at 160° C. for 4 hours. The solution was diluted EA and the organic layer washed with water (3×) then brine (2×), dried over magnesium sulfate and concentrated in vacuo. Purification by column chromatography (15% to 33% EA in heptanes) afforded the title compound (350 mg, 32%) as a yellow oil. HPLC (max plot) 97.9%; Rt 5.23 min.

Step 2: 4-(2-formyl-phenyl)-7-trifluoromethyl-[1,4]diazepane-1-carboxylic acid tert-butyl ester A solution of 2-(5-trifluoromethyl-[1,4]diazepan-1-yl)-benzaldehyde (350 mg; 1.29 mmol; 1 eq.), di-tert-butyl dicarbonate (309 mg; 1.41 mmol; 1.1 eq.) and dimethyl-pyridin-4-yl-amine (31 mg; 0.26 mmol; 0.2 eq.) in ACN was stirred at room temperature for 2 hours then at 50° C. for 1 hour. After concentration in vacuo, purification by column chromatography (5% to 25% in heptanes) afforded the title compound (160 mg, 33%) as a colourless oil. HPLC (max plot) 97.9%; Rt 5.23 min.

Step 3: 4-(2-carboxy-phenyl)-7-trifluoromethyl-[1,4]diazepane-1-carboxylic acid tert-butyl ester A solution of sodium chlorite (214 mg; 2.36 mmol; 5.5 eq.) and sodium dihydrogenphosphate (186 mg; 1.55 mmol; 3.6 eq.) in water (2 mL) was added dropwise to a mixture of 4-(2-formyl-phenyl)-7-trifluoromethyl-[1,4]diazepane-1-carboxylic acid tert-butyl ester (160 mg; 0.43 mmol; 1 eq.) in 1,4-dioxane (2 mL). The reaction mixture was stirred at room temperature for 1 hour and the 1,4-dioxane concentrated in vacuo. The aqueous solution was diluted with water, the pH made acidic with 0.1M HCl and extracted with EA (2×). The combined organic layer was washed with brine, dried over magnesium sulfate and concentrated in vacuo to afford the title compound (140 mg, 84%) as a yellow solid. UPLC/MS: (MS+) 389.2 ([M+H]$^+$).

Intermediate B15: (S)-3-(2-Carboxy-5-fluoro-phenoxy)-piperidine-1-carboxylic acid tert-butyl ester

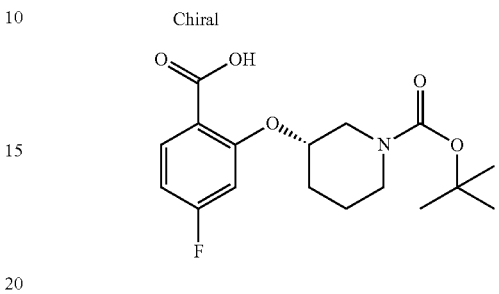

Step 1: (S)-3-(5-fluoro-2-formyl-phenoxy)-piperidine-1-carboxylic acid tert-butyl ester tBuOK (434 mg; 3.87 mmol; 1.1 eq.) was added to a solution of 2,4-difluoro-benzaldehyde (500 mg; 3.52 mmol; 1 eq.) and (S)-3-hydroxy-piperidine-1-carboxylic acid tert-butyl ester (779 mg; 3.87 mmol; 1.1 eq.) in 1,4-dioxane (3 mL) and reaction mixture was stirred at room temperature for 15 minutes. The solution was diluted with water and extracted with DCM. The organic layer was dried over magnesium sulfate and concentrated in vacuo. Purification by column chromatography (heptanes/EA) afforded the title compound (208 mg, 18%) as white solid. HPLC (max plot) 92.8%; Rt 4.46 min.

Step 2: (S)-3-(2-carboxy-5-fluoro-phenoxy)-piperidine-1-carboxylic acid tert-butyl ester A solution of sodium chlorite (320 mg; 3.54 mmol; 5.5 eq.) and sodium dihydrogenphosphate (278 mg; 2.32 mmol; 3.6 eq.) in water (2 mL) was added dropwise to a mixture of 2-methyl-2-butene (0.64 mL) and (S)-3-(5-fluoro-2-formyl-phenoxy)-piperidine-1-carboxylic acid tert-butyl ester (208 mg; 0.64 mmol; 1 eq.) in 1,4-dioxane (2 mL). The reaction mixture was stirred at room temperature for 16 hours and the 1,4-dioxane concentrated in vacuo. The aqueous solution was diluted with water and the pH made acidic with 0.1M HCl. The mixture was extracted with DCM (2×) and the combined organic phase was dried over magnesium sulfate and concentrated in vacuo to afford the title compound (202 mg, 93%) as a white solid. HPLC (max plot) 94.3%; Rt 3.89 min. UPLC/MS: (MS−) 338.4 ([M−H]$^−$).

Intermediate B16: 2-(1-methyl-piperidin-4-ylmethyl)-benzoic acid

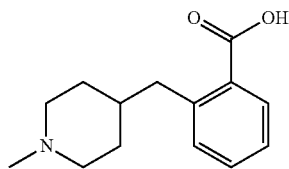 [SMILES: CN1CCC(Cc2ccccc2C(=O)O)CC1]

Step 1: 2-(1-methyl-piperidin-4-ylmethyl)-benzoic acid methyl ester

A mixture of 2-(1-methyl-piperidin-4-ylidenemethyl)-benzoic acid methyl ester (from Intermediate B12 step 1) (130 mg; 0.53 mmol; 1 eq.) and 10% Pd/C (~50% H$_2$O) (34 mg) in MeOH (1 mL) and THF (1 mL) was stirred at room temperature for 3 hours under a H$_2$ atmosphere (10 bars). The catalyst was filtered off and the solution concentrated in vacuo. Purification by column chromatography (heptane/EA) afforded the title compound (97 mg, 74%) as a white solid. UPLC/MS: (MS+) 248.2 ([M+H]$^+$).

Step 2: 2-(1-methyl-piperidin-4-ylmethyl)-benzoic acid

A mixture of 2-(1-methyl-piperidin-4-ylmethyl)-benzoic acid methyl ester (97 mg; 0.39 mmol; 1 eq.) and 5M NaOH (2 mL) in EtOH (3 mL) was stirred at 60° C. for 4 hours. After cooling down, the solution was neutralised with 1M HCl and freeze dried to afford the title compound as a white solid which was used without further purification. HPLC (max plot) 99.8% Rt 1.77 min. UPLC/MS: (MS+) 248.2 ([M+H]$^+$).

Intermediate B17: 4-(2-carboxy-benzyl)-piperidine-1-carboxylic acid tert-butyl ester

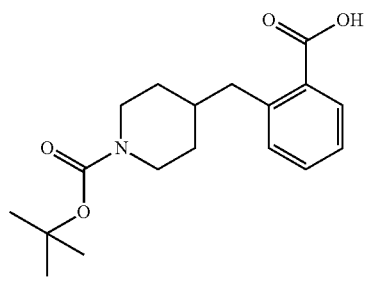 [SMILES: CC(C)(C)OC(=O)N1CCC(Cc2ccccc2C(=O)O)CC1]

Step 1: 4-(2-methoxycarbonyl-benzyl)-piperidine-1-carboxylic acid tert-butyl ester A mixture of 4-(2-methoxycarbonyl-benzylidene)-piperidine-1-carboxylic acid tert-butyl ester (from Intermediate B11 step 1) (350 mg; 1.06 mmol; 1 eq.) and 10% Pd/C (~50% H$_2$O) (67 mg) in MeOH (2 mL) and THF (2 mL) was stirred at room temperature for 3 hours under a H$_2$ atmosphere (10 bars). The catalyst was filtered off and the solution concentrated in vacuo. Purification by column chromatography (heptane/EA) afforded the title compound (330 mg, 94%) as a colourless oil. HPLC (max plot) 97.4%; Rt 5.20 min.

Step 2: 4-(2-carboxy-benzyl)-piperidine-1-carboxylic acid tert-butyl ester

A mixture of 4-(2-methoxycarbonyl-benzyl)-piperidine-1-carboxylic acid tert-butyl ester (330 mg; 0.99 mmol; 1 eq.) and 1M NaOH (2 mL; 2 mmol; 2 eq.) in EtOH (3 mL) was stirred at 60° C. for 16 hours. The pH was made acidic with 1M HCl and the mixture extracted with DCM (2×). The combined organic phase was dried over magnesium sulfate and concentrated in vacuo to afford the title compound (295 mg, 93%) as a white solid. HPLC (max plot) 99.8%; Rt 4.40 min. $^1$H NMR (300 MHz, CDCl$_3$) δ 11.17 (s, 1H), 8.07 (dd, J=7.9, 1.5 Hz, 1H), 7.50-7.44 (m, 1H), 7.31 (td, J=7.6, 1.3 Hz, 1H), 7.21 (dd, J=7.7, 1.3 Hz, 1H), 4.07 (s, 2H), 2.98 (d, J=6.8 Hz, 2H), 2.62 (t, J=12.7 Hz, 2H), 1.80-1.57 (m, 3H), 1.45 (s, 9H), 1.28-1.14 (m, 2H).

Intermediate B18: 2-(2-dimethylaminomethyl-imidazol-1-yl)-benzoic acid hydrochloride

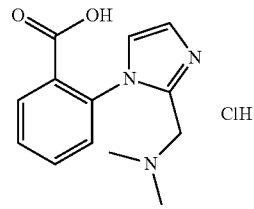 [SMILES: CN(C)Cc1nccn1-c1ccccc1C(=O)O ; Cl]

Step 1: 2-(2-dimethylaminomethyl-imidazol-1-yl)-benzoic acid ethyl ester

A mixture of 2-fluoro-benzoic acid ethyl ester (200 mg; 1.19 mmol; 10 eq.), (1H-imidazol-2-ylmethyl)-dimethyl-amine (149 mg; 1.19 mmol; 1 eq.) and cesium carbonate (775 mg; 2.38 mmol; 2 eq.) in DMSO (3 mL) was stirred at 120° C. for 16 hours. The mixture was diluted with EA, washed with water (3×), dried over magnesium sulfate and concentrated in vacuo to afford the title compound (58 mg, 18%) as a white solid. HPLC (max plot) 95.7%; Rt 1.80 min.

Step 2: 2-(2-dimethylaminomethyl-imidazol-1-yl)-benzoic acid hydrochloride

A mixture of 2-(2-dimethylaminomethyl-imidazol-1-yl)-benzoic acid ethyl ester (58 mg; 0.21 mmol; 1 eq.) and 5M NaOH (0.43 mL; 2.13 mmol; 10 eq.) in THF (2 mL) and EtOH (2 mL) was stirred at room temperature for 4 hours then concentrated in vacuo. 5M HCl was added and the solution was concentrated in vacuo to afford the title compound which was used without further purification.

Intermediate B19: (1S,3R,5R)-3-(2-carboxy-phenoxy)-8-aza-bicyclo[3.2.1]octane-8-carboxylic acid tert-butyl ester

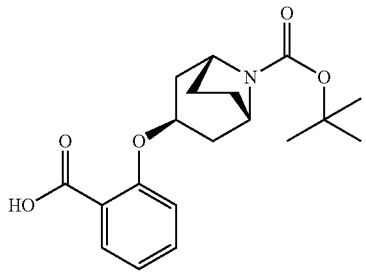 [SMILES: CC(C)(C)OC(=O)N1[C@@H]2CC[C@H]1C[C@@H](Oc1ccccc1C(=O)O)C2]

Step 1: (1S,3R,5R)-3-(2-cyano-phenoxy)-8-aza-bicyclo[3.2.1]octane-8-carboxylic acid tert-butyl ester tBuOK (1.43 g; 12.7 mmol; 2.2 eq.) was added to a solution of tert-butyl 3-hydroxy-8-azabicyclo[3.2.1]octane-8-carboxylate (2.63 g; 11.6 mmol; 2 eq.) in THF (10 mL) and the reaction mixture was stirred at room temperature for 15 minutes whereupon a solution of 2-fluorobenzonitrile (627 µL; 5.78 mmol; 1 eq.) in THF (10 mL) was added dropwise. The reaction mixture was stirred at room temperature for 2 hours then diluted with water and extracted with EA (2×). The combined organics were dried over magnesium sulfate and concentrated in vacuo. Purification by column chromatography (10% to 25% EA in heptane) afforded the title compound (2 g, 97%) as a white solid. HPLC (max plot) 99.3%; Rt 4.91 min. $^1$H NMR (300 MHz, DMSO-$d_6$) δ 7.74 (dd, J=7.7, 1.7 Hz, 1H), 7.64 (ddd, J=8.6, 7.5, 1.7 Hz, 1H), 7.16 (d, J=8.7 Hz, 1H), 7.07 (td, J=7.5, 0.8 Hz, 1H), 4.93 (t, J=4.5 Hz, 1H), 4.08 (s, 2H), 2.22-2.00 (m, 4H), 2.00-1.70 (m, 4H), 1.42 (s, 9H).

Step 2: (1S,3R,5R)-3-(2-carboxy-phenoxy)-8-aza-bicyclo[3.2.1]octane-8-carboxylic acid tert-butyl ester A mixture of (1S,3R,5R)-3-(2-cyano-phenoxy)-8-aza-bicyclo[3.2.1]octane-8-carboxylic acid tert-butyl ester (1.85 g; 5.63 mmol; 1.00 eq.) in 5M NaOH (10 mL) and ethylene glycol (5 mL) was stirred at reflux for 6 hours. The solution was washed with DCM (2×) and the pH made acidic with 5M HCl. The aqueous layer was extracted with EA (3×). The combined organic phase was dried over magnesium sulfate and concentrated in vacuo. The resulting oil was triturated in ACN and the precipitate was filtered off to afford the title compound (110 mg, 6%) as a white solid. HPLC (max plot) 97.2%; Rt 4.16 min. UPLC/MS: (MS−) 346.2 ([M−H]$^−$).

Intermediate B20: (1S,3R,5R)-3-(2-carboxy-5-fluoro-phenoxy)-8-aza-bicyclo[3.2.1]octane-8-carboxylic acid tert-butyl ester

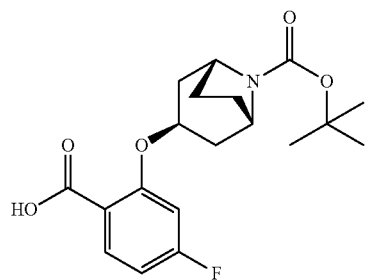 [SMILES: CC(C)(C)OC(=O)N1[C@@H]2CC[C@H]1C[C@@H](Oc1cc(F)ccc1C(=O)O)C2]

Step 1: (1S,3R,5R)-3-(2-bromo-5-fluoro-phenoxy)-8-aza-bicyclo[3.2.1]octane-8-carboxylic acid tert-butyl ester tBuOK (1.63 g; 14.5 mmol; 1.1 eq.) was added to a solution of (1R,5S)-3-hydroxy-8-aza-bicyclo[3.2.1]octane-8-carboxylic acid tert-butyl ester (3 g; 13.2 mmol; 1 eq.) in THF (7 mL) and the reaction mixture was stirred at reflux for 1 hour whereupon 1-bromo-2,4-difluoro-benzene (1.65 mL; 14.5 mmol; 1.1 eq.) was added dropwise maintaining a gentle reflux. The reaction mixture was stirred at reflux for a further 1.5 hour then diluted with water and extracted with MTBE (2×). The combined organics were washed with water then brine, dried over magnesium sulfate and concentrated in vacuo. Purification by column chromatography (5% EA in cyclohexane) afforded the title compound (4 g, 79%) as a white solid. HPLC (max plot) 99.8%; Rt 5.91 min.

Step 2: (1S,3R,5R)-3-(2-carboxy-5-fluoro-phenoxy)-8-aza-bicyclo[3.2.1]octane-8-carboxylic acid tert-butyl ester A 1.6M solution of nBuLi in hexanes (1.72 mL; 2.75 mL; 1.1 eq.) was added over 15 minutes to a cold (−78° C.) solution of (1S,3R,5R)-3-(2-bromo-5-fluoro-phenoxy)-8-aza-bicyclo[3.2.1]octane-8-carboxylic acid tert-butyl ester (1 g; 2.5 mmol; 1 eq.) in THF (15 mL) and the resulting mixture was stirred at −78° C. for 30 minutes whereupon carbon dioxide was bubbled into the reaction. The reaction mixture was allowed to return to room temperature while maintaining the bubbling. Sat. aq. NH$_4$Cl was added followed by EA and 0.1M HCl. The two phases were separated and the aqueous layer extracted with EA. The combined organics were dried over magnesium sulfate and concentrated in vacuo. Crystallization from heptane/EA afforded the title compound (522 mg, 57%) as a white solid. HPLC (max plot) 86.2%; Rt 4.36 min. UPLC/MS: (MS−) 364.3 ([M−H]$^−$).

Intermediate B21: 2-[2-(tert-butyl-dimethyl-silanyloxy)-1-methyl-ethoxy]-benzoic acid

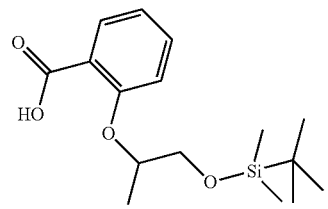 [SMILES: CC(CO[Si](C)(C)C(C)(C)C)Oc1ccccc1C(=O)O]

Step 1: 2-(2-formyl-phenoxy)-propionic acid methyl ester

A mixture of 2-hydroxy-benzaldehyde (1 g; 8.19 mmol; 1 eq.), K$_2$CO$_3$ (3.4 g; 24.6 mmol; 3 eq.) and 2-bromo-propionic acid methyl ester (3.42 g; 20.5 mmol; 2.5 eq.) in DMF (50 mL) was stirred at 120° C. for 45 minutes then diluted with EA. The solution was washed with water (3×) then brine, dried over magnesium sulfate and concentrated in vacuo. Purification by column chromatography (15% to 33% EA in cyclohexane) afforded the title compound (1.56 g, 91%) as a colourless oil. HPLC (max plot) 96.3%; Rt 3.18 min.

Step 2: 2-(2-hydroxymethyl-phenoxy)-propan-1-ol

Lithium borohydride (458 mg; 21 mmol; 3 eq.) was added to a solution of 2-(2-formyl-phenoxy)-propionic acid methyl ester (1.46 mg; 7 mmol; 1 eq.) in 1,4-dioxane (20 mL) and the resulting mixture was stirred at room temperature for 2 hours. After dilution with EA, the solution was washed with water, dried over magnesium sulfate and concentrated in vacuo to afford the title compound (960 mg, 75%) as colourless oil. $^1$H NMR (DMSO-$d_6$) δ 7.37-7.32 (m, 1H), 7.21-7.14 (m, 1H), 6.67 (d, J=8.3 Hz, 1H), 6.90 (dt, J=1.0, 7.4 Hz, 1H), 4.95 (t, J=5.7 Hz, 1H), 4.86 (t, J=5.7 Hz, 1H), 4.59-4.33 (m, 3H), 3.56-3.40 (m, 2H), 1.20 (d, J=6.2 Hz, 3H).

Step 3: 2-(2-hydroxy-1-methyl-ethoxy)-benzaldehyde

Manganese dioxide (4.02 g; 26.3 mmol; 5 eq.) was added to a solution of 2-(2-hydroxymethyl-phenoxy)-propan-1-ol (960 mg; 5.3 mmol; 1 eq.) in DCM (50 mL) and the resulting mixture was stirred at room temperature for 1.5 hour. The suspension was filtered through a short plug of Celite®. The solution was washed with water, dried over magnesium sulfate and concentrated in vacuo to afford the title compound (705 mg, 74%) as a colourless oil. UPLC/MS: (MS+) 181.1 ([M+H]$^+$).

Step 4: 2-[2-(tert-butyl-dimethyl-silanyloxy)-1-methyl-ethoxy]-benzaldehyde

Tert-butyl-chloro-dimethyl-silane (649 mg; 4.3 mmol; 1.1 eq.) was added to a solution of 2-(2-hydroxy-1-methyl-ethoxy)-benzaldehyde (705 mg; 3.91 mmol; 1 eq.), DIEA (867 μL; 4.69 mmol; 1.2 eq.) and 1H-imidazole (27 mg; 0.39 mmol; 0.1 eq.) in 1,4-dioxane (20 mL) and the resulting mixture was stirred at room temperature for 10 minutes. After dilution with EA, the solution was washed with sat. aq. NH4Cl (3×), dried over magnesium sulfate and concentrated in vacuo. Purification by column chromatography (20% to 50% EA in cyclohexane) to afford the title compound (690 mg, 60%) as a colourless oil. $^1$H NMR (300 MHz, DMSO-d$_6$) δ 10.47-10.33 (m, 1H), 7.72-7.55 (m, 2H), 7.30 (d, J=8.5 Hz, 1H), 7.05 (t, J=7.5 Hz, 1H), 4.71 (d, J=4.2 Hz, 1H), 3.77 (dd, J=4.8, 2.1 Hz, 2H), 1.28 (d, J=6.2 Hz, 3H), 0.84-0.75 (m, 9H), 0.04-0.07 (m, 6H).

Step 5: 2-[2-(tert-butyl-dimethyl-silanyloxy)-1-methyl-ethoxy]-benzoic acid

A solution of sodium chlorite (1.17 g; 12.9 mmol; 5.5 eq.) and sodium dihydrogenphosphate (1.01 g; 8.44 mmol; 3.6 eq.) in water (10 mL) was added dropwise to a mixture of 2-methyl-2-butene (2 mL) and 2-[2-(tert-butyl-dimethyl-silanyloxy)-1-methyl-ethoxy]-benzaldehyde (690 mg; 2.34 mmol; 1 eq.) in 1,4-dioxane (10 mL). The reaction mixture was stirred at room temperature for 1.5 hour. After dilution with EA, the solution was washed with 1M HCl, dried over magnesium sulfate and concentrated in vacuo to afford the title compound (690 mg, 95%) as a white solid. UPLC/MS: (MS−) 309.1 ([M−H]$^−$).

Intermediate B22: 2-[2-(tert-butoxycarbonyl-methyl-amino)-ethoxy]-benzoic acid

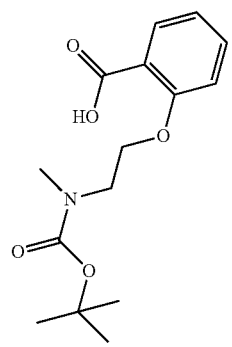 [SMILES: CN(CCOc1ccccc1C(=O)O)C(=O)OC(C)(C)C]

Step 1: (2-hydroxy-ethyl)-methyl-carbamic acid tert-butyl ester

A mixture of 2-methylamino-ethanol (2.5 g; 33.3 mmol; 1 eq.), di-tert-butyl dicarbonate (7.99 g; 36.6 mmol; 1.1 eq.) and dimethyl-pyridin-4-yl-amine (813 mg; 6.66 mmol; 0.2 eq.) in ACN (50 mL) and the resulting mixture was stirred at room temperature for 16 hours. After dilution with EA, the solution was washed with sat. aq. NH4Cl, dried over magnesium sulfate and concentrated in vacuo. Purification by column chromatography (25% to 70% EA in cyclohexane) afforded the title compound (4 g, 62%) as a colourless oil. $^1$H NMR (DMSO-d$_6$) δ 4.70-4.61 (m, 1H), 3.46 (q, J=5.8 Hz, 2H), 3.18 (t, J=6.1 Hz, 2H), 2.80 (br s, 3H), 1.38 (br s, 9H).

Step 2: [2-(2-formyl-phenoxy)-ethyl]methyl-carbamic acid tert-butyl ester tBuOK (2.69 g; 24 mmol; 1.2 eq.) was added portionwise to a solution of (2-hydroxy-ethyl)-methyl-carbamic acid tert-butyl ester (3.5 g; 20 mmol; 1 eq.) and 2-fluoro-benzaldehyde (2.97 g; 24 mmol; 1.2 eq.) in 1,4-dioxane (30 mL) and the reaction mixture was stirred at room temperature for 20 minutes. After dilution with EA, the solution was washed with water (2×) then brine, dried over magnesium sulfate and concentrated in vacuo. Purification by column chromatography (15% to 50% EA in cyclohexane) afforded the title compound (1.6 g, 29%) as a colourless oil. HPLC (max plot) 89.3%; Rt 4.21 min.

Step 3: 2-[2-(tert-butoxycarbonyl-methyl-amino)-ethoxy]-benzoic acid

A solution of sodium chlorite (2.85 g; 31.5 mmol; 5.5 eq.) and sodium dihydrogenphosphate (2.47 g; 20.6 mmol; 3.6 eq.) in water (25 mL) was added dropwise to a mixture of 2-methyl-2-butene (5.7 mL) and [2-(2-formyl-phenoxy)-ethyl]-methyl-carbamic acid tert-butyl ester (1.6 g; 5.73 mmol; 1 eq.) in 1,4-dioxane (25 mL). The reaction mixture was stirred at room temperature for 1.5 hour. After dilution with EA, the solution was washed with 1M HCl, dried over magnesium sulfate and concentrated in vacuo to afford the title compound (2.1 g, 93%) as a white solid. $^1$H NMR (300 MHz, DMSO-d$_6$) δ 7.66-7.59 (dd, J=7.7, 1.8 Hz, 1H), 7.52-7.42 (m, OH), 7.16-7.10 (d, J=8.4 Hz, 1H), 7.03-6.94 (td, J=7.5, 1.0 Hz, 1H), 4.18-4.07 (m, 1H), 3.54-3.48 (t, J=5.4 Hz, 2H), 2.96-2.86 (d, J=11.7 Hz, 3H), 1.42-1.31 (m, 9H).

Intermediate A11: 6-chloro-1,1,5,7-tetramethyl-2,3-dihydro-1H-2,4,7a,8-tetraaza-cyclopenta[a]indene hydrochloride

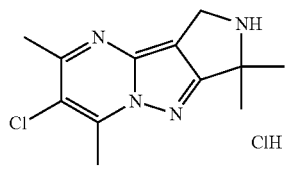

Step 1: 2-[(2-cyanoethyl)amino]-2-methylpropanoic acid

Acrylonitrile (5.13 g, 96.9 mmol) was added to a cold (0° C.) solution of 2-amino-2-methylpropanoic acid (10 g, 96.9 mmol) and sodium hydroxide (3.9 g, 96.9 mmol) in water (40 mL) and the resulting mixture was stirred at room temperature for 16 hours. AcOH (6 mL) was added and the precipitate filtered off. The solid was taken up in 95% EtOH (50 mL) and cooled down to 0° C. for 1 hour. The precipitate was filtered off, washed with EtOH (25 mL) and dried to afford the title compound (12 g, 80%) as a white solid. $^1$H NMR (DMSO-$d_6$) δ 3.37 (s, 1H), 2.70 (t, J=6.3 Hz, 2H), 2.58 (t, J=7.3 Hz, 2H), 1.16 (s, 6H).

Step 2: 2-[(tert-butoxycarbonyl)(2-cyanoethyl) amino]-2-methylpropanoic acid

A 40% solution of benzyltrimethylammonium hydroxide in MeOH (12.85 g, 76.8 mmol) was added to a solution of 2-[(2-cyanoethyl)amino]-2-methylpropanoic acid (12 g, 76.8 mmol) in acetonitrile (700 mL) and the reaction mixture was stirred at room temperature for 1 hour. Di-tert-butyldicarbonate (33.6 g, 153.6 mmol) was added and the resulting mixture was stirred at room temperature for 3 days. The solvent was removed in vacuo and the residue taken up in water (200 mL). The aqueous solution was washed with Et$_2$O (2×), the pH adjusted to 3.5 with citric acid and extracted with EA (2×). The combined organic layer was washed with brine, dried over sodium sulfate and concentrated in vacuo to afford the title compound (16.5 g, 84%) as a pale yellow liquid. $^1$H NMR (DMSO-$d_6$) δ 3.52 (t, J=6.8 Hz, 2H), 2.69 (t, J=6.8 Hz, 2H), 1.40-1.37 (m, 15H).

Step 3: methyl 2-[(tert-butoxycarbonyl)(2-cyanoethyl)amino]-2-methylpropanoate

Methyl iodide (12.5 mL, 193.2 mmol) was added to a mixture of 2-[(tert-butoxycarbonyl)(2-cyanoethyl)amino]-2-methylpropanoic acid (16.5 g, 64.4 mmol) and KHCO$_3$ (12.9 g, 193.2 mmol) in DMF (150 mL) and the reaction mixture was stirred at room temperature for 16 hours. After dilution with water, the solution was extracted with a 1/1 mixture of hexane/EA (2×). The combined organics were dried over magnesium sulfate and concentrated in vacuo to afford the title compound (16.5 g, 95%) as a yellow oil. $^1$H NMR (DMSO-$d_6$) δ 3.61-3.55 (m, 5H), 2.71 (t, J=6.76 Hz, 2H), 1.42-1.36 (m, 15H).

Step 4: tert-butyl 4-cyano-2,2-dimethyl-3-oxopyrrolidine-1-carboxylate

NaH (60%, 3 g; 73.2 mmol) was added to a solution of methyl 2-[(tert-butoxycarbonyl)(2-cyanoethyl)amino]-2-methylpropanoate (16.5 g, 61.0 mmol) in 1,4-dioxane (300 mL) and the reaction mixture was stirred at 100° C. for 4 hours then concentrated in vacuo. The residue was taken up in water (200 mL) and the pH adjusted to 3.5 with citric acid. The solution was extracted with EA (2×). The combined organics were washed with brine, dried over magnesium sulfate and concentrated in vacuo to afford the title compound (11.5 g, 79%) as an off-white solid. $^1$H NMR (DMSO-$d_6$) δ 12.24 (s, 1H), 4.02-3.98 (m, 2H), 1.46-1.39 (m, 15H).

Step 5: tert-butyl 3-amino-6,6-dimethyl-4,6-dihydropyrrolo[3,4-c]pyrazole-5(1H)-carboxylate Hydrazine hydrochloride (4.95 g, 72.4 mmol) was added to a solution of tert-butyl 4-cyano-2,2-dimethyl-3-oxopyrrolidine-1-carboxylate (11.5 g, 48.2 mmol) in EtOH (300 mL) and the reaction mixture was stirred at 85° C. for 18 hours then concentrated in vacuo. The residue was taken up in EA (200 mL), washed with sat. aq. NaHCO$_3$, dried over magnesium sulfate and concentrated in vacuo. Purification by column chromatography (3% MeOH in EA) afforded the title compound (5.5 g, 46%) as an off-white solid. $^1$H NMR (DMSO-$d_6$) δ 11.12 (s, 1H), 5.05 (s, 2H), 4.11-4.07 (m, 2H), 1.50-1.48 (m, 6H), 1.44-1.41 (m, 9H).

Step 6: 6-chloro-1,1,5,7-tetramethyl-2,3-dihydro-1H-2,4,7a,8-tetraaza-cyclopenta[a]indene hydrochloride A mixture of 3-amino-6,6-dimethyl-4,6-dihydro-1H-pyrrolo[3,4-c]pyrazole-5-carboxylic acid tert-butyl ester (500 mg; 1.98 mmol; 1 eq.) and 3-chloro-pentane-2,4-dione (226 μL; 1.98 mmol; 1.00 eq.) in AcOH (1.5 mL) was stirred at room temperature for 1 hour whereupon 32% aq. HCl (584 μL; 5.94 mmol; 3 eq.) was added. The resulting mixture was stirred for 4 hours then poured onto iPrOH (6 mL). The formed precipitate was filtered off and dried to afford the title compound (388 mg, 68%) as an off-white solid. $^1$H NMR (DMSO-$d_6$) δ 10.37 (brs, 2H), 4.59 (s, 2H), 2.83 (s, 3H), 2.62 (s, 3H), 1.74 (s, 6H). HPLC (max plot) 98.1%, Rt 1.97 min. UPLC/MS: (MS+) 234.1 ([M+H]$^+$).

Intermediate D1:
3-oxa-7,9-diaza-bicyclo[3.3.1]nonane-9-carboxylic acid 9H-fluoren-9-ylmethyl ester, hydrochloride salt

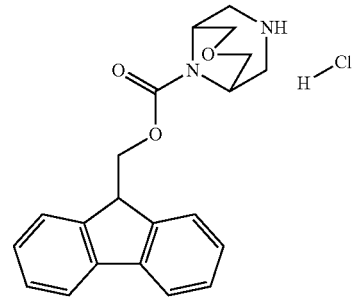

Step 1: 3-oxa-7,9-diaza-bicyclo[3.3.1]nonane-7,9-dicarboxylic acid 7-tert-butyl ester 9-(9H-fluoren-9-ylmethyl) ester A mixture of 3-oxa-7,9-diaza-bicyclo[3.3.1]nonane-7-carboxylic acid tert-butyl ester (716 mg, 3.14 mmol, WuXy AppTech) and 9-fluorenylmethoxycarbonyl-N-hydroxysuccinimide (1058 mg, 3.14 mmol) was prepared in anhydrous THF (11 mL) and stirred at RT for 2.5 hours. The reaction mixture was concentrated under vacuum to give a yellow oil. After purification by flash chromatography (silica, heptane/EtOAc), the title compound was obtained as a white foam (1.36 g, 93%). $^1$H NMR (300 MHz, CDCl$_3$) δ 7.77 (d, J=7.5 Hz, 2H), 7.55 (d, J=7.3 Hz, 2H), 7.45-7.37 (m, 2H), 7.36-7.28 (m, 2H), 4.65-4.57 (m, 2H), 4.35-3.49 (m, 9H), 3.17-2.78 (m, 2H), 1.46 (s, 9H). HPLC (max plot) 96.5%; Rt 5.07 min. UPLC/MS: (MS+) 451.4 ([M+H]$^+$).

Step 2:
3-oxa-7,9-diaza-bicyclo[3.3.1]nonane-9-carboxylic acid 9H-fluoren-9-ylmethyl ester hydrochloride 3-Oxa-7,9-diaza-bicyclo[3.3.1]nonane-7,9-dicarboxylic acid 7-tert-butyl ester 9-(9H-fluoren-9-ylmethyl) ester (1.29 g, 2.76 mmol) was dissolved into a 4N solution of HCl in 1,4-dioxane (10 mL). The resulting mixture was stirred at RT for 1.5 hours, and then concentrated under vacuum to give a colorless oil. The oil was taken up with Et$_2$O (20 ml) and a precipitation occurred. The precipitate was filtered off, washed with Et$_2$O (2×) and dried under vacuum to give the title compound as a white powder (1.06 g, 92%). $^1$H NMR (300 MHz, DMSO-d$_6$) δ 9.81 (s, 1H), 8.22 (s, 1H), 7.90 (d, J=7.3 Hz, 2H), 7.64 (d, J=7.4 Hz, 2H), 7.47-7.31 (m, 4H), 4.61-4.44 (m, 2H), 4.31 (t, J=6.0 Hz, 1H), 4.07 (s, 1H), 4.02-3.84 (m, 3H), 3.62-3.53 (m, 1H), 3.51-3.37 (m, 3H), 3.09-2.90 (m, 2H). HPLC (max plot) 97.4%; Rt 2.94 min. UPLC/MS: (MS+) 351.3 ([M+H]$^+$).

Intermediate A12: 6-chloro-5-methyl-2,3-dihydro-1H-2,4,7a,8-tetraaza-cyclopenta[a]indene

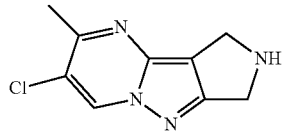

Step 1: 3-chloro-4,4-diethoxy-butan-2-one

A solution of BF$_3$.Et$_2$O (9.35 mL; 108 mmol; 2 eq.) in DCM (100 mL) was added dropwise at −30° C. over 50 minutes to diethoxymethoxy-ethane (18 mL; 108 mmol; 2 eq.). The reaction mixture was stirred at this temperature for a further 40 minutes then allowed to return to room temperature and was stirred at room temperature for 1 hour. After cooling down to −78° C., 1-chloro-propan-2-one (4.3 mL; 54 mmol; 1 eq.) was added dropwise followed by DIEA (28 mL; 162 mmol; 3 eq.) at such a rate to keep the temperature below −70° C. The resulting mixture was stirred at −70° C. for one hour then poured onto sat. aq. NaHCO$_3$. The two layers were separated and the aqueous phase extracted with DCM. The combined organics were washed with cold diluted H$_2$SO$_4$ then water, dried over magnesium sulfate and concentrated in vacuo to afford the title compound (6 g, 48%) as a brown oil which was used without further purification. $^1$H NMR (DMSO-d$_6$) δ 4.81 (d, J=6.0 Hz, 1H), 4.64 (d, J=6.0 Hz, 2H), 3.70-3.44 (m, 4H), 2.25 (s, 3H), 1.30-1.17 (m, 6H).

Step 2: 6-chloro-5-methyl-1H,3H-2,4,7a,8-tetraaza-cyclopenta[a]indene-2-carboxylic acid tea-butyl ester A solution of 3-amino-2,6-dihydro-4H-pyrrolo[3,4-c]pyrazole-5-carboxylic acid tert-butyl ester (5.8 g; 25.9 mmol; 1 eq.) and 3-chloro-4,4-diethoxy-butan-2-one (5.6 g; 25.9 mmol; 1 eq.) in AcOH (26 mL) was stirred at room temperature for 16 hours then concentrated in vacuo. The residue was poured onto sat. aq. NaHCO$_3$ and the formed precipitate was filtered off and dried. Purification by column chromatography (30% EA in heptane) afforded the title compound (1.7 g, 22%) as a white solid. $^1$H NMR (DMSO-d$_6$) δ 9.48 (s, 1H), 4.62-4.54 (m, 4H), 2.60-2.57 (m, 3H), 1.48 (s, 9H). HPLC (max plot) 97.0%, Rt 3.93 min. UPLC/MS: (MS+) 309.3 ([M+H]$^+$).

Step 3: 6-chloro-5-methyl-2,3-dihydro-1H-2,4,7a,8-tetraaza-cyclopenta[a]indene

A 32% solution of HCl (1.79 mL) was added to a solution of 6-chloro-5-methyl-1H,3H-2,4,7a,8-tetraaza-cyclopenta[a]indene-2-carboxylic acid tert-butyl ester (1.70 g; 5.51 mmol; 1 eq.) in AcOH (5.8 mL) and the reaction mixture was stirred at room temperature for 16 hours. The solution was diluted with DCM, washed with 1M NaOH (2×), dried over sodium sulfate and concentrated in vacuo to afford the title compound (900 mg, 78%) as a yellow solid. $^1$H NMR (DMSO-d$_6$) δ 9.37 (s, 1H), 4.09-3.98 (m, 4H), 3.70-3.53 (m, 1M), 2.55 (s, 3H). HPLC (max plot) 99.8%, Rt 1.20 min. UPLC/MS: (MS+) 209.1 ([M+H]$^+$).

Intermediate A13: 6-chloro-7-methyl-2,3-dihydro-1H-2,4,7a,8-tetraaza-cyclopenta[a]indene

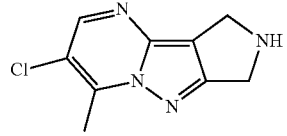

Step 1: 6-chloro-7-methyl-1H,3H-2,4,7a,8-tetraaza-cyclopenta[a]indene-2-carboxylic acid tert-butyl ester The title compound was isolated during the purification of Intermediate A12 step 2 (140 mg, 2%) as a white solid. $^1$H NMR (DMSO-d$_6$) δ 8.58 (s, 1H), 4.67-4.58 (m, 4H), 2.83 (s, 3H), 1.48 (s, 9H). HPLC (max plot) 96.4%, Rt 4.13 min. UPLC/MS: (MS+) 309.2 ([M+H]$^+$).

Step 2: 6-chloro-7-methyl-2,3-dihydro-1H-2,4,7a,8-tetraaza-cyclopenta[a]indene

A 32% solution of HCl (0.14 mL) was added to a solution of 6-chloro-7-methyl-1H,3H-2,4,7a,8-tetraaza-cyclopenta[a]indene-2-carboxylic acid tert-butyl ester (140 mg; 0.44 mmol; 1 eq.) in AcOH (0.5 mL) and the reaction mixture was stirred at room temperature for 16 hours. The solution was diluted with DCM, washed with 1M NaOH (2×), dried over sodium sulfate and concentrated in vacuo to afford the title compound (80 mg, 86%) as a yellow solid. $^1$H NMR (DMSO-d$_6$) δ 8.48 (s, 1H), 4.12-4.03 (m, 4H), 3.73-3.57 (m, 1H), 2.80 (s, 3H). HPLC (max plot) 99.6%, Rt 1.33 min. UPLC/MS: (MS+) 209.1 ([M+H]$^+$).

Intermediate Z7: (6-chloro-5-methyl-1H,3H-2,4,7a,8-tetraaza-cyclopenta[a]inden-2-yl)-(4-fluoro-2-hydroxy-phenyl)-methanone

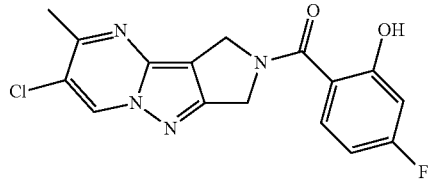 [SMILES: Cc1nc2c3c(nn2cc1Cl)CN(C(=O)c1ccc(F)cc1O)C3]

The title compound was prepared following procedure described in Method A starting from 4-fluoro-2-hydroxybenzoic acid and Intermediate A12. After completion, water was added and the precipitate was filtered off and dried to afford the title compound (400 mg, 79%) as a beige solid. $^1$H NMR (DMSO-d$_6$) δ 10.72-10.52 (m, 1H), 9.50 (d, J=4.6 Hz, 1H), 7.39-7.28 (m, 1H), 6.78-6.70 (m, 2H), 4.84-4.76 (m, 2H), 4.69-4.59 (m, 2H), 2.61 (s, 2H), 2.55 (s, 1H). HPLC (max plot) 98.4%, Rt 3.09 min. UPLC/MS: (MS+) 347.3 ([M+H]$^+$).

Intermediate B23: 4-(2-carboxy-phenoxy)-3-trifluoromethyl-piperidine-1-carboxylic acid tert-butyl ester

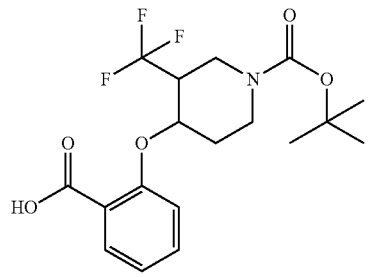 [SMILES: CC(C)(C)OC(=O)N1CCC(Oc2ccccc2C(=O)O)C(C(F)(F)F)C1]

Step 1: 4-(2-formyl-phenoxy)-3-trifluoromethyl-piperidine-1-carboxylic acid tert-butyl ester tBuOK (136 mg; 1.21 mmol; 1.5 eq.) was added to a solution of 4-hydroxy-3-trifluoromethyl-piperidine-1-carboxylic acid tert-butyl ester (239 mg; 0.89 mmol; 1.1 eq.) in 1,4-dioxane (10 mL) and the reaction mixture was stirred at 50° C. for 15 minutes. After cooling down to room temperature, 2-fluoro-benzaldehyde (100 mg; 0.81 mmol; 1 eq.) was added and the reaction was stirred at 50° C. for 30 minutes. The solution was diluted with water and extracted with EA (3×). The combined organics were dried over magnesium sulfate and concentrated in vacuo. Purification by column chromatography (10% to 30% EA in heptane) afforded the title compound (181 mg, 60%) as colourless oil. HPLC (max plot) 99.9%, Rt 5.02 min. UPLC/MS: (MS+) 274.2 ([M-(Boc)+H]$^+$).

Step 2: 4-(2-carboxy-phenoxy)-3-trifluoromethyl-piperidine-1-carboxylic acid tert-butyl ester A solution of sodium chlorite (219 mg; 2.42 mmol; 5 eq.) and sodium dihydrogenphosphate (233 mg; 1.94 mmol; 4 eq.) in water (1 mL) was added dropwise to a mixture of 2-methyl-2-butene (1 mL) and 4-(2-formyl-phenoxy)-3-trifluoromethyl-piperidine-1-carboxylic acid tert-butyl ester (181 mg; 0.48 mmol; 1 eq.) in 1,4-dioxane (4 mL). The reaction mixture was stirred at room temperature for 1 hour and the 1,4-dioxane concentrated in vacuo. The aqueous solution was diluted with water and the pH made acidic with 0.1M HCl. The mixture was extracted with DCM (2×) and the combined organic phase was dried over magnesium sulfate and concentrated in vacuo. Purification by mass directed preparative HPLC afforded the title compound (86 mg, 46%) as a white solid. HPLC (max plot) 97.3%, Rt 4.39 min. UPLC/MS: (MS−) 388.3 ([M−H]$^−$).

Intermediate Z8: (6-chloro-7-methyl-1H,3H-2,4,7a,8-tetraaza-cyclopenta[a]inden-2-yl)-(4-fluoro-2-hydroxy-phenyl)-methanone

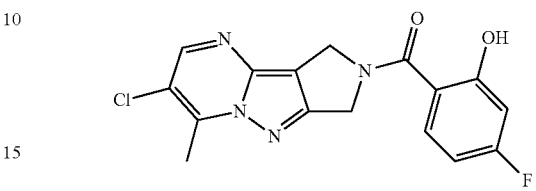

The title compound was prepared following procedure described in Method A starting from Intermediate A13 and 4-fluoro-2-hydroxybenzoic acid. After completion water was added and the precipitate was filtered off and dried to afford the title compound (110 mg, 62%) as a beige solid. $^1$H NMR (DMSO-d$_6$) δ 10.70-10.61 (m, 1H), 8.59 (d, J=10.6 Hz, 1H), 7.39-7.29 (m, 1H), 6.79-6.69 (m, 2H), 4.89-4.80 (m, 2H), 4.74-4.63 (m, 2H), 2.85 (s, 2H), 2.82 (s, 1H). UPLC/MS: (MS+) 347.3 ([M+H]$^+$).

Intermediate B24: 4-fluoro-2-((1R,5S,7S)-9-methyl-3-oxa-9-aza-bicyclo[3.3.1]non-7-yloxy)-benzoic acid

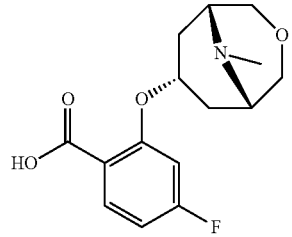 [SMILES: CN1[C@@H]2COC[C@H]1C[C@@H](Oc1cc(F)ccc1C(=O)O)C2]

Step 1: (1R,5S,7S)-9-methyl-3-oxa-9-aza-bicyclo[3.3.1]nonan-7-ol

A 1M solution of LiAlH$_4$ in THF (9.7 mL; 9.7 mmol; 1.5 eq.) was added dropwise at 0° C. to a solution of 9-methyl-3-oxa-9-aza-bicyclo[3.3.1]nonan-7-one (1 g; 6.44 mmol; 1 eq.) in THF (20 mL) and the reaction mixture was stirred at room temperature for 16 hours whereupon a 1M solution of LiAlH$_4$ in THF (3 mL; 3 mmol; 0.47 eq.) was added. The resulting mixture was stirred at room temperature for a 4 hours. Water (480 μL) was added followed by 1M NaOH (480 μL) and water (1.44 mL). The suspension was filtered through a short plug of Celite® and the solution concentrated in vacuo. Purification by column chromatography (5% to 30% MeOH in DCM) afforded the title compound (806 mg, 80%) as a white solid. $^1$H NMR (CDCl$_3$) δ 5.66 (d, J=12.5 Hz, 1H), 4.13-3.87 (m, 3H), 3.74 (dt, J=11.6, 0.9 Hz, 2H), 2.68-2.63 (m, 2H), 2.49 (s, 3H), 2.42-2.31 (m, 2H), 1.57 (dq, J=15.6, 1.3 Hz, 2H).

Step 2: (1R,5S,7S)-7-(2-bromo-5-fluoro-phenoxy)-9-methyl-3-oxa-9-aza-bicyclo[3.3.1]nonane tBuOK (416 mg; 3.7 mmol; 1.1 eq.) was added portionwise to a solution of (1R,5S,7S)-9-methyl-3-oxa-9-aza-bicyclo

[3.3.1]nonan-7-ol (530 mg; 3.4 mmol; 1 eq.) and 1-bromo-2, 4-difluoro-benzene (765 µL; 6.7 mmol; 2 eq.) in THF (10 mL) and the reaction mixture was stirred at room temperature for 16 hours. tBuOK (416 mg; 3.7 mmol; 1.1 eq.) was added and the resulting mixture was stirred at 50° C. for 16 hours. Water was added and the solution was extracted with EA (3×). The combined organics were washed with brine, dried over magnesium sulfate and concentrated in vacuo. Purification by column chromatography (EA/heptane) to afford the title compound (675 mg, 61%) as a yellow oil. $^1$H NMR (CDCl$_3$) δ 7.58 (dd, J=8.8, 6.4 Hz, 1H), 7.01 (dd, J=11.2, 2.9 Hz, 1H), 6.72 (ddd, J=8.8, 8.1, 2.8 Hz, 1H), 4.72 (quint, J=6.2 Hz, 1H), 3.78 (dd, J=11.0, 2.3 Hz, 2H), 3.37-3.31 (m, 2H), 2.72 (d, J=8.6 Hz, 2H), 2.49-2.40 (s, 5H), 1.72-1.53 (m, 2H). HPLC (max plot) 95.9%, Rt 2.45 min. UPLC/MS: (MS+) 330.2 and 332.2 ([M+H]$^+$).

Step 3: 4-fluoro-2-((1R,5S,7S)-9-methyl-3-oxa-9-aza-bicyclo[3.3.1]non-7-yloxy)-benzoic acid lithium salt A 1.6M solution of n-butyllithium in hexanes (625 µL; 1 mmol; 1 eq.) was added at −78° C. over 10 minutes to a solution of (1R,5S,7S)-7-(2-bromo-5-fluoro-phenoxy)-9-methyl-3-oxa-9-aza-bicyclo[3.3.1]nonane (300 mg; 0.91 mmol; 1 eq.) in THF (3 mL) and the reaction mixture was stirred at −78° C. for 30 minutes whereupon carbon dioxide was bubbled into the solution. The solution was allowed to return to room temperature while maintaining the bubbling then concentrated in vacuo to afford the title compound as a yellow solid which was used without further purification. UPLC/MS: (MS+) 296.2 ([M+H]$^+$).

Intermediate B25: 3-(2-carboxy-phenoxy)-3-trifluoromethyl-pyrrolidine-1-carboxylic acid tert-butyl ester

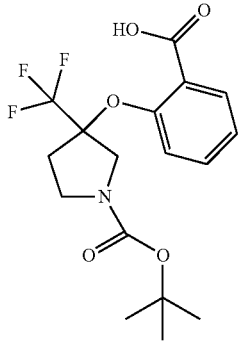 [SMILES: CC(C)(C)OC(=O)N1CCC(Oc2ccccc2C(=O)O)(C(F)(F)F)C1]

Step 1: 3-(2-formyl-phenoxy)-3-trifluoromethyl-pyrrolidine-1-carboxylic acid tert-butyl ester tBuOK (136 mg; 1.2 mmol; 1.5 eq.) was added at 10° C. to a solution of 3-hydroxy-3-trifluoromethyl-pyrrolidine-1-carboxylic acid tert-butyl ester (247 mg; 0.97 mmol; 1.2 eq.) in 1,4-dioxane (10 mL) and the reaction mixture was stirred at room temperature for 15 minutes whereupon 2-fluoro-benzaldehyde (100 mg; 0.81 mmol; 1 eq.) was added. The reaction mixture was stirred at 100° C. for 3 hours then diluted with sat. aq. NH$_4$Cl and extracted with EA (2×). The combined organics were washed with brine, dried over magnesium sulfate and concentrated in vacuo. Purification by column chromatography (DCM) afforded the title compound (95 mg, 33%) as a colourless oil. HPLC (max plot) 98.2%, Rt 4.87 min.

Step 2: 3-(2-carboxy-phenoxy)-3-trifluoromethyl-pyrrolidine-1-carboxylic acid tert-butyl ester A solution of sodium chlorite (120 mg; 1.32 mmol; 5 eq.) and sodium dihydrogenphosphate (127 mg; 1.06 mmol; 4 eq.) in water (2 mL) was added dropwise to a mixture of 2-methyl-2-butene (0.25 mL) and 3-(2-formyl-phenoxy)-3-trifluoromethyl-pyrrolidine-1-carboxylic acid tert-butyl ester (95 mg; 0.26 mmol; 1 eq.) in 1,4-dioxane (2 mL). The reaction mixture was stirred at room temperature for 3 hours and the 1,4-dioxane concentrated in vacuo. The aqueous solution was diluted with water and the pH made acidic with 0.1M HCl. The mixture was extracted with EA (2×) and the combined organic phase was dried over magnesium sulfate and concentrated in vacuo to afford the title compound (100 mg, quantitative) as a colourless oil. HPLC (max plot) 93.5%, Rt 4.22 min. UPLC/MS: (MS−) 374.3 ([M−H]$^−$).

Intermediate B26: 5-fluoro-2-(2-pyridazin-3-yl-ethoxy)-benzoic acid

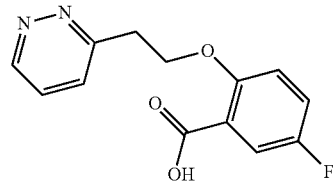 [SMILES: O=C(O)c1cc(F)ccc1OCCc1cccnn1]

Step 1: 5-fluoro-2-(2-pyridazin-3-yl-ethoxy)-benzoic acid methyl ester

The title compound was prepared following procedure described in Method G starting from 4-fluoro-2-hydroxy-benzoic acid methyl ester and 2-pyridazin-3-yl-ethanol. After work up, purification by column chromatography (10% EA in heptane to EA) afforded the title compound (60 mg, 23%) as a white solid. $^1$H NMR (DMSO-d$_6$) δ 9.12 (dd, J=4.8, 1.8 Hz, 1H), 7.77-7.63 (m, 3H), 7.13 (dd, J=11.6, 2.4 Hz, 1H), 6.90-6.80 (m, 1H), 4.48 (t, J=6.2 Hz, 2H), 3.69 (s, 3H), 3.39 (t, J=6.2 Hz, 2H). HPLC (max plot) 100%, Rt 2.84 min. UPLC/MS: (MS+) 277.2 ([M+H]$^+$).

Step 2: 5-fluoro-2-(2-pyridazin-3-yl-ethoxy)-benzoic acid

NaOH (87 mg; 2.17 mmol; 10 eq.) was added to a solution of 5-fluoro-2-(2-pyridazin-3-yl-ethoxy)-benzoic acid methyl ester (60 mg; 0.22 mmol; 1 eq.) on THF (1 mL) and the reaction mixture was stirred at room temperature for 16 hours. The solution was diluted with water acidified with 0.1M HCl and extracted with DCM (3×). The combined organics were dried over magnesium sulfate and concentrated in vacuo to give the title compound (57 mg, quantitative) as a yellow solid which was used without further purification. UPLC/MS: (MS+) 263.2 ([M+H]$^+$).

97

Intermediate Z9: (6-chloro-1H,3H-2,4,7a,8-tetraaza-cyclopenta[a]inden-2-yl)-(4-fluoro-2-hydroxy-phenyl)-methanone

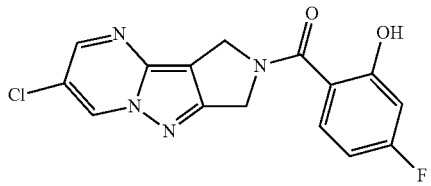 [SMILES: O=C(c1ccc(F)cc1O)N1Cc2nn3cc(Cl)cnc3c2C1]

The title compound was prepared following procedure described in Method A starting from Intermediate A4 and 4-fluoro-2-hydroxybenzoic acid. After completion, water was added and the precipitate was filtered off and dried to afford the title compound (480 mg, 66%) as a white solid. $^1$H NMR (DMSO-d$_6$) δ 10.88-10.29 (m, 1H), 9.60 (dd, J=5.0, 2.3 Hz, 1H), 8.61 (dd, J=10.6, 2.3 Hz, 1H), 7.37-7.29 (m, 1H), 6.78-6.70 (m, 2H), 4.88-4.81 (m, 2H), 4.72-4.63 (m, 2H). UPLC/MS: (MS+) 333.2 ([M+H]$^+$).

Preparation of Compounds of Formula (I)

Example 1

(6-chloro-5,7-dimethyl-1H,3H-2,4,7a,8-tetraaza-cyclopenta[a]inden-2-yl)-[2-(1-methyl-piperidin-4-yloxy)-phenyl]-methanone

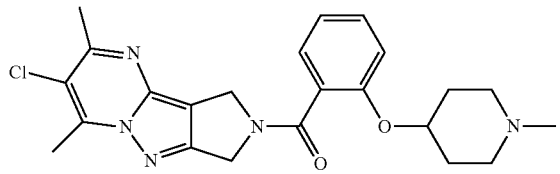 [SMILES: Cc1nc2c3c(nn2c(C)c1Cl)CN(C(=O)c1ccccc1OC1CCN(C)CC1)C3]

The title compound was prepared following procedure described in Method A starting Intermediate A3 and 2-(1-methyl-piperidin-4-yloxy)-benzoic acid hydrochloride. After purification by recrystallization from ACN, the title compound was obtained as a white solid (72 mg, 42%). $^1$H NMR (CDCl$_3$) δ 7.39-7.32 (m, 2H), 7.07-6.95 (m, 2H), 5.02-5.01 (m, 2H), 4.67 (br s, 2H), 4.39 (br s, 1H), 2.91 (s, 2H), 2.85 (s, 1H), 2.69 (s, 1H), 2.62 (s, 2H), 2.57-2.47 (m, 2H), 2.31-2.21 (m, 2H), 2.19 (s, 3H), 2.01-1.75 (m, 4H). HPLC (max plot) 99.2%; Rt 2.56 min. UPLC/MS: (MS+) 440.4 ([M+H]$^+$).

Example 2

(6-chloro-5,7-dimethyl-1H,3H-2,4,7a,8-tetraaza-cyclopenta[a]inden-2-yl)-[2-(1,1,2,2-tetrafluoro-ethoxy)-phenyl]-methanone

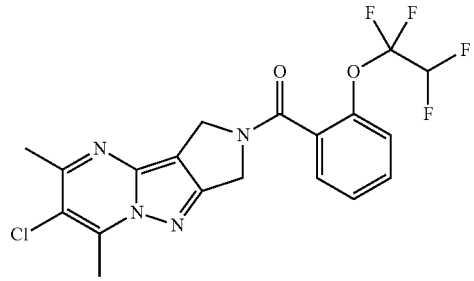 [SMILES: Cc1nc2c3c(nn2c(C)c1Cl)CN(C(=O)c1ccccc1OC(F)(F)C(F)F)C3]

98

The title compound was prepared following procedure described in Method A starting from Intermediate A3 and 2-(1,1,2,2-tetrafluoroethoxy)benzoic acid. After purification by crystallization (ACN), the title compound was obtained as a white powder (59 mg, 23%). $^1$H NMR (DMSO-d$_6$) δ 7.66-7.58 (m, 2H), 7.54-7.43 (m, 2H), 6.73 (t, J=51.6 Hz, 1H), 4.84 (s, 1H), 4.82 (s, 1H), 4.55 (s, 1H), 4.51 (s, 1H), 2.84 (s, 1.5H), 2.80 (s, 1.5H), 2.62 (s, 1.5H), 2.55 (s, 1.5H). HPLC (max plot) 99.9%, Rt 4.31 min. UPLC/MS: (MS+) 443.4 ([M+H]$^+$), (MS−) 441.4 ([M−H]$^−$). Melting point: 184-186° C. (ACN).

Example 3

(6-chloro-5,7-dimethyl-1H,3H-2,4,7a,8-tetraaza-cyclopenta[a]inden-2-yl)-[2-(piperidin-4-yloxy)-phenyl]-methanone

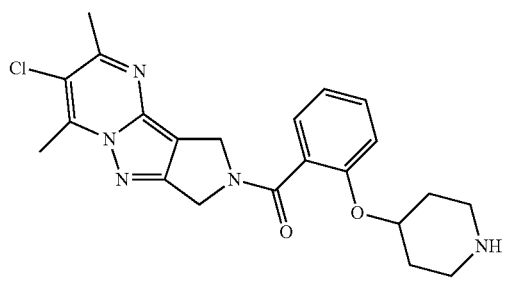 [SMILES: Cc1nc2c3c(nn2c(C)c1Cl)CN(C(=O)c1ccccc1OC1CCNCC1)C3]

Step 1: 4-[2-(6-chloro-5,7-dimethyl-1H,3H-2,4,7a,8-tetraaza-cyclopenta[a]indene-2-carbonyl)-phenoxy]-piperidine-1-carboxylic acid tert-butyl ester The title compound was prepared following procedure described in Method A starting from Intermediate A3 and Intermediate B3. After aqueous work-up the crude title compound was obtained (2.78 g) as a pale yellow solid and was used in the next step without further purification. $^1$H NMR (CDCl$_3$) δ 7.40-7.33 (m, 2H), 7.09-6.96 (m, 2H), 5.00-4.99 (m, 2H), 4.65 (br s, 2H), 4.56-4.49 (m, 1H), 3.56-3.46 (m, 2H), 3.38-3.28 (m, 2H), 2.90 (s, 2H), 2.85 (s, 1H), 2.69 (s, 1H), 2.61 (s, 2H), 1.90-1.65 (m, 4H), 1.41 (s, 9H). HPLC (max plot) 95.6%, Rt 4.39 min. UPLC/MS: (MS+) 426.4 ([M-Boc+2H]$^+$).

Step 2: (6-chloro-5,7-dimethyl-1H,3H-2,4,7a,8-tetraaza-cyclopenta[a]inden-2-yl)-[2-(piperidin-4-yloxy)-phenyl]-methanone A 4M solution of HCl in 1,4-dioxane (6.6 mL; 26.4 mmol; 5 eq.) was added to a solution of 4-[2-(6-chloro-5,7-dimethyl-1H,3H-2,4,7a,8-tetraaza-cyclopenta[a]indene-2-carbonyl)-phenoxy]-piperidine-1-carboxylic acid tert-butyl ester (2.78 g; 5.28 mmol; 1 eq.) in 1,4-dioxane (30 mL) and the reaction mixture was stirred at room temperature for 18 hours then concentrated in vacuo. The residue was partitioned between DCM and sat. aq. Na$_2$CO$_3$ and the two phases separated. The organic layer was dried over magnesium sulfate and concentrated in vacuo to afford the title compound (1.78 g, 79%) as a yellow solid. $^1$H NMR (DMSO-d$_6$) δ 7.46-7.39 (m, 1H), 7.33-7.29 (m, 1H), 7.21-7.19 (m, 1H), 7.07-7.01 (m, 1H), 4.85 (s, 1H), 4.82 (s, 1H), 4.58-4.49 (m, 3H), 2.92-2.76 (m, 2H), 2.84 (s, 1.5H), 2.80 (s, 1.5H), 2.69-2.58 (m, 2H), 2.62 (s, 1.5H), 2.55 (s, 1.5H), 1.93-1.68 (m, 2H), 1.54-1.43 (m, 2H). HPLC (max plot) 92.5%; Rt 2.69 min. UPLC/MS: (MS+) 426.4 ([M+H]+).

Example 4

[2-(1-methyl-piperidin-4-yloxy)-phenyl]-(5,6,7-trimethyl-1H,3H-2,4,7a,8-tetraaza-cyclopenta[a]inden-2-yl)-methanone

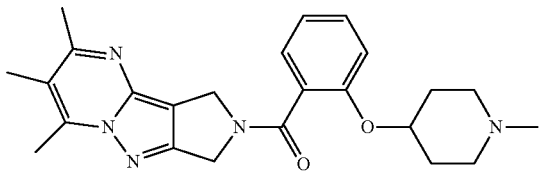

The title compound was prepared following procedure described in Method A starting from Intermediate A1 and 2-(1-methyl-piperidin-4-yloxy)-benzoic acid hydrochloride. After purification by mass directed preparative HPLC, the title compound was obtained as a white solid (65 mg, 31%). $^1$H NMR (CDCl$_3$) δ 7.45-7.34 (m, 2H), 7.13-6.99 (m, 2H), 5.00 (s, 0.7H), 4.97 (s, 1.3H), 4.76 (s, 1H), 4.62 (s, 1.3H), 4.59 (s, 0.7H), 3.32-3.24 (m, 2H), 3.14-3.10 (m, 2H), 2.78-2.77 (m, 5H), 2.72 (s, 1H), 2.59 (s, 1H), 2.51 (s, 2H), 2.31 (s, 1H), 2.30 (s, 2H), 2.27-2.23 (m, 2H), 2.13-2.08 (m, 2H). HPLC (max plot) 99.5%; Rt 2.25 min. UPLC/MS: (MS+) 420.5 ([M+H]+).

Example 5

(6-chloro-5,7-dimethyl-1H,3H-2,4,7a,8-tetraazacyclopenta[a]inden-2-yl)-(2-ethoxy-4-fluoro-phenyl)-methanone

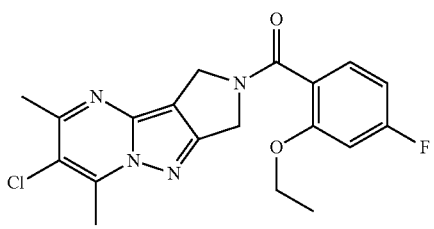 [SMILES: CCOc1cc(F)ccc1C(=O)N1Cc2nn3c(C)c(Cl)c(C)nc3c2C1]

The title compound was prepared following procedure described in Method A starting from Intermediate A3 and Intermediate B1. After purification by crystallization (ACN), the title compound was obtained as a white powder (135 mg, 60%). $^1$H NMR (DMSO-d$_6$) δ 7.39-7.31 (m, 1H), 7.06 (d, J=11.2 Hz, 1H), 6.91-6.81 (m, 1H), 4.82 (s, 1H), 4.79 (s, 1H), 4.56 (s, 1H), 4.51 (s, 1H), 4.14 (q, J=6.9 Hz, 1H), 4.13 (q, J=6.9 Hz, 1H), 2.83 (s, 1.5H), 2.80 (s, 1.5H), 2.61 (s, 1.5H), 2.55 (s, 1.5H), 1.24 (t, J=6.9 Hz, 1.5H), 1.23 (t, J=6.9 Hz, 1.5H). HPLC (max plot) 99.2%, Rt 4.05 min. UPLC/MS: (MS+) 389.4 ([M+H]+).

Example 6

(6-chloro-5,7-dimethyl-1H,3H-2,4,7a,8-tetraazacyclopenta[a]inden-2-yl)-[2-(4-methyl-[1,4]diazepan-1-yl)-phenyl]-methanone

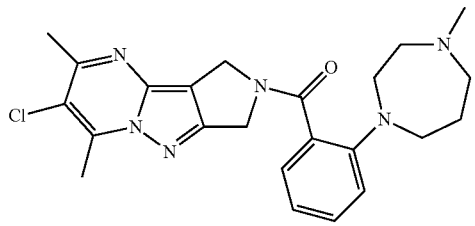 [SMILES: Cc1nc2c3c(nn2c(C)c1Cl)CN(C(=O)c1ccccc1N1CCCN(C)CC1)C3]

The title compound was prepared following procedure described in Method A starting from Intermediate A3 and 2-(4-methylperhydro-1,4-diazepin-1-yl)benzoic acid hydrochloride hemihydrate. After purification by crystallization (ACN), the title compound was obtained as a white powder (45 mg, 31%). HPLC (max plot) 95.6%, Rt 2.74 min. UPLC/MS: (MS+) 439.4 ([M+H]+), (MS−) 437.5 ([M−H]−).

Example 7

(6-chloro-5,7-dimethyl-1H,3H-2,4,7a,8-tetraazacyclopenta[a]inden-2-yl)-(2-pyrrolidin-1-yl-phenyl)-methanone

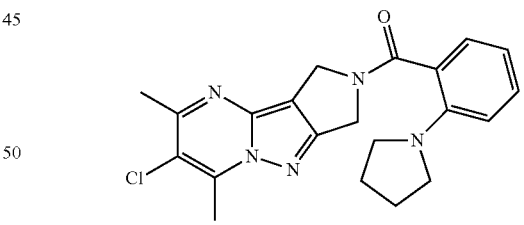

The title compound was prepared following procedure described in Method A starting from Intermediate A3 and 2-(pyrrolidin-1-yl)benzoic acid (Ukrorgsynthesis Ltd.), and has precipitated out from the reaction mixture. After filtration, washing twice with DMF and purification by crystallization (ACN), the title compound was obtained as a white powder (15 mg, 7%). $^1$H NMR (DMSO-d$_6$) δ 7.31-7.16 (m, 2H), 6.80-6.68 (m, 2H), 4.84 (s, 1H), 4.81 (s, 1H), 4.78-4.63 (m, 1H), 4.55-4.38 (m, 1H), 3.31-3.20 (m, 2H), 3.19-3.06 (m, 2H), 2.83 (s, 1.5H), 2.80 (s, 1.5H), 2.61 (s, 1.5H), 2.55 (s, 1.5H), 1.90-1.75 (m, 4H). HPLC (max plot) 99.3%, Rt 3.65 min. UPLC/MS: (MS+) 396.4 ([M+H]+).

Example 8

(6-chloro-5,7-dimethyl-1H,3H-2,4,7a,8-tetraaza-cyclopenta[a]inden-2-yl)-[2-(2-dimethylamino-ethoxy)-phenyl]-methanone

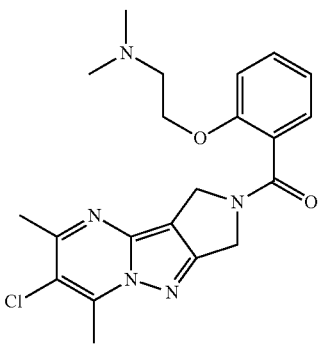 [SMILES: Cc1nc2c3c(nn2c(C)c1Cl)CN(C(=O)c1ccccc1OCCN(C)C)C3]

The title compound was prepared following procedure described in Method A starting from Intermediate A3 and 2-[2-(dimethylamino)ethoxy]benzoic acid hydrochloride (Enamine). After purification by flash chromatography (silica, DCM/EtOH/aqueous NH$_3$), followed by crystallization (MIBK), the title compound was obtained as a white powder (542 mg, 34%). $^1$H NMR (CDCl$_3$) δ 7.42-7.31 (m, 2H), 7.10-7.00 (m, 1H), 7.00-6.91 (m, 1H), 5.01-4.96 (m, 2H), 4.65 (s, 2H), 4.17 (t, J=5.8 Hz, 2H), 2.91 (s, 1.8H), 2.85 (s, 1.2H), 2.72 (t, J=5.8 Hz, 2H), 2.69 (s, 1.2H), 2.61 (s, 1.8H), 2.26 (s, 6H). HPLC (max plot) 99.4%, Rt 2.69 min. UPLC/MS: (MS+) 414.4 ([M+H]+). Melting point: 156-159° C. (MIBK). Elemental analysis (O$_{21}$H$_{24}$ClN$_6$O$_2$): calculated: C, 60.94%; H, 5.84%; N, 16.92%. found: C, 60.85%; H, 5.94%; N, 16.75%.

Example 9

(6-chloro-5,7-dimethyl-1H,3H-2,4,7a,8-tetraaza-cyclopenta[a]inden-2-yl)-(2-isopropoxy-phenyl)-methanone

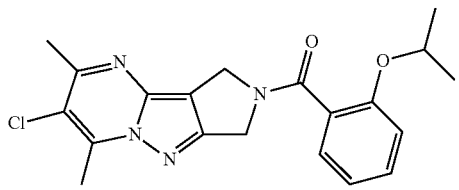 [SMILES: Cc1nc2c3c(nn2c(C)c1Cl)CN(C(=O)c1ccccc1OC(C)C)C3]

The title compound was prepared following procedure described in Method A starting from Intermediate A3 and 2-isopropoxybenzoic acid (Ukrorgsynthesis Ltd.). After purification by crystallization (ACN), the title compound was obtained as a pale beige powder (44 mg, 35%). $^1$H NMR (DMSO-d$_6$) δ 7.46-7.38 (m, 1H), 7.31-7.26 (m, 1H), 7.14 (d, J=8.3 Hz, 1H), 7.05-6.99 (m, 1H), 4.83 (s, 1H), 4.80 (s, 1H), 4.73-4.60 (m, 1H), 4.55 (s, 1H), 4.49 (s, 1H), 2.83 (s, 1.5H), 2.79 (s, 1.5H), 2.61 (s, 1.5H), 2.54 (s, 1.5H), 1.21 (d, J=6.0 Hz, 3H), 1.20 (d, J=6.0 Hz, 3H). HPLC (max plot) 98.0%, Rt 4.17 min. UPLC/MS: (MS+) 385.1 ([M+H]+), (MS−) 383.1 ([M−H]−).

Example 10

(6-chloro-5,7-dimethyl-1H,3H-2,4,7a,8-tetraaza-cyclopenta[a]inden-2-yl-(2-ethoxy-phenyl)-methanone

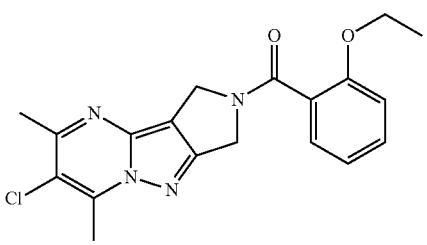 [SMILES: CCOc1ccccc1C(=O)N1Cc2nn3c(C)c(Cl)c(C)nc3c2C1]

The title compound was prepared following procedure described in Method A starting from Intermediate A3 and 2-ethoxybenzoic acid. After purification by crystallization (ACN), the title compound was obtained as a white powder (184 mg, 66%). $^1$H NMR (DMSO-d$_6$) δ 7.47-7.39 (m, 1H), 7.32-7.27 (m, 1H), 7.13 (d, J=8.4 Hz, 1H), 7.06-6.99 (m, 1H), 4.83 (s, 1H), 4.80 (s, 1H), 4.55 (s, 1H), 4.50 (s, 1H), 4.13 (q, J=6.9 Hz, 1H), 4.12 (q, J=6.9 Hz, 1H), 2.82 (s, 1.5H), 2.78 (s, 1.5H), 2.61 (s, 1.5H), 2.54 (s, 1.5H), 1.24 (t, J=6.9 Hz, 1.5H), 1.23 (t, J=6.9 Hz, 1.5H). HPLC (max plot) 98.6%, Rt 3.87 min. UPLC/MS: (MS+) 371.0 ([M+H]+). Melting point: 164-167° C. (ACN).

Example 11

(2-butoxy-phenyl)-(6-chloro-5,7-dimethyl-1H,3H-2,4,7a,8-tetraaza-cyclopenta[a]inden-2-yl)-methanone

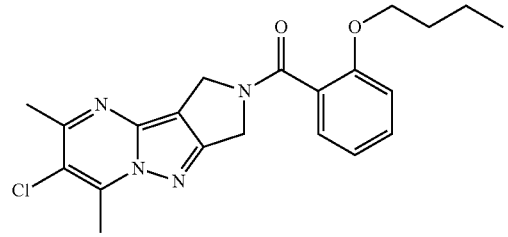 [SMILES: CCCCOc1ccccc1C(=O)N1Cc2nn3c(C)c(Cl)c(C)nc3c2C1]

The title compound was prepared following procedure described in Method A starting from Intermediate A3 and 2-butoxybenzoic acid. After purification by crystallization (ACN), the title compound was obtained as a white powder (142 mg, 61%). $^1$H NMR (DMSO-d$_6$) δ 7.47-7.39 (m, 1H), 7.32-7.27 (m, 1H), 7.14 (d, J=8.4 Hz, 1H), 7.07-7.00 (m, 1H), 4.82 (s, 1H), 4.79 (s, 1H), 4.53 (s, 1H), 4.48 (s, 1H), 4.05 (t, J=6.4 Hz, 1H), 4.04 (t, J=6.4 Hz, 1H), 2.83 (s, 1.5H), 2.79 (s, 1.5H), 2.61 (s, 1.5H), 2.54 (s, 1.5H), 1.65-1.53 (m, 2H), 1.35-1.20 (m, 2H), 0.77 (t, J=7.3 Hz, 1.5H), 0.75 (t, J=7.3 Hz, 1.5H). HPLC (max plot) 99.1%, Rt 4.55 min. UPLC/MS: (MS+) 399.4 ([M+H]⁺). Melting point: 167-169° C. (ACN).

Example 12

(2-ethoxy-phenyl)-(5,6,7-trimethyl-1H,3H-2,4,7a,8-tetraaza-cyclopenta[a]inden-2-yl)-methanone

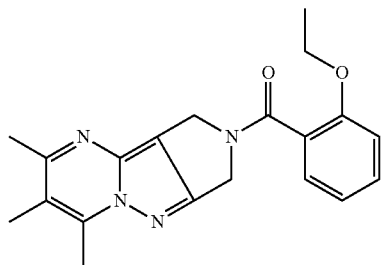 [SMILES: CCOc1ccccc1C(=O)N1Cc2nn3c(C)c(C)c(C)nc3c2C1]

The title compound was prepared following procedure described in Method B starting from Intermediate A1 and 2-ethoxybenzoic acid. After purification by flash chromatography (petroleum ether/EA, 50/50 to EA) the title compound was obtained as an white solid (29 mg, 38%). $^1$H NMR (CDCl$_3$) δ 7.39-7.28 (m, 2H), 7.01-6.88 (m, 2H), 5.10-4.95 (m, 2H), 4.68-4.60 (m, 2H), 4.16-4.06 (m, 2H), 2.74-2.68 (m, 3H), 2.54-2.48 (m, 3H), 2.26 (m, 3H), 1.35-1.19 (m, 3H). HPLC (max plot) 95.3%; Rt 3.22 min. UPLC/MS: (MS+) 351.0 ([M+H]⁺).

Example 13

(2-ethoxy-5-fluoro-phenyl)-(5,6,7-trimethyl-1H,3H-2,4,7a,8-tetraaza-cyclopenta[a]inden-2-yl)-methanone

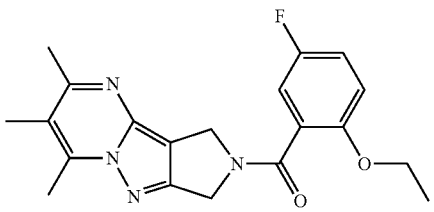 [SMILES: CCOc1ccc(F)cc1C(=O)N1Cc2nn3c(C)c(C)c(C)nc3c2C1]

The title compound was prepared following procedure described in Method B starting from Intermediate A1 and 2-ethoxy-5-fluorobenzoic acid. After purification by flash chromatography (petroleum ether/EA, 50/50 to EA), the title compound was obtained as a white solid (82 mg, 70%). $^1$H NMR (CDCl$_3$) δ 7.04-6.95 (m, 2H), 6.85-6.77 (m, 1H), 4.97-4.90 (m, 2H), 4.63-4.55 (m, 2H), 4.02-3.94 (m, 2H), 2.71-2.66 (m, 3H), 2.51-2.45 (m, 3H), 2.23 (s, 3H), 1.25-1.16 (m, 3H). HPLC (max plot) 96.7%; Rt 3.77 min. UPLC/MS: (MS+) 369.2 ([M+H]⁺).

Example 14

(6-chloro-5,7-dimethyl-1H,3H-2,4,7a,8-tetraaza-cyclopenta[a]inden-2-yl)-(2-trifluoromethoxy-phenyl)-methanone

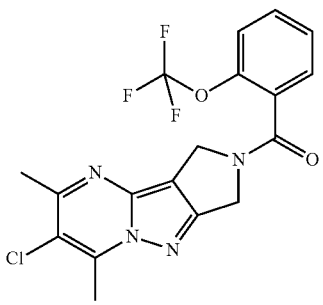 [SMILES: Cc1nc2c3c(nn2c(C)c1Cl)CN(C(=O)c1ccccc1OC(F)(F)F)C3]

The title compound was prepared following procedure described in Method A starting from Intermediate A3 and 2-(trifluoromethoxy)benzoic acid. After purification by crystallization (ACN), the title compound was obtained as a white powder (97 mg, 41%). $^1$H NMR (DMSO-d$_6$) δ 7.71-7.61 (m, 2H), 7.57-7.50 (m, 2H), 4.89 (s, 1H), 4.85 (s, 1H), 4.58 (s, 1H), 4.53 (s, 1H), 2.84 (s, 1.5H), 2.80 (s, 1.5H), 2.62 (s, 1.5H), 2.55 (s, 1.5H). HPLC (max plot) 100%, Rt 4.25 min. UPLC/MS: (MS+) 411.0 ([M+H]⁺). Melting point: 179-181° C. (ACN).

Example 15

(6-chloro-5,7-dimethyl-1H,3H-2,4,7a,8-tetraaza-cyclopenta[a]inden-2-yl)-[2-(2-methylsulfanyl-ethoxy)-phenyl]-methanone

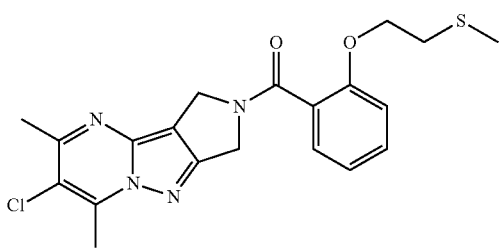

The title compound was prepared following procedure described in Method A starting from Intermediate A3 and 2-(2-methylsulfanyl-ethoxy)-benzoic acid (Ukrorgsynthesis Ltd.). After purification by crystallization (ACN), the title compound was obtained as a white powder (325 mg, 81%). $^1$H NMR (DMSO-d$_6$) δ 7.48-7.41 (m, 1H), 7.33-7.28 (m, 1H), 7.16 (d, J=8.3 Hz, 1H), 7.09-7.02 (m, 1H), 4.81 (s, 1H), 4.78 (s, 1H), 4.59 (s, 1H), 4.53 (s, 1H), 4.24 (t, J=6.1 Hz, 2H), 2.83 (s, 1.5H), 2.79 (s, 1.5H), 2.77 (t, J=6.1 Hz, 1H), 2.76 (t, J=6.1 Hz, 1H), 2.61 (s, 1.5H), 2.54 (s, 1.5H), 2.01 (s, 1.5H), 1.99 (s, 1.5H). HPLC (max plot) 99.4%, Rt 4.02 min. UPLC/

MS: (MS+) 417.3 ([M+H]+), (MS−) 415.5 ([M−H]−). Melting point: 183-185° C. (ACN).

Example 16

(6-chloro-5,7-dimethyl-1H,3H-2,4,7a,8-tetraaza-cyclopenta[a]inden-2-yl)-(3,5-difluoro-2-methoxy-phenyl)-methanone

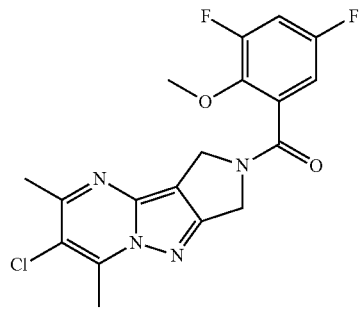 [SMILES: COc1c(F)cc(F)cc1C(=O)N1Cc2nn3c(C)c(Cl)c(C)nc3c2C1]

The title compound was prepared following procedure described in Method A starting from Intermediate A3 and 3,5-difluoro-2-methoxybenzoic acid (JRD Fluorochemicals Ltd.). After purification by crystallization (ACN), the title compound was obtained as a pale beige powder (80 mg, 35%). $^1$H NMR (DMSO-d$_6$) δ 7.54-7.45 (m, 1H), 7.25-7.17 (m, 1H), 4.86 (s, 1H), 4.83 (s, 1H), 4.62 (s, 1H), 4.57 (s, 1H), 3.84 (t, J=1.3 Hz, 3H), 2.84 (s, 1.5H), 2.81 (s, 1.5H), 2.62 (s, 1.5H), 2.56 (s, 1.5H). HPLC (max plot) 98.7%, Rt 3.99 min. UPLC/MS: (MS+) 393.4 ([M+H]+). Melting point: 185-187° C. (ACN).

Example 17

(2-trifluoromethoxy-phenyl)-(5,6,7-trimethyl-1H,3H-2,4,7a,8-tetraaza-cyclopenta[a]inden-2-yl)-methanone

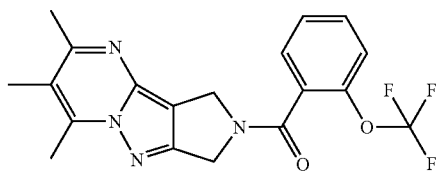 [SMILES: Cc1nc2c3c(nn2c(C)c1C)CN(C(=O)c1ccccc1OC(F)(F)F)C3]

The title compound was prepared following procedure described in Method B starting from Intermediate A1 and 2-(trifluoromethoxy)benzoic acid. After purification by flash chromatography (petroleum ether/EA, 50/50 to EA) the title compound was obtained as a colourless oil (30 mg, 37%). $^1$H NMR (CDCl$_3$) δ 7.53-7.46 (m, 2H), 7.43-7.33 (m, 2H), 5.06-5.01 (m, 2H), 4.65-4.58 (m, 2H), 2.79-2.77 (m, 3H), 2.59-2.58 (m, 3H), 2.32 (s, 3H). HPLC (max plot) 94.6%; Rt 4.02 min. UPLC/MS: (MS+) 391.1 ([M+H]+).

Example 18

(6-chloro-5,7-dimethyl-1H,3H-2,4,7a,8-tetraaza-cyclopenta[a]inden-2-yl)-[4-fluoro-2-(2-pyrazol-1-yl-ethoxy)-phenyl]-methanone

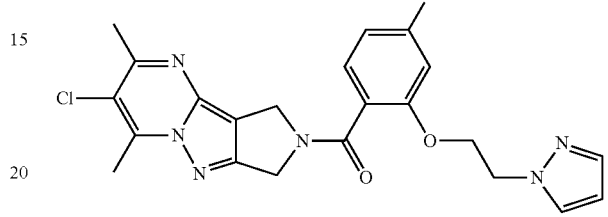

A mixture of Intermediate Z2 (100 mg; 0.28 mmol; 1 eq.), 1-(2-bromoethyl)-1H-pyrazole (97 mg; 0.55 mmol; 2 eq.) and K$_2$CO$_3$ (115 mg; 0.83 mmol; 3 eq.) in DMF (2.5 mL) was stirred at 150° C. for 20 min (MW heating). The reaction mixture was diluted with water and extracted with DCM. The organic layer was washed with brine, dried over MgSO$_4$ and concentrated in vacuo. Purification by mass directed preparative HPLC afforded the title compound (24 mg, 19%) as an off-white solid. $^1$H NMR (CDCl$_3$) δ 7.33-7.19 (m, 3H), 6.78-6.71 (m, 1H), 6.65-6.60 (m, 1H), 5.63-5.61 (m, 1H), 4.96 (s, 0.7H), 4.94 (s, 1.3H), 4.49-4.45 (m, 2H), 4.38-4.34 (m, 2H), 4.23 (s, 1.3H), 4.19 (s, 0.7H), 2.93 (s, 2H), 2.88 (s, 1H), 2.71 (s, 1H), 2.63 (s, 2H). HPLC (max plot) 96.3%; Rt 3.31 min. UPLC/MS: (MS+) 455.4 ([M+H]+).

Example 19

[2-(4-methyl-[1,4]diazepan-1-yl)-phenyl]-(5,6,7-trimethyl-1H,3H-2,4,7a,8-tetraaza-cyclopenta[a]inden-2-yl)-methanone

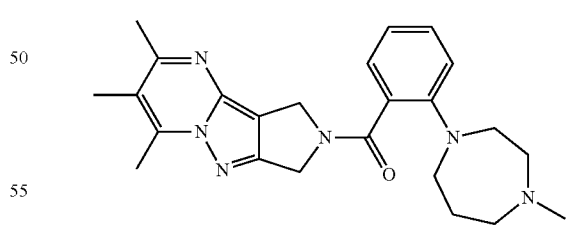

The title compound was prepared following procedure described in Method A starting from Intermediate A1 and 2-(4-methylperhydro-1,4-diazepin-1-yl)benzoic acid hydrochloride hemihydrate. After purification by mass directed preparative HPLC, the title compound was obtained as an off-white powder (80 mg, 46%). $^1$H NMR (CDCl$_3$) δ 7.35-7.27 (m, 2H), 6.99-6.89 (m, 2H), 5.10-4.77 (m, 3H), 4.52-4.28 (m, 1H), 3.57-3.39 (m, 4H), 2.79 (s, 2H), 2.73 (s, 1H), 2.70-2.58 (m, 4H), 2.59 (s, 1H), 2.52 (s, 2H), 2.34-2.26 (m, 6H), 1.97-1.87 (m, 2H). HPLC (max plot) 96.2%; Rt 2.25 min. UPLC/MS: (MS+) 419.2 ([M+H]+).

Example 20

[2-(2-piperidin-1-yl-ethoxy)-phenyl]-(5,6,7-trimethyl-1H,3H-2,4,7a,8-tetraaza-cyclopenta[a]inden-2-yl)-methanone

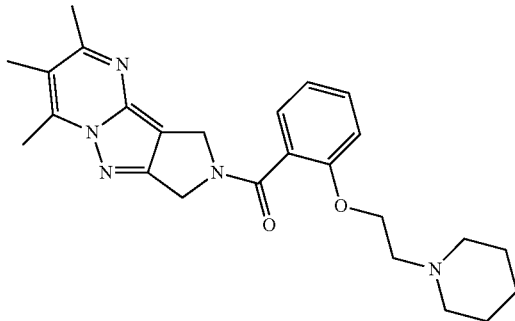

Intermediate Z1 (100 mg; 0.31 mmol; 1 eq.) was added to a suspension of NaH (60% in oil, 17.6 mg; 0.4 mmol; 1.3 eq.) in THF (3 mL) and DMF (2 mL) and the resulting mixture was stirred at room temperature for 10 minutes whereupon 1-(2-chloroethyl)piperidine hydrochloride (86 mg; 0.47 mmol; 1.5 eq.) was added. The reaction mixture was stirred at room temperature for 7 days, during which time several additions of NaH and 1-(2-chloroethyl)piperidine hydrochloride were made. The reaction mixture was partitioned between water and DCM and the two phases separated. The organic layer was washed with brine, dried over magnesium sulphate and concentrated in vacuo. Purification by mass directed preparative HPLC afforded the title compound (66 mg, 49%) as a white solid. $^1$H NMR (CDCl$_3$) δ 7.40-7.31 (m, 2H), 7.05-6.92 (m, 2H), 5.01 (s, 0.7H), 4.98 (s, 1.3H), 4.65 (s, 2H), 4.17-4.14 (m, 2H), 2.78 (s, 2H), 2.75-2.69 (m, 3H), 2.59 (s, 1H), 2.51 (s, 2H), 2.42 (br s, 2H), 2.31 (s, 1H), 2.30 (s, 2H), 1.59-1.26 (m, 8H). HPLC (max plot) 98.4%; Rt 2.33 min. UPLC/MS: (MS+) 434.5 ([M+H]+).

Example 21

(2-butoxy-phenyl)-(5,6,7-trimethyl-1H,3H-2,4,7a,8-tetraaza-cyclopenta[a]inden-2-yl)-methanone

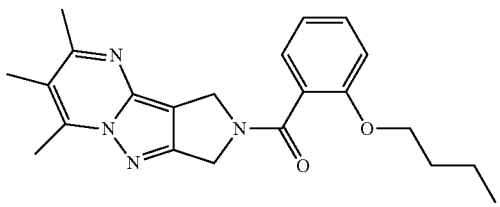 [SMILES: CCCCOc1ccccc1C(=O)N1Cc2nn3c(C)c(C)c(C)nc3c2C1]

The title compound was prepared following procedure described in Method A starting from Intermediate A1 and 2-butoxybenzoic acid. After purification by mass directed preparative HPLC, the title compound was obtained as a yellow solid (77 mg, 49%). $^1$H NMR (CDCl$_3$) δ 7.40-7.31 (m, 2H), 7.04-6.92 (m, 2H), 5.02 (s, 0.7H), 5.00 (s, 1.3H), 4.63 (br s, 2H), 4.04-3.98 (m, 2H), 2.79 (s, 2H), 2.73 (s, 1H), 2.59 (s, 1H), 2.52 (s, 2H), 2.31 (s, 1H), 2.30 (s, 2H), 1.73-1.64 (m, 2H), 1.42-1.30 (m, 2H), 0.86-0.81 (m, 3H). HPLC (max plot) 98.8%; Rt 3.74 min. UPLC/MS: (MS+) 379.1 ([M+H]+).

Example 22

[2-(2-dimethylamino-ethoxy)-phenyl]-(5,6,7-trimethyl-1H,3H-2,4,7a,8-tetraaza-cyclopenta[a]inden-2-yl)-methanone

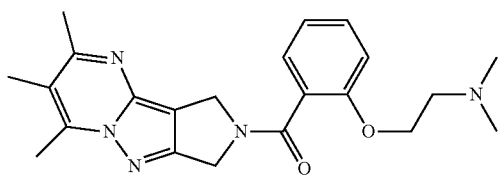

The title compound was prepared following procedure described in Method A starting from Intermediate A1 and 2-[2-(dimethylamino)ethoxy]benzoic acid. After purification by crystallization (DCM/Et$_2$O), the title compound was obtained as an off-white powder (110 mg, 21%). $^1$H NMR (DMSO-d$_6$) δ 7.47-7.39 (m, 1H), 7.32-7.27 (m, 1H), 7.14 (d, J=8.1 Hz, 1H), 7.07-7.00 (m, 1H), 4.77 (s, 1H), 4.75 (s, 1H), 4.56 (br s, 1H), 4.52 (br s, 1H), 4.12 (t, J=5.5 Hz, 2H), 2.72 (s, 1.5H), 2.68 (s, 1.5H), 2.55-2.50 (m, 3.5H), 2.45 (s, 1.5H), 2.26 (s, 1.5H), 2.25 (s, 1.5H), 2.05 (s, 3H), 2.04 (s, 3H). HPLC (max plot) 99.1%, Rt 2.22 min. UPLC/MS: (MS+) 394.2 ([M+H]+). Melting point: 148-150° C. (DCM/Et$_2$O).

Example 23 acetic acid 2-(5,6,7-trimethyl-1H,3H-2,4,7a,8-tetraaza-cyclopenta[a]indene-2-carbonyl)-phenyl ester

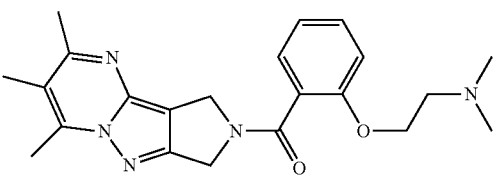

The title compound was prepared following procedure described in Method B starting from Intermediate A1 and acetylsalicylic acid. After purification by flash chromatography (petroleum ether/EA, 50/50 to EA) the title compound was obtained as a white solid (200 mg, 66%). $^1$H NMR (DMSO) δ 7.66-7.49 (m, 2H), 7.41-7.37 (m, 1H), 7.28-7.25 (m, 1H), 4.85-4.78 (m, 2H), 4.58-4.54 (m, 2H), 2.71 (s, 1.5H), 2.68 (s, 1.5H), 2.52 (s, 1.5H), 2.45 (s, 1.5H), 2.27 (s, 1.5H), 2.25 (s, 1.5H), 2.17 (s, 3H). HPLC (max plot) 89.1%; Rt 3.27 min. UPLC/MS: (MS+) 365.15 ([M+H]$^+$).

Example 24

[2-(2-pyrazol-1-yl-ethoxy)-phenyl]-(5,6,7-trimethyl-1H,3H-2,4,7a,8-tetraaza-cyclopenta[a]inden-2-yl)-methanone

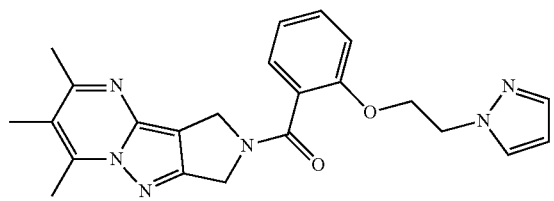 [SMILES: Cc1nc2c3c(nn2c(C)c1C)CN(C(=O)c1ccccc1OCCn1cccn1)C3]

A mixture of Intermediate Z1 (100 mg; 0.31 mmol; 1 eq.), 1-(2-bromoethyl)-1H-pyrazole (81 mg; 0.47 mmol; 1.5 eq.) and K$_2$CO$_3$ (129 mg; 0.93 mmol; 3 eq.) in DMF (2.5 mL) was stirred at 140° C. for 40 minutes (MW heating). 1-(2-bromoethyl)-1H-pyrazole (54.3 mg; 0.31 mmol; 1 eq.) was added and the reaction mixture was stirred at 140° C. for a further 20 minutes (MW heating). The reaction mixture was partitioned between DCM and water and the two phases separated. The organic layer was washed with brine, dried over MgSO4 and concentrated in vacuo. Purification by mass directed preparative HPLC afforded the title compound (46 mg, 36%) as a white solid. $^1$H NMR (CDCl$_3$) δ 7.38-7.27 (m, 3.3H), 7.20-7.19 (m, 0.7H), 7.06-6.99 (m, 1H), 6.90-6.87 (m, 1H), 5.63-5.62 (m, 0.7H), 5.61-5.59 (m, 0.3H), 5.00 (s, 0.7H), 4.97 (s, 1.3H), 4.48-4.45 (m, 2H), 4.37-4.34 (m, 2H), 4.26 (s, 1.3H), 4.22 (s, 0.7H), 2.80 (s, 2H), 2.74 (s, 1H), 2.61 (s, 1H), 2.52 (s, 2H), 2.33 (s, 1H), 2.32 (s, 2H). HPLC (max plot) 90.6%; Rt 2.69 min. UPLC/MS: (MS+) 417.4 ([M+H]$^+$).

Example 25

(2-methylsulfanyl-phenyl)-(5,6,7-trimethyl-1H,3H-2,4,7a,8-tetraaza-cyclopenta[a]inden-2-yl)-methanone

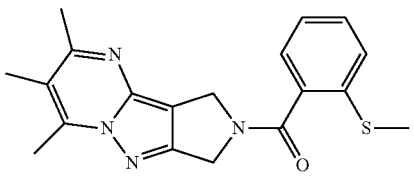

The title compound was prepared following procedure described in Method B starting from Intermediate A1 and 2-(methylthio)benzoic acid. After purification by flash chromatography (petroleum ether/EA, 50/50 to EA) the title compound was obtained as a white solid (31 mg, 42%). $^1$H NMR (CDCl$_3$) δ 7.38-7.20 (m, 4H), 5.04-5.02 (m, 2H), 4.59-4.56 (m, 2H), 2.76 (s, 2H), 2.70 (s, 1H), 2.57 (s, 1H), 2.52-2.45 (m, 5H). HPLC (max plot) 94.0%; Rt 3.56 min. UPLC/MS: (MS+) 353.14 ([M+H]$^+$).

Example 26

(2-isopropoxy-phenyl)-(5,6,7-trimethyl-1H,3H-2,4,7a,8-tetraaza-cyclopenta[a]inden-2-yl)-methanone

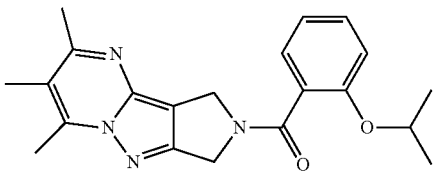 [SMILES: Cc1nc2c3c(nn2c(C)c1C)CN(C(=O)c1ccccc1OC(C)C)C3]

A mixture of Intermediate Z1 (50 mg; 0.15 mmol; 1 eq.), 2-iodopropane (77 mg; 0.45 mmol; 3 eq.) and K$_2$CO$_3$ (62 mg; 0.45 mmol; 3 eq.) in DMF (2.5 mL) was stirred at 140° C. for 20 minutes (MW heating). The reaction mixture was partitioned between DCM and water and the two phases separated. The organic layer was washed with brine, dried over MgSO$_4$ and concentrated in vacuo. Purification by mass directed preparative HPLC afforded the title compound (3.7 mg, 7%) as a brown solid. HPLC (max plot) 99.0%; Rt 3.89 min. UPLC/MS: (MS+) 365.1 ([M+H]$^+$).

Example 27

(2-ethoxy-phenyl)-(6-ethyl-5,7-dimethyl-1H,3H-2,4,7a,8-tetraaza-cyclopenta[a]inden-2-yl)-methanone

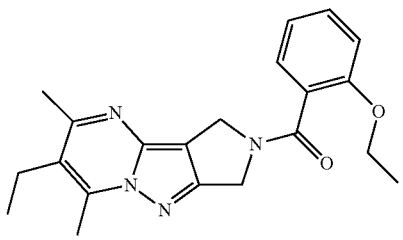 [SMILES: CCOc1ccccc1C(=O)N1Cc2nn3c(C)c(CC)c(C)nc3c2C1]

T3P (50% in DMF) (0.18 mL; 0.62 mmol; 1.3 eq.) was added to a solution of Intermediate A2 (100 mg; 0.46 mmol; 1 eq.), 2-ethoxy-benzoic acid (85 mg; 0.51 mmol; 1.1 eq.) and DIEA (243 µL; 1.43 mmol; 3.1 eq.) in DCE (10 mL) and the resulting mixture was stirred at room temperature for 16 hours. The solution was diluted with DCM and washed successively with sat. aq. NH$_4$Cl, sat. aq. NaHCO$_3$ and brine, dried over magnesium sulfate and concentrated in vacuo. Purification by column chromatography (EA) afforded the title compound (105 mg, 63%) as a white foam. $^1$H NMR (DMSO-d$_6$) δ 7.47-7.39 (m, 1H), 7.32-7.26 (m, 1H), 7.13 (d, J=8.3 Hz, 1H), 7.03 (t, J=7.4 Hz, 1H), 4.82-4.77 (m, 2H), 4.52 (br s, 1H), 4.47 (br s, 1H), 4.17-4.07 (m, 2H), 2.76-2.65 (m, 5H), 2.57 (s, 1.5H), 2.51 (s, 1.5H), 1.26-1.19 (m, 3H), 1.16-1.08 (m, 3H). HPLC (max plot) 98.6%; Rt 3.59 min. UPLC/MS: (MS+) 365.4 ([M+H]+).

Example 28

(6-chloro-5,7-dimethyl-1H,3H-2,4,7a,8-tetraaza-cyclopenta[a]inden-2-yl)-(2-ethoxy-3,5-difluoro-phenyl)-methanone

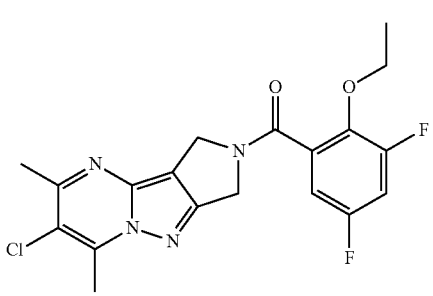 [SMILES: CCOc1c(F)cc(F)cc1C(=O)N1Cc2nn3c(C)c(Cl)c(C)nc3c2C1]

The title compound was prepared following procedure described in Method A starting from Intermediate A3 and Intermediate B2. After purification by crystallization (ACN/iPr$_2$O), the title compound was obtained as a pale beige powder (60 mg, 25%). $^1$H NMR (DMSO-d$_6$) δ 7.54-7.44 (m, 1H), 7.23-7.16 (m, 1H), 4.86 (s, 1H), 4.83 (s, 1H), 4.62 (s, 1H), 4.58 (s, 1H), 4.07 (q, J=7.0 Hz, 2H), 2.84 (s, 1.5H), 2.81 (s, 1.5H), 2.62 (s, 1.5H), 2.56 (s, 1.5H), 1.18 (t, J=7.0 Hz, 3H). HPLC (max plot) 99.9%, Rt 4.32 min. UPLC/MS: (MS+) 407.4 ([M+H]+), (MS−) 405.4 ([M−H]−). Melting point: 153-155° C. (ACN/iPr$_2$O).

Example 29

(2-benzyloxy-phenyl)-(5,6,7-trimethyl-1H,3H-2,4,7a,8-tetraaza-cyclopenta[a]inden-2-yl)-methanone

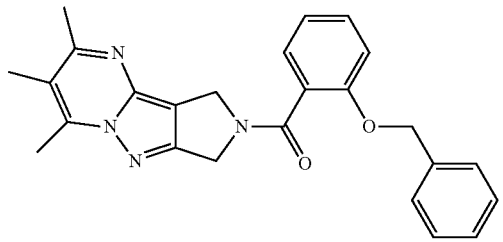 [SMILES: Cc1nc2c3c(nn2c(C)c1C)CN(C(=O)c1ccccc1OCc1ccccc1)C3]

The title compound was prepared following procedure described in Method B starting from Intermediate A1 and 2-benzyloxybenzoic acid. After purification by mass directed preparative HPLC the title compound was obtained as an off-white powder (76 mg, 44%). $^1$H NMR (CDCl$_3$) δ 7.39-7.32 (m, 4H), 7.29-7.21 (m, 3H), 7.07-6.99 (m, 2H), 5.15 (s, 0.7H), 5.14 (s, 1.3H), 5.04 (s, 0.7H), 5.01 (s, 1.3H), 4.64 (s, 1.3H), 4.63 (s, 0.7H), 2.77 (s, 2H), 2.71 (s, 1H), 2.58 (s, 1H), 2.50 (s, 2H), 2.30 (s, 1H), 2.29 (s, 2H). HPLC (max plot) 99.8%; Rt 3.69 min. UPLC/MS: (MS+) 419.2 ([M+H]+).

Example 30

(6-Chloro-5,7-dimethyl-1H,3H-2,4,7a,8-tetraaza-cyclopenta[a]inden-2-yl)-(2-isobutoxy-phenyl)-methanone

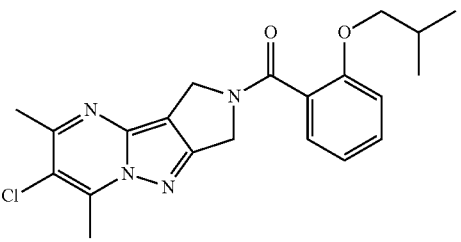 [SMILES: Cc1nc2c3c(nn2c(C)c1Cl)CN(C(=O)c1ccccc1OCC(C)C)C3]

The title compound was prepared following procedure described in Method A starting from Intermediate A3 and 2-(2-methylpropoxy)benzoic acid (Enamine Ltd.). After purification by crystallization (ACN), the title compound was obtained as a white powder (192 mg, 83%). $^1$H NMR (DMSO-d$_6$) δ 7.47-7.36 (m, 1H), 7.32-7.27 (m, 1H), 7.12 (d, J=8.4 Hz, 1H), 7.07-7.00 (m, 1H), 4.83 (s, 1H), 4.80 (s, 1H), 4.53 (s, 1H), 4.48 (s, 1H), 3.82 (d, J=6.2 Hz, 2H), 2.83 (s, 1.5H), 2.79 (s, 1.5H), 2.61 (s, 1.5H), 2.54 (s, 1.5H), 1.98-1.83 (m, 1H), 0.83 (d, J=6.7 Hz, 3H), 0.82 (d, J=6.7 Hz, 3H). HPLC (max plot) 99.7%, Rt 4.56 min. UPLC/MS: (MS+) 399.4 ([M+H]+). Melting point: 184-187° C. (ACN).

Example 31

(5,6-Dimethyl-1H,3H-2,4,7a,8-tetraaza-cyclopenta[a]inden-2-yl)-(2-ethoxy-phenyl)-methanone

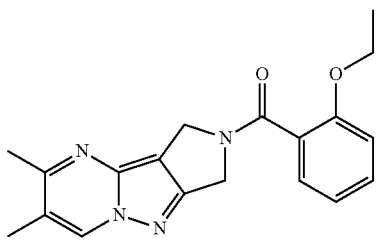 [SMILES: CCOc1ccccc1C(=O)N1Cc2nn3cc(C)c(C)nc3c2C1]

The title compound was prepared following procedure described in Method A starting from Intermediate A7 and 2-ethoxybenzoic acid. After purification by mass directed preparative HPLC the title compound was obtained as a white solid (28 mg, 36%). $^1$H NMR (CDCl$_3$) δ 8.40 (s, 0.5H), 8.35 (s, 0.5H), 7.46-7.40 (m, 1H), 7.31-7.28 (m, 1H), 7.15-7.12 (m, 1H), 7.05-7.00 (m, 1H), 4.83-4.82 (m, 2H), 4.55-4.51 (m, 2H), 4.16-4.08 (m, 2H), 2.70 (s, 1.5H), 2.67 (s, 1.5H), 2.33 (s, 1.5H), 2.32 (s, 1.5H), 1.26-1.20 (m, 3H). HPLC (max plot) 96.2%; Rt 3.02 min. UPLC/MS: (MS+) 337.4 ([M+H]+).

Example 32

[2-(2-dimethylamino-ethoxy)-phenyl]-(5,6-dimethyl-1H,3H-2,4,7a,8-tetraaza-cyclopenta[a]inden-2-yl)-methanone

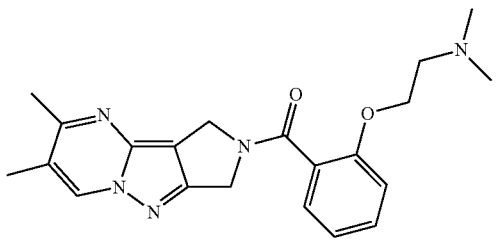

The title compound was prepared following procedure described in Method A starting from Intermediate A7 and 2-[2-(dimethylamino)ethoxy]benzoic acid. After purification by mass directed preparative HPLC the title compound was obtained as a yellow solid (80 mg, 61%). $^1$H NMR (DMSO-$d_6$) δ 8.40 (s, 0.5H), 8.35 (s, 0.5H), 7.46-7.40 (m, 1H), 7.32-7.28 (m, 1H), 7.17-7.14 (m, 1H), 7.06-7.01 (m, 1H), 4.80-4.39 (m, 2H), 4.59 (br s, 2H), 4.13 (t, J=5.5 Hz, 2H), 2.71 (s, 1.5H), 2.61 (s, 1.5H), 2.58-2.52 (m, 2H), 2.34 (s, 1.5H), 2.32 (s, 1.5H), 2.07 (s, 3H), 2.05 (s, 3H). HPLC (max plot) 94.8%; Rt 2.02 min. UPLC/MS: (MS+) 380.2 ([M+H]+).

Example 33

(5,6-dimethyl-1H,3H-2,4,7a,8-tetraaza-cyclopenta[a]inden-2-yl)-[2-(4-methyl-[1,4]diazepan-1-yl)-phenyl]-methanone

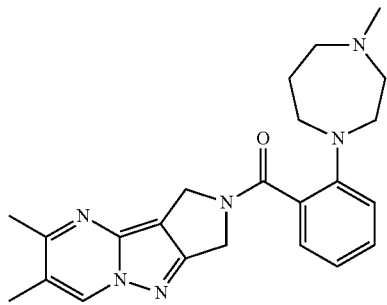 [SMILES: Cc1cn2nc3c(c2nc1C)CN(C(=O)c1ccccc1N1CCCN(C)CC1)C3]

The title compound was prepared following procedure described in Method A starting from Intermediate A7 and 2-(4-methylperhydro-1,4-diazepin-1-yl)benzoic acid hydrochloride. After purification mass directed preparative HPLC, the title compound was obtained as a pale brown solid (42 mg, 45%). $^1$H NMR (DMSO-$d_6$) δ 8.40 (s, 0.5H), 8.34 (s, 0.5H), 7.33-7.29 (m, 1H), 7.24-7.19 (m, 1H), 7.04-7.01 (m, 1H), 6.92-6.87 (m, 1H), 4.90-4.67 (m, 3H), 4.44-4.24 (m, 1H), 3.40-3.21 (m, 6H), 2.71 (s, 1.5H), 2.67 (s, 1.5H), 2.45-2.32 (m, 5H), 2.09 (s, 1.5H), 2.08 (s, 1.5H), 1.81-1.72 (m, 2H). HPLC (max plot) 96.8%; Rt 2.11 min. UPLC/MS: (MS+) 405.5 ([M+H]+).

Example 34

(5-chloro-2-ethoxy-phenyl)-(5,6,7-trimethyl-1H,3H-2,4,7a,8-tetraaza-cyclopenta[a]inden-2-yl)-methanone

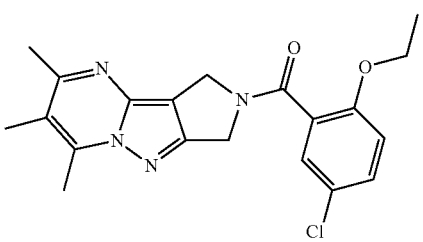 [SMILES: CCOc1ccc(Cl)cc1C(=O)N1Cc2nn3c(C)c(C)c(C)nc3c2C1]

The title compound was prepared following procedure described in Method A starting from Intermediate A1 and 5-chloro-2-ethoxy-benzoic acid (Ukrorgsynthesis Ltd.), and has precipitated out from the reaction mixture. After filtration and slurry in hot ACN, the title compound was obtained as a white powder (40 mg, 29%). $^1$H NMR (DMSO-$d_6$) δ 7.50-7.44 (m, 1H), 7.38-7.35 (m, 1H), 7.17 (d, J=8.9 Hz, 1H), 4.80 (s, 1H), 4.78 (s, 1H), 4.55 (s, 1H), 4.51 (s, 1H), 4.13 (q, J=6.9 Hz, 1H), 4.12 (q, J=6.9 Hz, 1H), 2.72 (s, 1.5H), 2.69 (s, 1.5H), 2.52 (s, 1.5H), 2.46 (s, 1.5H), 2.27 (s, 1.5H), 2.26 (s, 1.5H), 1.23 (t, J=6.9 Hz, 1.5H), 1.22 (t, J=6.9 Hz, 1.5H). HPLC (max plot) 99.5%, Rt 3.66 min. UPLC/MS: (MS+) 385.3 ([M+H]+).

Example 35

(6-chloro-5,7-dimethyl-1H,3H-2,4,7a,8-tetraaza-cyclopenta[a]inden-2-yl)-[2-(tetrahydro-pyran-4-yloxy)-phenyl]-methanone

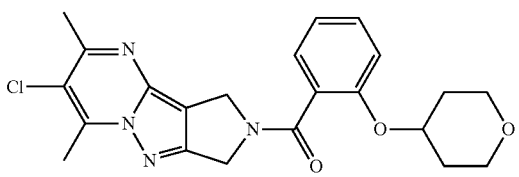 [SMILES: Cc1nc2c3c(nn2c(C)c1Cl)CN(C(=O)c1ccccc1OC1CCOCC1)C3]

The title compound was prepared following procedure described in Method A starting from Intermediate A3 and 2-(tetrahydropyran-4-yloxy)benzoic acid and has precipitated out from the reaction mixture. After filtration and drying, the title compound was obtained as a beige solid (138 mg, 84%). $^1$H NMR (CDCl$_3$) δ 7.40-7.33 (m, 2H), 7.09-6.96 (m, 2H), 5.02-5.01 (m, 2H), 4.67 (s, 2H), 4.58-4.50 (m, 1H), 3.89-3.81 (m, 2H), 3.56-3.49 (m, 2H), 2.91 (s, 2H), 2.85 (s, 1H), 2.69 (s, 1H), 2.62 (s, 2H), 2.00-1.93 (m, 2H), 1.80-1.69 (m, 2H). HPLC (max plot) 98.8%; Rt 3.42 min. UPLC/MS: (MS+) 427.4 ([M+H]$^+$).

Example 36

[2-(4-methyl-piperazin-1-yl)-phenyl]-(5,6,7-trimethyl-1H,3H-2,4,7a,8-tetraaza-cyclopenta[a]inden-2-yl)-methanone

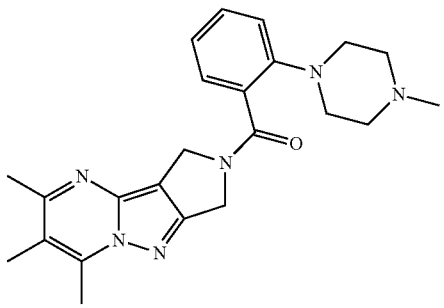

The title compound was prepared following procedure described in Method A starting from Intermediate A1 and 2-(4-methylpiperazin-1-yl)benzoic acid. After purification by flash chromatography (silica, DCM/acetone), followed by crystallization (EtOH), the title compound was obtained as a white powder (10 mg, 6%). $^1$H NMR (DMSO-d$_6$) δ 7.45-7.37 (m, 1H), 7.29-7.22 (m, 1H), 7.13-7.05 (m, 2H), 4.97-4.65 (br m, 3H), 4.27 (br s, 1H), 3.16 (br s, 2H), 2.89 (br s, 2H), 2.73 (s, 1.5H), 2.69 (s, 1.5H), 2.53 (s, 1.5H), 2.46 (s, 1.5H), 2.31-2.20 (m, 7H), 2.03 (s, 1.5H), 2.02 (s, 1.5H). HPLC (max plot) 96.7%; Rt 2.25 min. UPLC/MS: (MS+) 405.2 ([M+H]$^+$).

Example 37

(2-ethylamino-phenyl)-(5,6,7-trimethyl-1H,3H-2,4,7a,8-tetraaza-cyclopenta[a]inden-2-yl)-methanone

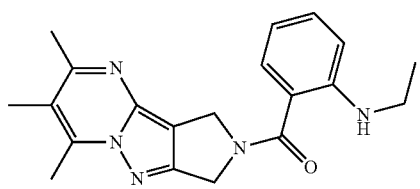 [SMILES: CCNc1ccccc1C(=O)N1Cc2nn3c(C)c(C)c(C)nc3c2C1]

The title compound was prepared following procedure described in Method B starting from Intermediate A1 and 2-ethylaminobenzoic acid. After purification by mass directed preparative HPLC, the title compound was obtained as a white solid (22 mg, 25%). $^1$H NMR (CDCl$_3$) δ 7.33-7.26 (m, 2H), 6.78-6.67 (m, 2H), 5.05-4.85 (m, 4H), 3.16 (q, J=7.0 Hz, 2H), 2.78 (br s, 3H), 2.55 (br s, 3H), 2.32 (s, 3H), 1.26 (t, J=7.0 Hz, 3H). HPLC (max plot) 91.6%; Rt 3.02 min. UPLC/MS: (MS+) 350.2 ([M+H]$^+$).

Example 38

[2-(2-dimethylamino-ethoxy)-phenyl]-(6,7-dimethyl-1H,3H-2,4,7a,8-tetraaza-cyclopenta[a]inden-2-yl)-methanone

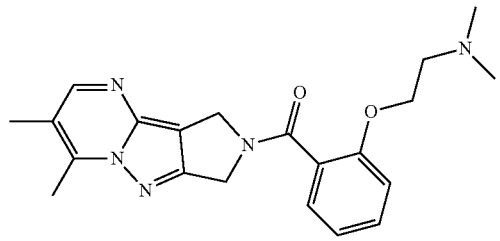

The title compound was prepared following procedure described in Method A starting from Intermediate A6 and 2-[2-(dimethylamino)ethoxy]benzoic acid. After purification by mass directed preparative HPLC, the title compound was obtained as a yellow solid (80 mg, 70%). $^1$H NMR (DMSO-d$_6$) δ 8.86 (s, 0.5H), 8.85 (s, 0.5H), 7.46-7.39 (m, 1H), 7.30-7.27 (m, 1H), 7.15-7.12 (m, 1H), 7.05-7.00 (m, 1H), 4.74 (s, 2H), 4.54-4.50 (m, 2H), 4.13 (t, J=4.5 Hz, 2H), 2.56-2.52 (m, 2H), 2.48 (s, 1.5H), 2.43 (s, 1.5H), 2.24 (br s, 3H), 2.06 (s, 3H), 2.05 (s, 3H). HPLC (max plot) 95.6%; Rt 1.95 min. UPLC/MS: (MS+) 380.2 ([M+H]$^+$).

Example 39

(2-pyrazol-1-yl-phenyl)-(5,6,7-trimethyl-1H,3H-2,4,7a,8-tetraaza-cyclopenta[a]inden-2-yl)-methanone

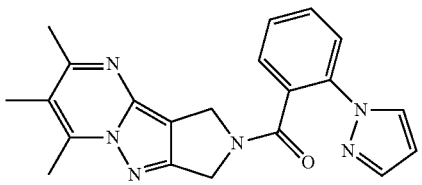 [SMILES: Cc1nc2c3c(nn2c(C)c1C)CN(C(=O)c1ccccc1-n1cccn1)C3]

The title compound was prepared following procedure described in Method A starting from Intermediate A1 and 2-(1H-pyrazol-1-yl)benzoic acid. After purification by mass directed preparative HPLC, the title compound was obtained as an off-white solid (91 mg, 49%). $^1$H NMR (CDCl$_3$) δ 7.91-7.89 (m, 1H), 7.68-7.40 (m, 5H), 6.38-6.36 (m, 1H), 4.89 (s, 2H), 4.37 (s, 1.3H), 4.31 (s, 0.7H), 2.74 (s, 2H), 2.69

(s, 1H), 2.56 (s, 1H), 2.48 (s, 2H), 2.28 (s, 1H), 2.27 (s, 2H). HPLC (max plot) 99.4%; Rt 2.81 min. UPLC/MS: (MS+) 373.4 ([M+H]+).

Example 40

[2-(2-cyclohexyl-ethoxy)-phenyl]-(5,6,7-trimethyl-1H,3H-2,4,7a,8-tetraaza-cyclopenta[a]inden-2-yl)-methanone

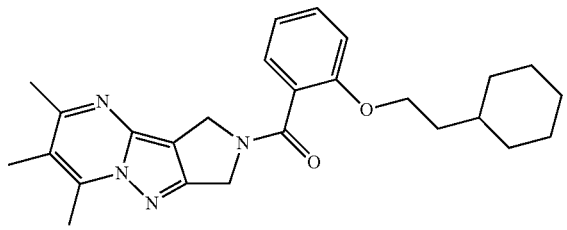 [SMILES: Cc1nc2c3c(nn2c(C)c1C)CN(C(=O)c1ccccc1OCCC1CCCCC1)C3]

A mixture of Intermediate Z1 (100 mg; 0.31 mmol; 1 eq.), (2-bromoethyl)cyclohexane, (74 μL; 0.47 mmol; 1.5 eq.) and K₂CO₃ (129 mg; 0.93 mmol; 3 eq.) in DMF (2.5 mL) was stirred at 140° C. for 20 minutes (MW heating). The reaction mixture was partitioned between DCM and water and the two phases separated. The organic layer was washed with brine, dried over MgSO₄ and concentrated in vacuo. Purification by mass directed preparative HPLC afforded the title compound (93 mg, 69%) as a white solid. ¹H NMR (CDCl₃) δ 7.39-7.31 (m, 2H), 7.04-6.91 (m, 2H), 5.02 (s, 0.7H), 5.00 (s, 1.3H), 4.62 (s, 2H), 4.06-4.01 (m, 2H), 2.78 (s, 2H), 2.72 (s, 1H), 2.59 (s, 1H), 2.51 (s, 2H), 2.31 (s, 1H), 2.30 (s, 2H), 1.65-1.28 (m, 8H), 1.00-0.79 (m, 5H). HPLC (max plot) 99.6%; Rt 4.46 min. UPLC/MS: (MS+) 433.4 ([M+H]+).

Example 41

(6,7-dimethyl-1H,3H-2,4,7a,8-tetraaza-cyclopenta[a]inden-2-yl)-[2-(4-methyl-[1,4]diazepan-1-yl)-phenyl]-methanone

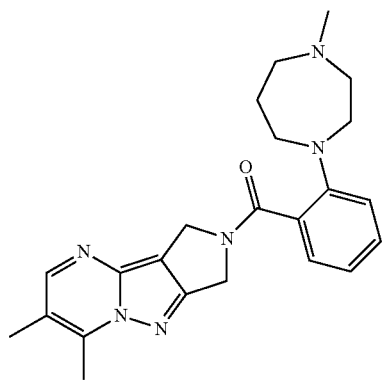 [SMILES: Cc1cnc2c3c(nn2c1C)CN(C(=O)c1ccccc1N1CCCN(C)CC1)C3]

The title compound was prepared following procedure described in Method A starting from Intermediate A6 and 2-(4-methylperhydro-1,4-diazepin-1-yl)benzoic acid hydrochloride hemihydrate. After purification by mass directed preparative HPLC, the title compound was obtained as a pale brown solid (19 mg, 31%). ¹H NMR (DMSO-d₆) δ 8.88 (m, 0.5H), 8.85 (m, 0.5H), 7.34-7.29 (m, 1H), 7.23-7.18 (m, 1H), 7.04-7.01 (m, 1H), 6.92-6.87 (m, 1H), 4.79-4.64 (m, 3H), 4.33-4.21 (m, 1H), 3.29-3.23 (m, 6H), 2.50-2.43 (m, 3H), 2.41-2.30 (m, 2H), 2.25-2.24 (m, 3H), 2.09 (s, 1.5H), 2.08 (s, 1.5H), 1.80-1.73 (m, 2H). HPLC (max plot) 98.2%; Rt 2.06 min. UPLC/MS: (MS+) 405.5 ([M+H]+).

Example 42

(6-chloro-1H,3H-2,4,7a,8-tetraaza-cyclopenta[a]inden-2-yl)-(2-isopropoxy-phenyl)-methanone

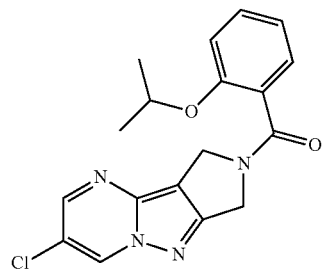

The title compound was prepared following procedure described in Method A starting from Intermediate A4 and 2-isopropoxybenzoic acid (Ukrorgsynthesis Ltd.). After purification by crystallization (ACN), the title compound was obtained as a pale yellow powder (49 mg, 27%). ¹H NMR (DMSO-d₆) δ 9.59 (d, J=2.3 Hz, 0.5H), 9.56 (d, J=2.3 Hz, 0.5H), 8.62 (d, J=2.3 Hz, 0.5H), 8.57 (d, J=2.3 Hz, 0.5H), 7.46-7.38 (m, 1H), 7.32-7.26 (m, 1H), 7.15 (d, J=8.3 Hz, 1H), 7.06-6.98 (m, 1H), 4.87-4.81 (m, 2H), 4.74-4.61 (m, 1H), 4.56 (s, 1H), 4.53 (s, 1H), 1.21 (d, J=6.0 Hz, 3H), 1.20 (d, J=6.0 Hz, 3H). HPLC (max plot) 100%, Rt 3.65 min. UPLC/MS: (MS+) 357.0 ([M+H]+). Melting point: 160° C.-161° C. (ACN).

Example 43

(2-trifluoromethyl-phenyl)-(5,6,7-trimethyl-1H,3H-2,4,7a,8-tetraaza-cyclopenta[a]inden-2-yl)-methanone

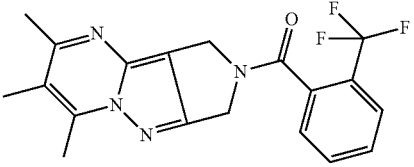 [SMILES: Cc1nc2c3c(nn2c(C)c1C)CN(C(=O)c1ccccc1C(F)(F)F)C3]

T3P (50% in DMF) (0.18 mL; 0.62 mmol; 3 eq.) was added to a solution of Intermediate A1 (50 mg; 0.21 mmol; 1 eq.), 2-trifluoromethyl-benzoic acid (43 mg; 0.23 mmol; 1.1 eq.) and DIEA (109 μL; 0.64 mmol; 3.1 eq.) in DCE and the resulting mixture was stirred at room temperature for 16 hours. The solution was diluted with DCM and washed successively with sat. aq. NH₄Cl, sat. aq. NaHCO₃ and brine, dried over magnesium sulfate and concentrated in vacuo. Purification by column chromatography (EA) afforded the title compound (35 mg, 45%) as a white foam. ¹H NMR (DMSO-d₆) δ 7.92-7.77 (m, 2H), 7.76-7.66 (m, 2H), 4.86-4.81 (m, 2H), 4.50-4.40 (m, 2H), 2.73 (s, 1.6H), 2.68 (s, 1.4H), 2.53 (s, 1.4H), 2.46 (s, 1.6H), 2.27 (s, 1.4H), 2.26 (s,1.6H). HPLC (max plot) 97.3%, Rt 3.45 min. UPLC/MS: (MS+) 375.4 ([M+H]$^+$).

Example 44

2-(5,6,7-trimethyl-1H,3H-2,4,7a,8-tetraaza-cyclopenta[a]indene-2-carbonyl)-benzoic acid methyl ester

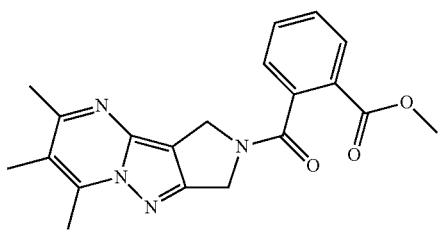

The title compound was prepared following procedure described in Method B starting from Intermediate A1 and monomethyl phthalate. After purification by flash chromatography (petroleum ether/EA, 50/50 to EA), the title compound was obtained as an off-white solid (203 mg, 66%). $^1$H NMR (CDCl$_3$) δ 8.04-8.01 (m, 1H), 7.63-7.38 (m, 3H), 5.02-5.00 (m, 2H), 4.45-4.42 (m, 2H), 3.80-3.65 (m, 3H), 2.72-2.65 (s,3H), 2.53-2.44 (s,3H), 2.25-2.24 (s, 3H). HPLC (max plot) 91.8%; Rt 3.20 min. UPLC/MS: (MS+) 365.2 ([M+H]$^+$).

Example 45

(5-bromo-2-ethoxy-phenyl)-(5,6,7-trimethyl-1H,3H-2,4,7a,8-tetraaza-cyclopenta[a]inden-2-yl)-methanone

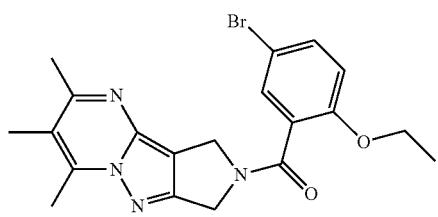 [SMILES: CCOc1ccc(Br)cc1C(=O)N1Cc2nn3c(C)c(C)c(C)nc3c2C1]

The title compound was prepared following procedure described in Method B starting from Intermediate A1 and 5-bromo-2-ethoxy-benzoic acid. After purification by crystallization (ACN), the title compound was obtained as an off-white solid (99 mg, 55%). $^1$H NMR (CDCl$_3$) δ 7.48-7.43 (m, 2H), 6.85-6.81 (m, 1H), 5.01-4.63 (m, 4H), 4.11-4.02 (m, 2H), 2.78-2.73 (m, 3H), 2.58-2.52 (m, 3H), 2.30 (s, 3H), 1.36-1.30 (m, 3H). HPLC (max plot) 98.0%; Rt 3.63 min. UPLC/MS: (MS+) 429.0 ([M+H]$^+$). Melting point: 208-215° C. (ACN).

Example 46

(6-chloro-1H,3H-2,4,7a,8-tetraaza-cyclopenta[a]inden-2-yl)-(2-ethoxy-phenyl)-methanone

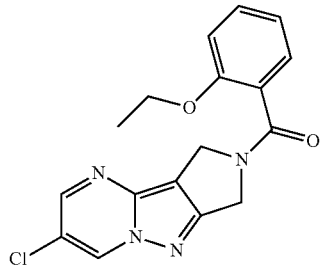

The title compound was prepared following procedure described in Method A starting from Intermediate A4 and 2-ethoxybenzoic acid, and has precipitated out from the reaction mixture. After filtration and washing with water (3×), the title compound was obtained as a white powder (132 mg, 48%). $^1$H NMR (DMSO-d$_6$) δ 9.60 (d, J=2.3 Hz, 0.5H), 9.57 (d, J=2.3 Hz, 0.5H), 8.63 (d, J=2.3 Hz, 0.5H), 8.58 (d, J=2.3 Hz, 0.5H), 7.47-7.40 (m, 1H), 7.33-7.27 (m, 1H), 7.14 (d, J=8.2 Hz, 1H), 7.06-7.00 (m, 1H), 4.85 (s, 1H), 4.84 (s, 1H), 4.57 (s, 1H), 4.54 (s, 1H), 4.13 (q, J=7.0 Hz, 1H), 4.12 (q, J=7.0 Hz, 1H), 1.24 (t, J=7.0 Hz, 1.5H), 1.23 (t, J=7.0 Hz, 1.5H). HPLC (max plot) 99.1%, Rt 3.35 min. UPLC/MS: (MS+) 343.0 ([M+H]$^+$).

Example 47

[2-(2-dimethylamino-ethoxy)-phenyl]-(6-methyl-1H,3H-2,4,7a,8-tetraaza-cyclopenta[a]inden-2-yl)-methanone

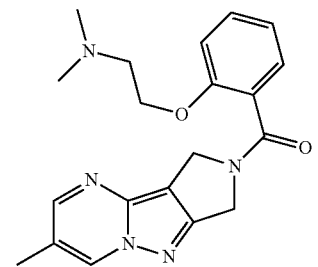 [SMILES: Cc1cnc2c3c(nn2c1)CN(C(=O)c1ccccc1OCCN(C)C)C3]

The title compound was prepared following procedure described in Method A starting from Intermediate A5 and 2-[2-(dimethylamino)ethoxy]benzoic acid. After purification by flash chromatography (silica, DCM/EtOH/aqueous NH$_3$), the title compound was obtained as a beige foam (28 mg, 9%). $^1$H NMR (DMSO-d$_6$) δ 9.01-8.97 (m, 1H), 8.46 (d, J=2.1 Hz, 0.5H), 8.41 (d, J=2.1 Hz, 0.5H), 7.47-7.40 (m, 1H), 7.32-7.28 (m, 1H), 7.16 (d, J=8.3 Hz, 1H), 7.07-7.01 (m, 1H), 4.79 (s, 2H), 4.58 (br s, 2H), 4.14 (t, J=5.2 Hz, 2H), 2.61-2.55 (m, 2H), 2.34-2.29 (m, 3H), 2.09 (s, 3H), 2.07 (s, 3H). HPLC (max plot) 98.5%, Rt 1.87 min. UPLC/MS: (MS+) 366.4 ([M+H]+).

Example 48

(6-bromo-1H,3H-2,4,7a,8-tetraaza-cyclopenta[a]inden-2-yl)-(2-ethoxy-phenyl)-methanone

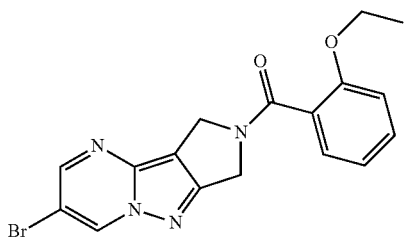 [SMILES: CCOc1ccccc1C(=O)N1Cc2nn3cc(Br)cnc3c2C1]

The title compound was prepared following procedure described in Method A starting from Intermediate A8 and 2-ethoxybenzoic acid, and has precipitated out from the reaction mixture. The reaction mixture was diluted with water and the precipitate was filtered off to give the title compound as a pale beige powder (1.97 g, 94%). $^1$H NMR (DMSO-$d_6$) δ 9.63 (d, J=2.2 Hz, 0.5H), 9.61 (d, J=2.2 Hz, 0.5H), 8.64 (d, J=2.2 Hz, 0.5H), 8.59 (d, J=2.2 Hz, 0.5H), 7.47-7.40 (m, 1H), 7.33-7.27 (m, 1H), 7.14 (d, J=8.2 Hz, 1H), 7.06-7.00 (m, 1H), 4.84 (s, 2H), 4.56 (s, 1H), 4.53 (s, 1H), 4.13 (q, J=7.0 Hz, 1H), 4.13 (q, J=7.0 Hz, 1H), 1.24 (t, J=7.0 Hz, 1.5H), 1.24 (t, J=7.0 Hz, 1.5H). HPLC (max plot) 99.5%, Rt 3.20 min. UPLC/MS: (MS+) 387.3 and 389.3 ([M+H]+).

Example 49

(2-bromo-phenyl)-(5,6,7-trimethyl-1H,3H-2,4,7a,8-tetraaza-cyclopenta[a]inden-2-yl)-methanone

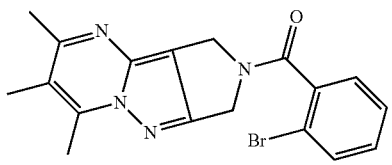 [SMILES: Cc1nc2c3c(nn2c(C)c1C)CN(C(=O)c1ccccc1Br)C3]

The title compound was prepared following procedure described in Method B starting from Intermediate A1 and 2-bromobenzoic acid. After purification by column chromatography (DCM/MeOH), the title compound was obtained as an off-white powder (570 mg, 35%). $^1$H NMR (CDCl$_3$) δ 7.65-7.61 (m, 1H), 7.45-7.36 (m, 2H), 7.33-7.27 (m, 1H), 5.05-5.03 (m, 2H), 4.59-4.56 (m, 2H), 2.78-2.72 (m, 3H), 2.59-2.51 (m, 3H), 2.31-2.30 (m, 3H). HPLC (max plot) 96.0%, Rt 3.09 min. UPLC/MS: (MS+) 385.0 and 387.0 ([M+H]+).

Example 50

(6-chloro-5,7-dimethyl-1H,3H-2,4,7a,8-tetraaza-cyclopenta[a]inden-2-yl)-(2-ethoxy-5-fluoro-phenyl)-methanone

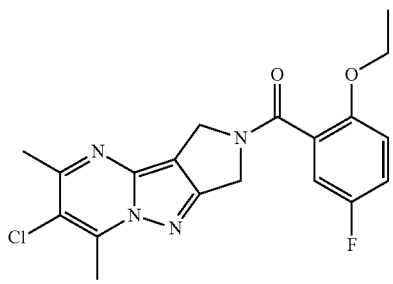 [SMILES: CCOc1ccc(F)cc1C(=O)N1Cc2nn3c(C)c(Cl)c(C)nc3c2C1]

The title compound was prepared following procedure described in Method A starting from Intermediate A3 and 2-ethoxy-5-fluorobenzoic acid (Ukrorgsyntez). After purification by slurry in hot ACN, the title compound was obtained as a white powder (140 mg, 69%). $^1$H NMR (300 MHz, DMSO-$d_6$) δ 7.33-7.23 (m, 1H), 7.23-7.11 (m, 2H), 4.83 (s, 1H), 4.80 (s, 1H), 4.58 (s, 1H), 4.53 (s, 1H), 4.10 (q, J=7.0 Hz, 1H), 4.09 (q, J=7.0 Hz, 1H), 2.83 (s, 1.5H), 2.80 (s, 1.5H), 2.61 (s, 1.5H), 2.55 (s, 1.5H), 1.22 (t, J=7.0 Hz, 1.5H), 1.21 (t, J=7.0 Hz, 1.5H). HPLC (max plot) 99.9%, Rt 4.03 min. UPLC/MS: (MS+) 389.4 ([M+H]+).

Example 51

(6-chloro-5,7-dimethyl-1H,3H-2,4,7a,8-tetraaza-cyclopenta[a]inden-2-yl)-[2-(2-methanesulfonyl-ethoxy)-phenyl]-methanone

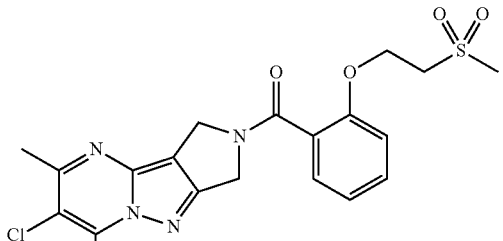

3-Chloroperbenzoic acid (77%, 276 mg, 1.12 mmol) was added portionwise into a solution of (6-chloro-5,7-dimethyl-1H,3H-2,4,7a,8-tetraaza-cyclopenta[a]inden-2-yl)-[2-(2-methylsulfanyl-ethoxy)-phenyl]-methanone (Example 15, 234 mg, 0.56 mmol) in DCM (4 mL) cooled at 0° C. After 5 minutes, the cooling bath was removed and the resulting mixture was stirred at RT for 30 minutes. The reaction mixture was diluted with DCM (50 mL) and washed with a aqueous solution of NaHSO$_3$ (2×20 mL), a 0.1N aqueous solution of NaOH (20 ml) and water (20 ml). The organic layer was dried (Na$_2$SO$_4$) and concentrated under vacuum.

After purification by slurry in hot ACN (3 mL), the title compound was obtained as a white powder (187 mg, 74%). $^1$H NMR (DMSO-d$_6$) δ 7.51-7.43 (m, 1H), 7.36-7.31 (m, 1H), 7.21 (d, J=8.3 Hz, 1H), 7.10 (dd, J=7.4, 7.3 Hz, 1H), 4.78 (s, 1H), 4.76 (s, 1H), 4.54 (s, 1H), 4.49 (s, 1H), 4.40 (t, J=5.2 Hz, 2H), 3.62-3.54 (m, 2H), 2.92 (s, 3H), 2.84 (s, 1.5H), 2.80 (s, 1.5H), 2.61 (s, 1.5H), 2.55 (s, 1.5H). HPLC (max plot) 99.2%, Rt 3.21 min. UPLC/MS: (MS+) 449.3 ([M+H]$^+$), (MS−) 447.4 ([M−H]−).

Example 52

(6-chloro-5,7-dimethyl-1H,3H-2,4,7a,8-tetraaza-cyclopenta[a]inden-2-yl)-[2-((R)-1-pyrrolidin-2-ylmethoxy)-phenyl]-methanone

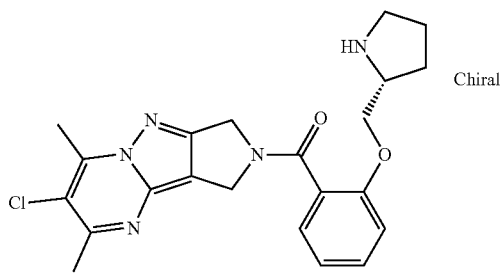 [SMILES: Cc1nc2c3c(nn2c(C)c1Cl)CN(C(=O)c1ccccc1OC[C@H]1CCCN1)C3]

Step 1: (R)-2-[2-(6-chloro-5,7-dimethyl-1H,3H-2,4,7a,8-tetraaza-cyclopenta[a]indene-2-carbonyl)-phenoxymethyl]-pyrrolidine-1-carboxylic acid tert-butyl ester The title compound was prepared following procedure described in Method G starting from Intermediate Z4 and N-Boc-D-prolinol. After purification by mass directed preparative HPLC, the title compound was obtained as white foam (107 mg, 69%). HPLC (max plot) 95.8%, Rt 4.61 min. UPLC/MS: (MS+) 526.3 ([M+H]$^+$).

Step 2: (6-chloro-5,7-dimethyl-1H,3H-2,4,7a,8-tetraaza-cyclopenta[a]inden-2-yl)-[2-((R)-1-pyrrolidin-2-ylmethoxy)-phenyl]-methanone A solution of (R)-2-[2-(6-chloro-5,7-dimethyl-1H,3H-2,4,7a,8-tetraaza-cyclopenta[a]indene-2-carbonyl)-phenoxymethyl]-pyrrolidine-1-carboxylic acid tert-butyl ester (90 mg; 0.17 mmol; 1 eq.) and 2M HCl (3 mL; 6 mmol; 35 eq.) in DCM (5 mL) was stirred at room temperature for 18 hours then concentrated to dryness. 1M NaOH was added and extracted several times with DCM. The combined organics were dried over magnesium sulfate and concentrated in vacuo. Crystallization from MTBE afforded the title compound (30 mg, 41%) as a yellow solid. $^1$H NMR (DMSO) δ 7.46-7.39 (m, 1H), 7.31-7.27 (m, 1H), 7.13 (d, J=8.4 Hz, 1H), 7.05-7.00 (m, 1H), 4.82-4.54 (m, 2H), 3.91-3.89 (m, 2H), 3.35-3.25 (m, 1H), 2.84 (s, 1.5H), 2.80 (s, 1.5H), 2.61-2.58 (m, 5H), 1.73-1.30 (m, 4H). HPLC (max plot) 97.1%, Rt 2.65 min. UPLC/MS: (MS+) 426.2 ([M+H]$^+$).

Example 53

(6-chloro-5,7-dimethyl-1H,3H-2,4,7a,8-tetraaza-cyclopenta[a]inden-2-yl)-[2-(1-methanesulfonyl-piperidin-4-yloxy)-phenyl]-methanone

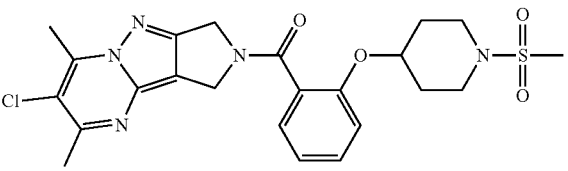 [SMILES: Cc1nc2c3c(nn2c(C)c1Cl)CN(C(=O)c1ccccc1OC1CCN(S(C)(=O)=O)CC1)C3]

To a solution of Example 3 (100 mg; 0.23 mmol; 1 eq.) and TEA (82 μL; 0.59 mmol; 2.5 eq.) in DCM (3 mL) at 0° C. was added methanesulfonyl chloride (22 μL; 0.28 mmol; 1.2 eq.). The reaction mixture was stirred at room temperature for 16 hours. The solution was diluted with DCM, washed successively with 0.1M HCl and brine, dried over magnesium sulfate and concentrated in vacuo. Purification by mass directed preparative HPLC afforded the title compound (42 mg, 35%) as a white solid. $^1$H NMR (CDCl$_3$) δ 7.43-7.34 (m, 2H), 7.12-7.05 (m, 1H), 7.01-6.96 (m, 1H), 4.98 (s, 0.7H), 4.97 (s, 1.3H), 4.69-4.64 (m, 3H), 3.39-3.32 (m, 2H), 3.18-3.08 (m, 2H), 2.91 (s, 2H), 2.86 (s, 1H), 2.72 (s, 3H), 2.70 (s, 1H), 2.62 (s, 2H), 2.00-1.93 (m, 4H). HPLC (max plot) 98.0%, Rt 3.61 min. UPLC/MS: (MS+) 504.4 ([M+H]$^+$).

Example 54

1-{4-[2-(6-chloro-5,7-dimethyl-1H,3H-2,4,7a,8-tetraaza-cyclopenta[a]indene-2-carbonyl)-phenoxy]-piperidin-1-yl}-ethanone

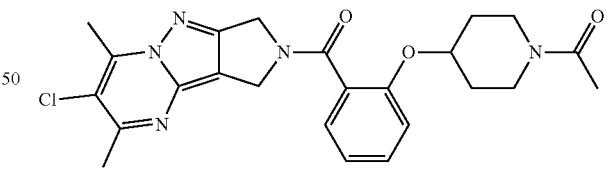

Acetic anhydride (27 μL; 0.28 mmol; 1.2 eq.) was added to a suspension of Example 3 (100 mg; 0.23 mmol; 1 eq.) and TEA (82 μL; 0.59 mmol; 2.5 eq.) in DCM (3 mLl) and the resulting mixture was stirred at room temperature for 2 hours. The solution was diluted with DCM, washed with 0.1M HCl and brine, dried over magnesium sulfate and concentrated in vacuo. Purification by mass directed preparative HPLC afforded the title compound (72 mg, 66%) as a white solid. $^1$H NMR (CDCl$_3$) δ 7.42-7.35 (m, 2H), 7.11-7.04 (m, 1H), 7.02-6.97 (m, 1H), 5.01-4.99 (m, 2H), 4.71-4.58 (m, 3H), 3.75-3.68 (m, 1H), 3.60-3.46 (m, 2H), 3.40-3.32 (m, 1H), 2.91 (s, 2H), 2.85 (s, 1H), 2.69 (s, 1H), 2.62 (s, 2H), 2.04 (s, 3H), 1.90-1.74 (m, 4H). HPLC (max plot) 99.4%, Rt 3.16 min. UPLC/MS: (MS+) 468.4 ([M+H]⁺).

Example 55

[2-(3-dimethylamino-pyrrolidin-1-yl)-phenyl]-(5,6,7-trimethyl-1H,3H-2,4,7a,8-tetraaza-cyclopenta[a]inden-2-yl)-methanone

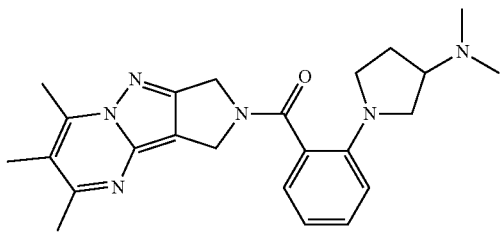

A mixture of intermediate Z5 (55 mg; 0.17 mmol; 1 eq.) and 3-(dimethylamino)pyrrolidine (1 mL) was stirred at 150° C. (MW heating) 1.5 hour. The solution was diluted with water and extracted with DCM (3×). The combined organic phase was washed with brine, dried over magnesium sulfate and concentrated in vacuo. Purification by mass directed preparative HPLC followed by washing with 1M NaOH afforded the title compound (36 mg, 51%) as a white solid. ¹H NMR (CDCl₃) δ 7.35-7.23 (m, 2H), 6.84-6.68 (m, 2H), 5.11-4.73 (m, 3H), 4.32-4.23 (m, 1H), 3.61-3.14 (m, 4H), 2.78 (s, 2H), 2.72 (s, 1H), 2.66-2.56 (m, 1H), 2.58 (s, 1H), 2.52 (s, 2H), 2.31 (s, 1H), 2.30 (s, 2H), 2.23 (s, 3H), 2.22 (s, 3H), 2.16-2.09 (m, 1H), 1.82-1.72 (m, 1H). HPLC (max plot) 99.6%, Rt 2.3 min. UPLC/MS: (MS+) 419.5 ([M+H]⁺).

Example 56

(6-chloro-5,7-dimethyl-1H,3H-2,4,7a,8-tetraaza-cyclopenta[a]inden-2-yl)-[2-(2-pyrazol-1-yl-ethoxy)-phenyl]-methanone

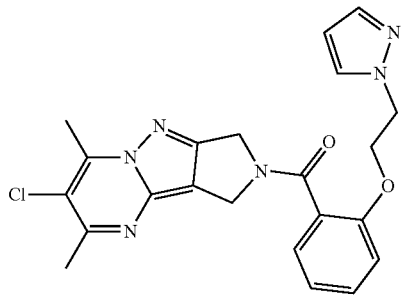 [SMILES: Cc1nc2c3c(nn2c(C)c1Cl)CN(C(=O)c1ccccc1OCCn1cccn1)C3]

A mixture of Intermediate Z4 (100 mg; 0.29 mmol; 1 eq.) 1-(2-bromoethyl)-1H-pyrazole (102 mg; 0.58 mmol; 2 eq.) and K₂CO₃ (121 mg; 0.88 mmol; 3 eq.) in DMF (2.5 mL) was stirred at 150° C. (MW heating) for 40 min. The mixture was diluted with water and extracted with DCM. The combined organic layer was washed with brine, dried over magnesium sulfate and concentrated in vacuo. Purification by mass directed preparative HPLC followed by filtration through a SPE-NH₂ column afforded the title compound (27 mg, 21%) as a white solid. ¹H NMR (CDCl₃) δ 7.39-7.26 (m, 3.5H), 7.19-7.18 (m, 0.5H), 7.07-7.00 (m, 1H), 6.91-6.88 (m, 1H), 5.63-5.60 (m, 1H), 4.98 (s, 0.7H), 4.96 (s, 1.3H), 4.49-4.45 (m, 2H), 4.40-4.36 (m, 2H), 4.24 (s, 1.3H), 4.21 (s, 0.7H), 2.93 (s, 2H), 2.87 (s, 1H), 2.71 (s, 1H), 2.62 (s, 2H). HPLC (max plot) 98.9%, Rt 3.16 min. UPLC/MS: (MS+) 437.4 ([M+H]⁺).

Example 57

(2-ethoxy-phenyl)-(6-fluoro-5,7-dimethyl-1H,3H-2,4,7a,8-tetraaza-cyclopenta[a]inden-2-yl)-methanone

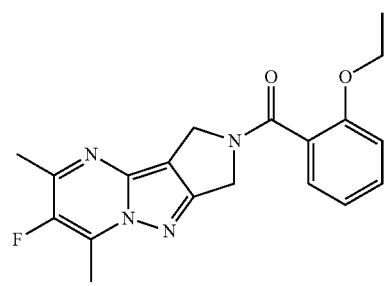 [SMILES: CCOc1ccccc1C(=O)N1Cc2nn3c(C)c(F)c(C)nc3c2C1]

The title compound was prepared following procedure described in Method A starting from 2-ethoxybenzoic acid and intermediate A9. After work up, the residue was triturated in diethyl ether and the solid filtered off to afford the title compound (82 mg, 56%) as a white solid. ¹H NMR (DMSO-d₆) δ 7.46-7.40 (m, 1H), 7.29 (ddd, J=7.4, 3.3, 1.7 Hz, 1H), 7.13 (d, J=8.2 Hz, 1H), 7.03 (t, J=7.2 Hz, 1H), 4.83 (br s, 1H), 4.81 (br s, 1H), 4.55 (br s, 1H), 4.50 (br s, 1H), 4.16-4.08 (m, 2H), 2.70 (d, J=2.7 Hz, 1.5H), 2.66 (d, J=2.7 Hz, 1.5H), 2.55 (d, J=3.2 Hz, 1.5H), 2.47 (d, J=3.2 Hz, 1.5H), 1.25-1.20 (m, 3H). HPLC (max plot) 99.3%, Rt 3.41 min; UPLC/MS: (MS+) 355.4 ([M+H]⁺).

Example 58

[2-(2-dimethylamino-ethoxy)-phenyl]-(6-fluoro-5,7-dimethyl-1H,3H-2,4,7a,8-tetraaza-cyclopenta[a]inden-2-yl)-methanone

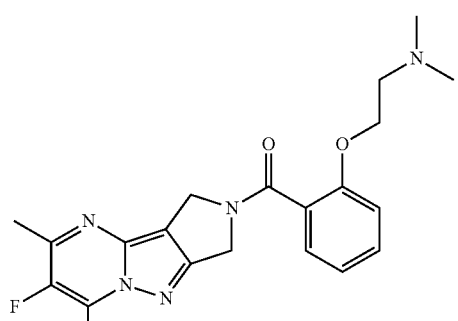

The title compound was prepared following procedure described in Method A starting from 2-[2-(dimethylamino)ethoxy]benzoic acid and intermediate A9. After work up, the residue was purified by mass directed preparative HPLC to afford the title compound (51 mg, 31%) as a white solid. ¹H NMR (DMSO-d₆) δ 7.46-7.39 (m, 1H), 7.29 (ddd, J=7.4, 2.9, 1.7 Hz, 1H), 7.14 (d, J=8.2 Hz, 1H), 7.03 (t, J=7.2 Hz, 1H), 4.80 (br s, 1H), 4.78 (br s, 1H), 4.67-4.44 (m, 2H), 4.12 (t, J=5.4 Hz, 2H), 2.69 (d, J=2.7 Hz, 1.5H), 2.66 (d, J=2.7 Hz, 1.5H), 2.54-2.47 (m, 5H), 2.05 (s, 3H), 2.04 (s, 3H). HPLC (max plot) 100%, Rt 2.27 min. UPLC/MS: (MS+) 398.3 ([M+H]+).

Example 59

(6-fluoro-5,7-dimethyl-1H,3H-2,4,7a,8-tetraaza-cyclopenta[a]inden-2-yl)-[2-(4-methyl-[1,4]diazepan-1-yl)-phenyl]-methanone

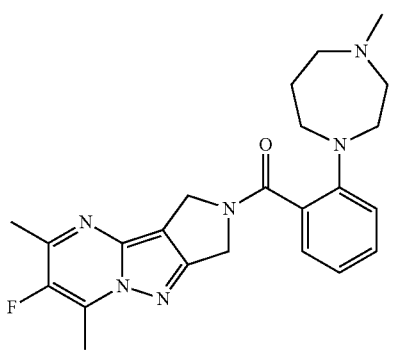 [SMILES: Cc1nc2c3c(nn2c(C)c1F)CN(C(=O)c1ccccc1N1CCCN(C)CC1)C3]

The title compound was prepared following procedure described in Method A starting from 2-(4-methylperhydro-1,4-diazepin-1-yl)benzoic acid hydrochloride hemihydrate and intermediate A9. After work up, the residue was purified by mass directed preparative HPLC to afford the title compound (89 mg, 51%) as a white solid. HPLC (max plot) 100%, Rt 2.42 min. UPLC/MS: (MS+) 423.5 ([M+H]+).

Example 60

(6-fluoro-5,7-dimethyl-1H,3H-2,4,7a,8-tetraaza-cyclopentafanden-2-yl)-[2-(1-methyl-piperidin-4-yloxy)-phenyl]-methanone

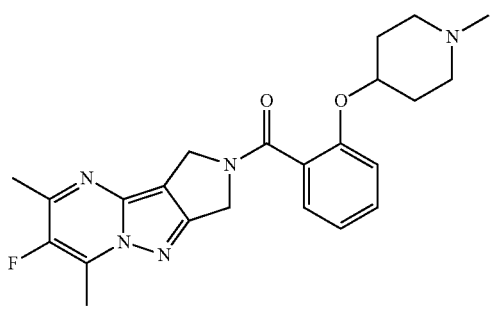

The title compound was prepared following procedure described in Method A starting from 2-(1-methyl-piperidin-4-yloxy)-benzoic acid; hydrochloride and intermediate A9. After work up, the residue was purified by mass directed preparative HPLC to afford the title compound (50 mg, 29%) as a white solid. $^1$H NMR (DMSO-d$_6$) δ 7.43-7.38 (m, 1H), 7.31-7.29 (m, 1H), 7.19-7.16 (m, 1H), 7.05-7.00 (m, 1H), 4.83-4.41 (m, 5H), 2.69 (d, J=2.8 Hz, 1.5H), 2.66 (d, J=2.8 Hz, 1.5H), 2.54-2.47 (m, 3H), 2.42-2.24 (m, 2H), 2.24-2.07 (m, 2H), 2.06-1.92 (m, 3H), 1.90-1.76 (m, 2H), 1.64-1.47 (m, 2H). HPLC (max plot) 99.5%, Rt 2.42 min. UPLC/MS: (MS+) 424.5 ([M+H]+).

Example 61

[2-(azepan-4-yloxy)-phenyl]-(6-chloro-5,7-dimethyl-1H,3H-2,4,7a,8-tetraaza-cyclopenta[a]inden-2-yl)-methanone

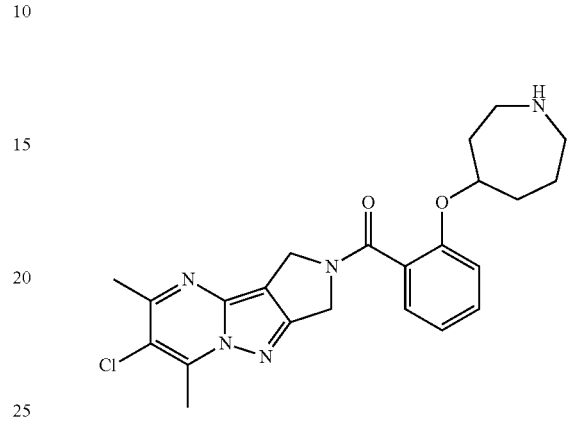

The title compound was prepared following procedure described in Method G starting from 4-hydroxyazepane-1-carboxylic acid tert-butyl ester and intermediate Z4. After work up, the residue was taken up in DCM (5 mL) and TFA (5 mL) was added. The reaction mixture was stirred for 5 minutes then concentrated in vacuo. After dilution with 1M NaOH extraction with DCM, the combined organic phase was dried over magnesium sulfate and concentrated in vacuo. Purification by mass directed preparative HPLC afforded the title compound (50 mg, 39%) as a white solid. $^1$H NMR (DMSO-d$_6$) δ 7.45-7.39 (m, 1H), 7.31-7.27 (m, 1H), 7.12-7.09 (m, 1H), 7.04-6.93 (m, 1H), 4.28-4.80 (m, 2H), 4.72-4.51 (m, 3H), 2.84-2.55 (m, 10H), 1.96-1.35 (m, 7H). HPLC (max plot) 98.4%, Rt 2.78 min. UPLC/MS: (MS+) 440.4 ([M+H]+).

Example 62

(6-chloro-5,7-dimethyl-1H,3H-2,4,7a,8-tetraaza-cyclopenta[a]inden-2-yl)-(2-piperidin-1-yl-phenyl)-methanone

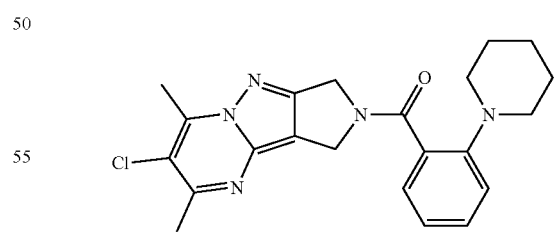

A mixture of intermediate Z6 (100 mg; 0.29 mmol; 1 eq.) and piperidine (1 mL; 10.1 mmol; 35 eq.) was stirred at 160° C. (MW heating) for 4 hours. The reaction mixture was diluted with water and extracted with DCM (2×). The organic layers were washed with brine, dried over magnesium sulfate and concentrated in vacuo. Recrystallization from ACN afforded the title compound (58 mg, 49%) as a white solid. $^1$H NMR (CDCl$_3$) δ 7.38-7.31 (m, 2H), 7.07-7.00 (m, 2H), 5.19-

4.89 (m, 3H), 4.37-4.27 (m, 1H), 3.22 (br s, 2H), 2.95-2.85 (m, 2H), 2.91 (s, 2H), 2.86 (s, 1H), 2.69 (s, 1H), 2.63 (s, 2H), 1.57-1.42 (m, 6H). HPLC (max plot) 97.3%, Rt 3.16 min. UPLC/MS: (MS+) 410.4 ([M+H]+).

Example 63

[2-(2-pyridin-2-yl-ethoxy)-phenyl]-(5,6,7-trimethyl-1H,3H-2,4,7a,8-tetraaza-cyclopenta[a]inden-2-yl)-methanone

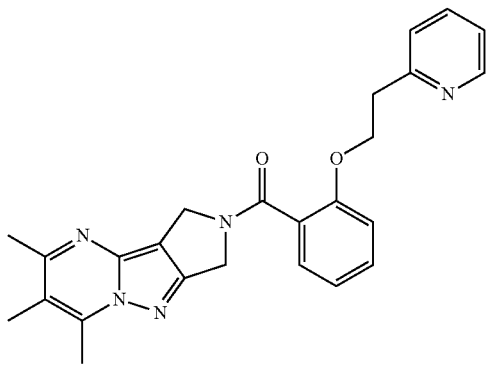 [SMILES: Cc1nc2c3c(nn2c(C)c1C)CN(C(=O)c1ccccc1OCCc1ccccn1)C3]

The title compound was prepared following procedure described in Method G starting from 2-(2-hydroxyethyl)pyridine and intermediate Z1. After work up, the residue was purified by mass directed preparative HPLC to afford the title compound (52 mg, 39%) as a white solid. $^1$H NMR (DMSO-d$_6$) δ 8.24-8.09 (m, 1H), 7.45-7.38 (m, 1H), 7.25-6.98 (m, 5H), 6.59-6.36 (m, 1H), 4.63 (br s, 2H), 4.41 (t, J=5.9 Hz, 2H), 4.05-3.99 (m, 2H), 3.08-3.04 (m, 2H), 2.75 (s, 1.5H), 2.71 (s, 1.5H), 2.54 (s, 1.5H), 2.49 (s, 1.5H), 2.29 (s, 3H). HPLC (max plot) 93.2%, Rt 2.22 min. UPLC/MS: (MS+) 428.5 ([M+H]+).

Example 64

(6-chloro-5,7-dimethyl-1H,3H-2,4,7a,8-tetraaza-cyclopenta[a]inden-2-yl)-[4-fluoro-2-(piperidin-4-yloxy)-phenyl]-methanone

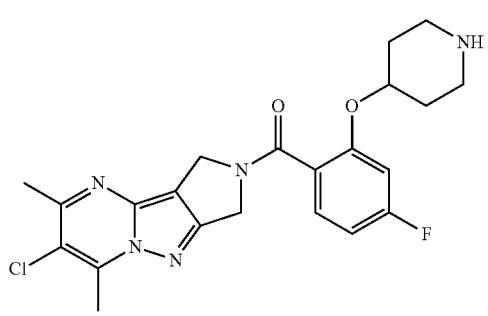 [SMILES: Cc1nc2c3c(nn2c(C)c1Cl)CN(C(=O)c1ccc(F)cc1OC1CCNCC1)C3]

The title compound was prepared following procedure described in Method G starting from 1-Boc-4-hydroxypiperidine and intermediate Z2. After work up, the residue was taken up in DCM (5 mL) and TFA (5 mL) was added. The reaction mixture was stirred for 5 minutes then concentrated in vacuo. After dilution with 1M NaOH extraction with DCM, the combined organic phase was dried over magnesium sulfate and concentrated in vacuo. Purification by mass directed preparative HPLC afforded the title compound (45 mg, 37%) as a white solid. HPLC (max plot) 96%, Rt 2.80 min. UPLC/MS: (MS+) 444.1 ([M+H]+).

Example 65

(6-chloro-5,7-dimethyl-1H,3H-2,4,7a,8-tetraaza-cyclopenta[a]inden-2-yl)-[2-(1-isopropyl-piperidin-4-yloxy)-phenyl]-methanone

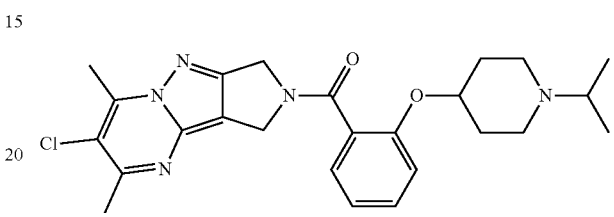

To a solution of Example 3 (100 mg; 0.23 mmol; 1 eq.) in DCM (3 mL) was added acetone (52 μL; 0.70 mmol; 3 eq.) and AcOH (16 μL; 0.28 mmol; 1.2 eq.) and then after few minutes sodium triacetoxyborohydride (149 mg; 0.70 mmol; 3 eq.). The reaction mixture was stirred at room temperature for 60 hours and acetone (104 μL; 1.41 mmol; 6 eq.) and sodium triacetoxyborohydride (50 mg; 0.23 mmol; 1 eq.). The reaction mixture was stirred for 5 hours then diluted with DCM. The organic phase was washed with sat. aq. NaHCO$_3$, dried over magnesium sulfate and concentrated in vacuo. Purification by mass directed preparative HPLC afforded the title compound (45 mg, 41%). $^1$H NMR (CDCl$_3$) δ 7.41-7.33 (m, 2H), 7.08-6.96 (m, 2H), 4.99 (s, 0.8H), 4.98 (s, 1.2H), 4.66-4.49 (m, 3H), 2.98-2.14 (m, 5H), 2.91 (s, 2H), 2.86 (s, 1H), 2.70 (s, 1H), 2.62 (s, 2H), 1.89-1.61 (m, 4H), 1.09 (s, 6H). HPLC (max plot) 93.8%; Rt 2.80 min. UPLC/MS: (MS+) 468.5 ([M+H]+).

Example 66

(6-chloro-5,7-dimethyl-1H,3H-2,4,7a,8-tetraaza-cyclopenta[a]inden-2-yl)-[2-(4-methyl-piperazin-1-ylmethyl)-phenyl]-methanone

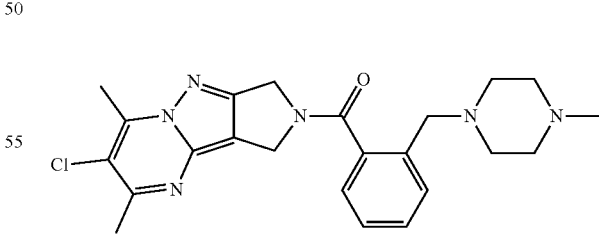

The title compound was prepared following procedure described in Method F starting from lithium 2-[(4-methylpiperazin-1-yl)methyl]benzoate (Apollo scientific) and intermediate A3. After work up, recrystallization from ACN afforded the title compound (79 mg, 47%) as a white solid. $^1$H NMR (CDCl$_3$) δ 7.37-7.30 (m, 4H), 5.01 (br s, 2H), 4.57 (br s, 2H), 3.59 (br s, 2H), 2.92 (s, 2H), 2.86 (s, 1H), 2.70 (s, 1H), 2.62 (s, 2H), 2.57-1.75 (m, 6H), 1.89 (s, 1H), 1.84 (s, 2H), 1.63 (br s, 2H). HPLC (max plot) 99.5%, Rt 2.27 min. UPLC/MS: (MS+) 439.5 ([M+H]+).

Example 67

(6-chloro-5,7-dimethyl-1H,3H-2,4,7a,8-tetraaza-cyclopenta[a]inden-2-yl)-(2-difluoromethoxy-phenyl)-methanone

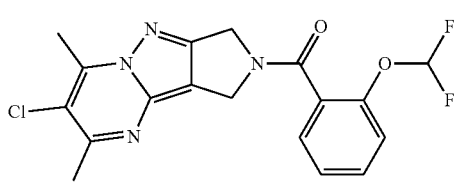 [SMILES: Cc1nc2c3c(nn2c(C)c1Cl)CN(C(=O)c1ccccc1OC(F)F)C3]

The title compound was prepared following procedure described in Method A starting from 2-(difluoromethoxy) benzoic acid and Intermediate A3. After work up, recrystallization from ACN afforded the title compound (140 mg, 92%) as a white solid. ¹H NMR (CDCl₃) δ 7.50-7.44 (m, 2H), 7.36-7.24 (m, 2H), 6.58 (t, J=73.9 Hz, 1H), 5.03-5.02 (m, 2H), 4.64-4.62 (m, 2H), 2.91 (s, 2H), 2.85 (s, 1H), 2.69 (s, 1H), 2.62 (s, 2H). HPLC (max plot) 99.2%, Rt 3.82 min. UPLC/MS: (MS+) 393.4 ([M+H]+).

Example 68

(6-chloro-5,7-dimethyl-1H,3H-2,4,7a,8-tetraaza-cyclopenta[a]inden-2-yl)-[2-(pyrrolidin-3-yloxy)-phenyl]-methanone

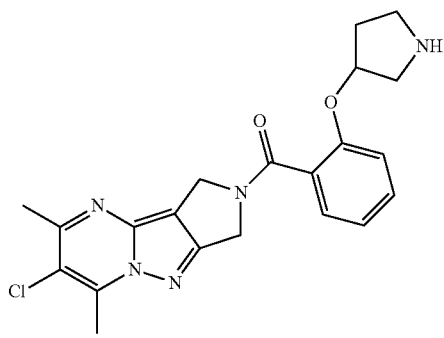 [SMILES: Cc1nc2c3c(nn2c(C)c1Cl)CN(C(=O)c1ccccc1OC1CCNC1)C3]

The title compound was prepared following procedure described in Method G starting from DL-3-pyrrolidinol and Intermediate Z4. After work up, the residue was purified by column chromatography (DCM/MeOH/TEA, 97/3/2) to afford the title compound (221 mg, 92%) as a yellow foam. ¹H NMR (DMSO-d₆) δ 7.48-7.39 (m, 1H), 7.34-7.27 (m, 1H), 7.15-7.09 (m, 1H), 7.09-7.00 (m, 1H), 4.98-4.90 (m, 1H), 4.87-4.78 (m, 2H), 4.60-4.44 (m, 2H), 3.12-3.00 (m, 1H), 2.89-2.75 (m, 5H), 2.62 (s, 1.5H), 2.56 (s, 1.5H), 2.03-1.88 (m, 1H), 1.78-1.63 (m, 1H), 1.46-1.29 (m, 1H). HPLC (max plot) 96.3%, Rt 2.67 min. UPLC/MS: (MS+) 412.4 ([M+H]+).

Example 69

(6-chloro-5,7-dimethyl-1H,3H-2,4,7a,8-tetraaza-cyclopenta[a]inden-2-yl)-[4-fluoro-2-(2-pyridin-2-yl-ethoxy)-phenyl]-methanone

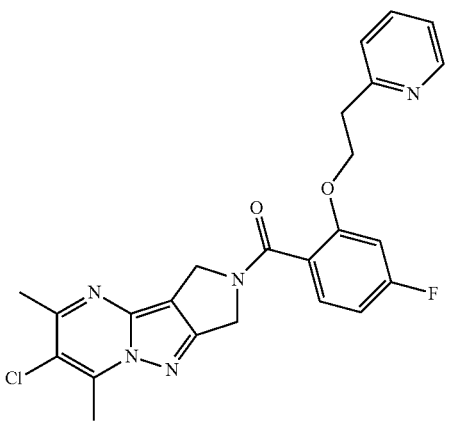 [SMILES: Cc1nc2c3c(nn2c(C)c1Cl)CN(C(=O)c1ccc(F)cc1OCCc1ccccn1)C3]

The title compound was prepared following procedure described in Method G starting from 2-(2-hydroxyethyl)pyridine and Intermediate Z2. After work up, the residue was purified by column chromatography (EA) followed by trituration in MeOH and filtration to afford the title compound (221 mg, 92%) as a white solid. ¹H NMR (DMSO-d₆) δ 8.24-8.11 (m, 1H), 7.30-7.24 (m, 1H), 7.18-7.08 (m, 3H), 6.87-6.81 (m, 1H), 6.62-6.39 (m, 1H), 4.64 (br s, 2H), 4.46-4.42 (m, 2H), 4.06-3.99 (m, 2H), 3.11-3.01 (m, 2H), 2.88 (s, 1.5H), 2.84 (s, 1.5H), 2.64 (s, 1.5H), 2.59 (s, 1.5H). HPLC (max plot) 98.7%, Rt 2.64 min; UPLC/MS: (MS+) 446.4 ([M+H]+).

Example 70

(6-chloro-5,7-dimethyl-1H,3H-2,4,7a,8-tetraaza-cyclopenta[a]inden-2-yl)-[4-fluoro-2-(1-methyl-piperidin-4-yloxy)-phenyl]-methanone

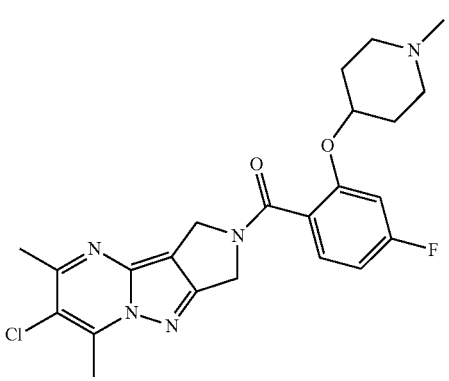 [SMILES: Cc1nc2c3c(nn2c(C)c1Cl)CN(C(=O)c1ccc(F)cc1OC1CCN(C)CC1)C3]

A mixture of Example 64 (100 mg; 0.21 mmol; 1 eq.), paraformaldehyde (56 mg; 0.62 mmol; 3 eq.) and sodium triacetoxyborohydride (88 mg; 0.42 mmol; 2 eq.) in DCE (7 mL) was stirred at reflux for 16 hours. Paraformaldehyde (56 mg; 0.62 mmol; 3 eq.) and sodium triacetoxyborohydride (88 mg; 0.42 mmol; 2 eq.) were added and the reaction mixture was stirred at reflux for one hour. The mixture was partitioned between EA and 1M NaOH and the aqueous layer extracted with EA. The combined organic phase was dried over magnesium sulfate and concentrated in vacuo. Purification by column chromatography (2% to 5% MeOH in DCM) followed by recrystallization from ACN afforded the title compound (34 mg, 35%) as a white powder. $^1$H NMR (DMSO-d$_6$) δ 7.44-7.25 (m, 1H), 7.13 (d, J=11.4 Hz, 1H), 6.86 (td, J=8.3, 2.0 Hz, 1H), 4.92-4.69 (m, 2H), 4.69-4.37 (m, 3H), 2.93-2.70 (m, 3H), 2.61 (s, 1.5H), 2.55 (s, 1.5H), 2.42-2.23 (m, 2H), 2.23 2.04 (m, 2H), 2.04-1.93 (m, 3H), 1.91-1.73 (m, 2H), 1.64-1.47 (m, 2H). HPLC (max plot) 97.4%, Rt 2.81 min. UPLC/MS: (MS+) 458.5 ([M+H]$^+$).

Example 71

(6-chloro-5,7-dimethyl-1H,3H-2,4,7a,8-tetraaza-cyclopenta[a]inden-2-yl)-[2-(1-methyl-pyrrolidin-3-yloxy)-phenyl]-methanone

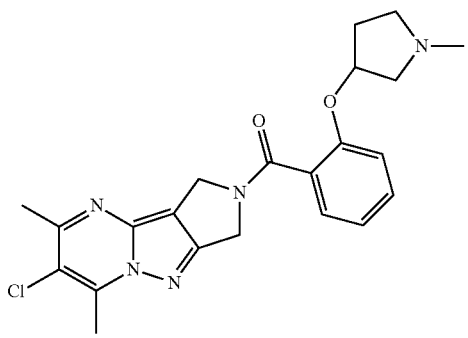 [SMILES: Cc1nc2c3c(nn2c(C)c1Cl)CN(C(=O)c1ccccc1OC1CCN(C)C1)C3]

A mixture of Example 68 (150 mg; 0.36 mmol; 1 eq.), formaldehyde (0.27 mL; 3.64 mmol; 10 eq.) and NaBH$_4$ (69 mg; 1.82 mmol; 5 eq.) in THF (12 mL) was cooled to 0° C. and TFA (1 mL) was added. The reaction mixture was stirred at room temperature for 18 hours then diluted with EA. The organic phase was washed with 0.1M NaOH (2×), dried over magnesium sulfate and concentrated in vacuo. Purification by column chromatography (DCM/MeOH/TEA) afforded the title compound (75 mg, 48%) as white foam. $^1$H NMR (DMSO-d$_6$) δ 7.47-7.38 (m, 1H), 7.33-7.25 (m, 1H), 7.09-6.99 (m, 2H), 4.99-4.89 (m, 1H), 4.82 (m, 2H), 4.65-4.42 (m, 2H), 2.88-2.75 (m, 4H), 2.62 (s, 1.5H), 2.60-2.52 (m, 2.5H), 2.37-2.20 (m, 2H), 2.19 (s, 1.5H), 2.18 (s, 1.5H), 1.80-1.66 (m, 1H), 1.46-1.31 (m, 1H). HPLC (max plot) 95.6%, Rt 2.63 min. UPLC/MS: (MS+) 426.5 ([M+H]$^+$).

Example 72

(6-chloro-5,7-dimethyl-1H,3H-2,4,7a,8-tetraaza-cyclopenta[a]inden-2-yl)-[2-(3-hydroxy-pyrrolidin-1-ylmethyl)-phenyl]-methanone

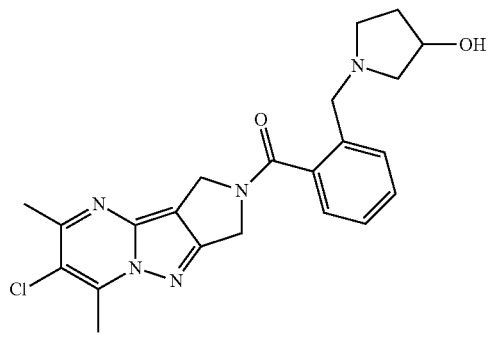 [SMILES: Cc1nc2c3c(nn2c(C)c1Cl)CN(C(=O)c1ccccc1CN1CCC(O)C1)C3]

The title compound was prepared following procedure described in Method C starting from Intermediate Z3 and 3-pyrrolidinol. After purification by slurry in hot ACN, the title compound was obtained as a pale beige powder (65 mg, 64%). $^1$H NMR (DMSO-d$_6$) δ 7.44-7.31 (m, 4H), 4.83 (s, 1H), 4.81 (s, 1H), 4.57-4.37 (m, 3H), 3.95-3.83 (m, 1H), 3.59 (br s, 2H), 2.84 (s, 1.5H), 2.80 (s, 1.5H), 2.69-2.59 (m, 2.5H), 2.54 (s, 1.5H), 2.49-2.42 (m, 1H), 2.42-2.30 (m, 1H), 2.25-2.16 (m, 1H), 1.74-1.58 (m, 1H), 1.38-1.24 (m, 1H). HPLC (max plot) 97.4%, Rt 2.59 min. UPLC/MS: (MS+) 426.5 ([M+H]$^+$), (MS−) 424.5 ([M−H]−). Melting point: 210-217° C. (ACN).

Example 73

(6-chloro-5,7-dimethyl-1H,3H-2,4,7a,8-tetraaza-cyclopenta[a]inden-2-yl)-[4-fluoro-2-(2-pyridin-3-yl-ethoxy)-phenyl]-methanone

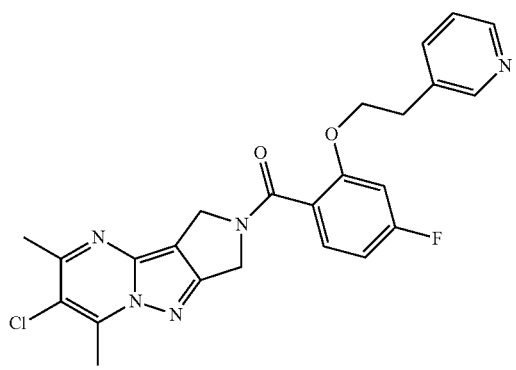 [SMILES: Cc1nc2c3c(nn2c(C)c1Cl)CN(C(=O)c1ccc(F)cc1OCCc1cccnc1)C3]

The title compound was prepared following procedure described in Method G starting from 2-(3-pyridyl)ethan-1-ol and intermediate Z2. After work up, the residue was purified by column chromatography (50% to 100% EA in heptanes) followed by recrystallization from EtOH to afford the title compound (104 mg, 40%) as white powder. $^1$H NMR (DMSO-d$_6$) δ 8.35 (s, 1H), 7.88 (dd, J=1.4, 4.7 Hz, 0.5H), 7.78 (dd, J=1.4, 4.7 Hz, 0.5H), 7.64-7.50 (m, 1H), 7.30 (ddd, J=3.7, 6.8, 8.3 Hz, 1H), 7.08 (d, J=10.0 Hz, 1H), 6.95-6.75 (m, 2H), 4.74 (d, J=5.6 Hz, 2H), 4.32 (t, J=5.9 Hz, 2H), 4.23-3.98 (m, 2H), 2.96 (t, J=5.6 Hz, 2H), 2.89 (s, 1.5H), 2.83 (s, 1.5H), 2.65 (s, 1.5H), 2.57 (s, 1.5H). HPLC (max plot) 99.7%, Rt 2.78 min. UPLC/MS: (MS+) 466.4 ([M+H]$^+$).

Example 74

(6-chloro-5,7-dimethyl-1H,3H-2,4,7a,8-tetraaza-cyclopenta[a]inden-2-yl)-[4-fluoro-2-(2-pyridin-4-yl-ethoxy)-phenyl]-methanone

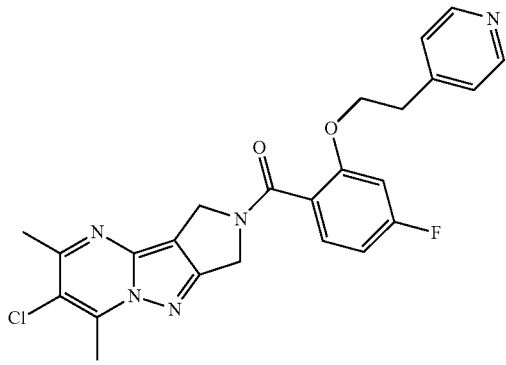 [SMILES: Cc1nc2c3c(nn2c(C)c1Cl)CN(C(=O)c1ccc(F)cc1OCCc1ccncc1)C3]

The title compound was prepared following procedure described in Method G starting from 4-(2-hydroxyethyl)pyridine and intermediate Z2. After work up, the residue was purified by column chromatography (50% to 100% EA in heptanes) followed by recrystallization from EtOH to afford the title compound (95 mg, 37%) as white powder. $^1$H NMR (DMSO) δ 8.01 (dd, J=1.5, 4.4 Hz, 1H), 7.94 (dd, J=1.5, 4.4 Hz, 1H), 7.31 (dd, J=4.1, 6.8, 8.4 Hz, 1H), 7.19-7.01 (m, 3H), 6.86 (td, J=2.1, 8.4 Hz, H), 4.72 (d, J=11.5 Hz, 2H), 4.35 (t, J=5.7 Hz, 2H), 4.16 (s, 1H), 4.07 (s, 1H), 2.95 (t, J=2.1 Hz, 2H), 2.88 (s, 1.5H), 2.83 (s, 1.5H), 2.65 (s, 1.5H), 2.57 (s, 1.5H). HPLC (max plot) 99.7%, Rt 2.68 min. UPLC/MS: (MS+) 466.4 ([M+H]$^+$).

Example 75

(6-chloro-5,7-dimethyl-1H,3H-2,4,7a,8-tetraaza-cyclopenta[a]inden-2-yl)-[2-(morpholin-3-yl-methoxy)-phenyl]-methanone

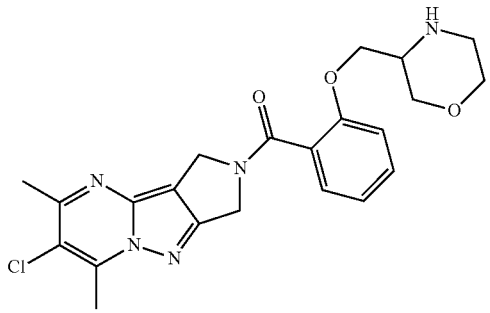 [SMILES: Cc1nc2c3c(nn2c(C)c1Cl)CN(C(=O)c1ccccc1OCC1COCCN1)C3]

Step 1: tert-butyl 3-(hydroxymethyl)morpholine-4-carboxylate

A 1M solution of borane-tetrahydrofuran complex in THF (8.65 mL; 8.65 mmol; 2 eq.) was added to a cold (0° C.) solution of morpholine-3,4-dicarboxylic acid 4-tert-butyl ester (1 g; 4.32 mmol; 1 eq.) in THF (10 mL) and the resulting mixture was stirred at room temperature for 1 hour. The solution was diluted with EA, washed with sat. aq. NaHCO3 then brine, dried over magnesium sulfate and concentrated in vacuo. Purification by column chromatography (EA/heptane) afforded the title compound (600 mg, 64%) as a colourless oil.

Step 2: 3-[2-(6-chloro-5,7-dimethyl-1H,3H-2,4,7a,8-tetraaza-cyclopenta[a]indene-2-carbonyl)-phenoxymethyl]-morpholine-4-carboxylic acid tert-butyl ester The title compound was prepared following procedure described in Method G starting from tert-butyl 3-(hydroxymethyl)morpholine-4-carboxylate and Intermediate Z4. After work up, the residue was purified by column chromatography (DCM to 20% MeOH in DCM) to afford the title compound (694 mg, 93%) as a yellow oil which was used without further purification. HPLC (max plot) 97.3%, Rt 4.42 min. UPLC/MS: (MS+) 542.6 and 544.6 ([M+H]$^+$).

Step 3: (6-chloro-5,7-dimethyl-1H,3H-2,4,7a,8-tetraaza-cyclopenta[a]inden-2-yl)-[2-(morpholin-3-ylmethoxy)-phenyl]-methanone A 4M solution of HCl in 1,4-dioxane (3.2 mL; 12.7 mmol; 10 eq.) was added to a suspension of 3-[2-(6-chloro-5,7-dimethyl-1H,3H-2,4,7a,8-tetraaza-cyclopenta[a]indene-2-carbonyl)-phenoxymethyl]-morpholine-4-carboxylic acid tert-butyl ester (690 mg; 1.27 mmol; 1 eq.) in 1,4-dioxane (10 mL) followed by WATER (130 µL) and the resulting mixture was stirred at room temperature for 16 hours. After concentration in vacuo, the residue was partitioned between DCM and 1M NaOH and the aqueous layer was extracted with DCM. The combined organic phase was dried over sodium sulfate and concentrated in vacuo. Crystallization from EA afforded the title compound (240 mg, 43%) as a yellow solid. $^1$H NMR (CDCl$_3$) δ 7.44-7.30 (m, 2H), 7.13-7.01 (m, 1H), 6.96 (dd, J=8.2, 4.0 Hz, 1H), 5.07-4.96 (m, 2H), 4.68-4.55 (m, 2H), 4.03-3.89 (m, 2H), 3.85-3.76 (m, 1H), 3.76-3.66 (m, 1H), 3.51-3.39 (m, 1H), 3.31 (t, J=10.0 Hz, 1H), 3.25-3.12 (m, 1H), 2.95-2.76 (m, 5H), 2.69 (s, 1.1H), 2.61 (s, 1.9H), 1.94 (brs, 1H). HPLC (max plot) 94.4%, Rt 2.72 min. UPLC/MS: (MS+) 442.5 ([M+H]$^+$).

Example 76

(6-chloro-5,7-dimethyl-1H,3H-2,4,7a,8-tetraaza-cyclopenta[a]inden-2-yl)-[4-fluoro-2-(1-oxetan-3-yl-piperidin-4-yloxy)-phenyl]-methanone

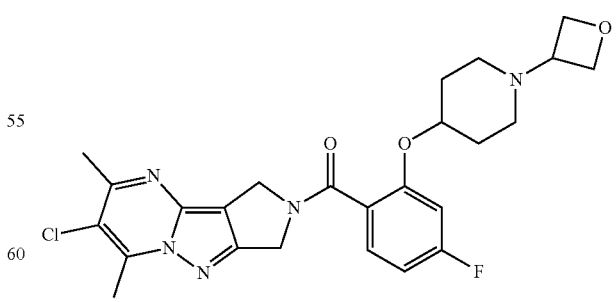

A mixture of Example 64 (110 mg; 0.25 mmol; 1 eq.), 3-oxetanone (22 µL; 0.37 mmol; 1.5 eq.) and sodium triacetoxyborohydride (53 mg; 0.25 mmol; 1 eq.) in DCE (6 mL) was stirred at 50° C. for 16 hours. The reaction mixture was diluted with DCM, washed with sat. aq. NaHCO$_3$, dried over sodium sulfate and concentrated in vacuo. Crystallization from EA afforded the title compound (86 mg, 69%) as an off-white solid. $^1$H NMR (CDCl$_3$) δ 7.34 (td, J=8.1, 6.6 Hz, 1H), 6.80-6.63 (m, 2H), 5.07-4.92 (m, 2H), 4.66 (br s, 2H), 4.61-4.47 (m, 4H), 4.47-4.33 (m, 1H), 3.43-3.28 (m, 1H), 2.92 (s, 1.8H), 2.86 (s, 1.2H), 2.70 (s, 1.2H), 2.63 (s, 1.8H), 2.44-2.28 (m, 2H), 2.23-2.10 (m, 2H), 2.03-1.90 (m, 2H), 1.90-1.73 (m, 2H). HPLC (max plot) 97.1%, Rt 2.90 min. UPLC/MS: (MS+) 500.5 ([M+H]$^+$).

Example 77

(6-chloro-5,7-dimethyl-1H,3H-2,4,7a,8-tetraaza-cyclopenta[a]inden-2-yl)-[4-fluoro-2-((S)-1-isopropyl-pyrrolidin-3-yloxy)-phenyl]-methanone

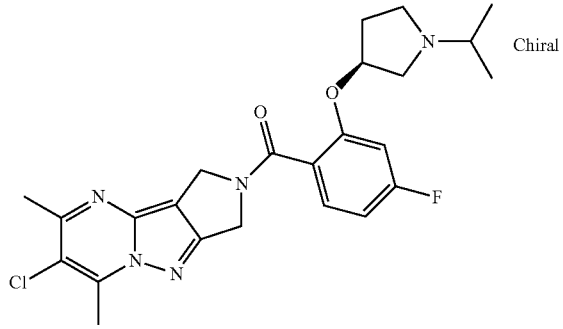 [SMILES: Cc1nc2c3c(nn2c(C)c1Cl)CN(C(=O)c1ccc(F)cc1O[C@H]1CCN(C(C)C)C1)C3]

A mixture Example 83 (150 mg; 0.35 mmol; 1 eq.) acetone (0.13 mL; 1.74 mmol; 5 eq.) and sodium triacetoxyborohydride (74 mg; 0.35 mmol; 1 eq.) in DCE (4 mL) was stirred 50° C. for 16 hours. The reaction mixture was diluted with DCM, washed with sat. aq. NaHCO$_3$, dried over sodium sulfate and concentrated in vacuo. Purification by column chromatography (EA to EA/MeOH/TEA 90/10/2) afforded the title compound (66 mg, 40%) as white foam. $^1$H NMR (DMSO-d$_6$) δ 7.40-7.31 (m, 1H), 6.99 (dd, J=11.5, 2.3 Hz, 1H), 6.91-6.82 (m, 1H), 5.02-4.93 (m, 1H), 4.85-4.80 (m, 2H), 4.76-4.44 (m, 2H), 2.84 (s, 1.5H), 2.79 (s, 1.5H), 2.79-2.74 (m, 1H), 2.71-2.63 (m, 1H), 2.61 (s, 1.5H), 2.56 (s, 1.5H), 2.38-2.13 (m, 3H), 1.78-1.65 (m, 1H), 1.40-1.28 (m, 1H), 0.95-0.80 (m, 6H). HPLC (max plot) 98.5%, Rt 2.88 min. UPLC/MS: (MS+) 472.4 ([M+H]$^+$).

Example 78

(6-chloro-5,7-dimethyl-1H,3H-2,4,7a,8-tetraaza-cyclopenta[a]inden-2-yl)-[4-fluoro-2-((R)-1-isopropyl-pyrrolidin-3-yloxy)-phenyl]-methanone

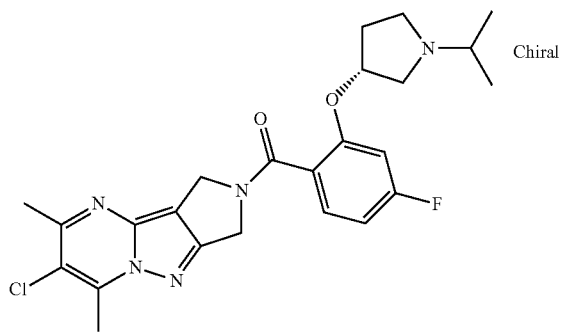 [SMILES: Cc1nc2c3c(nn2c(C)c1Cl)CN(C(=O)c1ccc(F)cc1O[C@@H]1CCN(C(C)C)C1)C3]

A mixture Example 80 (150 mg; 0.35 mmol; 1 eq.) acetone (0.13 mL; 1.74 mmol; 5 eq.) and sodium triacetoxyborohydride (74 mg; 0.35 mmol; 1 eq.) in DCE (4 mL) was stirred 50° C. for 16 hours. The reaction mixture was diluted with DCM, washed with sat. aq. NaHCO$_3$, dried over magnesium sulfate and concentrated in vacuo to afford the title compound (140 mg, 85%) as yellow foam. $^1$H NMR (DMSO-d$_6$) δ 7.40-7.31 (m, 1H), 6.99 (dd, J=11.5, 2.3 Hz, 1H), 6.91-6.82 (m, 1H), 5.02-4.93 (m, 1H), 4.85-4.78 (m, 2H), 4.76-4.44 (m, 2H), 2.86-2.77 (m, 2H), 2.79-2.74 (m, 1H), 2.71-2.63 (m, 1H), 2.61 (s, 1.5H), 2.56 (s, 1.5H), 2.38-2.13 (m, 3H), 1.78-1.65 (m, 1H), 1.40-1.28 (m, 1H), 0.95-0.80 (m, 6H). HPLC (max plot) 92.6%, Rt 2.89 min. UPLC/MS: (MS+) 472.5 ([M+H]$^+$).

Example 79

(6-chloro-5,7-dimethyl-1H,3H-2,4,7a,8-tetraaza-cyclopenta[a]inden-2-yl)-{4-fluoro-2-[(R)-1-(2,2,2-trifluoro-ethyl)-pyrrolidin-3-yloxy]-phenyl}-methanone

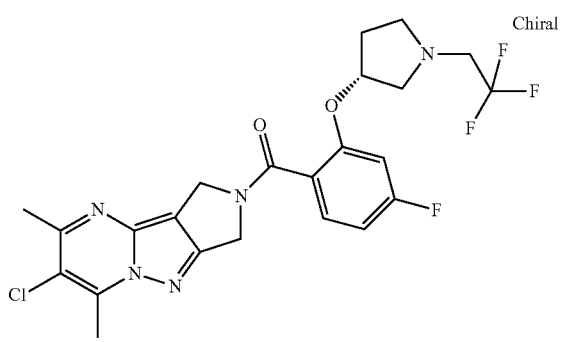 [SMILES: Cc1nc2c3c(nn2c(C)c1Cl)CN(C(=O)c1ccc(F)cc1O[C@@H]1CCN(CC(F)(F)F)C1)C3]

2,2,2-Trifluoroethyl trifluoromethanesulfonate (97 mg; 0.42 mmol; 1.2 eq.) was added dropwise to a cold (0° C.) solution of Example 80 (150 mg; 0.35 mmol; 1 eq.) and TEA (0.19 mL; 1.4 mmol; 4 eq.) in DCM (4 mL) and the reaction mixture was stirred at room temperature for 16 hours. 2,2,2-Trifluoroethyl trifluoromethanesulfonate (97 mg; 0.42 mmol; 1.2 eq.) was added and the reaction mixture was stirred at room temperature for 24 hours. The reaction mixture was diluted with DCM, washed with sat. aq. NaHCO$_3$, dried over magnesium sulfate and concentrated in vacuo to afford the title compound (144 mg, 81%) as yellow foam. $^1$H NMR (DMSO-d$_6$) δ 7.41-7.32 (m, 1H), 7.03 (dd, J=11.5, 2.3 Hz, 1H), 6.89 (td, J=8.5, 2.3 Hz, 1H), 5.05-4.97 (m, 1H), 4.81 (d, J=8.7 Hz, 2H), 4.55 (d, J=14.3 Hz, 2H), 3.29-3.04 (m, 3H), 2.85 (s, 1.5H), 2.81 (s, 1.5H), 2.79-2.64 (m, 2H), 2.62 (s, 1.5H), 2.56 (s, 1.5H), 2.31-2.15 (m, 1H), 1.85-1.72 (m, 1H), 0.93-0.81 (m, 1H) HPLC (max plot) 93.6%, Rt 3.29 min. UPLC/MS: (MS+) 512.5 ([M+H]+).

Example 80

(6-chloro-5,7-dimethyl-1H,3H-2,4,7a,8-tetraaza-cyclopenta[a]inden-2-yl)-[4-fluoro-2-((R)-pyrrolidin-3-yloxy)-phenyl]-methanone

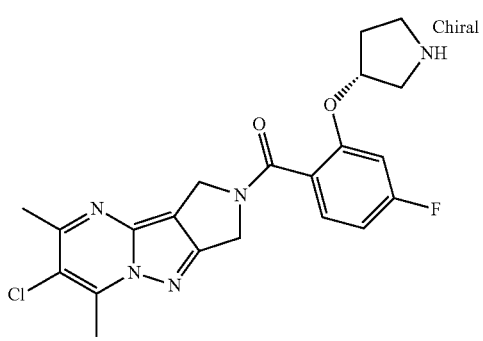 [SMILES: Cc1nc2c3c(nn2c(C)c1Cl)CN(C(=O)c1ccc(F)cc1O[C@@H]1CCNC1)C3]

Step 1: (R)-3-[2-(6-chloro-5,7-dimethyl-1H,3H-2,4,7a,8-tetraaza-cyclopenta[a]indene-2-carbonyl)-5-fluoro-phenoxy]-pyrrolidine-1-carboxylic acid tert-butyl ester The title compound was prepared following procedure described in Method G starting from N-tert-butoxycarbonyl-(R)-(+)-3-pyrrolidine and Intermediate Z2. After work up, the residue was purified by column chromatography (EA/heptane, 1/4 to 1/1) to afford the title compound (640 mg, 44%) as yellow oil. HPLC (max plot) 96.6%, Rt 4.50 min. UPLC/MS: (MS+) 530.4 ([M+H]+).

Step 2: (6-chloro-5,7-dimethyl-1H,3H-2,4,7a,8-tetraaza-cyclopenta[a]inden-2-yl)-[4-fluoro-2-((R)-pyrrolidin-3-yloxy)-phenyl]-methanone HCl (1.3 mL) was added to a solution of (R)-3-[2-(6-chloro-5,7-dimethyl-1H,3H-2,4,7a,8-tetraaza-cyclopenta[a]indene-2-carbonyl)-5-fluoro-phenoxy]-pyrrolidine-1-carboxylic acid tert-butyl ester (700 mg; 1.32 mmol; 1 eq.) in 1,4-dioxane (10 mL) was stirred at room temperature for 16 hours then concentrated in vacuo. The reaction mixture was diluted with DCM, washed with 0.1M NaOH, dried over magnesium sulfate and concentrated in vacuo to afford the title compound (550 mg, 97%) as yellow foam. $^1$H NMR (DMSO-d$_6$) δ 7.40-7.31 (m, 1H), 7.09-7.01 (m, 1H), 6.93-6.83 (m, 1H), 5.03-4.93 (m, 1H), 4.86-4.76 (m, 2H), 4.62-4.43 (m, 2H), 3.13-3.02 (m, 1H), 2.84 (s, 1.5H), 2.81 (s, 1.5H), 2.78-2.69 (m, 2H), 2.62 (s, 1.5H), 2.57 (s, 1.5H), 2.07-1.89 (m, 1H), 1.79-1.61 (m, 2H). HPLC (max plot) 97.2%, Rt 2.74 min. UPLC/MS: (MS+) 430.4 ([M+H]+).

Example 81

[2-(4-dimethylamino-piperidin-1-yl)-phenyl]-(5,6,7-trimethyl-1H,3H-2,4,7a,8-tetraaza-cyclopenta[a]inden-2-yl)-methanone

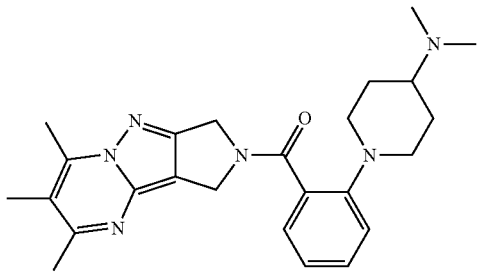

A mixture of Intermediate Z5 (100 mg; 0.31 mmol; 1 eq.) and 4-(dimethylamino)piperidine (0.3 mL) was stirred at 150° C. for 7 hours. 4-(dimethylamino)piperidine (0.2 mL) was added and the reaction mixture was stirred at 150° C. for 2 hours. The reaction mixture was diluted with DCM, washed with 0.1M NaOH, dried over magnesium sulfate and concentrated in vacuo. Purification by mass directed preparative HPLC afforded the title compound (55 mg, 41%) as an off-white solid. $^1$H NMR (CDCl$_3$) δ 7.38-7.31 (m, 2H), 7.09-7.00 (m, 2H), 5.11-4.92 (m, 3H), 4.35 (s, 1H), 3.72 (s, 1H), 3.32 (s, 1H), 2.89 (s, 1H), 2.78 (s, 2H), 2.72 (s, 1H), 2.59 (s, 2H), 2.51 (s, 2H), 2.32 (s, 1H), 2.31 (s, 2H), 2.17 (s, 3H), 2.15 (s, 3H), 2.10-1.82 (m, 3H), 1.43-1.30 (m, 2H). HPLC (max plot) 99.6%, Rt 2.33 min. UPLC/MS: (MS+) 433.5 ([M+H]+).

Example 82

(6-chloro-5,7-dimethyl-1H,3H-2,4,7a,8-tetraaza-cyclopenta[a]inden-2-yl)-[4-fluoro-2-((R)-1-oxetan-3-yl-pyrrolidin-3-yloxy)-phenyl]-methanone

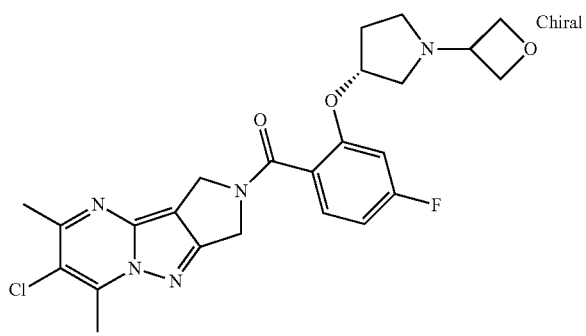 [SMILES: Cc1nc2c3c(nn2c(C)c1Cl)CN(C(=O)c1ccc(F)cc1O[C@@H]1CCN(C2COC2)C1)C3]

A mixture of Example 80 (150 mg; 0.35 mmol; 1 eq.), 3-oxetanone (38 mg; 0.52 mmol; 1.5 eq.) and sodium triacetoxyborohydride (74 mg; 0.35 mmol; 1 eq.) in DCE (4 mL) was stirred at 50° C. for 16 hours. The reaction mixture was diluted with DCM, washed with 0.1M NaOH, dried over magnesium sulfate and concentrated in vacuo. Purification by mass directed preparative HPLC afforded the title compound (55 mg, 41%) as white foam. $^1$H NMR (DMSO-d$_6$) δ 7.41-

7.31 (m, 1H), 7.01 (dd, J=11.5, 2.2 Hz, 1H), 6.88 (td, J=8.4, 2.3 Hz, 1H), 5.05-4.95 (m, 1H), 4.85-4.78 (m, 2H), 4.69-4.48 (m, 2H), 4.47-4.37 (m, 2H), 4.37-4.21 (m, 2H), 3.60-3.48 (m, 1H), 2.90-2.70 (m, 1H), 2.84 (s, 1.5H), 2.80 (s, 1.5H), 2.62 (s, 1.5H), 2.59-2.53 (m, 2H), 2.56 (s, 1.5H), 2.42-2.15 (m, 2H), 1.84-1.70 (m, 1H). HPLC (max plot) 99.5%, Rt 2.74 min. UPLC/MS: (MS+) 486.5 ([M+H]$^+$).

Example 83

(6-chloro-5,7-dimethyl-1H,3H-2,4,7a,8-tetraaza-cyclopenta[a]inden-2-yl)-[4-fluoro-2-((S)-pyrrolidin-3-yloxy)-phenyl]-methanone formic acid salt

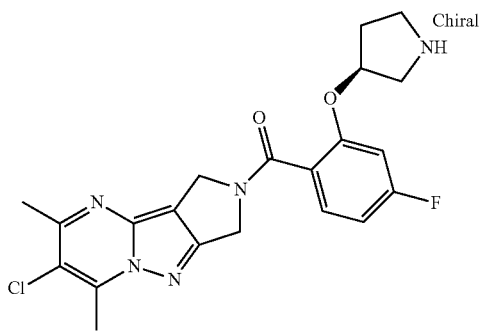 [SMILES: Cc1nc2c3c(nn2c(C)c1Cl)CN(C(=O)c1ccc(F)cc1O[C@H]1CCNC1)C3]

Step 1: (S)-3-[2-(6-chloro-5,7-dimethyl-1H,3H-2,4,7a,8-tetraaza-cyclopenta[a]indene-2-carbonyl)-5-fluoro-phenoxy]-pyrrolidine-1-carboxylic acid tert-butyl ester The title compound was prepared following procedure described in Method G starting from N-boc-(S)-3-hydroxy-pyrrolidine and Intermediate Z2. After work up, the residue was purified by column chromatography (20% to 50% EA in heptane) to afford the title compound (1 g, 95%) as a yellow oil. HPLC (max plot) 96.7%, Rt 4.51 min. UPLC/MS: (MS+) 530.4 ([M+H]$^+$).

Step 2: (6-chloro-5,7-dimethyl-1H,3H-2,4,7a,8-tetraaza-cyclopenta[a]inden-2-yl)-[4-fluoro-2-((S)-pyrrolidin-3-yloxy)-phenyl]-methanone formic acid salt HCl (2.64 mL) was added to a solution of (S)-3-[2-(6-chloro-5,7-dimethyl-1H,3H-2,4,7a,8-tetraaza-cyclopenta[a]indene-2-carbonyl)-5-fluoro-phenoxy]-pyrrolidine-1-carboxylic acid tert-butyl ester (1.4 g; 2.64 mmol; 1 eq.) in 1,4-dioxane (10 mL) and the reaction mixture was stirred at room temperature for 16 hours then concentrated in vacuo. The residue was taken up in DCM, washed with 0.1M NaOH, dried over magnesium sulfate and concentrated in vacuo. Purification by mass directed preparative HPLC afforded the title compound (48 mg, 4%) as a yellow solid. $^1$H NMR (DMSO-d$_6$) δ 8.28 (s, 1H), 7.44-7.33 (m, 1H), 7.17-7.09 (m, 1H), 6.91 (td, J=8.4, 2.3 Hz, 1H), 5.14-5.06 (m, 1H), 4.86-4.78 (m, 2H), 4.63-4.42 (m, 2H), 3.35-3.21 (m, 1H), 3.08-2.85 (m, 3H), 2.83 (s, 1.5H), 2.80 (s, 1.5H), 2.61 (s, 1.5H), 2.55 (s, 1.5H), 2.16-1.97 (m, 1H), 1.95-1.83 (m, 1H). HPLC (max plot) 93.3%, Rt 2.67 min. UPLC/MS: (MS+) 430.4 ([M+H]$^+$).

Example 84

(6-chloro-5,7-dimethyl-1H,3H-2,4,7a,8-tetraaza-cyclopenta[a]inden-2-yl)-[2-(1-isopropyl-pwrolidin-3-ylmethoxy)-phenyl]-methanone

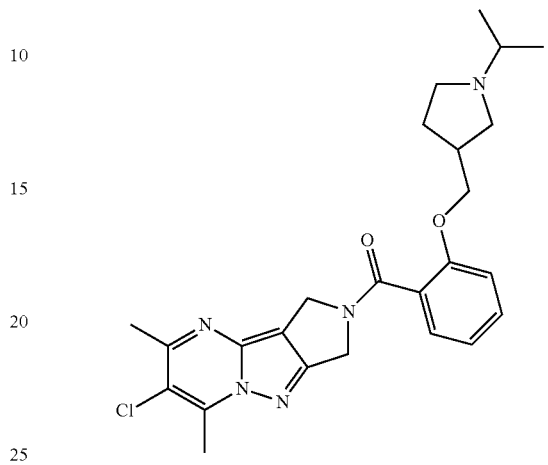

Step 1: 3-[2-(6-chloro-5,7-dimethyl-1H,3H-2,4,7a,8-tetraaza-cyclopenta[a]indene-2-carbonyl)-phenoxymethyl]-pyrrolidine-1-carboxylic acid tert-butyl ester The title compound was prepared following procedure described in Method G starting from tert-butyl 3-(hydroxymethyl)pyrrolidine-1-carboxylate and Intermediate Z2. After work up, the residue was purified by column chromatography (20% EA in cyclohexane to EA) to afford the title compound (321 mg, 38%) as yellow solid. HPLC (max plot) 98.2%, Rt 4.58 min. UPLC/MS: (MS+) 526.4 ([M+H]$^+$).

Step 2: (6-chloro-5,7-dimethyl-1H,3H-2,4,7a,8-tetraaza-cyclopenta[a]inden-2-yl)-[2-(pyrrolidin-3-ylmethoxy)-phenyl]-methanone formic acid salt A 4M solution of HCl in 1,4-dioxane (1.5 mL; 5.99 mmol; 10 eq.) was added to a suspension of 3-[2-(6-chloro-5,7-dimethyl-1H,3H-2,4,7a,8-tetraaza-cyclopenta[a]indene-2-carbonyl)-phenoxymethyl]-pyrrolidine-1-carboxylic acid tert-butyl ester (315 mg; 0.6 mmol; 1 eq.) in 1,4-dioxane (10 mL) followed by water (30 µL) and the resulting mixture was stirred at room temperature for 5 hours. After concentration in vacuo, the residue was partitioned between DCM and 1M NaOH and the aqueous layer was extracted with DCM. The combined organic phase was dried over sodium sulfate and concentrated in vacuo. Purification by mass directed preparative HPLC afforded the title compound (51 mg, 18%) as a white solid. HPLC (max plot) 97.4%, Rt 2.74 min. UPLC/MS: (MS+) 426.4 ([M+H]$^+$).

Step 3: (6-chloro-5,7-dimethyl-1H,3H-2,4,7a,8-tetraaza-cyclopenta[a]inden-2-yl)-[2-(1-isopropyl-pyrrolidin-3-ylmethoxy)-phenyl]-methanone Sodium triacetoxyborohydride (90 mg; 0.42 mmol; 4 eq.) was added to a solution of (6-chloro-5,7-dimethyl-1H,3H-2,4,7a,8-tetraaza-cyclopenta[a]inden-2-yl)-[2-(pyrrolidin-3-ylmethoxy)-phenyl]-methanone formic acid salt (50 mg; 0.11 mmol; 1 eq.), acetone (47 µL; 0.64 mmol; 6 eq.) and AcOH (7 µL; 0.13 mmol; 1.2 eq.) in DCM (3 mL) and the reaction mixture was stirred at room temperature for 16 hours. The solution was diluted with DCM, washed with sat. aq. NaHCO₃, dried over sodium sulfate and concentrated in vacuo. Purification by mass directed preparative HPLC afforded the title compound (47 mg, 76%) as a white solid. ¹H NMR (CDCl₃) δ 7.44-7.30 (m, 2H), 7.12-6.98 (m, 1H), 6.98-6.87 (m, 1H), 5.07-4.92 (m, 2H), 4.63 (br s, 2H), 4.09-3.86 (m, 2H), 2.88 (d, J=18.2 Hz, 4H), 2.65 (d, J=23.0 Hz, 5H), 2.50-2.05 (m, 3H), 2.04-1.84 (m, 1H), 1.58 (dt, J=13.2, 5.8 Hz, 1H), 1.02-0.81 (m, 6H). HPLC (max plot) 94.3%, Rt 2.92 min. UPLC/MS: (MS+) 468.5 ([M+H]⁺).

Example 85

(6-chloro-5,7-dimethyl-1H,3H-2,4,7a,8-tetraaza-cyclopenta[a]inden-2-yl)-[4-fluoro-2-(1-isopropyl-piperidin-4-yloxy)-phenyl]-methanone

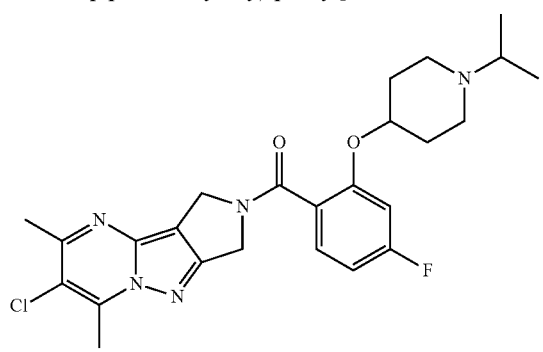

A mixture of Example 64 (110 mg; 0.25 mmol; 1 eq.), acetone (109 μL; 1.49 mmol; 6 eq.) and sodium triacetoxyborohydride (210 mg; 0.99 mmol; 4 eq.) in DCM (6 mL) was stirred at room temperature for 60 hours. The reaction mixture was diluted with DCM, washed with sat. aq. NaHCO₃, dried over sodium sulfate and concentrated in vacuo. Purification by mass directed preparative HPLC afforded the title compound (68 mg, 56%) as a yellow powder. ¹H NMR (CDCl₃) δ 7.33 (td, J=8.2, 6.7 Hz, 1H), 6.80-6.63 (m, 2H), 5.05-4.91 (m, 2H), 4.67 (br s, 2H), 4.36 (br s, 1H), 2.91 (s, 2H), 2.86 (s, 1H), 2.78-0.52 (m, 6H), 2.46-2.24 (m, 2H), 2.06-1.88 (m, 2H), 1.88-1.70 (m, 2H), 0.94 (d, J=6.5 Hz, 6H). HPLC (max plot) 94.1%, Rt 3.02 min. UPLC/MS: (MS+) 486.5 ([M+H]⁺).

Example 86

(6-chloro-5,7-dimethyl-1H,3H-2,4,7a,8-tetraaza-cyclopenta[a]inden-2-yl)-{4-fluoro-2-[(S)-1-(tetrahydro-pyran-4-yl)-pyrolidin-3-yloxy]-phenyl}-methanone

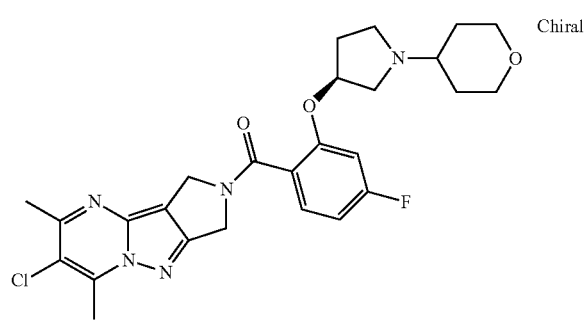 [SMILES: Cc1nc2c3c(nn2c(C)c1Cl)CN(C(=O)c1ccc(F)cc1O[C@H]1CCN(C2CCOCC2)C1)C3]

A mixture of Example 83 (150 mg; 0.35 mmol; 1 eq.), tetrahydropyran-4-one (52 mg; 0.52 mmol; 1.5 eq.) and sodium triacetoxyborohydride (74 mg; 0.35 mmol; 1 eq.) in DCE (4 mL) was stirred at 50° C. for 16 hours. The reaction mixture was diluted with DCM, washed with sat. aq. NaHCO₃, dried over magnesium sulfate and concentrated in vacuo. Purification by column chromatography (EA to EA/MeOH/TEA, 90/10/2) afforded the title compound (100 mg, 56%) as white foam. ¹H NMR (DMSO-d₆) δ 7.41-7.30 (m, 1H), 6.99 (dd, J=11.5, 2.2 Hz, 1H), 6.87 (td, J=8.4, 2.3 Hz, 1H), 5.04-4.94 (m, 1H), 4.84-4.78 (m, 2H), 4.73-4.45 (m, 2H), 3.75-3.58 (m, 2H), 3.21-3.05 (m, 2H), 2.84 (s, 1.5H), 2.81 (s, 1.5H), 2.79-2.63 (m, 3H), 2.62 (s, 1.5H), 2.56 (s, 1.5H), 2.35-2.14 (m, 2H), 2.14-2.00 (m, 1H), 1.80-1.67 (m, 1H), 1.62-1.50 (m, 2H), 1.30-1.02 (m, 2H). HPLC (max plot) 94.2%, Rt 2.83 min. UPLC/MS: (MS+) 514.6 ([M+H]⁺).

Example 87

(6-chloro-5,7-dimethyl-1H,3H-2,4,7a,8-tetraaza-cyclopenta[a]inden-2-yl)-[4-fluoro-2-((S)-1-methyl-pwrolidin-3-yloxy)-phenyl]-methanone

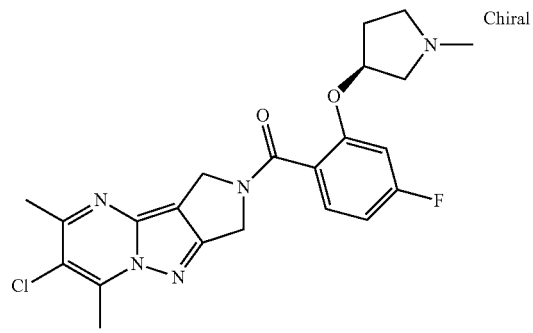

TFA (1 mL) was added to a cold (0° C.) mixture of Example 83 (150 mg; 0.35 mmol; 1 eq.), formaldehyde (0.26 mL; 3.49 mmol; 10 eq.) and NaBH₄ (66 mg; 1.74 mmol; 5 eq.) in THF (12 mL) and the resulting mixture was stirred at room temperature for 16 hours. The reaction mixture was diluted with EA, washed with 0.1M NaOH, dried over magnesium sulfate and concentrated in vacuo. Purification by column chromatography (EA to EA/MeOH/TEA, 90/10/2) afforded the title compound (35 mg, 23%) as yellow foam. ¹H NMR (DMSO-d₆) δ 7.40-7.31 (m, 1H), 6.98 (dd, J=11.5, 2.2 Hz, 1H), 6.87 (td, J=8.4, 2.3 Hz, 1H), 5.02-4.90 (m, 1H), 4.85-4.79 (m, 2H), 4.66-4.40 (m, 2H), 2.84 (s, 1.5H), 2.81 (s, 1.5H), 2.79-2.70 (m, 1H), 2.62 (s, 1.5H), 2.59-2.53 (m, 2H), 2.55 (s, 1.5H), 2.37-2.20 (m, 2H), 2.17 (s, 1.5H), 2.16 (s, 1.5H), 1.78-1.63 (m, 1H). HPLC (max plot) 94.9%, Rt 2.74 min. UPLC/MS: (MS+) 444.5 ([M+H]⁺).

Example 88

(6-chloro-5,7-dimethyl-1H,3H-2,4,7a,8-tetraaza-cyclopenta[a]inden-2-yl)-[4-fluoro-2-((R)-1-methyl-pyrrolidin-3-yloxy)-phenyl]-methanone

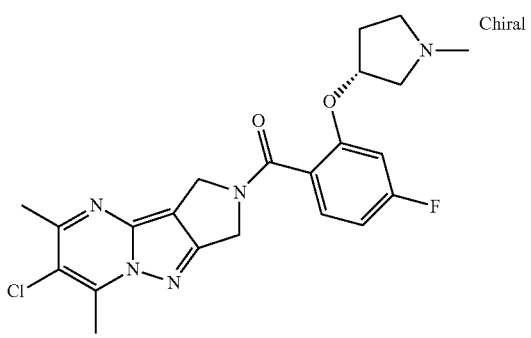

TFA (15 µL) was added to a cold (0° C.) mixture of Example 80 (150 mg; 0.35 mmol; 1 eq.), formaldehyde (0.26 mL; 3.49 mmol; 10 eq.) and NaBH$_4$ (66 mg; 1.74 mmol; 5 eq.) in THF (12 mL) and the resulting mixture was stirred at room temperature for 16 hours. The reaction mixture was diluted with EA, washed with 0.1M NaOH, dried over magnesium sulfate and concentrated in vacuo. Purification by column chromatography (EA to EA/MeOH/TEA, 90/10/2) afforded the title compound (50 mg, 32%) as yellow foam. $^1$H NMR (DMSO-d$_6$) δ 7.39-7.30 (m, 1H), 6.98 (dd, J=11.5, 2.3 Hz, 1H), 6.87 (td, J=8.4, 2.3 Hz, 1H), 5.01-4.92 (m, 1H), 4.85-4.78 (m, 2H), 4.66-4.45 (m, 2H), 2.85 (s, 1.5H), 2.81 (s, 1.5H), 2.79-2.70 (m, 1H), 2.62 (s, 1.5H), 2.60-2.52 (m, 2H), 2.55 (s, 1.5H), 2.35-2.2.20 (m, 2H), 2.17 (s, 1.5H), 2.16 (s, 1.5H), 1.81-1.60 (m, 1H). HPLC (max plot) 96.7%, Rt 2.74 min. UPLC/MS: (MS+) 444.5 ([M+H]$^+$).

Example 89

(6-chloro-5,7-dimethyl-1H,3H-2,4,7a,8-tetraaza-cyclopenta[a]inden-2-yl)-{4-fluoro-2-[(R)-1-(tetrahydro-pyran-4-yl)-pyrrolidin-3-yloxy]-phenyl}-methanone

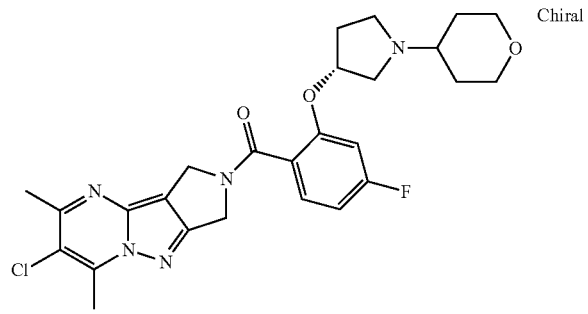 [SMILES: Cc1nc2c3c(nn2c(C)c1Cl)CN(C(=O)c1ccc(F)cc1O[C@@H]1CCN(C2CCOCC2)C1)C3]

A mixture of Example 80 (150 mg; 0.35 mmol; 1 eq.), tetrahydropyran-4-one (52 mg; 0.52 mmol; 1.5 eq.) and sodium triacetoxyborohydride (74 mg; 0.35 mmol; 1 eq.) in DCE (4 mL) was stirred at 50° C. for 16 hours. The reaction mixture was diluted with DCM, washed with sat. aq. NaHCO$_3$, dried over magnesium sulfate and concentrated in vacuo. Purification by column chromatography (EA to EA/MeOH/TEA, 90/10/2) afforded the title compound (80 mg, 45%) as white foam. $^1$H NMR (DMSO-d$_6$) δ 7.41-7.31 (m, 1H), 6.99 (dd, J=11.5, 2.2 Hz, 1H), 6.87 (td, J=8.4, 2.3 Hz, 1H), 5.03-4.94 (m, 1H), 4.85-4.77 (m, 2H), 4.75-4.44 (m, 2H), 3.74-3.59 (m, 2H), 3.22-3.06 (m, 2H), 2.85 (s, 1.5H), 2.81 (s, 1.5H), 2.79-2.64 (m, 3H), 2.62 (s, 1.5H), 2.56 (s, 1.5H), 2.35-2.15 (m, 2H), 2.14-2.00 (m, 1H), 1.82-1.68 (m, 1H), 1.63-1.50 (m, 2H), 1.31-1.03 (m, 2H). HPLC (max plot) 95.1%, Rt 2.83 min. UPLC/MS: (MS+) 514.5 ([M+H]$^+$).

Example 90

(6-chloro-5,7-dimethyl-1H,3H-2,4,7a,8-tetraaza-cyclopenta[a]inden-2-yl)-[2-(4-hydroxy-4-trifluoromethyl-piperidin-1-ylmethyl)-phenyl]-methanone

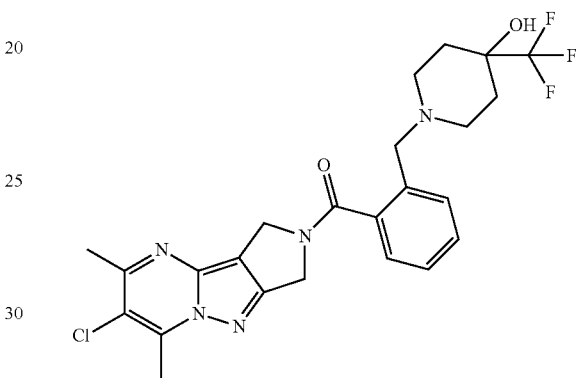

The title compound was prepared following procedure described in Method D starting from Intermediate Z3 and 4-(trifluoromethyl)piperidin-4-ol hydrochloride (Enamine). After purification by crystallization from hot ACN, the title compound was obtained as a white powder (64 mg, 53%). $^1$H NMR (DMSO-d$_6$) δ 7.47-7.31 (m, 4H), 5.61 (d, J=3.7 Hz, 1H), 4.90-4.76 (m, 2H), 4.53-4.33 (m, 2H), 3.47 (br s, 2H), 2.83 (s, 1.5H), 2.77 (s, 1.5H), 2.62 (s, 1.5H), 2.53 (s, 1.5H), 2.25-2.10 (m, 2H), 1.36 (m, 2H), 1.07-0.87 (m, 2H). HPLC (max plot) 98.9%, Rt 3.06 min. UPLC/MS: (MS+) 508.5 ([M+H]$^+$), (MS−) 506.5 ([M−H]−). Melting point: 223-227° C. (ACN).

Example 91

(6-chloro-5,7-dimethyl-1H,3H-2,4,7a,8-tetraaza-cyclopenta[a]inden-2-yl)-{4-fluoro-2-[1-(2-fluoroethyl)-piperidin-4-yloxy]-phenyl}-methanone

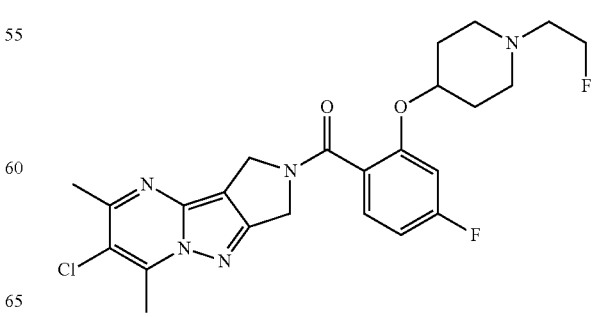

1-Bromo-2-fluoro-ethane (19 mg; 0.15 mmol; 1.1 eq.) was added to a suspension of Example 64 (60 mg; 0.14 mmol; 1 eq.) and NaHCO₃ (114 mg; 1.35 mmol; 10 eq.) in DMF (2 mL) and the reaction mixture was stirred at 100° C. (MW heating) for 30 minutes. 1-Bromo-2-fluoro-ethane (9 mg; 0.07 mmol; 0.5 eq.) was added and the reaction mixture was stirred at 100° C. (MW heating) for 30 minutes. The precipitate was filtered off and the mother liquor was concentrated in vacuo. The residue was diluted with DCM, washed with 1M NaOH, dried over magnesium sulfate and concentrated in vacuo. Purification by column chromatography (5% to 20% MeOH in DCM) followed by crystallization from EA afforded the title compound (33 mg, 49%) as yellow solid. ¹H NMR (CDCl₃) δ 7.40-7.28 (m, 1H), 6.84-6.61 (m, 2H), 5.11-4.90 (m, 2H), 4.66 (br s, 2H), 4.56 (t, J=4.9 Hz, 1H), 4.46-4.29 (m, 2H), 2.91 (s, 1.8H), 2.86 (s, 1.2H), 2.73-2.48 (m, 7H), 2.47-2.30 (m, 2H), 2.07-1.91 (m, 2H), 1.91-1.73 (m, 2H). HPLC (max plot) 98.5%, Rt 2.96 min. UPLC/MS: (MS+) 490.3 ([M+H]⁺).

Example 92

(6-chloro-5,7-dimethyl-1H,3H-2,4,7a,8-tetraaza-cyclopenta[a]inden-2-yl)-(2-piperazin-1-ylmethyl-phenyl)-methanone

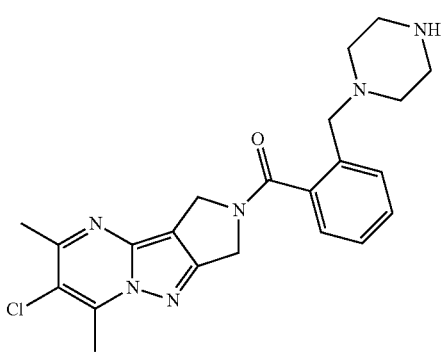 [SMILES: Cc1nc2c3c(nn2c(C)c1Cl)CN(C(=O)c1ccccc1CN1CCNCC1)C3]

The title compound was prepared following procedure described in Method C starting from Intermediate Z3 and piperazine. After purification by flash chromatography (silica, DCM/EtOH/28% aqueous ammonia), the title compound was obtained as a white powder (145 mg, 72%). ¹H NMR (CDCl₃) δ 7.39-7.27 (m, 4H), 5.04-4.96 (m, 2H), 4.62-4.54 (m, 2H), 3.56 (br s, 2H), 2.91 (s, 2H), 2.85 (s, 1H), 2.69 (s, 1H), 2.60 (s, 2H), 2.52 (br s, 4H), 2.37 (br s, 4H). HPLC (max plot) 95.9%, Rt 2.29 min. UPLC/MS: (MS+) 425.4 ([M+H]⁺).

Example 93

(6-chloro-5,7-dimethyl-1H,3H-2,4,7a,8-tetraaza-cyclopenta[a]inden-2-yl)-(2-piperidin-3-yl-phenyl)-methanone

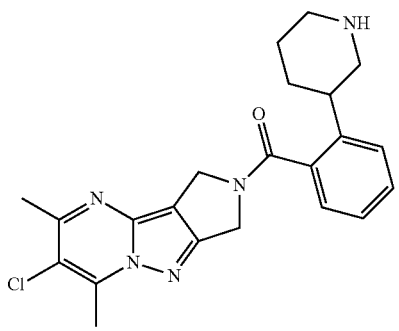 [SMILES: Cc1nc2c3c(nn2c(C)c1Cl)CN(C(=O)c1ccccc1C1CCCNC1)C3]

Step 1: 3-[2-(6-chloro-5,7-dimethyl-1H,3H-2,4,7a,8-tetraaza-cyclopenta[a]indene-2-carbonyl)-phenyl]-piperidine-1-carboxylic acid tert-butyl ester The title compound was prepared following procedure described in Method A starting from Intermediate A3 and 3-(2-carboxy-phenyl)-piperidine-1-carboxylic acid tert-butyl ester (Bio Farma). After purification by flash chromatography (silica, heptane/EtOAc), the title compound was obtained as a white powder (606 mg, 77%). ¹H NMR (CDCl₃) δ 7.44-7.27 (m, 4H), 5.07-5.00 (m, 2H), 4.61-4.46 (m, 2H), 4.26-4.03 (m, 2H), 2.94-2.57 (m, 9H), 2.04 (br s, 1H), 1.75-1.47 (m, 3H), 1.33 (s, 9H). HPLC (max plot) 99.8%, Rt 4.82 min. UPLC/MS: (MS+) 510.6 ([M+H]⁺).

Step 2: (6-chloro-5,7-dimethyl-1H,3H-2,4,7a,8-tetraaza-cyclopenta[a]inden-2-yl)-(2-piperidin-3-yl-phenyl)-methanone The title compound was prepared following procedure described in Method E starting from 3-[2-(6-chloro-5,7-dimethyl-1H,3H-2,4,7a,8-tetraaza-cyclopenta[a]indene-2-carbonyl)-phenyl]-piperidine-1-carboxylic acid tert-butyl ester. After purification by flash chromatography (silica, DCM/EtOH/28% aqueous ammonia), the title compound was obtained as a pale yellow foam (336 mg, 76%). ¹H NMR (DMSO-d₆) δ 7.46-7.39 (m, 2H), 7.39-7.25 (m, 2H), 4.89 (s, 1H), 4.86 (s, 1H), 4.47 (s, 1H), 4.41 (s, 1H), 2.97-2.75 (m, 5H), 2.74-2.37 (m, 6H), 2.20 (s, 1H), 1.89-1.76 (m, 1H), 1.68-1.50 (m, 2H), 1.44-1.25 (m, 1H). HPLC (max plot) 96.8%, Rt 2.80 min. UPLC/MS: (MS+) 410.4 ([M+H]⁺).

Example 94

(6-chloro-5,7-dimethyl-1H,3H-2,4,7a,8-tetraaza-cyclopenta[a]inden-2-yl)-[2-((3aR,6aS)-5-methyl-hexahydro-pyrrolo[3,4-c]pyrrol-2-ylmethyl)-phenyl]-methanone

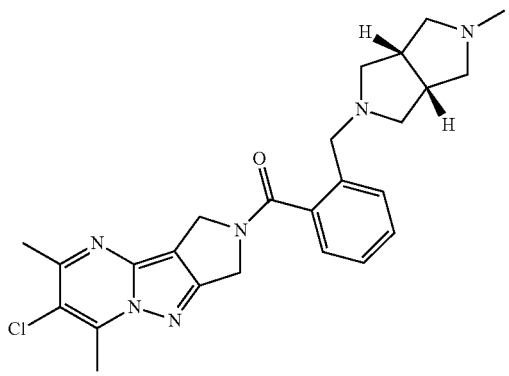

The title compound was prepared following procedure described in Method D starting from Intermediate Z3 and (3aR,6aS)-2-methyl-octahydro-pyrrolo[3,4-c]pyrrole dihydrochloride (ChemBridge). After purification by flash chromatography (silica, DCM/EtOH/28% aqueous ammonia), followed by a crystallization from ACN, the title compound was obtained as a white powder (91 mg, 41%). $^1$H NMR (DMSO-$d_6$) δ 7.48-7.32 (m, 4H), 4.85 (s, 1H), 4.82 (s, 1H), 4.55 (s, 1H), 4.50 (s, 1H), 3.56 (s, 2H), 2.83 (s, 1.5H), 2.78 (s, 1.5H), 2.62 (s, 1.5H), 2.54 (s, 1.5H), 2.42-2.22 (m, 8H), 1.79-1.69 (m, 2H), 1.67 (s, 1.5H), 1.60 (s, 1.5H). HPLC (max plot) 99.8%, Rt 2.24 min. UPLC/MS: (MS+) 465.5 ([M+H]$^+$). Melting point: 174-177° C. (ACN).

Example 95

(6-Chloro-5,7-dimethyl-1H,3H-2,4,7a,8-tetraaza-cyclopenta[a]inden-2-yl)-[2-(4-methyl-[1,4]diazepan-1-ylmethyl)-phenyl]-methanone

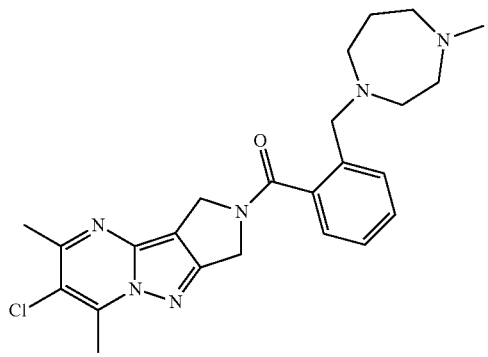

The title compound was prepared following procedure described in Method C starting from Intermediate Z3 and 1-methyl-[1,4]diazepane. After purification by flash chromatography (silica, DCM/EtOH/28% aqueous ammonia), followed by a crystallization from ACN, the title compound was obtained as a white powder (91 mg, 41%). $^1$H NMR (CDCl$_3$) δ 7.37-7.27 (m, 4H), 5.05-4.99 (m, 2H), 4.62-4.57 (m, 2H), 3.71 (br s, 2H), 2.91 (s, 1.9H), 2.85 (s, 1.1H), 2.70 (s, 1.1H), 2.68-2.62 (m, 4H), 2.61 (s, 1.9H), 2.42-2.31 (m, 4H), 2.09 (s, 1.1H), 2.07 (s, 1.9H), 1.66-1.55 (m, 2H). HPLC (max plot) 99.9%, Rt 2.21 min. UPLC/MS: (MS+) 453.5 ([M+H]$^+$). Melting point: 138-141° C. (ACN).

Example 96

(6-chloro-5,7-dimethyl-1H,3H-2,4,7a,8-tetraaza-cyclopenta[a]inden-2-yl)-{4-fluoro-2-[2-(1-methyl-1H-pyrazol-4-yl)-ethoxy]-phenyl}-methanone

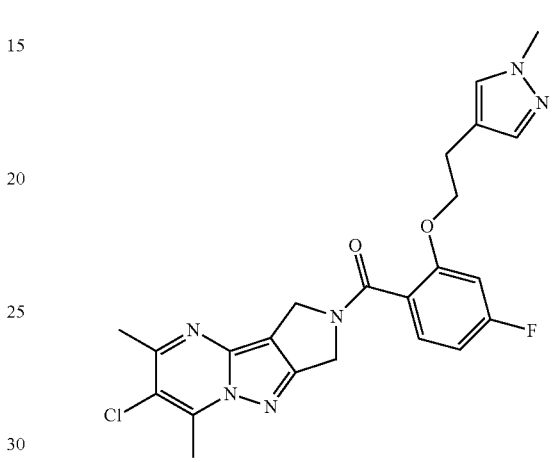

The title compound was prepared following procedure described in Method G starting from 2-(1-methyl-1H-pyrazol-4-yl)-ethanol (104 mg; 0.82 mmol; 1.5 eq.) and Intermediate Z2. After work up, the residue was purified by column chromatography (2% MeOH in DCM) followed by mass directed preparative HPLC to afford the title compound (60 mg, 23%) as a white solid. $^1$H NMR (DMSO-$d_6$) δ 7.39 (s, 1H), 7.33 (ddd, J=8.4, 6.8, 3.0 Hz, 1H), 7.17 (dd, J=6.0, 0.8 Hz, 1H), 7.07 (dd, J=11.8, 2.3 Hz, 1H), 6.86 (td, J=8.4, 2.3 Hz, 1H), 4.83 (s, 1H), 4.80 (s, 1H), 4.36 (s, 1H), 4.32 (s, 1H), 4.16 (m, 2H), 3.46 (s, 1.5H), 3.41 (s, 1.5H), 2.85 (s, 1.5H), 2.81 (s, 1.5H), 2.75 (m, 2H), 2.63 (s, 1.5H), 2.56 (s, 1.5H). HPLC (max plot) 99.5%, Rt 3.56 min; UPLC/MS: (MS+) 469.2 ([M+H]$^+$).

Example 97

(6-chloro-5,7-dimethyl-1H,3H-2,4,7a,8-tetraaza-cyclopenta[a]inden-2-yl)-[2-(hexahydro-pyrrolo[1,2-a]pyrazin-2-ylmethyl)-phenyl]-methanone

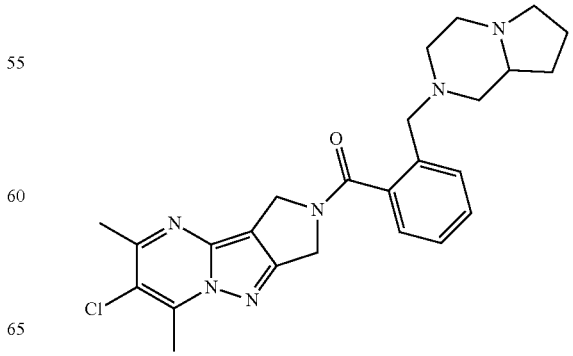

The title compound was prepared following procedure described in Method C starting from Intermediate Z3 and octahydro-pyrrolo[1,2-a]pyrazine (ChemBridge). After purification by flash chromatography (silica, DCM/EtOH/28% aqueous ammonia), followed by a crystallization from ACN, the title compound was obtained as a white powder (111 mg, 67%). ¹H NMR (CDCl₃) δ 7.38-7.27 (m, 4H), 5.00 (s, 2H), 4.56 (s, 2H), 3.63 (br s, 2H), 2.94-2.59 (m, 10H), 2.29-2.13 (m, 1H), 1.91-1.77 (m, 1H), 1.76-1.15 (m, 7H). HPLC (max plot) 99.6%, Rt 2.41 min. UPLC/MS: (MS+) 465.4 ([M+H]⁺). Melting point: 180-182° C. (ACN).

Example 98

(6-chloro-5,7-dimethyl-1H,3H-2,4,7a,8-tetraaza-cyclopenta[a]inden-2-yl)-[2-(2-dimethylamino-ethoxy)-4-fluoro-phenyl]-methanone

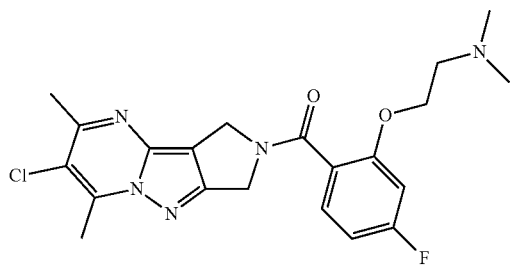 [SMILES: Cc1nc2c3c(nn2c(C)c1Cl)CN(C(=O)c1ccc(F)cc1OCCN(C)C)C3]

A mixture of Intermediate Z2 (1 g; 2.74 mmol; 1 eq.), (2-chloro-ethyl)-dimethyl-amine hydrochloride (474 mg; 3.29 mmol; 1.2 eq.) and K₂CO₃ (947 mg; 6.85 mmol; 2.5 eq.) in DMA (20 mL) was stirred at 60° C. for 6 hours. The reaction mixture was diluted with DCM, washed with brine, dried over sodium sulfate and concentrated in vacuo. Purification by column chromatography (DCM/EtOH/NH₄OH, 90/9.5/0.5) followed by recrystallization from ACN afforded the title compound (400 mg, 34%) as white solid. ¹H NMR (CDCl₃) δ 7.39-7.31 (m, 1H), 6.83-6.68 (m, 2H), 5.02-4.97 (m, 2H), 4.68 (br s, 2H), 4.20 (t, J=5.6 Hz, 2H), 2.93 (s, 1.8H), 2.88 (s, 1.2H), 2.85-2.75 (m, 2H), 2.71 (s, 1.2H), 2.64 (s, 1.8H), 2.32 (br s, 6H). HPLC (max plot) 99.7%, Rt 2.65 min. UPLC/MS: (MS+) 432.4 ([M+H]⁺).

Example 99

(6-chloro-5,7-dimethyl-1H,3H-2,4,7a,8-tetraaza-cyclopenta[a]inden-2-yl)-[2-((S)-piperidin-3-yloxy)-phenyl]-methanone Chiral

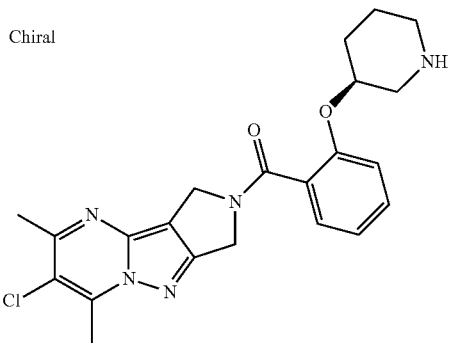 [SMILES: Cc1nc2c3c(nn2c(C)c1Cl)CN(C(=O)c1ccccc1O[C@H]1CCCNC1)C3]

Step 1: (S)-3-[2-(6-chloro-5,7-dimethyl-1H,3H-2,4,7a,8-tetraaza-cyclopenta[a]indene-2-carbonyl)-phenoxy]-piperidine-1-carboxylic acid tert-butyl ester The title compound was prepared following procedure described in Method G starting from Intermediate B6 and Intermediate Z4. After work up, the residue was purified by column chromatography (EA/heptane) to afford the title compound (270 mg, 76%) as a white solid. ¹H NMR (CDCl₃) δ 7.41-7.32 (m, 2H), 7.08-7.02 (m, 2H), 5.01-5.00 (m, 2H), 4.63 (br s, 2H), 4.29-4.03 (m, 2H), 3.74 (br s, 1H), 3.01-2.83 (m, 2H), 2.90 (s, 2H), 2.85 (s, 1H), 2.69 (s, 1H), 2.61 (s, 2H), 2.06-2.04 (m, 1H), 1.77-1.68 (m, 1H), 1.63-1.38 (m, 2H), 1.42 (s, 9H). HPLC (max plot) 99.1%, Rt 4.60 min. UPLC/MS: (MS+) 526.4 ([M+H]⁺).

Step 2: (6-chloro-5,7-dimethyl-1H,3H-2,4,7a,8-tetraaza-cyclopenta[a]inden-2-yl)-[2-((S)-piperidin-3-yloxy)-phenyl]-methanone A mixture of (S)-3-[2-(6-chloro-5,7-dimethyl-1H,3H-2,4,7a,8-tetraaza-cyclopenta[a]indene-2-carbonyl)-phenoxy]-piperidine-1-carboxylic acid tert-butyl ester (270 mg; 0.51 mmol; 1 eq.) and TFA (2 mL) in DCM (2 mL) was stirred at room temperature for 1 hour then concentrated in vacuo. The residue was taken up in water, the pH made basic with 5M NaOH and extracted with DCM (2×). The combined organic layer was dried over magnesium sulfate and concentrated in vacuo to afford the title compound (176 mg, 81%) as white foam. ¹H NMR (CDCl₃) δ 7.41-7.33 (m, 2H), 7.08-6.98 (m, 2H), 5.02-5.01 (m, 2H), 4.67 (br s, 2H), 4.33 (br s, 1H), 3.11-3.06 (m, 1H), 2.91 (s, 2H), 2.85 (s, 1H), 2.84-2.72 (m, 3H), 2.69 (s, 1H), 2.62 (s, 2H), 1.98-1.91 (m, 1H), 1.80-1.69 (m, 3H), 1.50-1.40 (m, 1H). HPLC (max plot) 98.9%, Rt 2.85 min. UPLC/MS: (MS+) 426.4 ([M+H]⁺).

Example 100

(6-chloro-1,1,5,7-tetramethyl-1H,3H-2,4,7a,8-tetraaza-cyclopenta[a]inden-2-yl)-[2-(piperidin-4-yloxy)-phenyl]-methanone hydrochloride

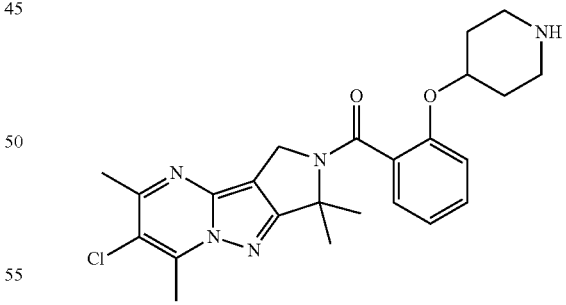

Step 1: 4-[2-(6-chloro-1,1,5,7-tetramethyl-1H,3H-2,4,7a,8-tetraaza-cyclopenta[a]indene-2-carbonyl)-phenoxy]-piperidine-1-carboxylic acid tert-butyl ester The title compound was prepared following procedure described in Method A starting from Intermediate A11 and Intermediate B3. After work up, the residue was purified by column chromatography (heptane to 50% EA in heptane) to afford the title compound (306 mg, 79%) as white solid. HPLC (max plot) 99.9%, Rt 5.18 min. UPLC/MS: (MS+) 554.5 ([M+H]⁺).

Step 2: (6-chloro-1,1,5,7-tetramethyl-1H,3H-2,4,7a, 8-tetraaza-cyclopenta[a]inden-2-yl)-[2-(piperidin-4-yloxy)-phenyl]-methanone hydrochloride A 4M solution of HCl in 1,4-dioxane (0.55 mL; 2.21 mmol; 4 eq.) was added to a suspension of 4-[2-(6-chloro-1,1,5,7-tetramethyl-1H,3H-2,4,7a,8-tetraaza-cyclopenta[a]indene-2-carbonyl)-phenoxy]-piperidine-1-carboxylic acid tert-butyl ester (306 mg; 0.55 mmol; 1 eq.) in 1,4-dioxane (6 mL) followed by water (604) and the resulting mixture was stirred at room temperature for 16 hours. A 4M solution of HCl in 1,4-dioxane (0.55 mL; 2.21 mmol; 4 eq.) was added and the resulting mixture was stirred at room temperature for 3 hours. Concentration in afforded the title compound (34 mg, quantitative) as an orange solid. ¹H NMR (DMSO-d₆) δ 9.09 (br s, 1H), 8.76 (br s, 1H), 7.48-7.38 (m, 1H), 7.37-7.17 (m, 2H), 7.06 (t, J=7.1 Hz, 1H), 4.85-4.67 (m, 1H), 4.41 (s, 2H), 3.05 (s, 4H), 2.84 (s, 3H), 2.54 (s, 3H), 2.06 (br s, 2H), 1.90 (s, 6H), 1.87-1.71 (m, 2H). HPLC (max plot) 99.8%, Rt 3.09 min. UPLC/MS: (MS+) 454.5 ([M+H]⁺).

Example 101

(6-chloro-5,7-dimethyl-1H,3H-2,4,7a,8-tetraaza-cyclopenta[a]inden-2-yl)-[2-(morpholin-2-yl-methoxy)-phenyl]-methanone hydrochloride

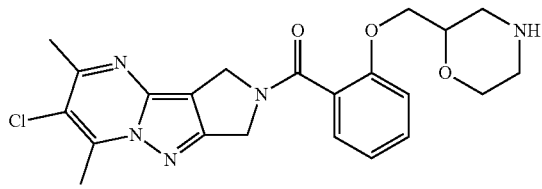 [SMILES: Cc1nc2c3c(nn2c(C)c1Cl)CN(C(=O)c1ccccc1OCC1CNCCO1)C3]

Step 1: 2-[2-(6-chloro-5,7-dimethyl-1H,3H-2,4,7a,8-tetraaza-cyclopenta[a]indene-2-carbonyl)-phenoxymethyl]-morpholine-4-carboxylic acid tert-butyl ester The title compound was prepared following procedure described in Method A starting from Intermediate B7 and Intermediate A3. After work up, the residue was purified by column chromatography (40% to 70% EA in heptane) to afford the title compound (367 mg, 98%) as yellow oil. ¹H NMR (CDCl₃) δ 7.45-7.30 (m, 2H), 7.13-7.00 (m, 1H), 6.96 (d, J=8.4 Hz, 1H), 5.09-4.96 (m, 2H), 4.84-4.53 (m, 2H), 4.19-3.98 (m, 2H), 3.91 (br s, 1H), 3.84-3.55 (m, 3H), 3.52-3.30 (m, 1H), 2.90 (s, 2H), 2.85 (s, 1H), 2.78-2.65 (m, 3H), 2.61 (s, 2H), 1.47-1.32 (m, 9H).). UPLC/MS: (MS+) 542.5 ([M+H]⁺).

Step 2: (6-chloro-5,7-dimethyl-1H,3H-2,4,7a,8-tetraaza-cyclopenta[a]inden-2-yl)-[2-(morpholin-2-ylmethoxy)-phenyl]-methanone A 4M solution of HCl in 1,4-dioxane (0.6 mL; 2.39 mmol; 4 eq.) was added to a suspension of 2-[2-(6-chloro-5,7-dimethyl-1H,3H-2,4,7a,8-tetraaza-cyclopenta[a]indene-2-carbonyl)-phenoxymethyl]-morpholine-4-carboxylic acid tert-butyl ester (366 mg; 0.6 mmol; 1 eq.) in 1,4-dioxane (3 mL) followed by water (304) and the resulting mixture was stirred at room temperature for 16 hours. A 4M solution of HCl in 1,4-dioxane (0.3 mL; 1.2 mmol; 2 eq.) was added and the resulting mixture was stirred at room temperature for 3 hours. Concentration in vacuo afforded the title compound (298 mg, quantitative) as an orange solid. ¹H NMR (DMSO-d₆) δ 7.46 (t, J=7.9 Hz, 1H), 7.38-7.28 (m, 1H), 7.15 (d, J=8.5 Hz, 1H), 7.08 (t, J=7.4 Hz, 1H), 4.95-4.77 (m, 2H), 4.69-4.39 (m, 2H), 4.27-4.06 (m, 2H), 4.06-3.87 (m, 1H), 3.77-3.53 (m, 2H), 3.30-3.17 (m, 1H), 3.12-2.94 (m, 1H), 2.92-2.74 (m, 4H), 2.72-2.53 (m, 4H). HPLC (max plot) 99.5%, Rt 2.70 min. UPLC/MS: (MS+) 442.4 ([M+H]⁺).

Example 102

(6-chloro-5,7-dimethyl-1H,3H-2,4,7a,8-tetraaza-cyclopenta[a]inden-2-yl)-[2-(1,1-difluoro-2-hydroxy-ethoxy)-phenyl]-methanone

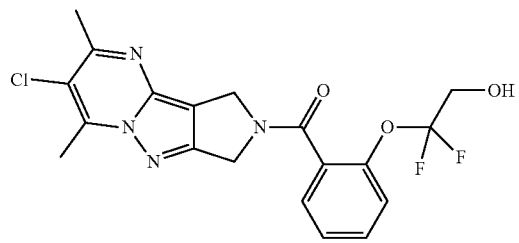 [SMILES: Cc1nc2c3c(nn2c(C)c1Cl)CN(C(=O)c1ccccc1OC(F)(F)CO)C3]

Step 1: [2-(6-chloro-5,7-dimethyl-1H,3H-2,4,7a,8-tetraaza-cyclopenta[a]indene-2-carbonyl)-phenoxy]-difluoro-acetic acid ethyl ester Sodium hydride (55-65%; 98 mg; 2.45 mmol; 1.2 eq.) was added to a solution of Intermediate Z4 (700 mg; 2.04 mmol; 1 eq.) in DMF (10 mL) and the resulting mixture was stirred at room temperature for 5 minutes whereupon ethyl bromodifluoroacetate (315 μL); 2.45 mmol; 1.2 eq.) was added. The reaction mixture was stirred at 100° C. (MW heating) for 20 minutes then diluted with EA. The solution was washed with water (3×) dried on magnesium sulfate and concentrated in vacuo. Purification by column chromatography (25% to 35% ethyl acetate in cyclohexane) afforded the title compound (60 mg, 6%) as a colourless oil. UPLC/MS: (MS+) 464.5 ([M+H]⁺).

Step 2: (6-chloro-5,7-dimethyl-1H,3H-2,4,7a,8-tetraaza-cyclopenta[a]inden-2-yl)-[2-(1,1-difluoro-2-hydroxy-ethoxy)-phenyl]-methanone Lithium borohydride (2.81 mg; 0.13 mmol; 1 eq.) was added to a solution of [2-(6-chloro-5,7-dimethyl-1H,3H-2,4,7a,8-tetraaza-cyclopenta[a]indene-2-carbonyl)-phenoxy]-difluoro-acetic acid ethyl ester (60 mg; 0.13 mmol; 1 eq.) in 1,4-dioxane (1 mL) and the resulting mixture was stirred at room temperature for 1.5 hour. The solution was diluted with EA, washed with brine, dried over magnesium sulfate and concentrated in vacuo. Purification by column chromatography (30% to 75% EA in cyclohexane) followed by crystallization from ACN afforded the title compound (12 mg, 22%). HPLC (max plot) 98.4%, Rt 3.46 min. UPLC/MS: (MS+) 423.2 ([M+H]+).

Example 103

2-[2-(6-chloro-5,7-dimethyl-1H,3H-2,4,7a,8-tetraaza-cyclopenta[a]indene-2-carbonyl)-phenoxy]-2,2-difluoro-acetamide

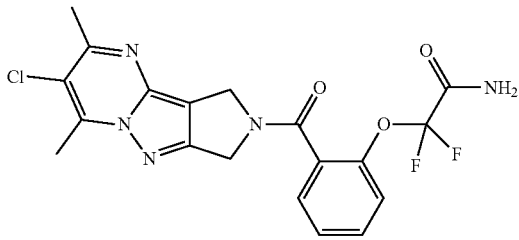 [SMILES: Cc1nc2c3c(nn2c(C)c1Cl)CN(C(=O)c1ccccc1OC(F)(F)C(N)=O)C3]

To [2-(6-chloro-5,7-dimethyl-1H,3H-2,4,7a,8-tetraaza-cyclopenta[a]indene-2-carbonyl)-phenoxy]-difluoro-acetic acid ethyl ester (from example 102 step 1) (70 mg; 0.15 mmol; 1 eq.) was added NH₄OH/MeOH and the reaction mixture was stirred at room temperature for 1.5 hour then concentrated in vacuo. The residue taken up in EA, washed sat. aq. NH₄Cl, dried over magnesium sulfate and concentrated in vacuo. Purification by mass directed preparative HPLC afforded the title compound (25 mg, 38%) as a white solid. HPLC (max plot) 99.6%, Rt 3.28 min. UPLC/MS: (MS+) 436.4 ([M+H]+).

Example 104

[2-(azetidin-3-yloxy)-phenyl]-(6-chloro-5,7-dimethyl-1H,3H-2,4,7a,8-tetraaza-cyclopenta[a]inden-2-yl)-methanone formic acid salt

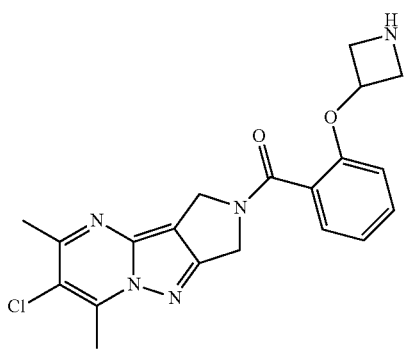 [SMILES: Cc1nc2c3c(nn2c(C)c1Cl)CN(C(=O)c1ccccc1OC1CNC1)C3]

Step 1: 3-[2-(6-chloro-5,7-dimethyl-1H,3H-2,4,7a,8-tetraaza-cyclopenta[a]indene-2-carbonyl)-phenoxy]-azetidine-1-carboxylic acid tert-butyl ester The title compound was prepared following procedure described in Method A starting from Intermediate B8 and Intermediate A3. After work up, the residue was purified by recrystallization from ACN to afford the title compound (1.07 g, 66%) as a white solid. ¹H NMR (CDCl₃) δ 7.41-7.33 (m, 2H), 7.12-7.05 (m, 1H), 6.61-6.59 (m, 1H), 5.03-5.02 (m, 2H), 4.95-4.89 (m, 1H), 4.63 (s, 2H), 4.30-4.25 (m, 2H), 4.00-3.95 (m, 2H), 2.91 (s, 2H), 2.85 (m, 1H), 2.70 (s, 1H), 2.62 (s, 2H). HPLC (max plot) 99.1%, Rt 4.24 min. UPLC/MS: (MS−) 496.5 ([M−H]−).

Step 2: [2-(azetidin-3-yloxy)-phenyl]-(6-chloro-5,7-dimethyl-1H,3H-2,4,7a,8-tetraaza-cyclopenta[a]inden-2-yl)-methanone formic acid salt A 4M solution of HCl in 1,4-dioxane (2.51 mL; 10.04 mmol; 5 eq.) was added to a solution of 3-[2-(6-chloro-5,7-dimethyl-1H,3H-2,4,7a,8-tetraaza-cyclopenta[a]indene-2-carbonyl)-phenoxy]-azetidine-1-carboxylic acid tert-butyl ester (1 g; 2.01 mmol; 1 eq.) in 1,4-dioxane (15 mL) and the resulting mixture was stirred at room temperature for 3.5 hours. A 4M solution of HCl in 1,4-dioxane (1 mL; 4 mmol; 2 eq.) was added and the reaction mixture was stirred at room temperature for 2.5 hours then concentrated in vacuo. The residue was taken up in water and the pH made basic. The solution was extracted with DCM and the organic layer dried over magnesium sulfate and concentrated in vacuo. Purification by mass directed preparative HPLC afforded the title compound (60 mg, 7%) as a white solid. ¹H NMR (CDCl₃) δ 8.41 (s, 1H), 7.40-7.33 (m, 4H), 7.14-7.07 (m, 1H), 6.66-6.62 (m, 1H), 5.13-5.07 (m, 1H), 4.97 (s, 2H), 4.59 (s, 2H), 4.29-4.23 (m, 2H), 3.97-3.92 (m, 2H), 2.88 (s, 2H), 2.83 (s, 1H), 2.67 (s, 1H), 2.60 (s, 2H). HPLC (max plot) 97.3%, Rt 2.45 min. UPLC/MS: (MS+) 398.4 ([M+H]+).

Example 105

(6-chloro-5,7-dimethyl-1H,3H-2,4,7a,8-tetraaza-cyclopenta[a]inden-2-yl)-[2-((S)-1-methyl-piperidin-3-yloxy)-phenyl]-methanone

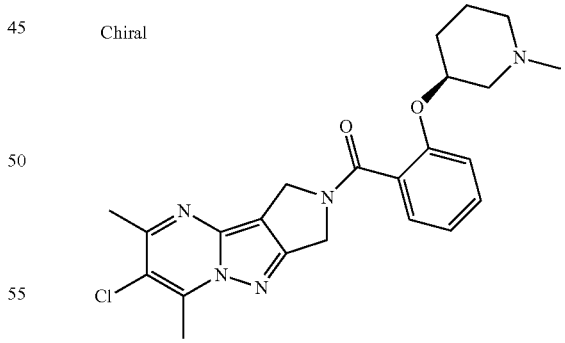

Give 89 mg (86%) of the title compound as a white solid. ¹H NMR (CDCl₃) δ 7.39-7.31 (m, 2H), 7.05-6.99 (m, 2H), 5.00 (br s, 2H), 4.65 (br s, 2H), 4.43-4.34 (m, 1H), 3.00-2.96 (m, 1H), 2.91 (s, 2H), 2.85 (s, 1H), 2.69 (s, 1H), 2.64-2.62 (m, 3H), 2.24 (br s, 3H), 2.07-1.87 (m, 3H), 1.77-1.50 (m, 2H), 1.42-1.25 (m, 1H). HPLC (max plot) 98%; Rt 2.71 min. UPLC/MS: (MS+) 440.5 ([M+H]⁺).

Example 106

(6-chloro-1H,3H-2,4,7a,8-tetraaza-cyclopenta[a]inden-2-yl)-[2-(1,1,2,2-tetrafluoro-ethoxy)-phenyl]-methanone

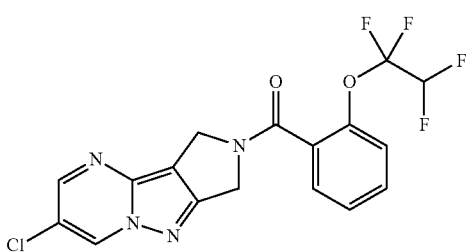 [SMILES: O=C(c1ccccc1OC(F)(F)C(F)F)N1Cc2nn3cc(Cl)cnc3c2C1]

The title compound was prepared following procedure described in Method A starting from Intermediate A4 and 2-(1,1,2,2-tetrafluoro-ethoxy)-benzoic acid. After purification by crystallization from hot ACN, the title compound was obtained as a pale yellow powder (112 mg, 62%). ¹H NMR (CDCl₃) δ 8.72 (d, J=2.3 Hz, 0.6H), 8.69 (d, J=2.3 Hz, 0.4H), 8.44 (d, J=2.3 Hz, 0.4H), 8.37 (d, J=2.3 Hz, 0.6H), 7.55-7.45 (m, 2H), 7.44-7.36 (m, 2H), 5.87 (tt, J=53.0, 2.8 Hz, 1H), 5.05-4.99 (m, 2H), 4.67-4.61 (m, 2H). HPLC (max plot) 99.8%, Rt 3.86 min. UPLC/MS: (MS+) 415.3 ([M+H]⁺). Melting point: 194-196° C. (ACN).

Example 107

(6-chloro-1,1,5,7-tetramethyl-1H,3H-2,4,7a,8-tetraaza-cyclopenta[a]inden-2-yl)-[2-(1-methyl-piperidin-4-yloxy)-phenyl]-methanone

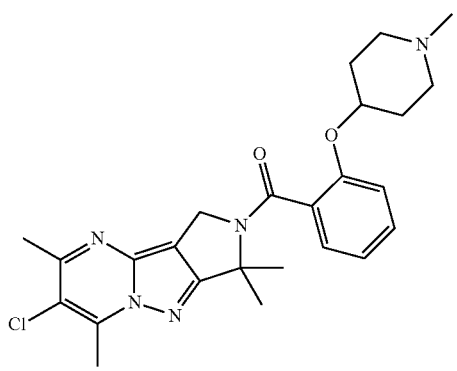

A mixture of Example 100 (100 mg; 0.22 mmol; 1 eq.), paraformaldehyde (60 mg; 0.66 mmol; 3 eq.), sodium triacetoxyborohydride (93 mg; 0.44 mmol; 2 eq.) and AcOH (13 µL; 0.22 mmol; 1 eq.) in DCE (5 mL) was stirred at 65° C. for 16 hours. 1M NaOH was added and the two phases separated. The aqueous layer was extracted with DCM (2×). The combined organic phase was dried over magnesium sulfate and concentrated in vacuo. Purification by column chromatography (5% to 20% MeOH in DCM) afforded the title compound (82 mg, 80%) as a colourless oil. ¹H NMR (DMSO-d₆) δ 7.44-7.32 (m, 1H), 7.24 (dd, J=7.4, 1.7 Hz, 1H), 7.16 (d, J=8.2 Hz, 1H), 7.06-6.96 (m, 1H), 4.58-4.42 (m, 2H), 4.42-4.25 (m, 1H), 2.83 (s, 3H), 2.54 (s, 3H), 2.48-2.34 (m, 2H), 2.15 (br s, 2H), 2.04 (s, 3H), 1.94-1.75 (m, 8H), 1.56 (br s, 2H). HPLC (max plot) 98.6%, Rt 3.15 min. UPLC/MS: (MS+) 468.5 ([M+H]⁺).

Example 108

(6-chloro-5,7-dimethyl-1H,3H-2,4,7a,8-tetraaza-cyclopenta[a]inden-2-yl)-[2-(1-methyl-azetidin-3-yloxy)-phenyl]-methanone

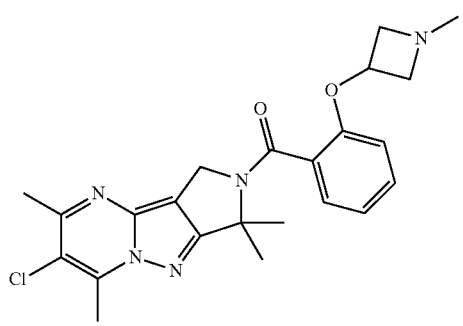

A mixture of Example 104 (112 mg; 0.25 mmol; 1 eq.), paraformaldehyde (68 mg; 0.76 mmol; 3.00 eq.) and sodium triacetoxyborohydride (107 mg; 0.50 mmol; 2 eq.) in DCE (5 mL) was stirred at reflux for 2 hours. 1M NaOH was added and extracted several times with EtOAc. The combined organics were dried over magnesium sulfate and concentrated in vacuo. Purification by mass directed preparative HPLC afforded the title compound (22 mg, 21%) as a white solid. ¹H NMR (CDCl₃) δ 7.40-7.33 (m, 2H), 7.11-7.05 (m, 1H), 6.73-6.69 (m, 1H), 5.03-5.01 (m, 2H), 4.97-4.89 (m, 1H), 4.61-4.60 (m, 2H), 4.16-4.10 (m, 2H), 3.34-3.28 (m, 2H), 2.91 (s, 2H), 2.85 (s, 1H), 2.69 (s, 1H), 2.62 (s, 2H), 2.51 (s, 3H). HPLC (max plot) 98%, Rt 1.92 min. UPLC/MS: (MS+) 412.4 ([M+H]⁺).

Example 109

(6-chloro-5,7-dimethyl-1H,3H-2,4,7a,8-tetraaza-cyclopenta[a]inden-2-yl)-[2-(3-fluoro-1-methyl-piperidin-4-yloxy)-phenyl]-methanone

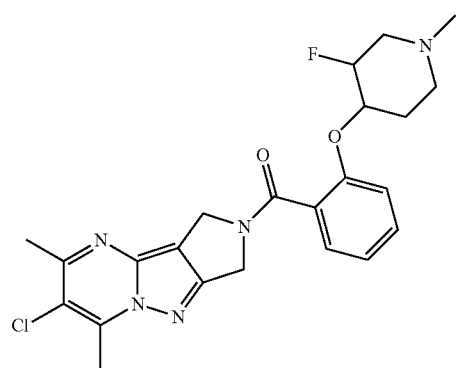

Step 1: 4-[2-(6-chloro-5,7-dimethyl-1H,3H-2,4,7a,8-tetraaza-cyclopenta[a]indene-2-carbonyl)-phenoxy]-3-fluoro-piperidine-1-carboxylic acid tert-butyl ester The title compound was prepared following procedure described in Method A starting from Intermediate B9 and Intermediate A3. After work up, the residue was purified by column chromatography (50% to 100% EA in heptane) to afford the title compound (1.07 g, 66%) as an off-white solid. HPLC (max plot) 93.8%, Rt 4.44 min. UPLC/MS: (MS+) 544.5 ([M+H]$^+$).

Step 2: (6-chloro-5,7-dimethyl-1H,3H-2,4,7a,8-tetraaza-cyclopenta[a]inden-2-yl)-[2-(3-fluoro-piperidin-4-yloxy)-phenyl]-methanone hydrochloride A 4M solution of HCl in 1,4-dioxane (10 mL; 400 mmol; 136 eq.) was added to a solution of 4-[2-(6-chloro-5,7-dimethyl-1H,3H-2,4,7a,8-tetraaza-cyclopenta[a]indene-2-carbonyl)-phenoxy]-3-fluoro-piperidine-1-carboxylic acid tert-butyl ester (160 mg; 0.29 mmol; 1 eq.) and the reaction mixture was stirred at room temperature for 16 hours then concentrated in vacuo. The residue was triturated in Et$_2$O and concentrated to dryness to afford the title compound (140 mg, 99%) as a pale yellow solid. UPLC/MS: (MS+) 444.4 ([M+H]$^+$).

Step 3: (6-chloro-5,7-dimethyl-1H,3H-2,4,7a,8-tetraaza-cyclopenta[a]inden-2-yl)-[2-(3-fluoro-1-methyl-piperidin-4-yloxy)-phenyl]-methanone A mixture of (6-chloro-5,7-dimethyl-1H,3H-2,4,7a,8-tetraaza-cyclopenta[a]inden-2-yl)-[2-(3-fluoro-piperidin-4-yloxy)-phenyl]-methanone hydrochloride (124 mg; 0.26 mmol; 1 eq.), paraformaldehyde (70 mg; 0.78 mmol; 1 eq.), sodium triacetoxyborohydride (110 mg; 0.52 mmol; 2 eq.) and AcOH (30 µL; 0.52 mmol; 2 eq.) in DCE (1.5 mL) was stirred at reflux for 1.5 hour. The reaction mixture was diluted with sat. aq. Na$_2$CO$_3$ and extracted with EA (3×). The combined organic layer was dried over magnesium sulfate and concentrated in vacuo. Purification by mass directed preparative HPLC afforded the title compound (20 mg, 6%) as a white solid. HPLC (max plot) 97.0%, Rt 2.70 min. UPLC/MS: (MS+) 458.4 ([M+H]$^+$).

Example 110

[2-(azetidin-3-ylmethoxy)-phenyl]-(6-chloro-5,7-dimethyl-1H,3H-2,4,7a,8-tetraaza-cyclopenta[a]inden-2-yl)-methanone hydrochloride

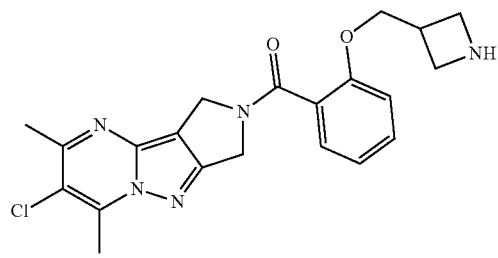 [SMILES: Cc1nc2c3c(nn2c(C)c1Cl)CN(C(=O)c1ccccc1OCC1CNC1)C3]

Step 1: 3-[2-(6-chloro-5,7-dimethyl-1H,3H-2,4,7a,8-tetraaza-cyclopenta[a]indene-2-carbonyl)-phenoxymethyl]-azetidine-1-carboxylic acid tert-butyl ester The title compound was prepared following procedure described in Method A starting from Intermediate B10 and Intermediate A3. After work up, the residue was purified recrystallization from ACN to afford the title compound (952 mg, 71%) as a white solid. $^1$H NMR (CDCl$_3$) δ 7.43-7.33 (m, 2H), 7.10-7.03 (m, 1H), 6.99-6.95 (m, 1H), 5.00-4.99 (m, 2H), 4.61-4.59 (m, 2H), 4.17-4.14 (m, 2H), 3.97-3.91 (m, 2H), 3.70-3.65 (m, 2H), 2.90 (s, 3H), 2.85 (s, 1H), 2.69 (s, 1H), 2.61 (s, 2H), 1.36 (s, 9H). HPLC (max plot) 97.3%, Rt 4.26 min. UPLC/MS: (MS+) 5.12.5 ([M+H]$^+$).

Step 2: 2-(azetidin-3-ylmethoxy)-phenyl]-(6-chloro-5,7-dimethyl-1H,3H-2,4,7a,8-tetraaza-cyclopenta[a]inden-2-yl)-methanone hydrochloride A solution of 3-[2-(6-chloro-5,7-dimethyl-1H,3H-2,4,7a,8-tetraaza-cyclopenta[a]indene-2-carbonyl)-phenoxymethyl]-azetidine-1-carboxylic acid tert-butyl ester (920 mg; 1.8 mmol; 1 eq.) in TFA (5 mL) and DCM (5 mL) was stirred at room temperature for 1 hour and then concentrated in vacuo. The residue was taken up in water, the pH made basic with 5M NaOH and extracted with DCM (2×). The combined organic layer was dried over magnesium sulfate and concentrated in vacuo. Purification by mass directed preparative HPLC afforded the title compound (10 mg, 1%) a yellow gum. $^1$H NMR (CDCl$_3$) δ 10.56 (s, 1H), 8.82 (s, 1H), 7.50-7.40 (m, 2H), 7.15-7.02 (m, 2H), 5.09 (s, 0.6H), 5.05 (s, 1.4H), 4.83 (s, 1.4H), 4.70 (s, 0.6H), 4.43-4.27 (m, 3H), 3.93-3.78 (m, 1H), 3.21-3.09 (m, 1H), 3.03 (s, 2H), 2.92 (s, 1H), 2.79 (s, 2H), 2.78 (s, 1H). HPLC (max plot) 99.3%, Rt 2.65 min. UPLC/MS: (MS+) 412.4 ([M+H]$^+$).

Example 111

(6-chloro-1H,3H-2,4,7a,8-tetraaza-cyclopenta[a]inden-2-yl)-[2-(piperidin-4-yloxy)-phenyl]-methanone

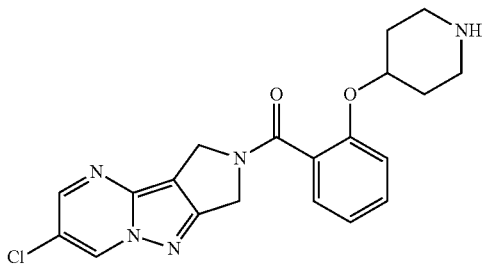 [SMILES: O=C(c1ccccc1OC1CCNCC1)N1Cc2nn3cc(Cl)cnc3c2C1]

Step 1: 4-[2-(6-chloro-1H,3H-2,4,7a,8-tetraaza-cyclopenta[a]indene-2-carbonyl)-phenoxy]-piperidine-1-carboxylic acid tert-butyl ester The title compound was prepared following procedure described in Method A starting from Intermediate A4 and Intermediate B3. After purification by flash chromatography (silica, heptanes/EtOAc), the title compound was obtained as a pale yellow foam (177 mg, 82%). $^1$H NMR (CDCl$_3$) δ 8.72 (d, J=2.3 Hz, 0.55H), 8.68 (d, J=2.3 Hz, 0.45H), 8.44 (d, J=2.4

Hz, 0.45H), 8.36 (d, J=2.3 Hz, 0.55H), 7.42-7.33 (m, 2H), 7.11-6.97 (m, 2H), 5.04 (s, 0.9H), 5.01 (s, 1.1H), 4.69 (br s, 2H), 4.59-4.49 (m, 1H), 3.59-3.48 (m, 2H), 3.38-3.27 (m, 2H), 1.94-1.79 (m, 2H), 1.79-1.65 (m, 2H), 1.42 (s, 9H). HPLC (max plot) 100%, Rt 4.26 min. UPLC/MS: (MS+) 498.5 ([M+H]$^+$).

Step 2: (6-chloro-1H,3H-2,4,7a,8-tetraaza-cyclopenta[a]inden-2-yl)-[2-(piperidin-4-yloxy)-phenyl]-methanone The title compound was prepared following procedure described in Method E starting from 4-[2-(6-chloro-1H,3H-2,4,7a,8-tetraaza-cyclopenta[a]indene-2-carbonyl)-phenoxy]-piperidine-1-carboxylic acid tert-butyl ester. The title compound was obtained as a pale yellow foam (112 mg, 82%) without further purification. $^1$H NMR (CDCl$_3$) δ 8.72 (d, J=2.3 Hz, 0.55H), 8.68 (d, J=2.4 Hz, 0.45H), 8.43 (d, J=2.4 Hz, 0.45H), 8.36 (d, J=2.3 Hz, 0.55H), 7.41-7.31 (m, 2H), 7.09-6.94 (m, 2H), 5.04 (s, 0.9H), 5.01 (s, 1.1H), 4.70 (br s, 2H), 4.51-4.40 (m, 1H), 3.10-2.98 (m, 2H), 2.76-2.63 (m, 2H), 2.15-1.90 (m, 3H), 1.75-1.58 (m, 2H). HPLC (max plot) 99.9%, Rt 2.27 min. UPLC/MS: (MS+) 398.4 ([M+H]$^+$).

Example 112

(6-chloro-5,7-dimethyl-1H,3H-2,4,7a,8-tetraaza-cyclopenta[a]inden-2-yl)-[2-((1R,4R)-5-methyl-2,5-diaza-bicyclo[2.2.1]hept-2-ylmethyl)-phenyl]-methanone

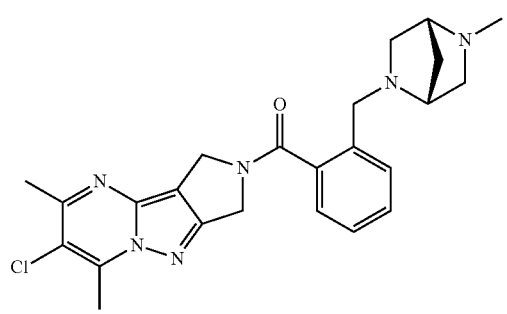 [SMILES: Cc1nc2c3c(nn2c(C)c1Cl)CN(C(=O)c1ccccc1CN1C[C@H]2C[C@@H]1CN2C)C3]

The title compound was prepared following procedure described in Method D starting from Intermediate Z3 and (1R,4R)-2-methyl-2,5-diaza-bicyclo[2.2.1]heptane dihydrobromide (Enamine). After purification by flash chromatography (silica, DCM/EtOH/28% aqueous ammonia), the title compound was obtained as a white foam (97 mg, 60%). $^1$H NMR (CDCl$_3$) δ 7.39-7.26 (m, 4H), 5.09-4.93 (m, 2H), 4.65-4.53 (m, 2H), 3.90-3.68 (m, 2H), 3.21 (s, 1H), 3.07 (s, 1H), 2.91 (s, 1.8H), 2.85 (s, 1.2H), 2.72-2.50 (m, 7H), 2.21 (s, 1.2H), 2.18 (s, 1.8H), 1.55 (d, J=9.5 Hz, 1H), 1.41-1.32 (m, 1H). HPLC (max plot) 98.9%, Rt 2.21 min. UPLC/MS: (MS+) 451.5 ([M+H]$^+$).

Example 113

(6-chloro-5,7-dimethyl-1H,3H-2,4,7a,8-tetraaza-cyclopenta[a]inden-2-yl)-[2-(3,8-diaza-bicyclo[3.2.1]oct-3-ylmethyl)-phenyl]-methanone

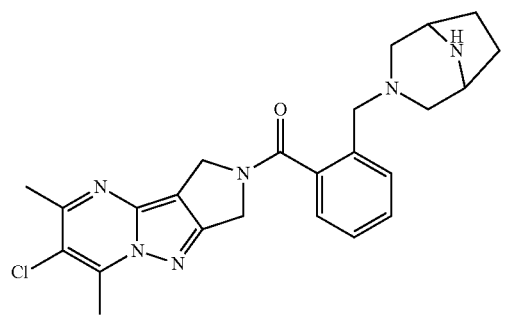 [SMILES: Cc1nc2c3c(nn2c(C)c1Cl)CN(C(=O)c1ccccc1CN1CC2CCC(C1)N2)C3]

Step 1: 3-[2-(6-chloro-5,7-dimethyl-1H,3H-2,4,7a,8-tetraaza-cyclopenta[a]indene-2-carbonyl)-benzyl]-3,8-diaza-bicyclo[3.2.1]octane-8-carboxylic acid tert-butyl ester The title compound was prepared following procedure described in Method D starting from Intermediate Z3 and 3,8-diaza-bicyclo[3.2.1]octane-8-carboxylic acid tert-butyl ester hydrochloride (Chem Impex). After purification by flash chromatography (silica, heptane/EtOAc), the title compound was obtained as a white foam (181 mg, 92%). $^1$H NMR (CDCl$_3$) δ 7.46-7.27 (m, 4H), 5.06-4.98 (m, 2H), 4.65-4.55 (m, 2H), 4.14-3.94 (m, 2H), 3.56 (br s, 2H), 2.91 (s, 2H), 2.85 (s, 1H), 2.70 (s, 1H), 2.65-2.56 (m, 4H), 2.32-2.17 (m, 2H), 1.58-1.48 (m, 4H), 1.44-1.38 (m, 9H). HPLC (max plot) 99.4%, Rt 3.80 min. UPLC/MS: (MS+) 551.5 ([M+H]$^+$), (MS−) 549.6 ([M−H]$^-$).

Step 2: (6-chloro-5,7-dimethyl-1H,3H-2,4,7a,8-tetraaza-cyclopenta[a]inden-2-yl)-[2-(3,8-diaza-bicyclo[3.2.1]oct-3-ylmethyl)-phenyl]-methanone The title compound was prepared following procedure described in Method E starting from 3-[2-(6-chloro-5,7-dimethyl-1H,3H-2,4,7a,8-tetraaza-cyclopenta[a]indene-2-carbonyl)-benzyl]-3,8-diaza-bicyclo[3.2.1]octane-8-carboxylic acid tert-butyl ester. After purification by crystallization from hot EtOH, the title compound was obtained as a white powder (64 mg, 45%). $^1$H NMR (CDCl$_3$) δ 7.46-7.27 (m, 4H), 5.06-5.00 (m, 2H), 4.63-4.58 (m, 2H), 3.54 (br s, 2H), 3.34-3.27 (m, 2H), 2.92 (s, 2H), 2.85 (s, 1H), 2.70 (s, 1H), 2.65 (dd, J=10.9, 2.7 Hz, 2H), 2.61 (s, 2H), 2.18-2.10 (m, 2H), 1.59-1.35 (m, 4H). HPLC (max plot) 99.2%, Rt 2.40 min. UPLC/MS: (MS+) 451.5 ([M+H]$^+$).

Example 114

(6-chloro-5,7-dimethyl-1H,3H-2,4,7a,8-tetraaza-cyclopenta[a]inden-2-yl)-[2-(2-hydroxy-ethoxy)-phenyl]-methanone

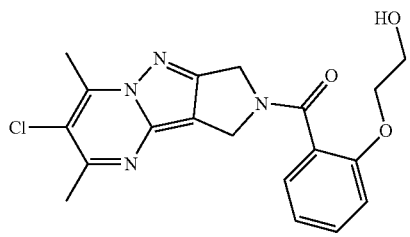 [SMILES: Cc1nc2c3c(nn2c(C)c1Cl)CN(C(=O)c1ccccc1OCCO)C3]

The title compound was prepared following procedure described in Method F starting from 2-(2-hydroxy-ethoxy)-benzoic acid and Intermediate A3. After work up, the residue was purified by mass directed preparative HPLC to afford the title compound (43 mg, 14%) as a white solid. $^1$H NMR (CDCl$_3$) δ 7.43-7.33 (m, 2H), 7.11-7.04 (m, 2H), 5.03 (s, 0.7H), 5.02 (s, 1.3H), 4.68 (s, 1.3H), 4.65 (s, 0.7H), 4.24-4.21 (m, 2H), 3.83-3.80 (m, 2H), 2.91 (s, 2H), 2.85 (s, 1H), 2.69 (s, 1H), 2.61 (s, 2H). HPLC (max plot) 100%, Rt 3.06 min. UPLC/MS: (MS+) 387.4 ([M+H]$^+$).

Example 115

(6-chloro-1,1,5,7-tetramethyl-1H,3H-2,4,7a,8-tetraaza-cyclopenta[a]inden-2-yl)-[2-(1-isopropyl-piperidin-4-yloxy)-phenyl]-methanone

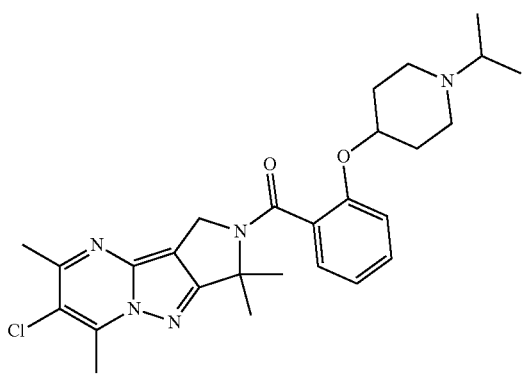 [SMILES: Cc1nc2c3c(nn2c(C)c1Cl)C(C)(C)N(C(=O)c1ccccc1OC1CCN(C(C)C)CC1)C3]

A mixture of Example 100 (98 mg; 0.22 mmol; 1 eq.), acetone (95 μL; 1.3 mmol; 6 eq.), sodium triacetoxyborohydride (183 mg; 0.86 mmol; 4 eq.) and AcOH (15 μL; 0.26 mmol; 1 eq.) in DCE (5 mL) was stirred at room temperature for 16 hours. Acetone (95 μL; 1.3 mmol; 6 eq.), sodium triacetoxyborohydride (183 mg; 0.86 mmol; 4 eq.) and AcOH (15 μL; 0.26 mmol; 1 eq.) were added and the resulting mixture was stirred at room temperature for 24 hours. 1M NaOH was added and the two phases separated. The aqueous layer was extracted with DCM (2×). The combined organic phase was dried over magnesium sulfate and concentrated in vacuo. Purification by column chromatography (5% to 20% MeOH in DCM) afforded the title compound (78 mg, 72%) as a colourless oil. $^1$H NMR (DMSO-d$_6$) δ 7.44-7.33 (m, 1H), 7.24 (dd, J=7.4, 1.7 Hz, 1H), 7.18-7.09 (m, 1H), 7.00 (t, J=7.4 Hz, 1H), 4.61-4.42 (m, 2H), 4.42-4.27 (m, 1H), 2.83 (s, 3H), 2.63-2.52 (m, 4H), 2.36-2.21 (m, 2H), 1.98-1.74 (m, 8H), 1.68-1.44 (m, 2H), 0.79 (d, J=6.2 Hz, 6H). HPLC (max plot) 86.3%, Rt 3.27 min. UPLC/MS: (MS+) 496.5 ([M+H]$^+$).

Example 116

(6-chloro-5,7-dimethyl-1H,3H-2,4,7a,8-tetraaza-cyclopenta[a]inden-2-yl)-[2-(3-methyl-piperazin-1-ylmethyl)-phenyl]-methanone

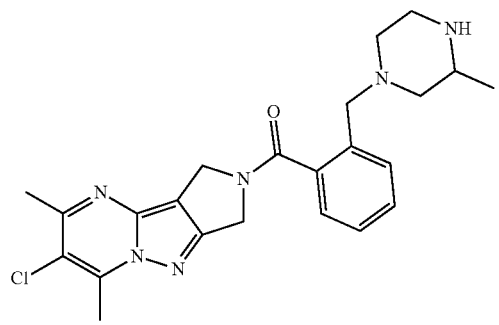 [SMILES: Cc1nc2c3c(nn2c(C)c1Cl)CN(C(=O)c1ccccc1CN1CCNC(C)C1)C3]

Step 1: 4-[2-(6-chloro-5,7-dimethyl-1H,3H-2,4,7a,8-tetraaza-cyclopenta[a]indene-2-carbonyl)-benzyl]-2-methyl-piperazine-1-carboxylic acid tert-butyl ester The title compound was prepared following procedure described in Method C starting from Intermediate Z3 and 2-methyl-piperazine-1-carboxylic acid tert-butyl ester (Apollo Scientific). After purification by flash chromatography (silica, heptane/EtOAc), the title compound was obtained as a white foam (177 mg, 85%). $^1$H NMR (CDCl$_3$) δ 7.42-7.28 (m, 4H), 5.11-4.90 (m, 2H), 4.71-4.49 (m, 2H), 4.16-4.03 (m, 1H), 3.80 (br s, 1H), 3.75-3.64 (m, 1H), 3.29 (br s, 1H), 2.93-2.59 (m, 9H), 2.23-2.13 (m, 1H), 1.95-1.81 (m, 1H), 1.42-1.34 (m, 9H), 0.94-0.86 (m, 3H). HPLC (max plot) 99.9%, Rt 3.70 min. UPLC/MS: (MS+) 539.6 ([M+H]$^+$), (MS−) 537.7 ([M−H]$^-$).

Step 2: (6-chloro-5,7-dimethyl-1H,3H-2,4,7a,8-tetraaza-cyclopenta[a]inden-2-yl)-[2-(3-methyl-piperazin-1-ylmethyl)-phenyl]-methanone The title compound was prepared following procedure described in Method E starting from 4-[2-(6-chloro-5,7-dimethyl-1H,3H-2,4,7a,8-tetraaza-cyclopenta[a]indene-2-carbonyl)-benzyl]-2-methyl-piperazine-1-carboxylic acid tert-butyl ester. After purification by crystallization from hot ACN, the title compound was obtained as a white powder (62 mg, 49%). $^1$H NMR (CDCl$_3$) δ 7.38-7.27 (m, 4H), 5.02-4.96 (m, 2H), 4.64-4.50 (m, 2H), 3.56 (br s, 2H), 2.91 (s, 1.9H), 2.85 (s, 1.1H), 2.82-2.63 (m, 4.1H), 2.60 (s, 1.9H), 2.44-2.29 (m, 2H), 2.03-1.88 (m, 1H), 1.66 (t, J=10.4 Hz, 1H), 0.91-

0.84 (m, 3H). HPLC (max plot) 98.9%, Rt 2.30 min. UPLC/MS: (MS+) 439.4 ([M+H]⁺). Melting point: 195-200° C. (ACN).

Example 117

1-[2-(6-chloro-5,7-dimethyl-1H,3H-2,4,7a,8-tet-raaza-cyclopenta[a]indene-2-carbonyl)-benzyl]-piperazin-2-one

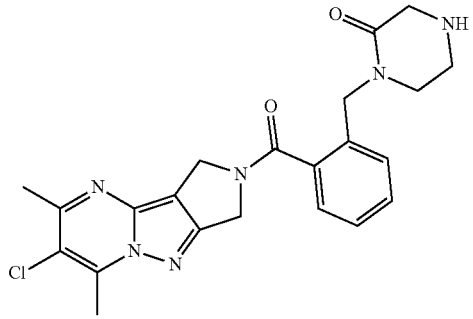 [SMILES: Cc1nc2c3c(nn2c(C)c1Cl)CN(C(=O)c1ccccc1CN1CCNCC1=O)C3]

Step 1: 4-[2-(6-chloro-5,7-dimethyl-1H,3H-2,4,7a,8-tetraaza-cyclopenta[a]indene-2-carbonyl)-benzyl]-3-oxo-piperazine-1-carboxylic acid tert-butyl ester Sodium hydride (55-65%, 21 mg, 0.54 mmol) was added to a solution of 3-oxo-piperazine-1-carboxylic acid tert-butyl ester (107 mg, 0.54 mmol) in anhydrous THF (3 mL). The resulting mixture was stirred at RT for 45 minutes, then Intermediate Z3 (150 mg, 0.36 mmol) was added. After 24 hours of stirring at RT, the reaction mixture was diluted with THF/DCM (2:1, 150 mL) and washed with brine (100 mL). The organic layer was dried (MgSO4) and concentrated under vacuum. After purification by flash chromatography (silica, DCM/THF), the title compound was obtained as a white foam (101 mg, 52%). ¹H NMR (300 MHz, CDCl₃) δ 7.47-7.33 (m, 4H), 5.02-4.96 (m, 2H), 4.71 (s, 2H), 4.57-4.51 (m, 2H), 4.11 (s, 2H), 3.63-3.55 (m, 2H), 3.36-3.27 (m, 2H), 2.90 (s, 1.9H), 2.84 (s, 1.1H), 2.69 (s, 1.1H), 2.61 (s, 1.9H), 1.47-1.41 (m, 9H). HPLC (max plot) 98.7%, Rt 3.95 min. UPLC/MS: (MS+) 539.5 ([M+H]⁺), (MS-) 537.5 ([M-H]⁻).

Step 2: 1-[2-(6-chloro-5,7-dimethyl-1H,3H-2,4,7a,8-tetraaza-cyclopenta[a]indene-2-carbonyl)-benzyl]-piperazin-2-one The title compound was prepared following procedure described in Method E starting from 4-[2-(6-chloro-5,7-dimethyl-1H,3H-2,4,7a,8-tetraaza-cyclopenta[a]indene-2-carbonyl)-benzyl]-3-oxo-piperazine-1-carboxylic acid tert-butyl ester. After purification by crystallization from ACN, the title compound was obtained as a white powder (34 mg, 44%). ¹H NMR (CDCl₃) δ 7.47-7.32 (m, 4H), 5.02-4.96 (m, 2H), 4.71 (s, 2H), 4.57-4.51 (m, 2H), 3.53 (s, 2H), 3.30-3.21 (m, 2H), 3.06-3.00 (m, 2H), 2.90 (s, 1.9H), 2.84 (s, 1.1H), 2.68 (s, 1.1H), 2.60 (s, 1.9H). HPLC (max plot) 99.2%, Rt 2.48 min. UPLC/MS: (MS+) 439.4 ([M+H]⁺), (MS-) 437.4 ([M-H]⁻). Melting point: 176-183° C. (ACN).

Example 118

(6-chloro-5,7-dimethyl-1H,3H-2,4,7a,8-tetraaza-cyclopenta[a]inden-2-yl)-(2-[1,4]diazepan-1-ylm-ethyl-phenyl)-methanone

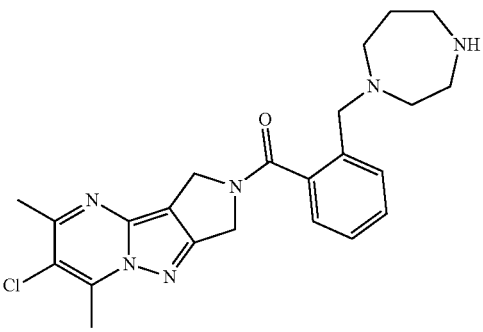 [SMILES: Cc1nc2c3c(nn2c(C)c1Cl)CN(C(=O)c1ccccc1CN1CCCNCC1)C3]

Step 1: 4-[2-(6-chloro-5,7-dimethyl-1H,3H-2,4,7a,8-tetraaza-cyclopenta[a]indene-2-carbonyl)-benzyl]-[1,4]diazepane-1-carboxylic acid tert-butyl ester The title compound was prepared following procedure described in Method D starting from Intermediate Z3 and [1,4]diazepane-1-carboxylic acid tert-butyl ester. After purification by flash chromatography (silica, heptane/EtOAc), the title compound was obtained as a white foam (170 mg, 88%). ¹H NMR (CDCl₃) δ 7.40-7.27 (m, 4H), 5.03-4.97 (m, 2H), 4.60-4.53 (m, 2H), 3.69 (br s, 2H), 3.31-3.14 (m, 4H), 2.91 (s, 1.9H), 2.85 (s, 1.1H), 2.70 (s, 1.1H), 2.61 (s, 1.9H), 2.60-2.52 (m, 4H), 1.65-1.54 (m, 2H), 1.43-1.35 (m, 9H). HPLC (max plot) 98.4%, Rt 3.55 min. UPLC/MS: (MS+) 539.5 ([M+H]⁺), (MS-) 537.5 ([M-H]⁻).

Step 2: (6-chloro-5,7-dimethyl-1H,3H-2,4,7a,8-tetraaza-cyclopenta[a]inden-2-yl)-(2-[1,4]diazepan-1-ylmethyl-phenyl)-methanone The title compound was prepared following procedure described in Method E starting from 4-[2-(6-chloro-5,7-dimethyl-1H,3H-2,4,7a,8-tetraaza-cyclopenta[a]indene-2-carbonyl)-benzyl]-[1,4]diazepane-1-carboxylic acid tert-butyl ester. After purification by slurry in hot ACN, the title compound was obtained as an off-white powder (87 mg, 67%). ¹H NMR (CDCl₃) δ 7.38-7.27 (m, 4H), 5.06-4.98 (m, 2H), 4.60 (s, 2H), 3.72 (br s, 2H), 2.91 (s, 1.8H), 2.85 (s, 1.2H), 2.72-

2.54 (m, 11H), 1.62-1.51 (m, 2H). HPLC (max plot) 99.6%, Rt 2.20 min. UPLC/MS: (MS+) 439.4 ([M+H]+). Melting point: 185-192° C. (ACN).

Example 119

(6-chloro-5,7-dimethyl-1H,3H-2,4,7a,8-tetraaza-cyclopenta[a]inden-2-yl)-(2-piperidin-4-ylidenem-ethyl-phenyl)-methanone

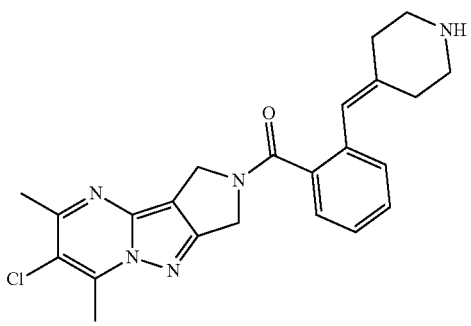 [SMILES: Cc1nc2c3c(nn2c(C)c1Cl)CN(C(=O)c1ccccc1C=C1CCNCC1)C3]

Step 1: 4-[2-(6-chloro-5,7-dimethyl-1H,3H-2,4,7a,8-tetraaza-cyclopenta[a]indene-2-carbonyl)-ben-zylidene]-piperidine-1-carboxylic acid tert-butyl ester The title compound was prepared following procedure described in Method F starting from Intermediate B11 and Intermediate A3. After work up, the residue was purified by recrystallization from ACN to afford the title compound (80 mg, 58%) as a white solid. ¹H NMR (CDCl₃) δ 7.40-7.31 (m, 3H), 7.26-7.23 (m, 1H), 6.41 (s, 1H), 5.00 (s, 0.7H), 4.99 (s, 1.3H), 4.46 (s, 1.3H), 4.43 (s, 0.7H), 3.41-3.33 (m, 4H), 2.90 (s, 2H), 2.84 (s, 1H), 2.69 (s, 1H), 2.61 (s, 2H), 2.40-2.36 (m, 2H), 2.26-2.22 (m, 2H), 1.44 (s, 3H), 1.43 (s, 6H). HPLC (max plot) 98.8%, Rt 4.84 min. UPLC/MS: (MS+) 522.4 ([M+H]+).

Step 2: (6-chloro-5,7-dimethyl-1H,3H-2,4,7a,8-tetraaza-cyclopenta[a]inden-2-yl)-(2-piperidin-4-ylidenemethyl-phenyl)-methanone A mixture of 4-[2-(6-chloro-5,7-dimethyl-1H,3H-2,4,7a,8-tetraaza-cyclopenta[a]indene-2-carbonyl)-benzylidene]-piperidine-1-carboxylic acid tert-butyl ester (80 mg; 0.15 mmol; 1 eq.) and TFA (1 mL) in DCM (1 mL) was stirred at room temperature for 30 min then concentrated in vacuo. The residue was taken up in water, the pH made basic with 5M NaOH and extracted with DCM (2×). The combined organics were dried over magnesium sulfate and concentrated in vacuo to afford the title compound (40 mg, 62%) as a white solid. ¹H NMR (CDCl₃) δ 7.41-7.25 (m, 4H), 6.33 (s, 1H), 5.01-5.00 (m, 2H), 4.47-4.45 (m, 2H), 2.90 (s, 2H), 2.85-2.78 (m, 5H), 2.69 (s, 1H), 2.61 (s, 2H), 2.41-2.38 (m, 2H), 2.26-2.23 (m, 2H). HPLC (max plot) 96%, Rt 2.63 min. UPLC/MS: (MS+) 422.2 ([M+H]+).

Example 120

(6-chloro-5,7-dimethyl-1H,3H-2,4,7a,8-tetraaza-cyclopenta[a]inden-2-yl)-[2-((R)-2-methyl-piper-azin-1-ylmethyl)-phenyl]-methanone

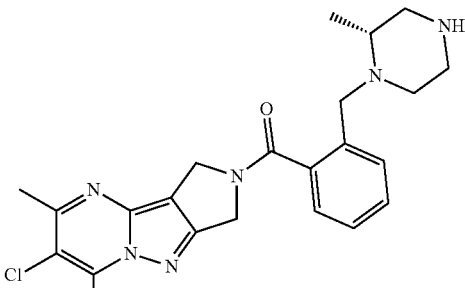

Step 1: (R)-4-[2-(6-chloro-5,7-dimethyl-1H,3H-2,4,7a,8-tetraaza-cyclopenta[a]indene-2-carbonyl)-ben-zyl]-3-methyl-piperazine-1-carboxylic acid tert-butyl ester The title compound was prepared following procedure described in Method D starting from Intermediate Z3 and (R)-3-methyl-piperazine-1-carboxylic acid tert-butyl ester. After purification by flash chromatography (silica, heptane/EtOAc), the title compound was obtained as a white foam (150 mg, 76%). HPLC (max plot) 97.2%, Rt 3.55 min. UPLC/MS: (MS+) 539.5 ([M+H]+).

Step 2: (6-chloro-5,7-dimethyl-1H,3H-2,4,7a,8-tetraaza-cyclopenta[a]inden-2-yl)-[2-((R)-2-methyl-piperazin-1-ylmethyl)-phenyl]-methanone The title compound was prepared following procedure described in Method E starting from (R)-4-[2-(6-chloro-5,7-dimethyl-1H,3H-2,4,7a,8-tetraaza-cyclopenta[a]indene-2-carbonyl)-benzyl]-3-methyl-piperazine-1-carboxylic acid tert-butyl ester. After purification by crystallization from hot ACN, the title compound was obtained as an off-white powder (55 mg, 47%). ¹H NMR (CDCl₃) δ 7.37-7.27 (m, 4H), 5.11-4.91 (m, 2H), 4.66-4.54 (m, 2H), 4.23 (br s, 1H), 3.07 (br s, 1H), 2.91 (s, 1.8H), 2.85 (s, 1.2H), 2.71-2.56 (m, 6H), 2.54-2.38 (m, 1H), 2.38-2.21 (m, 1H), 2.21-1.94 (m, 2H), 1.06-0.98 (m, 3H). HPLC (max plot) 99.1%, Rt 2.31 min. UPLC/MS: (MS+) 439.3 ([M+H]+).

Example 121

(6-chloro-5,7-dimethyl-1H,3H-2,4,7a,8-tetraaza-cyclopenta[a]inden-2-yl)-[2-((S)-2-methyl-piperazin-1-ylmethyl)-phenyl]-methanone

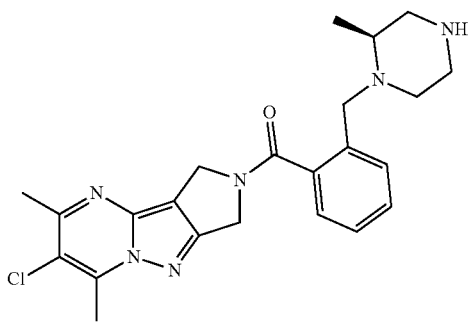 [SMILES: Cc1nc2c3c(nn2c(C)c1Cl)CN(C(=O)c1ccccc1CN1CCNC[C@@H]1C)C3]

Step 1: (S)-4-[2-(6-chloro-5,7-dimethyl-1H,3H-2,4,7a,8-tetraaza-cyclopenta[a]indene-2-carbonyl)-benzyl]-3-methyl-piperazine-1-carboxylic acid tert-butyl ester The title compound was prepared following procedure described in Method D starting from Intermediate Z3 and (S)-3-methyl-piperazine-1-carboxylic acid tert-butyl ester. After purification by flash chromatography (silica, heptane/EtOAc), the title compound was obtained as a white foam (159 mg, 80%). HPLC (max plot) 97.2%, Rt 3.55 min. UPLC/MS: (MS+) 539.5 ([M+H]$^+$).

Step 2: (6-chloro-5,7-dimethyl-1H,3H-2,4,7a,8-tetraaza-cyclopenta[a]inden-2-yl)-[2-((S)-2-methyl-piperazin-1-ylmethyl)-phenyl]-methanone The title compound was prepared following procedure described in Method E starting from (S)-4-[2-(6-chloro-5,7-dimethyl-1H,3H-2,4,7a,8-tetraaza-cyclopenta[a]indene-2-carbonyl)-benzyl]-3-methyl-piperazine-1-carboxylic acid tert-butyl ester. After purification by crystallization from hot ACN, the title compound was obtained as an off-white powder (54 mg, 48%). $^1$H NMR (CDCl$_3$) δ 7.37-7.27 (m, 4H), 5.11-4.91 (m, 2H), 4.66-4.54 (m, 2H), 4.23 (br s, 1H), 3.07 (br s, 1H), 2.91 (s, 1.8H), 2.85 (s, 1.2H), 2.71-2.56 (m, 6H), 2.54-2.38 (m, 1H), 2.38-2.21 (m, 1H), 2.21-1.94 (m, 2H), 1.06-0.98 (m, 3H). HPLC (max plot) 98.9%, Rt 2.29 min. UPLC/MS: (MS+) 439.3 ([M+H]$^+$).

Example 122

2-[2-(6-chloro-5,7-dimethyl-1H,3H-2,4,7a,8-tetraaza-cyclopenta[a]indene-2-carbonyl)-phenoxy]-2,2-difluoro-1-(4-methyl-piperazin-1-yl)-ethanone

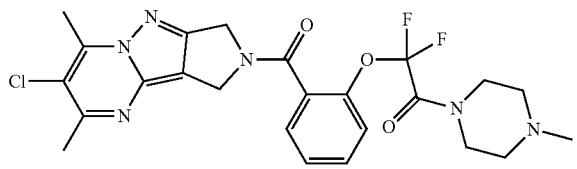 [SMILES: Cc1nc2c3c(nn2c(C)c1Cl)CN(C(=O)c1ccccc1OC(F)(F)C(=O)N1CCN(C)CC1)C3]

Step 1: 2-bromo-2,2-difluoro-1-(4-methyl-piperazin-1-yl)-ethanone

1-Methyl-piperazine (1.23 g; 12.3 mmol; 5 eq.) was added to a solution of bromo-difluoro-acetic acid ethyl ester (500 mg; 2.46 mmol; 1 eq.) in THF (50 mL) and the reaction mixture was stirred at room temperature for 16 hours then concentrated in vacuo. The residue was taken up in EA, washed with water, dried over magnesium sulfate and concentrated in vacuo to afford the title compound (450 mg, 71%) as a yellow oil.

Step 2: 2-[2-(6-chloro-5,7-dimethyl-1H,3H-2,4,7a,8-tetraaza-cyclopenta[a]indene-2-carbonyl)-phenoxy]-2,2-difluoro-1-(4-methyl-piperazin-1-yl)-ethanone NaH (55-65%, 16 mg; 0.4 mmol; 1.1 eq.) was added to a solution of Intermediate Z4 (125 mg; 0.36 mmol; 1 eq.) in DMF (2 mL) and the resulting mixture was stirred at room temperature for 5 minutes whereupon 2-bromo-2,2-difluoro-1-(4-methyl-piperazin-1-yl)-ethanone (94 mg; 0.36 mmol; 1 eq.) was added. The reaction mixture was stirred at 90° C. for 2 hours. After concentration in vacuo, purification by mass directed preparative HPLC afforded the title compound (30 mg, 16%) as a white foam. HPLC (max plot) 94.3%, Rt 2.95 min. UPLC/MS: (MS+) 519.3 ([M+H]$^+$).

Example 123

(6-chloro-5,7-dimethyl-1H,3H-2,4,7a,8-tetraaza-cyclopenta[a]inden-2-yl)-[2-(1-methyl-piperidin-4-ylidenemethyl)-phenyl]-methanone

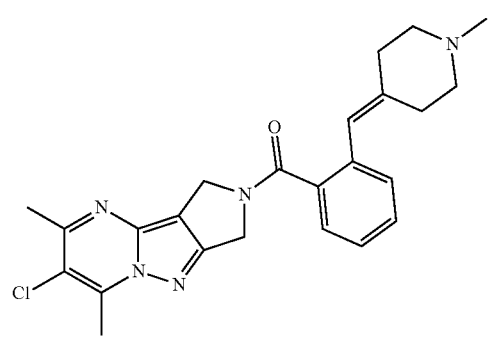 [SMILES: Cc1nc2c3c(nn2c(C)c1Cl)CN(C(=O)c1ccccc1C=C1CCN(C)CC1)C3]

The title compound was prepared following procedure described in Method F starting from Intermediate B12 and Intermediate A3. After work up, the residue was purified by mass directed preparative HPLC to afford the title compound (71 mg, 38%) as an off-white solid. $^1$H NMR (CDCl$_3$) δ 8.47 (s, 1H), 7.47-7.29 (m, 3H), 7.25-7.20 (m, 1H), 6.40 (s, 1H), 5.00-4.98 (m, 2H), 4.58-4.44 (m, 2H), 2.91 (s, 2H), 2.84 (s, 1H), 2.83-2.72 (m, 4H), 2.69 (s, 1H), 2.64-2.60 (m, 4H), 2.53-2.49 (m, 3H), 2.46 (s, 2H). HPLC (max plot) 100%, Rt 2.70 min. UPLC/MS: (MS+) 436.2 ([M+H]$^+$).

Example 124

(5,7-dimethyl-1H,3H-2,4,7a,8-tetraaza-cyclopenta[a]inden-2-yl)-[2-(1,1,2,2-tetrafluoro-ethoxy)-phenyl]-methanone

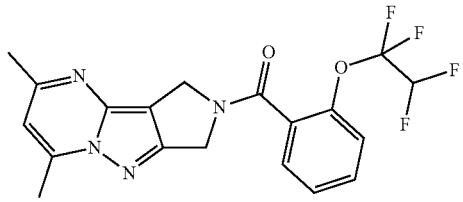 [SMILES: Cc1cc(C)n2nc3c(c2n1)CN(C(=O)c1ccccc1OC(F)(F)C(F)F)C3]

The title compound was prepared following procedure described in Method A starting from 2-(1,1,2,2-tetrafluoro-ethoxy)-benzoic acid and Intermediate A10. After work up, the residue was purified by column chromatography (DCM to 2% MeOH in DCM) to afford the title compound (98 mg, 54%) as an off-white solid. $^1$H NMR (DMSO-d$_6$) δ 7.66-7.58 (m, 2H), 7.54-7.44 (m, 2H), 6.94-6.83 (m, 1H), 6.75-6.52 (m, 1H), 4.85-4.78 (m, 2H), 4.56-4.47 (m, 2H), 2.68 (br s, 2H), 2.65 (br s, 1H), 2.50 (s, 1H), 2.45 (s, 2H). HPLC (max plot) 99.0%, Rt 3.47 min. UPLC/MS: (MS+) 409.2 ([M+H]+).

Example 125

[2-(3-amino-piperidin-1-ylmethyl)-phenyl]-(6-chloro-5,7-dimethyl-1H,3H-2,4,7a,8-tetraaza-cyclopenta[a]inden-2-yl)-methanone

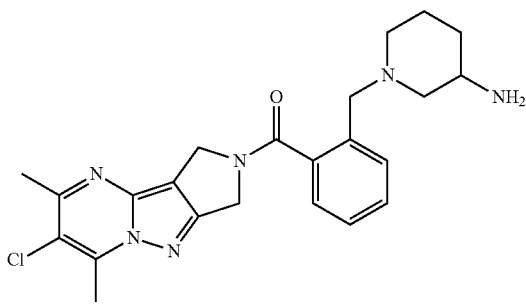 [SMILES: Cc1nc2c3c(nn2c(C)c1Cl)CN(C(=O)c1ccccc1CN1CCCC(N)C1)C3]

Step 1: {1-[2-(6-chloro-5,7-dimethyl-1H,3H-2,4,7a,8-tetraaza-cyclopenta[a]indene-2-carbonyl)-benzyl]-piperidin-3-yl}-carbamic acid tert-butyl ester The title compound was prepared following procedure described in Method D starting from Intermediate Z3 and piperidin-3-yl-carbamic acid tert-butyl ester. After purification by flash chromatography (silica, heptane/EtOAc), the title compound was obtained as a white foam (168 mg, 85%). ¹H NMR (CDCl₃) δ 7.43-7.27 (m, 4H), 5.14-4.80 (m, 3H), 4.67-4.47 (m, 2H), 3.75-3.33 (m, 3H), 2.91 (s, 2H), 2.85 (s, 1H), 2.68 (s, 1H), 2.65-2.50 (m, 3H), 2.27 (br s, 3H), 1.62-1.18 (m, 13H). HPLC (max plot) 97.9%, Rt 3.49 min. UPLC/MS: (MS+) 539.5 ([M+H]+), (MS−) 537.5 ([M−H]−).

Step 2: [2-(3-amino-piperidin-1-ylmethyl)-phenyl]-(6-chloro-5,7-dimethyl-1H,3H-2,4,7a,8-tetraaza-cyclopenta[a]inden-2-yl)-methanone {1-[2-(6-Chloro-5,7-dimethyl-1H,3H-2,4,7a,8-tetraaza-cyclopenta[a]indene-2-carbonyl)-benzyl]-piperidin-3-yl}-carbamic acid tert-butyl ester (160 mg, 0.30 mmol) was added into a 4N solution of HCl in dioxane (2 mL, 8 mmol), followed by water (0.5 mL). The resulting mixture was stirred at RT for 2 hours, then concentrated under vacuum. The residue was taken up with water (5 mL) and a 1N aqueous solution of NaOH (15 mL), then extracted with DCM (2×25 mL). The organic layers were combined, dried (Na2SO4) and concentrated under vacuum. After purification by crystallization from ACN, the title compound was obtained as a white powder (46 mg, 35%). ¹H NMR (DMSO-d₆) δ 7.47-7.31 (m, 4H), 4.83 (s, 1H), 4.81 (s, 1H), 4.52 (s, 1H), 4.47 (s, 1H), 3.42 (br s, 2H), 2.85 (s, 1.5H), 2.80 (s, 1.5H), 2.70-2.43 (m, 5H), 2.23-2.09 (m, 1H), 1.88-1.74 (m, 1H), 1.65-1.52 (m, 1H), 1.46-1.31 (m, 2H), 1.25 (s, 2H), 1.02-0.83 (m, 1H), 0.83-0.65 (m, 1H). HPLC (max plot) 99.4%, Rt 2.21 min. UPLC/MS: (MS+) 439.3 ([M+H]+). Melting point: 165-170° C. (ACN).

Example 126

(6-chloro-5,7-dimethyl-1H,3H-2,4,7a,8-tetraaza-cyclopenta[a]inden-2-yl)-[2-(3-dimethylamino-azetidin-1-ylmethyl)-phenyl]-methanone

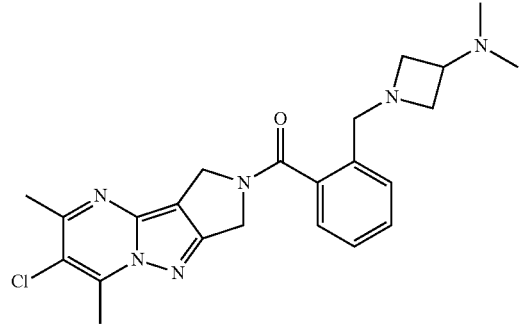

The title compound was prepared following procedure described in Method D starting from Intermediate Z3 and azetidin-3-yl-dimethyl-amine dihydrochloride (Matrix Scientific). After purification by crystallization from ACN, the title compound was obtained as a white powder (71 mg, 44%). ¹H NMR (DMSO-d₆) δ 7.46-7.30 (m, 4H), 4.87 (s, 1H), 4.84 (s, 1H), 4.53 (s, 1H), 4.47 (s, 1H), 3.56 (s, 2H), 3.29-3.20 (m, 2H), 2.85 (s, 1.5H), 2.80 (s, 1.5H), 2.78-2.69 (m, 2H), 2.64-2.49 (m, 4H), 1.87 (s, 3H), 1.85 (s, 3H). HPLC (max plot) 96.6%, Rt 2.28 min. UPLC/MS: (MS+) 439.3 ([M+H]+). Melting point: 159-162° C. (ACN).

Example 127

[2-(azetidin-3-yloxy)-4-fluoro-phenyl]-(6-chloro-5,7-dimethyl-1H,3H-2,4,7a,8-tetraaza-cyclopenta[a]inden-2-yl)-methanone

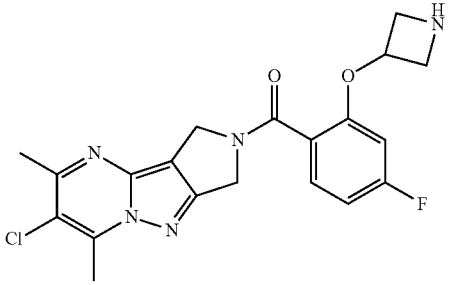 [SMILES: Cc1nc2c3c(nn2c(C)c1Cl)CN(C(=O)c1ccc(F)cc1OC1CNC1)C3]

Step 1: 3-[2-(6-chloro-5,7-dimethyl-1H,3H-2,4,7a,8-tetraaza-cyclopenta[a]indene-2-carbonyl)-5-fluoro-phenoxy]-azetidine-1-carboxylic acid tert-butyl ester The title compound was prepared following procedure described in Method A starting from Intermediate B13 and Intermediate A3. After work up, purification by column chromatography (heptanes/EA) afforded the title compound (472 mg, 95%) as a white solid. HPLC (max plot) 98.4%, Rt 4.41 min. UPLC/MS: (MS+) 516.2 ([M+H]+).

Step 2: [2-(azetidin-3-yloxy)-4-fluoro-phenyl]-(6-chloro-5,7-dimethyl-1H,3H-2,4,7a,8-tetraaza-cyclopenta[a]inden-2-yl)-methanone A solution of 3-[2-(6-chloro-5,7-dimethyl-1H,3H-2,4,7a,8-tetraaza-cyclopenta[a]indene-2-carbonyl)-5-fluoro-phenoxy]-azetidine-1-carboxylic acid tert-butyl ester (472 mg; 0.91 mmol; 1 eq.) and TFA (4 mL) in DCM (4 mL) was stirred at room temperature for 1 hour then concentrated in vacuo. The residue was taken up in water, the pH was made basic with 5M NaOH and extracted with DCM (2×). The combined organic phase was dried over magnesium sulfate and concentrated in vacuo. The resulting solid was triturated in water and filtered off to afford the title compound (70 mg, 18%) as a white solid. ¹H NMR (CDCl₃) δ 7.38-7.31 (m, 1H), 6.80-6.72 (m, 1H), 6.38 (dt, J=10.5, 2.0 Hz, 1H), 5.04-4.96 (m, 3H), 4.65 (s, 2H), 3.93-3.87 (m, 2H), 3.79-3.72 (m, 2H), 2.91 (s, 2H), 2.86 (s, 1H), 2.69 (s, 1H), 2.63 (s, 2H). HPLC (max plot) 94.9%, Rt 2.56 min. UPLC/MS: (MS+) 416.2 ([M+H]+).

Example 128

(6-chloro-5,7-dimethyl-1H,3H-2,4,7a,8-tetraaza-cyclopenta[a]inden-2-yl)-[2-(5-trifluoromethyl-[1,4]diazepan-1-yl)-phenyl]-methanone hydrochloride

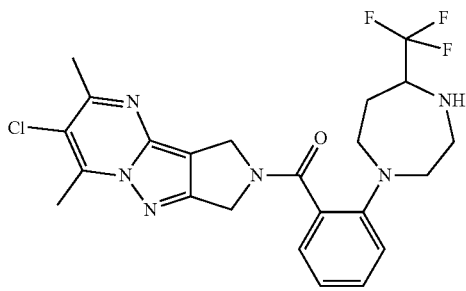 [SMILES: Cc1nc2c3c(nn2c(C)c1Cl)CN(C(=O)c1ccccc1N1CCNC(C(F)(F)F)CC1)C3]

Step 1: 4-[2-(6-chloro-5,7-dimethyl-1H,3H-2,4,7a,8-tetraaza-cyclopenta[a]indene-2-carbonyl)-phenyl]-7-trifluoromethyl-[1,4]diazepane-1-carboxylic acid tert-butyl ester The title compound was prepared following procedure described in Method A starting from Intermediate B14 and Intermediate A3. After work up, purification by column chromatography (25% to 50% EA in heptane) afforded the title compound (90 mg, 42%) as a colourless oil. HPLC (max plot) 88.2%, Rt 5.29 min. UPLC/MS: (MS+) 593.4 ([M+H]+).

Step 2: (6-chloro-5,7-dimethyl-1H,3H-2,4,7a,8-tetraaza-cyclopenta[a]inden-2-yl)-[2-(5-trifluoromethyl-[1,4]diazepan-1-yl)-phenyl]-methanone A suspension of 4-[2-(6-chloro-5,7-dimethyl-1H,3H-2,4,7a,8-tetraaza-cyclopenta[a]indene-2-carbonyl)-phenyl]-7-trifluoromethyl-[1,4]diazepane-1-carboxylic acid tert-butyl ester (90 mg; 0.15 mmol; 1 eq.) in a 4M solution of HCl in 1,4-dioxane (0.38 mL; 1.52 mmol; 10 eq.) was stirred at room temperature for 3 hours. A 4M solution of HCl in 1,4-dioxane (0.38 mL; 1.52 mmol; 10 eq.) was added and the reaction mixture was stirred at room temperature for a 45 minutes. After concentration in vacuo, purification by mass directed preparative HPLC afforded the title compound (14 mg, 17%) as a white solid. ¹H NMR (DMSO-d₆) 10.12 (br s, 2H), 7.46-7.35 (m, 1H), 7.35-7.26 (m, 1H), 7.18-7.10 (m, 1H), 7.04 (t, J=7.4 Hz, 1H), 4.85 (d, J=8.3 Hz, 2H), 4.67-4.28 (m, 3H), 4.22-3.74 (m, 4H), 3.62-3.45 (m, 2H), 2.85 (s, 1.5H), 2.81 (s, 1.5H), 2.62 (s, 1.5H), 2.56 (s, 1.5H), 2.34-2.19 (m, 1H), 2.17-1.98 (m, 1H). HPLC (max plot) 94.6%, Rt 2.94 min. UPLC/MS: (MS+) 493.2 ([M+H]+).

Example 129

(6-chloro-5,7-dimethyl-1H,3H-2,4,7a,8-tetraaza-cyclopenta[a]inden-2-yl)-[4-fluoro-2-((S)-piperidin-3-yloxy)-phenyl]-methanone

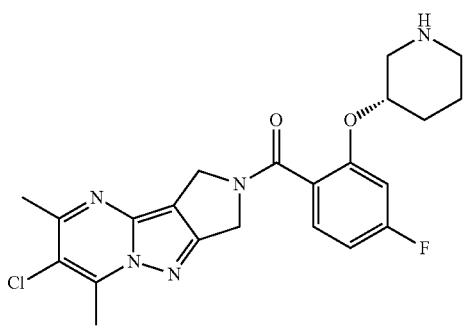

Chiral

Step 1: (S)-3-[2-(6-chloro-5,7-dimethyl-1H,3H-2,4,7a,8-tetraaza-cyclopenta[a]indene-2-carbonyl)-5-fluoro-phenoxy]-piperidine-1-carboxylic acid tert-butyl ester The title compound was prepared following procedure described in Method A starting from Intermediate B15 and Intermediate A3. After work up, purification by column chromatography (heptanes/EA) afforded the title compound (288 mg, 91%) as an off-white solid. HPLC (max plot) 98.8%, Rt 4.73 min. UPLC/MS: (MS+) 544.3 ([M+H]+).

Step 2: (6-chloro-5,7-dimethyl-1H,3H-2,4,7a,8-tetraaza-cyclopenta[a]inden-2-yl)-[4-fluoro-2-((S)-piperidin-3-yloxy)-phenyl]-methanone A mixture of (S)-3-[2-(6-chloro-5,7-dimethyl-1H,3H-2,4,7a,8-tetraaza-cyclopenta[a]indene-2-carbonyl)-5-fluoro-phenoxy]-piperidine-1-carboxylic acid tert-butyl ester (288 mg; 0.53 mmol; 1 eq.) and TFA (3 mL) in DCM (3 mL) was stirred at room temperature for 1 hour then concentrated in vacuo. The residue was taken up in water, the pH made basic with 5M NaOH extracted with DCM (2×). The combined organic layer was dried over magnesium sulfate and concentrated in vacuo. The resulting solid was triturated in water and filtered off to afford the title compound (82 mg, 35%) as an off-white solid. ¹H NMR (CDCl₃) δ 7.36-7.29 (m, 1H), 6.78-6.68 (m, 2H), 5.01-4.99 (m, 2H), 4.66 (s, 2H), 4.29-0.23 (m, 1H), 3.13-3.06 (m, 1H), 2.91 (s, 2H), 2.86 (s, 1H), 2.84-2.75 (m, 2H), 2.71-2.65 (m, 2H), 2.62 (s, 2H), 2.03-1.91 (m, 1H), 1.78-1.56 (m, 3H), 1.51-1.36 (m, 1H). HPLC (max plot) 98.7%, Rt 2.82 min. UPLC/MS: (MS+) 444.4 ([M+H]+).

Example 130

(6-chloro-5,7-dimethyl-1H,3H-2,4,7a,8-tetraaza-cyclopenta[a]inden-2-yl)-[2-(1-methyl-piperidin-4-ylmethyl)-phenyl]-methanone

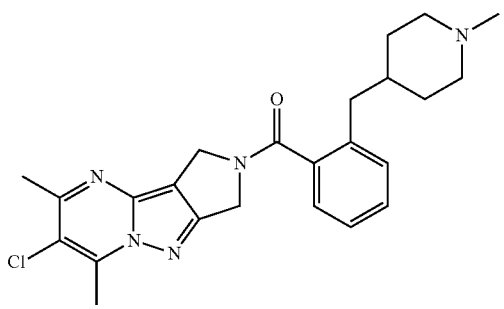

The title compound was prepared following procedure described in Method F starting from Intermediate B16 and Intermediate A3. After work up, purification by mass directed preparative HPLC afforded the title compound (35 mg, 22%) as a white solid. ¹H NMR (CDCl₃) δ 7.37-7.23 (m, 4H), 5.03-5.00 (m, 2H), 4.52-4.48 (m, 2H), 2.92 (s, 2H), 2.85 (s, 1H), 2.79-2.72 (m, 2H), 2.70 (s, 1H), 2.61-2.58 (m, 4H), 2.18 (s, 3H), 1.85-1.74 (m, 2H), 1.66-1.53 (m, 3H), 1.34-1.19 (m, 2H). HPLC (max plot) 100%, Rt 2.75 min. UPLC/MS: (MS+) 438.4 ([M+H]+).

Example 131

(6-chloro-5,7-dimethyl-1H,3H-2,4,7a,8-tetraaza-cyclopenta[a]inden-2-yl)-(2-piperidin-4-ylmethyl-phenyl)-methanone

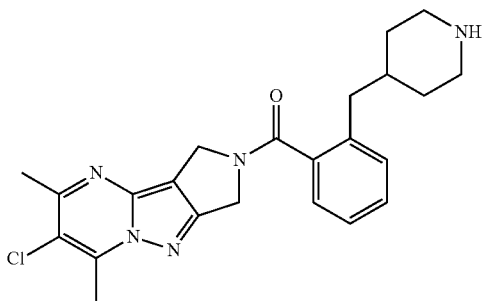 [SMILES: Cc1nc2c3c(nn2c(C)c1Cl)CN(C(=O)c1ccccc1CC1CCNCC1)C3]

Step 1: 4-[2-(6-chloro-5,7-dimethyl-1H,3H-2,4,7a,8-tetraaza-cyclopenta[a]indene-2-carbonyl)-benzyl]-piperidine-1-carboxylic acid tert-butyl ester The title compound was prepared following procedure described in Method F starting from Intermediate B17 and Intermediate A3. After work up, purification by mass directed preparative HPLC afforded the title compound (210 mg, 47%) as a white solid. HPLC (max plot) 99.8%, Rt 4.93 min. UPLC/MS: (MS+) 524.5 ([M+H]+).

Step 2: (6-chloro-5,7-dimethyl-1H,3H-2,4,7a,8-tetraaza-cyclopenta[a]inden-2-yl)-(2-piperidin-4-ylmethyl-phenyl)-methanone A mixture of 4-[2-(6-chloro-5,7-dimethyl-1H,3H-2,4,7a,8-tetraaza-cyclopenta[a]indene-2-carbonyl)-benzyl]-piperidine-1-carboxylic acid tert-butyl ester (210 mg; 0.4 mmol; 1 eq.) and TFA (2 mL) in DCM (2 mL) was stirred at room temperature for 2 hours then concentrated in vacuo. The residue was taken up in water, the pH made basic with 5M NaOH and extracted with DCM (2×). The combined organic layer was dried over magnesium sulfate and concentrated in to afford the title compound (131 mg, 77%) as an off-white solid. ¹H NMR (CDCl₃) δ 7.38-7.24 (m, 4H), 5.04-5.01 (m, 2H), 4.51 (s, 1.3H), 4.48 (s, 0.7H), 3.04-2.96 (m, 2H), 2.91 (s, 2H), 2.85 (s, 1H), 2.70 (s, 1H), 2.61-2.57 (m, 4H), 2.53-2.43 (m, 2H), 1.80-1.57 (m, 4H), 1.19-1.06 (m, 2H). HPLC (max plot) 100%, Rt 2.75 min. UPLC/MS: (MS+) 424.4 ([M+H]+).

Example 132

(6-chloro-5,7-dimethyl-1H,3H-2,4,7a,8-tetraaza-cyclopenta[a]inden-2-yl)-(4-fluoro-2-piperazin-1-ylmethyl-phenyl)-methanone, dihydrochloride

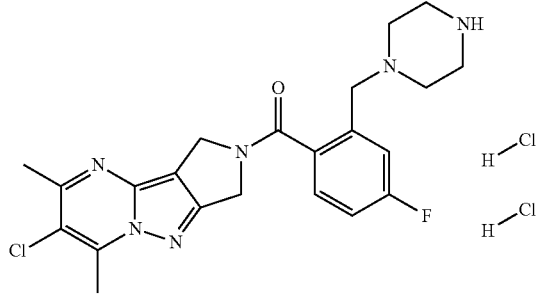 [SMILES: Cc1nc2c3c(nn2c(C)c1Cl)CN(C(=O)c1ccc(F)cc1CN1CCNCC1)C3 ; Cl ; Cl]

Step 1: 4-[2-(6-chloro-5,7-dimethyl-1H,3H-2,4,7a,8-tetraaza-cyclopenta[a]indene-2-carbonyl)-5-fluoro-benzyl]-piperazine-1-carboxylic acid tert-butyl ester A mixture of Intermediate B4 (80%, 391 mg, 0.92 mmol), Intermediate A3 (287 mg, 1.11 mmol), T3P (50% in DMF, 1.00 mL, 1.68 mmol) and DIEA (0.47 mL, 2.77 mmol) was prepared in anhydrous DMF (6 mL) and heated at 60° C. for 24 hours. The reaction mixture was diluted with a 1N aqueous solution of NaOH and extracted with EtOAc (50+25 mL). The organic layers were combined, dried (Na₂SO₄) and concentrated under vacuum to give a yellow oil. After purification by flash chromatography (silica, heptane/EtOAc), the title compound was obtained as a yellow foam (141 mg, 24%). ¹H NMR (CDCl₃) δ 7.38-7.31 (m, 1H), 7.19-6.92 (m, 2H), 5.01-4.95 (m, 2H), 4.58-4.51 (m, 2H), 3.58 (br s, 2H), 3.17-3.09 (m, 4H), 2.91 (s, 2H), 2.86 (s, 1H), 2.70 (s, 1H), 2.62 (s, 2H), 2.43-2.29 (m, 4H), 1.37 (s, 9H). HPLC (max plot) 84.6%, Rt 3.46 min. UPLC/MS: (MS+) 543.5 ([M+H]+), (MS−) 541.5 ([M−H]−).

Step 2: (6-chloro-5,7-dimethyl-1H,3H-2,4,7a,8-tetraaza-cyclopenta[a]inden-2-yl)-(4-fluoro-2-piperazin-1-ylmethyl-phenyl)-methanone, dihydrochloride 4-[2-(6-chloro-5,7-dimethyl-1H,3H-2,4,7a,8-tetraaza-cyclopenta[a]indene-2-carbonyl)-5-fluoro-benzyl]-piperazine-1-carboxylic acid tert-butyl ester (133 mg, 0.21 mmol) was added into a mixture of a 4N solution of HCl in dioxane (2 mL, 8.0 mmol) and water (0.4 mL). After 1 hour of stirring at RT, the reaction mixture was diluted with a 1N aqueous solution of NaOH (15 mL) and extracted with DCM (3×25 mL). The organic layers were combined, dried (Na₂SO₄) and concentrated under vacuum. After purification by flash chromatography (silica, DCM/EtOH/28% aqueous ammonia), the parent compound was obtained as a white solid. The solid was dissolved in DCM (2 ml), then a 2N solution of HCl in Et$_2$O (0.5 mL) was added, followed by Et$_2$O (2 mL). The precipitate was filtered off, washed with Et$_2$O (3×) and dried under vacuum to give the title compound as a white powder (34 mg, 32%). $^1$H NMR (D$_2$O) δ 7.76-7.67 (m, 1H), 7.47-7.34 (m, 2H), 5.01 (s, 1H), 4.98 (s, 1H), 4.72 (s, 1H), 4.67 (s, 1H), 4.15 (s, 2H), 3.40-3.21 (m, 8H), 2.80 (s, 1.5H), 2.76 (s, 1.5H), 2.63 (s, 1.5H), 2.57 (s, 1.5H). HPLC (max plot) 99.9%, Rt 2.39 min. UPLC/MS: (MS+) 443.4 ([M+H]$^+$), (MS−) 441.4 ([M−H]$^-$).

Example 133

(6-chloro-5,7-dimethyl-1H,3H-2,4,7a,8-tetraaza-cyclopenta[a]inden-2-yl)-[2-(2-dimethylaminomethyl-imidazol-1-yl)-phenyl]-methanone

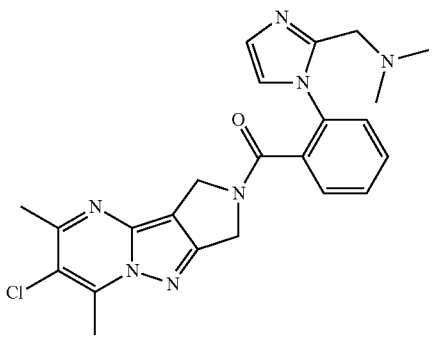

The title compound was prepared following procedure described in Method A starting from Intermediate B18 and Intermediate A3. After work up, purification by column chromatography (DCM/MeOH/NH$_4$OH) afforded the title compound (45 mg, 47%) as a white solid. $^1$H NMR (DMSO-d$_6$) δ 7.81-7.55 (m, 4H), 7.40-7.32 (m, 1H), 7.02-6.90 (m, 1H), 4.84-4.51 (m, 4H), 3.68 (s, 2H), 2.87-2.75 (m, 3H), 2.63-2.53 (m, 3H), 2.38-2.12 (m, 6H). HPLC (max plot) 97.2%, Rt 2.55 min. UPLC/MS: (MS+) 450.4 ([M+H]$^+$).

Example 134

{2-[(1S,3R,5R)-(8-aza-bicyclo[3.2.1]oct-3-yl)oxy]-phenyl}-(6-chloro-5,7-dimethyl-1H,3H-2,4,7a,8-tetraaza-cyclopenta[a]inden-2-yl)-methanone

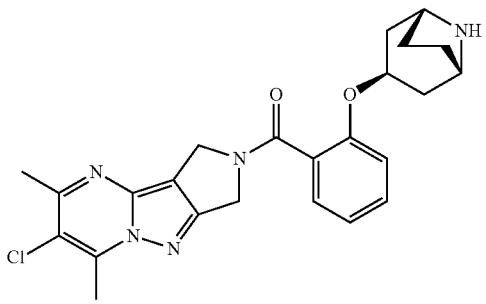 [SMILES: Cc1nc2c3c(nn2c(C)c1Cl)CN(C(=O)c1ccccc1O[C@H]1C[C@H]2CC[C@@H](C1)N2)C3]

Step 1: (1S,3R,5R)-3-[2-(6-chloro-5,7-dimethyl-1H,3H-2,4,7a,8-tetraaza-cyclopenta[a]indene-2-carbonyl)-phenoxy]-8-aza-bicyclo[3.2.1]octane-8-carboxylic acid tert-butyl ester The title compound was prepared following procedure described in Method A starting from Intermediate B19 and Intermediate A3. After completion, water was added and the precipitate was filtered off to afford the title compound (114 mg, 65%) as a pale yellow solid. HPLC (max plot) 98.9%, Rt 4.76 min. UPLC/MS: (MS+) 552.3 ([M+H]$^+$).

Step 2: {2-[(1S,3R,5R)-(8-aza-bicyclo[3.2.1]oct-3-yl)oxy]-phenyl}-(6-chloro-5,7-dimethyl-1H,3H-2,4,7a,8-tetraaza-cyclopenta[a]inden-2-yl)-methanone A mixture of (1S,3R,5R)-3-[2-(6-chloro-5,7-dimethyl-1H,3H-2,4,7a,8-tetraaza-cyclopenta[a]indene-2-carbonyl)-phenoxy]-8-aza-bicyclo[3.2.1]octane-8-carboxylic acid tert-butyl ester (114 mg; 0.21 mmol; 1 eq.) and a 4M solution of HCl in 1,4-dioxane (2 mL; 8 mmol; 38.7 eq.) was stirred at room temperature for 16 hours then concentrated in vacuo. The residue was diluted with 0.1M NaOH and extracted with DCM (2×). The combined organic phase was dried over magnesium sulfate and concentrated in vacuo. Crystallizaton from ACN afforded the title compound (66 mg, 71%) as a white solid. $^1$H NMR (DMSO-d$_6$) δ 7.49-7.35 (m, 1H), 7.35-7.23 (m, 1H), 7.10-6.92 (m, 2H), 4.96-4.67 (m, 3H), 4.67-4.40 (m, 2H), 3.23 (br s, 2H), 2.84 (s, 1.5H), 2.80 (s, 1.5H), 2.62 (s, 1.5H), 2.55 (s, 1.5H), 2.43-2.15 (m, 1H), 2.03-1.84 (m, 2H), 1.84-1.72 (m, 2H), 1.72-1.55 (m, 22H), 1.55-1.32 (m, 2H). HPLC (max plot) 98.4%, Rt 2.66 min. UPLC/MS: (MS+) 452.2 ([M+H]$^+$).

Example 135

(6-chloro-5,7-dimethyl-1H,3H-2,4,7a,8-tetraaza-cyclopenta[a]inden-2-yl)-[2-((S)-pyrrolidin-3-yloxymethyl)-phenyl]-methanone

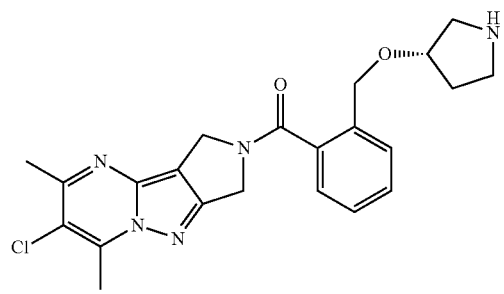

Chiral

Step 1: (S)-3-[2-(6-chloro-5,7-dimethyl-1H,3H-2,4,7a,8-tetraaza-cyclopenta[a]indene-2-carbonyl)-benzyloxy]-pyrrolidine-1-carboxylic acid tert-butyl ester Sodium hydride (55-65%; 23.4 mg; 0.54 mmol; 1.5 eq.) was added to a solution of (S)-3-hydroxy-pyrrolidine-1-carboxylic acid tert-butyl ester (100 mg; 0.54 mmol; 1.5 eq.) in THF (3 mL) and the mixture was stirred at room temperature for 30 minutes whereupon Intermediate Z3 (150 mg; 0.36 mmol; 1 eq.) was added. The reaction mixture was stirred at room temperature for 2 hours then diluted with DCM. The solution was washed with water then brine, dried over magnesium sulfate and concentrated in vacuo. Purification by column chromatography (heptanes/EA) afforded the title compound (60 mg, 32%) as a white solid. HPLC (max plot) 100%, Rt 4.36 min.

Step 2: (6-chloro-5,7-dimethyl-1H,3H-2,4,7a,8-tetraaza-cyclopenta[a]inden-2-yl)-[2-((S)-pyrrolidin-3-yloxymethyl)-phenyl]-methanone A mixture of (S)-3-[2-(6-chloro-5,7-dimethyl-1H,3H-2,4,7a,8-tetraaza-cyclopenta[a]indene-2-carbonyl)-benzyloxy]-pyrrolidine-1-carboxylic acid tert-butyl ester (60 mg; 0.11 mmol; 1 eq.) and TFA (2 mL) in DCM (2 mL) was stirred at room temperature for 15 minutes then concentrated in vacuo. The residue was taken up in water, the pH made basic with 5M NaOH and extracted with DCM (2×). The combined organic layer was dried over magnesium sulfate and concentrated in to afford the title compound (49 mg, quantitative) as an off-white solid. $^1$H NMR (CDCl$_3$) δ 7.46-7.33 (m, 4H), 5.02-4.95 (m, 2H), 4.68-4.46 (m, 4H), 4.21 (m, 1H), 3.26-2.97 (m, 1H), 2.92-2.82 (m, 3H), 2.70-2.58 (m, 3H), 1.96-1.59 (m, 2H). HPLC (max plot) 100%, Rt 2.56 min. UPLC/MS: (MS+) 426.2 ([M+H]$^+$).

Example 136

(6-chloro-5,7-dimethyl-1H,3H-2,4,7a,8-tetraaza-cyclopenta[a]inden-2-yl)-[2-((S)-piperidin-3-yloxymethyl)-phenyl]-methanone

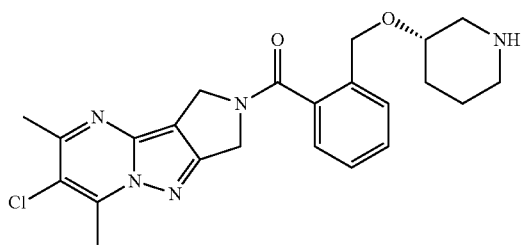

Chiral

Step 1: (S)-3-[2-(6-chloro-5,7-dimethyl-1H,3H-2,4,7a,8-tetraaza-cyclopenta[a]indene-2-carbonyl)-benzyloxy]-piperidine-1-carboxylic acid tert-butyl ester Sodium hydride (55-65%; 23.4 mg; 0.54 mmol; 1.5 eq.) was added to a solution of (S)-3-hydroxy-piperidine-1-carboxylic acid tert-butyl ester (108 mg; 0.54 mmol; 1.5 eq.) in THF (3 mL) and the mixture was stirred at room temperature for 30 minutes whereupon Intermediate Z3 (150 mg; 0.36 mmol; 1 eq.) was added. The reaction mixture was stirred at room temperature for 2 hours then diluted with DCM. The solution was washed with water then brine, dried over magnesium sulfate and concentrated in vacuo. Purification by column chromatography (heptane/EA) afforded the title compound (50 mg, 26%) as a white solid. HPLC (max plot) 99.2%, Rt 4.71 min. UPLC/MS: (MS+) 540.5 ([M+H]$^+$).

Step 2: (6-chloro-5,7-dimethyl-1H,3H-2,4,7a,8-tetraaza-cyclopenta[a]inden-2-yl)-[2-((S)-piperidin-3-yloxymethyl)-phenyl]-methanone A mixture of (S)-3-[2-(6-chloro-5,7-dimethyl-1H,3H-2,4,7a,8-tetraaza-cyclopenta[a]indene-2- carbonyl)-benzyloxy]-piperidine-1-carboxylic acid tert-butyl ester (50 mg; 0.09 mmol; 1 eq.) and TFA (2 mL) in DCM (2 mL) was stirred at room temperature for 30 minutes then concentrated in vacuo. The residue was taken up in water, the pH made basic with 5M NaOH and extracted with DCM (2×). The combined organic layer was dried over magnesium sulfate and concentrated in to afford the title compound (40 mg, 98%) as an off-white solid. $^1$H NMR (CDCl$_3$) δ 7.39-7.26 (m, 4H), 5.03-4.88 (m, 2H), 4.63-4.47 (m, 4H), 3.63-3.30 (m, 1H), 2.94-2.71 (m, 5H), 2.62-2.53 (m, 3H), 1.83-0.72 (m, 7H). HPLC (max plot) 100%, Rt 2.63 min. UPLC/MS: (MS+) 440.2 ([M+H]$^+$).

Example 138

(6-chloro-1H,3H-2,4,7a,8-tetraaza-cyclopenta[a]inden-2-yl)-[4-fluoro-2-(1,1,2,2-tetrafluoro-ethoxy)-phenyl]-methanone

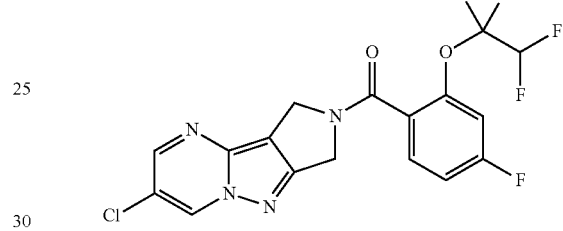

The title compound was prepared following procedure described in Method A starting from Intermediate A4 and Intermediate B5. After purification by flash chromatography (silica, DCM/EtOH) and slurry in ACN, the title compound was obtained as an off-white powder (409 mg, 54%). $^1$H NMR (DMSO-d$_6$) δ 9.61 (d, J=2.3 Hz, 0.5H), 9.59 (d, J=2.3 Hz, 0.5H), 8.64 (d, J=2.3 Hz, 0.5H), 8.60 (d, J=2.3 Hz, 0.5H), 7.76-7.66 (m, 1H), 7.48-7.36 (m, 2H), 6.76 (tt, J=51.5, 3.2 Hz, 1H), 4.85 (s, 2H), 4.59 (s, 1H), 4.56 (s, 1H). HPLC (max plot) 99.7%, Rt 4.02 min. UPLC/MS: (MS+) 433.1 ([M+H]$^+$). Melting point: 208-210° C.

Example 139

[2-((S)-azepan-4-yloxy)-4-fluoro-phenyl]-(6-chloro-5,7-dimethyl-1H,3H-2,4,7a,8-tetraaza-cyclopenta[a]inden-2-yl)-methanone

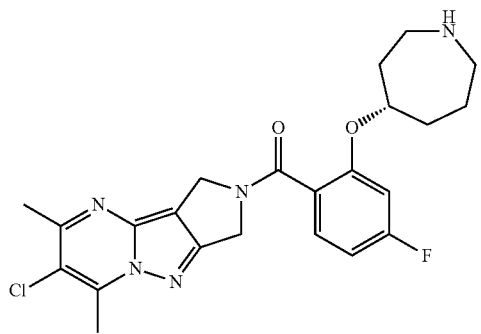

Chiral

Step 1: (S)-4-[2-(6-chloro-5,7-dimethyl-1H,3H-2,4, 7a,8-tetraaza-cyclopenta[a]indene-2-carbonyl)-5-fluoro-phenoxy]-azepane-1-carboxylic acid tert-butyl ester The title compound was prepared following procedure described in Method G starting from Intermediate Z2 and 4-hydroxyazepane-1-carboxylic acid tert-butyl ester. After work up purification by column chromatography (50% to 80% EA in heptane) followed by chiral separation (SFC-Chiralcel OJ-H) afforded the title compound (180 mg, 28%) as a white solid. HPLC (max plot) 90.6%, Rt 4.96 min. UPLC/MS: (MS+) 558.5 ([M+H]$^+$).

Step 2: [2-((S)-azepan-4-yloxy)-4-fluoro-phenyl]-(6-chloro-5,7-dimethyl-1H,3H-2,4,7a,8-tetraaza-cyclopenta[a]inden-2-yl)-methanone formic acid salt A solution of (S)-4-[2-(6-chloro-5,7-dimethyl-1H,3H-2,4, 7a,8-tetraaza-cyclopenta[a]indene-2-carbonyl)-5-fluoro-phenoxy]-azepane-1-carboxylic acid tert-butyl ester (180 mg; 1.11 mmol; 1 eq.) in a 4M solution of HCl in 1,4-dioxane (2 mL) was stirred at room temperature for 16 hours. The residue was diluted with 0.1M NaOH and extracted with DCM (2×). The combined organic phase was dried over magnesium sulfate and concentrated in vacuo. Purification by mass directed preparative HPLC afforded the title compound (38 mg, 7%) as a yellow solid. $^1$H NMR (DMSO-d$_6$) δ 8.34 (s, 1H), 7.37 (ddd, J=8.5, 6.8, 3.2 Hz, 1H), 7.12 (dd, J=11.7, 2.3 Hz, 1H), 6.88 (td, J=8.4, 2.3 Hz, 1H), 4.93-4.72 (m, 3H), 4.54 (d, J=15.1 Hz, 2H), 3.03-2.75 (m, 6.7H), 2.62 (s, 1.5H), 2.56 (s, 1.5H), 2.11-1.49 (m, 6.3H). HPLC (max plot) 90.3%, Rt 2.91 min. UPLC/MS: (MS+) 458.4 ([M+H]$^+$).

Example 140

[2-((R)-azepan-4-yloxy)-4-fluoro-phenyl]-(6-chloro-5,7-dimethyl-1H,3H-2,4,7a,8-tetraaza-cyclopenta[a]inden-2-yl)-methanone

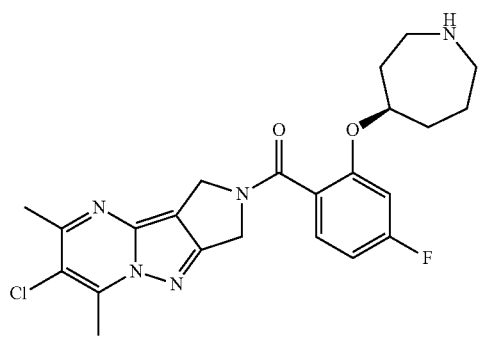

Chiral

Step 1: (R)-4-[2-(6-Chloro-5,7-dimethyl-1H,3H-2,4, 7a,8-tetraaza-cyclopenta[a]indene-2-carbonyl)-5-fluoro-phenoxy]-azepane-1-carboxylic acid tert-butyl ester The title compound was isolated (173 mg, 28%) as a white solid during the chiral separation described in Example 139 step 1. HPLC (max plot) 99.2%, Rt 4.95 min. UPLC/MS: (MS+) 558.5 ([M+H]$^+$).

Step 2: [2-((R)-azepan-4-yloxy)-4-fluoro-phenyl]-(6-chloro-5,7-dimethyl-1H,3H-2,4,7a,8-tetraaza-cyclopenta[a]inden-2-yl)-methanone A solution of (R)-4-[2-(6-chloro-5,7-dimethyl-1H,3H-2,4, 7a,8-tetraaza-cyclopenta[a]indene-2-carbonyl)-5-fluoro-phenoxy]-azepane-1-carboxylic acid tert-butyl ester (173 mg; 0.31 mmol; 1 eq.) in a 4M solution of HCl in 1,4-dioxane (2 mL) was stirred at room temperature for 16 hours. The residue was diluted with 0.1M NaOH and extracted with DCM (2×). The combined organic phase was dried over magnesium sulfate and concentrated in vacuo. Purification by mass directed preparative HPLC afforded the title compound (27 mg, 17%) as a yellow solid. $^1$H NMR (DMSO-d$_6$) δ 8.34 (s, 1H), 7.37 (ddd, J=8.5, 6.8, 3.2 Hz, 1H), 7.12 (dd, J=11.8, 2.3 Hz, 1H), 6.87 (td, J=8.4, 2.3 Hz, 1H), 4.88-4.72 (m, 2H), 4.54 (d, J=15.8 Hz, 2H), 3.10-2.74 (m, 7H), 2.61 (s, 1.5H), 2.56 (s, 1.5H), 2.11-1.49 (m, 6H). HPLC (max plot) 96.2%, Rt 2.91 min. UPLC/MS: (MS+) 458.4 ([M+H]$^+$).

Example 141

{2-[(1S,3R,5R)-(8-aza-bicyclo[3.2.1]oct-3-yl)oxy]-4-fluoro-phenyl}-(6-chloro-5,7-dimethyl-1H,3H-2,4, 7a,8-tetraaza-cyclopenta[a]inden-2-yl)-methanone

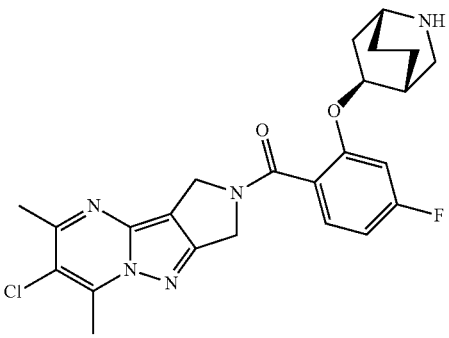 [SMILES: Cc1nc2c3c(nn2c(C)c1Cl)CN(C(=O)c1ccc(F)cc1O[C@H]1C[C@H]2CC[C@@H]1CN2)C3]

Step 1: (1S,3R,5R)-3-[2-(6-chloro-5,7-dimethyl-1H, 3H-2,4,7a,8-tetraaza-cyclopenta[a]indene-2-carbonyl)-5-fluoro-phenoxy]-8-aza-bicyclo[3.2.1]octane-8-carboxylic acid tert-butyl ester The title compound was prepared following procedure described in Method A starting from Intermediate B20 and Intermediate A3. After work-up, purification by column chromatography (20% to 60% EA in heptane) afforded the title compound (532 mg, 85%) as a white solid. HPLC (max plot) 96.2%, Rt 5.00 min. UPLC/MS: (MS+) 570.3 ([M+H]$^+$).

Step 2: {2-[(1S,3R,5R)-(8-aza-bicyclo[3.2.1]oct-3-yl)oxy]-4-fluoro-phenyl}-(6-chloro-5,7-dimethyl-1H,3H-2,4,7a,8-tetraaza-cyclopenta[a]inden-2-yl)-methanone hydrochloride A solution of (1S,3R,5R)-3-[2-(6-chloro-5,7-dimethyl-1H,3H-2,4,7a,8-tetraaza-cyclopenta[a]indene-2-carbonyl)-5-fluoro-phenoxy]-8-aza-bicyclo[3.2.1]octane-8-carboxylic acid tert-butyl ester (532 mg; 0.93 mmol; 1 eq.) in a 4M solution of HCl 1,4-dioxane (5 mL; 20.00 mmol; 21.4 eq.) and MeOH (1 mL) was stirred at room temperature for 16 hours then concentrated in vacuo. Water was added and the resulting solution was concentrated in vacuo. The residue was suspended in toluene and concentrated in vacuo. Crystallization from iPrOH afforded the title compound (116 mg, 25%) as a white solid. $^1$H NMR (DMSO-$d_6$) δ 9.02 (s, 2H), 7.40 (ddd, J=8.4, 6.8, 2.9 Hz, 1H), 7.16 (dt, J=11.8, 2.2 Hz, 1H), 6.88 (td, J=8.4, 2.2 Hz, 1H), 4.82 (t, J=9.2 Hz, 3H), 4.58 (d, J=14.1 Hz, 2H), 3.86 (s, 2H), 2.84 (s, 1H), 2.81 (s, 1H), 2.62 (s, 1H), 2.56 (s, 2H), 2.29 (d, J=15.0 Hz, 2H), 2.13-1.67 (m, 6H). HPLC (max plot) 99.8%, Rt 2.84 min. UPLC/MS: (MS+) 470.4 ([M+H]$^+$).

Example 142

{2-[(1S,3R,5R)-(8-aza-bicyclo[3.2.1]oct-3-yl)oxy]-4-fluoro-phenyl}-(6-chloro-1H,3H-2,4,7a,8-tetraaza-cyclopenta[a]inden-2-yl)-methanone hydrochloride

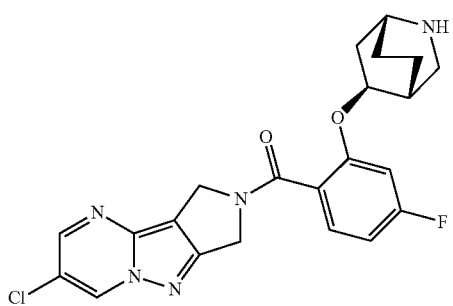 [SMILES: O=C(c1ccc(F)cc1O[C@H]1C[C@H]2CC[C@@H]1CN2)N1Cc2nn3cc(Cl)cnc3c2C1]

Step 1: (1S,3R,5R)-3-[2-(6-chloro-1H,3H-2,4,7a,8-tetraaza-cyclopenta[a]indene-2-carbonyl)-5-fluoro-phenoxy]-8-aza-bicyclo[3.2.1]octane-8-carboxylic acid tert-butyl ester The title compound was prepared following procedure described in Method A starting from Intermediate B20 and Intermediate A4. After work-up, purification by crystallization from heptane/MTBE afforded the title compound (135 mg, 76%) as a white solid. HPLC (max plot) 97.5%, Rt 4.58 min. UPLC/MS: (MS+) 542.2 ([M+H]$^+$).

Step 2: {2-[(1S,3R,5R)-(8-aza-bicyclo[3.2.1]oct-3-yl)oxy]-4-fluoro-phenyl}-(6-chloro-1H,3H-2,4,7a,8-tetraaza-cyclopenta[a]inden-2-yl)-methanone hydrochloride A solution of (1S,3R,5R)-3-[2-(6-chloro-1H,3H-2,4,7a,8-tetraaza-cyclopenta[a]indene-2-carbonyl)-5-fluoro-phenoxy]-8-aza-bicyclo[3.2.1]octane-8-carboxylic acid tert-butyl ester (135 mg; 0.25 mmol; 1 eq.) in a 4M solution of HCl 1,4-dioxane (1 mL; 4 mmol; 16 eq.) and MeOH (5 mL) was stirred at room temperature for 16 hours then concentrated in vacuo. Water was added and the resulting solution was concentrated in vacuo. The residue was suspended in toluene and concentrated in vacuo. Crystallization from iPrOH afforded the title compound (27 mg, 22%) as a white solid. $^1$H NMR (DMSO-$d_6$) δ 9.60 (dd, J=4.9, 2.3 Hz, 1H), 9.00 (s, 2H), 8.62 (dd, J=11.6, 2.3 Hz, 1H), 7.41 (ddd, J=8.6, 6.9, 2.2 Hz, 1H), 7.16 (d, J=11.8 Hz, 1H), 6.89 (td, J=8.4, 2.3 Hz, 1H), 4.83 (br s, 3H), 4.61 (d, J=9.0 Hz, 2H), 3.86 (s, 2H), 2.29 (d, J=14.3 Hz, 2H), 2.08-1.71 (m, 6H). HPLC (max plot) 96.7%, Rt 2.44 min. UPLC/MS: (MS+) 442.3 ([M+H]$^+$).

Example 143

(6-chloro-5,7-dimethyl-1H,3H-2,4,7a,8-tetraaza-cyclopenta[a]inden-2-yl)-[2-(2-hydroxy-1-methyl-ethoxy)-phenyl]-methanone

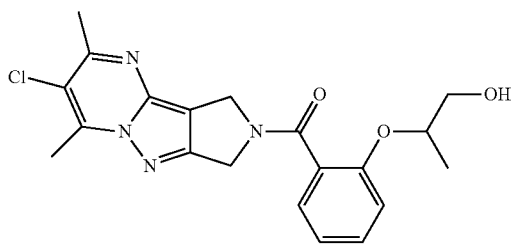 [SMILES: Cc1nc2c3c(nn2c(C)c1Cl)CN(C(=O)c1ccccc1OC(C)CO)C3]

Step 1: {2-[2-(tert-butyl-dimethyl-silanyloxy)-1-methyl-ethoxy]-phenyl}-(6-chloro-5,7-dimethyl-1H,3H-2,4,7a,8-tetraaza-cyclopenta[a]inden-2-yl)-methanone The title compound was prepared following procedure described in Method A starting from Intermediate B21 and Intermediate A3. After work-up, purification by column chromatography (15% to 30% EA in cyclohexane) afforded the title compound (540 mg, 47%) as a yellow foam. HPLC (max plot) 94.4%, Rt 3.34 min. UPLC/MS: (MS+) 515.4 ([M+H]$^+$).

Step 2: (6-chloro-5,7-dimethyl-1H,3H-2,4,7a,8-tetraaza-cyclopenta[a]inden-2-yl)-[2-(2-hydroxy-1-methyl-ethoxy)-phenyl]-methanone A 1M solution of tetrabutyl-ammonium fluoride in THF (1.26 mL; 1.26 mmol; 1.2 eq.) was added to a cold (0° C.) solution of {2-[2-(tert-butyl-dimethyl-silanyloxy)-1-methyl-ethoxy]-phenyl}-(6-chloro-5,7-dimethyl-1H,3H-2,4,7a,8-tetraaza-cyclopenta[a]inden-2-yl)-methanone (540 mg; 1.05 mmol; 1 eq.) in THF (5 mL) and the resulting mixture was stirred at room temperature for 2.5 hours. After dilution with EA, the solution was washed with sat. aq. NaHCO$_3$, dried over magnesium sulfate and concentrated in vacuo. Purification by column chromatography (50% EA in cyclohexane to EA) afforded the title compound (200 mg, 48%) as a white foam. $^1$H NMR (DMSO-$d_6$) δ 7.52-7.36 (m, 1H), 7.37-7.23 (m, 1H), 7.23-7.14 (d, J=8.4 Hz, 1H), 7.09-6.96 (m, 1H), 4.96-4.73 (m, 3H), 4.55-4.38 (m, 2H), 3.51-3.37 (m, 2H), 2.84 (s, 1.5H), 2.80 (s, 1.5H), 2.62 (s, 1.5H), 2.55 (s, 1.5H), 1.24-1.11 (dd, J=6.2, 2.3 Hz, 2H). HPLC (max plot) 99.1%, Rt 3.35 min. UPLC/MS: (MS+) 401.2 ([M+H]$^+$).

Example 144

(6-chloro-5,7-dimethyl-1H,3H-2,4,7a,8-tetraaza-cyclopenta[a]inden-2-yl)-[2-(2-methylamino-ethoxy)-phenyl]-methanone

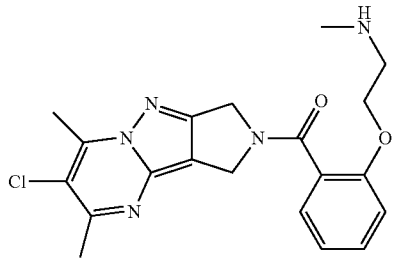 [SMILES: CNCCOc1ccccc1C(=O)N1Cc2nn3c(C)c(Cl)c(C)nc3c2C1]

Step 1: {2-[2-(6-chloro-5,7-dimethyl-1H,3H-2,4,7a,8-tetraaza-cyclopenta[a]indene-2-carbonyl)-phenoxy]-ethyl}-methyl-carbamic acid tert-butyl ester The title compound was prepared following procedure described in Method A starting from Intermediate B22 and Intermediate A3. After work-up, purification by column chromatography (25% to 50% EA in heptane) afforded the title compound (1.54 g, 81%) as a yellow foam. HPLC (max plot) 94.5%, Rt 4.44 min. UPLC/MS: (MS+) 500.2 ([M+H]$^+$).

Step 2: (6-chloro-5,7-dimethyl-1H,3H-2,4,7a,8-tetraaza-cyclopenta[a]inden-2-yl)-[2-(2-methylamino-ethoxy)-phenyl]-methanone A solution of {2-[2-(6-chloro-5,7-dimethyl-1H,3H-2,4,7a,8-tetraaza-cyclopenta[a]indene-2-carbonyl)-phenoxy]-ethyl}-methyl-carbamic acid tert-butyl ester (1.54 mg; 3.08 mmol; 1 eq.) in a 4M solution of HCl 1,4-dioxane (7.7 mL; 30.8 mmol; 10 eq.) and DCM (25 mL) was stirred at room temperature for 2 hours then concentrated in vacuo. After dilution with DCM, the solution was washed with sat. aq. Na$_2$CO$_3$, dried over magnesium sulfate and concentrated in vacuo to afford the title compound (1.2 g, 89%) as a yellow powder. $^1$H NMR (DMSO-d$_6$) δ 10.12 (br s, 2H), 7.46-7.35 (m, 1H), 7.35-7.26 (m, 1H), 7.18-7.10 (m, 1H), 7.04 (t, J=7.4 Hz, 1H), 4.85 (d, J=8.3 Hz, 2H), 4.67-4.28 (m, 3H), 4.22-3.74 (m, 4H), 3.62-3.45 (m, 2H), 2.85 (s, 1.5H), 2.81 (s, 1.5H), 2.62 (s, 1.5H), 2.56 (s, 1.5H), 2.34-2.19 (m, 1H), 2.17-1.98 (m, 1H). HPLC (max plot) 94.7%, Rt 2.61 min. UPLC/MS: (MS+) 400.2 ([M+H]$^+$).

Example 145

(6-chloro-1H,3H-2,4,7a,8-tetraaza-cyclopenta[a]inden-2-yl)-[4-fluoro-2-(2-pyridin-3-yl-ethoxy)-phenyl]-methanone

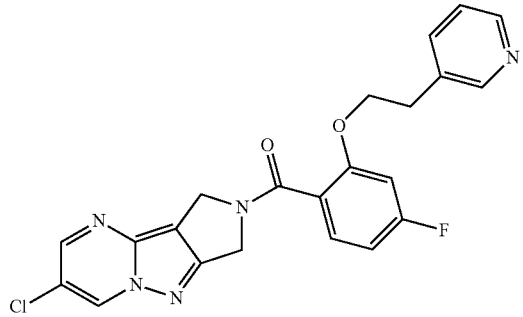 [SMILES: O=C(c1ccc(F)cc1OCCc1cccnc1)N1Cc2nn3cc(Cl)cnc3c2C1]

The title compound was prepared following procedure described in Method G starting from Intermediate Z2 and 2-pyridin-3-yl-ethanol. After work-up, purification by column chromatography (40% EA in heptane to EA) followed by recrystallization from EA afforded the title compound (60 mg, 46%) as a white solid. $^1$H NMR (DMSO-d$_6$) δ 9.63 (d, J=2.3 Hz, 0.5H), 9.60 (d, J=2.3 Hz, 0.5H), 8.66 (d, J=2.3 Hz, 0.5H), 8.59 (d, J=2.3 Hz, 0.5H), 8.39-8.28 (m, 1H), 7.92-7.68 (m, 1H), 7.64-7.53 (m, 1H), 7.35-7.23 (m, 1H), 7.14-7.03 (m, 1H), 6.96-6.74 (m, 2H), 4.84-4.67 (m, 2H), 4.32 (t, J=5.9 Hz, 2H), 4.20-3.98 (m, 2H), 2.96 (t, J=5.8 Hz, 2H). HPLC (max plot) 98.0%, Rt 2.40 min. UPLC/MS: (MS+) 438.3 ([M+H]$^+$).

Example 146

(6-chloro-5,7-dimethyl-1H,3H-2,4,7a,8-tetraaza-cyclopenta[a]inden-2-yl)-(2-{2-[(2-fluoro-ethyl)-methyl-amino]-ethoxy}-phenyl)-methanone

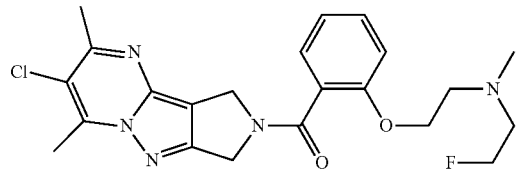 [SMILES: Cc1nc2c3c(nn2c(C)c1Cl)CN(C(=O)c1ccccc1OCCN(C)CCF)C3]

A mixture of Example 144 (100 mg; 0.23 mmol; 1 eq.), 1-bromo-2-fluoro-ethane (47 mg; 0.37 mmol; 1.6 eq.) and NaHCO$_3$ (193 mg; 2.29 mmol; 10 eq.) in DMF was stirred at 100° C. for 30 minutes. 1-Bromo-2-fluoro-ethane (47 mg; 0.37 mmol; 1.6 eq.) was added and the resulting mixture was stirred at 100° C. for 30 minutes then concentrated in vacuo. After dilution with EA, the solution was washed with sat. aq. NaHCO$_3$ then brine, dried over magnesium sulfate and concentrated in vacuo. Purification by column chromatography (EA to 10% MeOH in EA) afforded the title compound (50 mg, 49%) as a white foam. $^1$H NMR (DMSO-d$_6$) δ 7.51-7.39 (m, 1H), 7.36-7.24 (m, 1H), 7.15 (d, J=8.3 Hz, 1H), 7.04 (t, J=7.3 Hz, 1H), 4.80 (d, J=7.3 Hz, 2H), 4.59 (d, J=19.7 Hz, 2H), 4.37 (td, J=5.0, 3.2 Hz, 1H), 4.21 (td, J=5.1, 3.3 Hz, 1H), 4.12 (t, J=5.3 Hz, 2H), 2.84 (s, 2H), 2.81 (s, 1H), 2.71 (t, J=5.2 Hz, 2H), 2.67-2.60 (m, 2H), 2.60-2.53 (m, 2H), 2.15 (s, 3H). HPLC (max plot) 97.5%, Rt 2.65 min. UPLC/MS: (MS+) 446.2 ([M+H]$^+$).

Example 147

(6-chloro-5,7-dimethyl-1H,3H-2,4,7a,8-tetraaza-cyclopenta[a]inden-2-yl)-[4-fluoro-2-((1S,3R,5R)-8-methyl-8-aza-bicyclo[3.2.1]oct-3-yloxy)-phenyl]-methanone hydrochloride

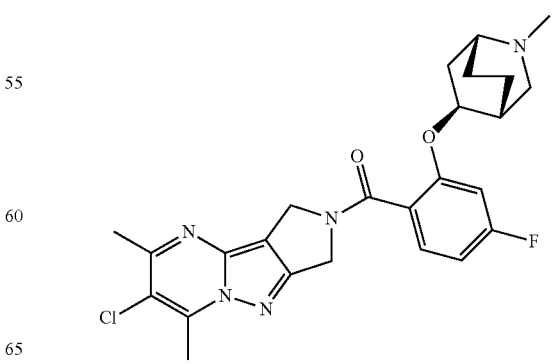

A mixture of Example 141 (256 mg; 0.54 mmol; 1 eq.), paraformaldehyde (491 mg; 5.45 mmol; 10 eq.) and sodium triacetoxyborohydride (231 mg; 1.09 mmol; 2 eq.) in DCE (5 mL) was stirred at reflux for 3 days. 0.1M NaOH was added and the two phases separated. The aqueous layer was extracted with DCM (3×) and the combined organics were dried over magnesium sulfate and concentrated in vacuo. The residue was suspended in a 1.25M solution of HCl in MeOH and the solvent evaporated in vacuo. The solid was taken up in iPrOH and the solution cooled down to 0° C. for 2 hours. The precipitate was filtered off and dried to afford the title compound (39 mg, 14%) as a pale yellow solid. $^1$H NMR (DMSO-$d_6$) δ 10.22 (br s, 1H), 7.41 (ddd, J=8.4, 6.8, 3.2 Hz, 1H), 7.18 (dt, J=11.7, 2.3 Hz, 1H), 6.89 (td, J=8.4, 2.2 Hz, 1H), 4.83-4.78 (m, 3H), 4.59 (d, J=13.8 Hz, 2H), 3.75 (br s, 2H), 2.85 (s, 1.5H), 2.81 (s, 1.5H), 2.66-2.54 (m, 6H), 2.50-2.39 (m, 2H), 2.04-1.97 (m, 6H). HPLC (max plot) 98.0%, Rt 2.85 min. UPLC/MS: (MS+) 484.4 ([M+H]$^+$).

Example 148

(6-chloro-5,7-dimethyl-1H,3H-2,4,7a,8-tetraaza-cyclopenta[a]inden-2-yl)-[4-fluoro-2-(2-methylamino-ethoxy)-phenyl]-methanone hydrochloride

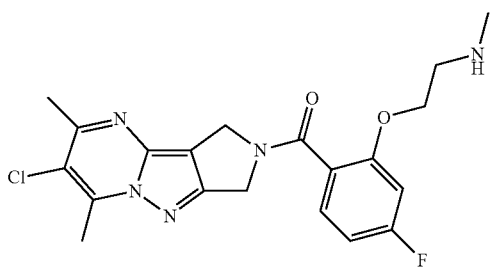 [SMILES: CNCCOc1cc(F)ccc1C(=O)N1Cc2nn3c(C)c(Cl)c(C)nc3c2C1]

Step 1: {2-[2-(6-chloro-5,7-dimethyl-1H,3H-2,4,7a,8-tetraaza-cyclopenta[a]indene-2-carbonyl)-5-fluoro-phenoxy]-ethyl}-methyl-carbamic acid tert-butyl ester The title compound was prepared following procedure described in Method G starting from Intermediate Z2 and (2-hydroxy-ethyl)-methyl-carbamic acid tert-butyl ester (from Intermediate B22 step 1). After work-up, purification by column chromatography (25% to 65% EA in heptane) afforded the title compound (100 mg, 70%) as a white solid. HPLC (max plot) 97.9%, Rt 4.60 min. UPLC/MS: (MS+) 518.4 ([M+H]$^+$).

Step 2: (6-chloro-5,7-dimethyl-1H,3H-2,4,7a,8-tetraaza-cyclopenta[a]inden-2-yl)-[4-fluoro-2-(2-methylamino-ethoxy)-phenyl]-methanone hydrochloride A 4M solution of HCl in 1,4-dioxane (0.72 mL; 2.9 mmol; 15 eq.) was added to a solution of {2-[2-(6-chloro-5,7-dimethyl-1H,3H-2,4,7a,8-tetraaza-cyclopenta[a]indene-2-carbonyl)-5-fluoro-phenoxy]-ethyl}-methyl-carbamic acid tert-butyl ester (100 mg; 0.19 mmol; 1 eq.) in DCM (5 mL) and the reaction mixture was stirred at room temperature for 2 hours. The residue was suspended in hot MTBE, filtered and dried to afford the title compound (60 mg, 68%) as a pale yellow solid. $^1$H NMR (DMSO-$d_6$) δ 8.92-8.69 (m, 2H), 7.50-7.38 (m, 1H), 7.24-7.13 (m, 1H), 7.00-6.90 (td, J=8.5, 8.0, 2.2 Hz, 1H), 4.89-4.77 (d, J=8.6 Hz, 2H), 4.65-4.51 (m, 2H), 4.41-4.32 (m, 2H), 3.27 (br s, 2H), 2.85 (s, 1.7H), 2.81 (s, 1.3H), 2.62 (s, 1.3H), 2.57 (s, 1.7H), 2.53 (s, 3H). HPLC (max plot) 97.0%, Rt 2.73 min. UPLC/MS: (MS+) 418.3 ([M+H]$^+$).

Example 149

(6-chloro-5,7-dimethyl-1H,3H-2,4,7a,8-tetraaza-cyclopenta[a]inden-2-yl)-[2-(2-dimethylamino-1-methyl-ethoxy)-phenyl]-methanone hydrochloride

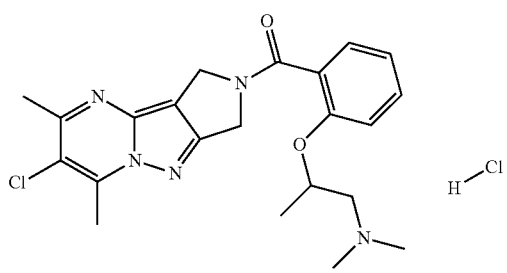

Step 1: 2-[2-(6-chloro-5,7-dimethyl-1H,3H-2,4,7a,8-tetraaza-cyclopenta[a]indene-2-carbonyl)-phenoxy]-propionaldehyde DMP (291 mg; 0.69 mmol; 1.25 eq.) was added at 0° C. to a solution of Example 143 (220 mg; 0.55 mmol; 1 eq.) in DCM (10 mL) and the reaction mixture was stirred at room temperature for 16 hours. The solution was diluted with DCM, washed with sat. aq. NaHCO$_3$ then brine, dried over magnesium sulfate and concentrated in vacuo. Purification by column chromatography (25% to 65% EA in cyclohexane) afforded the title compound (170 mg, 78%) as a white solid. UPLC/MS: (MS+) 399.1 ([M+H]$^+$).

Step 2: (6-chloro-5,7-dimethyl-1H,3H-2,4,7a,8-tetraaza-cyclopenta[a]inden-2-yl)-[2-(2-dimethylamino-1-methyl-ethoxy)-phenyl]-methanone hydrochloride A mixture of 2-[2-(6-chloro-5,7-dimethyl-1H,3H-2,4,7a,8-tetraaza-cyclopenta[a]indene-2-carbonyl)-phenoxy]-propionaldehyde (170 mg; 0.43 mmol; 1 eq.), a 1M solution of dimethyl-amine in THF (2.1 mL; 2.1 mmol; 5 eq.) and sodium triacetoxyborohydride (117 mg; 0.55 mmol; 1.3 eq.) in DCE (10 mL) was stirred at 70° C. for 16 hours. The solution was diluted with DCM, washed with sat. aq. NaHCO$_3$ then brine, dried over magnesium sulfate and concentrated in vacuo. Purification by column chromatography (DCM to 20% MeOH in DCM) followed by hydrochloride formation with a 4M solution of HCl in 1,4-dioxane and crystallization from hot MTBE afforded the title compound (40 mg, 20%) as a pale yellow solid. $^1$H NMR (DMSO-$d_6$) δ 9.83 (br s, 1H), 7.54-7.45 (m, 1H), 7.41 (ddd, J=7.6, 3.9, 1.7 Hz, 1H), 7.26 (d, J=8.5 Hz, 1H), 7.13 (t, J=7.4 Hz, 1H), 5.04-4.91 (m, 1H), 4.90-4.80 (d, J=7.9 Hz, 2H), 4.71-4.41 (m, 2H), 2.85 (s, 1.5H), 2.82 (s, 1.5H), 2.75 (br s, 6H), 2.63 (s, 1.5H), 2.56 (s, 1.5H), 1.30-1.22 (m, 3H). HPLC (max plot) 98.7%, Rt 2.79 min. UPLC/MS: (MS+) 428.3 ([M+H]+).

Example 150

[2-(4-amino-piperidin-1-ylmethyl)-phenyl]-(6-chloro-5,7-dimethyl-1H,3H-2,4,7a,8-tetraaza-cyclopenta[a]inden-2-yl)-methanone dihydrochloride

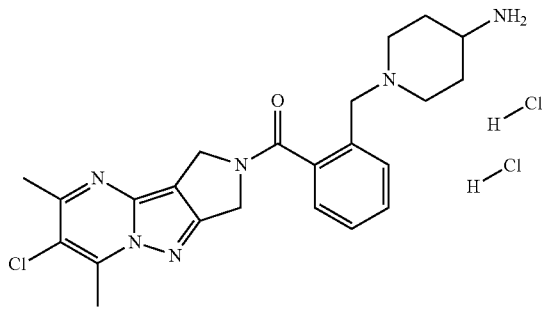

Step 1: {1-[2-(6-chloro-5,7-dimethyl-1H,3H-2,4,7a,8-tetraaza-cyclopenta[a]indene-2-carbonyl)-benzyl]-piperidin-4-yl}-carbamic acid tert-butyl ester The title compound was prepared following procedure described in Method D starting from Intermediate Z3 and 4-N-Boc-amino-piperidine. After purification by flash chromatography (silica, heptane/EtOAc), the title compound was obtained as a white foam (136 mg, 68%). ¹H NMR (300 MHz, CDCl₃) δ 7.36-7.27 (m, 4H), 5.05-4.95 (m, 2H), 4.56 (s, 2H), 4.05-3.01 (m, 4H), 2.93 (s, 2H), 2.87 (s, 1H), 2.75-2.60 (m, 5H), 2.15-2.00 (m, 2H), 1.71-1.57 (m, 2H), 1.37 (s, 9H), 0.99-0.80 (m, 2H). HPLC (max plot) 96.1%, Rt 3.36 min. UPLC/MS: (MS+) 539.3 ([M+H]+), (MS−) 537.2 ([M−H]−).

Step 2: [2-(4-amino-piperidin-1-ylmethyl)-phenyl]-(6-chloro-5,7-dimethyl-1H,3H-2,4,7a,8-tetraaza-cyclopenta[a]inden-2-yl)-methanone, dihydrochloride salt A 4N solution of HCl in dioxane (1.0 mL, 4 mmol) was added to a solution of {1-[2-(6-chloro-5,7-dimethyl-1H,3H-2,4,7a,8-tetraaza-cyclopenta[a]indene-2-carbonyl)-benzyl]-piperidin-4-yl}-carbamic acid tert-butyl ester (136 mg, 0.24 mmol) in dioxane (1.0 mL). After 3 hours of stirring at RT, the precipitate was filtered off and washed with dioxane (2×). The solid was dissolved in water (2 ml) and lyophilized to give the title compound as an off-white powder (82 mg, 64%). ¹H NMR (300 MHz, DMSO-d₆) δ 10.97-10.60 (m, 1H), 8.63-8.24 (m, 3H), 8.15-7.98 (m, 1H), 7.76-7.41 (m, 3H), 5.08-4.86 (m, 2H), 4.73-4.48 (m, 2H), 4.44-4.17 (m, 2H), 3.60-2.96 (m, 5H), 2.85 (s, 1.5H), 2.81 (s, 1.5H), 2.63 (s, 1.5H), 2.56 (s, 1.5H), 2.23-1.78 (m, 4H). HPLC (max plot) 96.1%, Rt 2.23 min. UPLC/MS: (MS+) 439.4 ([M+H]+).

Example 151

(6-chloro-1H,3H-2,4,7a,8-tetraaza-cyclopenta[a]inden-2-yl)-[4-fluoro-2-(3,3,3-trifluoro-2-hydroxy-propoxy)-phenyl]-methanone

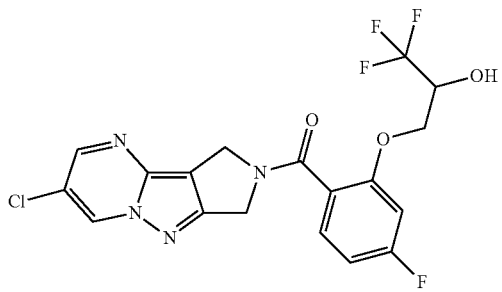 [SMILES: O=C(c1ccc(F)cc1OCC(O)C(F)(F)F)N1Cc2nn3cc(Cl)cnc3c2C1]

Cesium fluoride (45 mg; 0.3 mmol; 1 eq.) was added to a solution of Intermediate Z9 (100 mg; 0.3 mmol; 1 eq.) in DMF (2.3 mL) and the reaction mixture was stirred at room temperature for 30 minutes whereupon 2-trifluoromethyloxirane (37 mg; 0.33 mmol; 1.1 eq.) was added. The resulting mixture was stirred at 130° C. (microwave heating) for 30 minutes. The precipitate was filtered off and the filtrate concentrated in vacuo. Purification by column chromatography (50% EA in heptane to EA) afforded the title compound (66 mg, 49%) as a beige solid. ¹H NMR (DMSO-d₆) δ 9.58 (dd, J=6.3, 2.3 Hz, 1H), 8.60 (dd, J=14.0, 2.4 Hz, 1H), 7.49-7.29 (m, 1H), 7.18 (dd, J=10.5, 2.1 Hz, 1H), 6.92 (td, J=8.4, 2.4 Hz, 1H), 6.61 (dd, J=6.3, 3.9 Hz, 1H), 4.81 (s, 2H), 4.69-4.47 (m, 2H), 4.42-4.05 (m, 3H). HPLC (max plot) 98.8%, Rt 3.56 min. UPLC/MS: (MS+) 445.2 ([M+H]+).

Example 152

(6-chloro-5,7-dimethyl-1H,3H-2,4,7a,8-tetraaza-cyclopenta[a]inden-2-yl)-(2-{2-[(2-hydroxy-ethyl)-methyl-amino]-ethoxy}-phenyl)-methanone

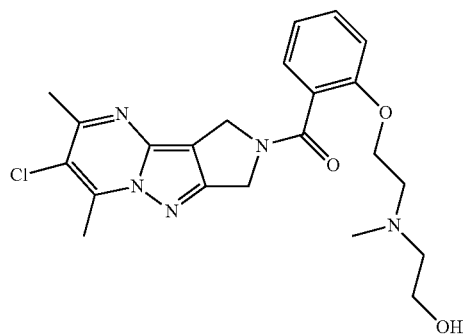 [SMILES: Cc1nc2c3c(nn2c(C)c1Cl)CN(C(=O)c1ccccc1OCCN(C)CCO)C3]

Step 1: [2-(2-{[2-(tert-butyl-dimethyl-silanyloxy)-ethyl]-methyl-amino}-ethoxy)-phenyl]-(6-chloro-5,7-dimethyl-1H,3H-2,4,7a,8-tetraaza-cyclopenta[a]inden-2-yl)-methanone A mixture of Example 144 (100 mg; 0.25 mmol; 1 eq.), (tert-butyl-dimethyl-silanyloxy)-acetaldehyde (87 mg; 0.50 mmol; 2 eq.) and sodium triacetoxyborohydride (58 mg; 0.28 mmol; 1.1 eq.) in DCE (10 mL) was stirred at 70° C. for 1 hour. The solution was washed with 0.1M NaOH (2×), dried over sodium sulfate and concentrated in vacuo. Purification by column chromatography (EA to 10% MeOH in EA) afforded the title compound (45 mg, 32%) as a yellow oil. HPLC (max plot) 95.0%, Rt 4.26 min. UPLC/MS: (MS+) 558.3 ([M+H]+).

Step 2: (6-chloro-5,7-dimethyl-1H,3H-2,4,7a,8-tetraaza-cyclopenta[a]inden-2-yl)-(2-{2-[(2-hydroxy-ethyl)-methyl-amino]-ethoxy}-phenyl)-methanone A mixture of [2-(2-{[2-(tert-butyl-dimethyl-silanyloxy)-ethyl]-methyl-amino}-ethoxy)-phenyl]-(6-chloro-5,7-dimethyl-1H,3H-2,4,7a,8-tetraaza-cyclopenta[a]inden-2-yl)-methanone (40 mg; 0.07 mmol; 1 eq.) and a 1M solution of tetrabutyl-ammonium fluoride in THF (0.09 mL; 0.09 mmol; 1.2 eq.) was stirred at room temperature for 3 hours. The solution was diluted with EA, washed with water, dried over magnesium sulfate and concentrated in vacuo. Purification by column chromatography (EA to 20% MeOH in EA) afforded the title compound (12 mg, 38%) as a colourless oil. HPLC (max plot) 95.8%, Rt 2.56 min. UPLC/MS: (MS+) 444.3 ([M+H]+).

Example 153

3-[2-(6-chloro-5,7-dimethyl-1H,3H-2,4,7a,8-tetraaza-cyclopenta[a]indene-2-carbonyl)-5-fluoro-phenoxy]-cyclobutanecarbonitrile

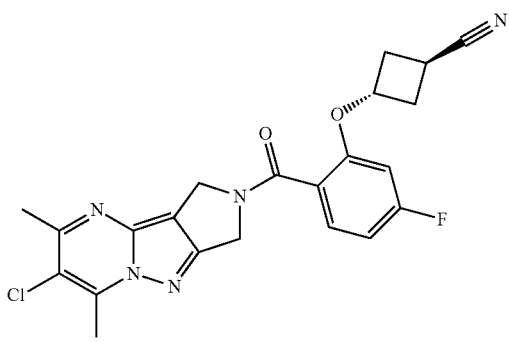 [SMILES: Cc1nc2c3c(nn2c(C)c1Cl)CN(C(=O)c1ccc(F)cc1O[C@H]1C[C@H](C#N)C1)C3]

The title compound was prepared following procedure described in Method G starting from Intermediate Z2 and 3-hydroxy-cyclobutanecarbonitrile (mixture cis/trans, 7/3). After work-up, purification by column chromatography (5% EA in heptane to EA) followed by recrystallization from ACN/MTBE afforded the title compound (33 mg, 13%) as a yellow solid. 1H NMR (CDCl3) δ 7.43-7.31 (m, 1H), 6.91-6.73 (m, 1H), 6.49 (dt, J=10.4, 2.5 Hz, 1H), 5.10-4.91 (m, 3H), 4.72-4.51 (m, 2H), 3.31-3.11 (m, 1H), 3.03-2.78 (m, 5H), 2.78-2.51 (m, 5H). HPLC (max plot) 92.2%, Rt 4.01 min. UPLC/MS: (MS+) 440.3 ([M+H]+).

Example 154

(6-chloro-5,7-dimethyl-1H,3H-2,4,7a,8-tetraaza-cyclopenta[a]inden-2-yl)-(2-{[(2-dimethylamino-ethyl)-(2,2,2-trifluoro-ethyl)-amino]-methyl}-phenyl)-methanone

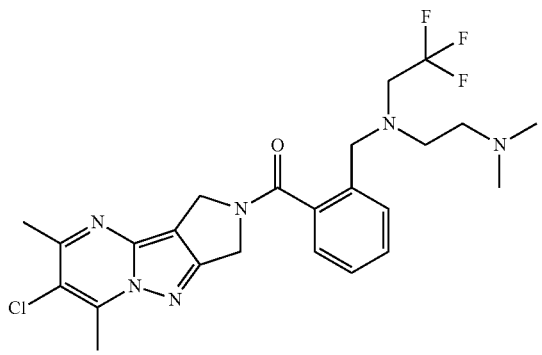

The title compound was prepared following procedure described in Method D starting from Intermediate Z3 and N,N-dimethyl-N'-(2,2,2-trifluoro-ethyl)-ethane-1,2-diamine (Enamine Ltd). After purification by crystallization (ACN), the title compound was obtained as a white powder (157 mg, 42%). 1H NMR (300 MHz, CDCl3) δ 8.03-7.91 (m, 1H), 7.67-7.58 (m, 2H), 7.58-7.51 (m, 1H), 5.12 (s, 0.8H), 5.10 (s, 1.2H), 5.05-4.97 (m, 2H), 4.46 (s, 1.2H), 4.42 (s, 0.8H), 4.03-3.94 (m, 2H), 3.39-3.27 (m, 7H), 3.27-3.13 (m, 2H), 2.90 (s, 1.8H), 2.84 (s, 1.2H), 2.74-2.59 (m, 4H). HPLC (max plot) 97.8%, Rt 2.97 min. UPLC/MS: (MS+) 509.4 ([M+H]+), (MS−) 567.4 ([M+OAc]−). Melting point: 168-174° C. (ACN).

Example 155

(6-chloro-5,7-dimethyl-1H,3H-2,4,7a,8-tetraaza-cyclopenta[a]inden-2-yl)-[4-fluoro-2-((2R,4R)-2-trifluoromethyl-piperidin-4-yloxy)-phenyl]-methanone

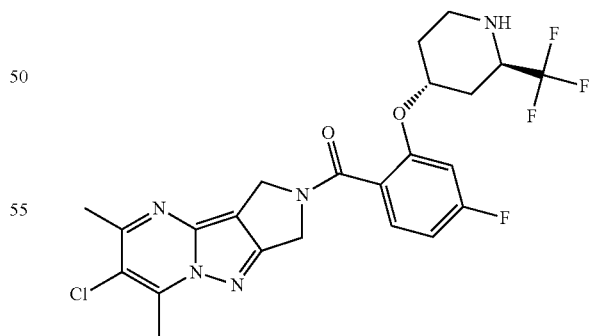

Step 1: cis-4-hydroxy-2-trifluoromethyl-piperidine-1-carboxylic acid tea-butyl ester NaBH4 (76 mg; 2 mmol; 2 eq.) was added at −10° C. to a solution of 1-Boc-2-trifluoromethyl-piperidin-4-one (Small Molecules inc.) (267 mg; 1 mmol; 1 eq.) in MeOH (8 mL) and the reaction mixture was stirred at −10° C. for 1 hour. Sat. aq. NH₄Cl (3 mL) was added and the resulting mixture was allowed to return to room temperature. The MeOH was evaporated in vacuo and the resulting aqueous layer extracted with DCM (4×). The combined organics were washed with brine, dried over magnesium sulfate and concentrated in vacuo to afford the title compound (269 mg, 100%) as a colourless oil. ¹H NMR (CDCl₃) δ 4.74 (br s, 1H), 4.19-3.93 (m, 2H), 3.42-3.17 (m, 1H), 2.14-1.90 (m, 2H), 1.90-1.52 (m, 3H), 1.52-1.37 (m, 9H).

Step 2: trans-4-[2-(6-chloro-5,7-dimethyl-1H,3H-2,4,7a,8-tetraaza-cyclopenta[a]indene-2-carbonyl)-5-fluoro-phenoxy]-2-trifluoromethyl-piperidine-1-carboxylic acid tert-butyl ester The title compound was prepared following procedure described in Method G starting from Intermediate Z2 and cis-4-hydroxy-2-trifluoromethyl-piperidine-1-carboxylic acid tert-butyl ester. After work-up, purification by column chromatography (5% EA in heptane to EA) afforded the title compound (115 mg, 38%) as a white foam. HPLC (max plot) 91.4%, Rt 5.44 min. UPLC/MS: (MS+) 612.4 ([M+H]⁺).

Step 3: (6-chloro-5,7-dimethyl-1H,3H-2,4,7a,8-tetraaza-cyclopenta[a]inden-2-yl)-[4-fluoro-2-((2R,4R)-2-trifluoromethyl-piperidin-4-yloxy)-phenyl]-methanone A 4M solution of HCl in 1,4-dioxane (0.47 mL; 1.87 mmol; 10 eq.) was added to a solution of trans-4-[2-(6-chloro-5,7-dimethyl-1H,3H-2,4,7a,8-tetraaza-cyclopenta[a]indene-2-carbonyl)-5-fluoro-phenoxy]-2-trifluoromethyl-piperidine-1-carboxylic acid tert-butyl ester (115 mg; 0.19 mmol; 1 eq.) in 1,4-dioxane (5 mL) and the reaction mixture was stirred at room temperature for 16 hours. 5M NaOH was added and the mixture extracted with DCM (3×). The combined organics were washed with brine, dried over sodium sulfate and concentrated in vacuo. The residue was dissolved in ACN/water and freeze-dried to afford the title compound (34 mg, 35%) as a yellow solid. ¹H NMR (CDCl₃) δ 7.45-7.29 (m, 1H), 6.91-6.74 (m, 1H), 6.74-6.60 (m, 1H), 5.12-4.91 (m, 2H), 4.84-4.53 (m, 3H), 3.56-3.29 (m, 1H), 3.07-2.79 (m, 5H), 2.78-2.55 (m, 3H), 2.22-1.99 (m, 1H), 1.99-1.86 (m, 1H), 1.86-1.56 (m, 3H). HPLC (max plot) 92.5%, Rt 3.10 min. UPLC/MS: (MS+) 512.3 ([M+H]⁺).

Example 156

(2-butoxy-4-fluoro-phenyl)-(6-chloro-5,7-dimethyl-1H,3H-2,4,7a,8-tetraaza-cyclopenta[a]inden-2-yl)-methanone

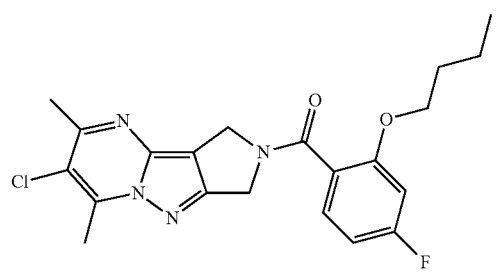 [SMILES: CCCCOc1cc(F)ccc1C(=O)N1Cc2nn3c(C)c(Cl)c(C)nc3c2C1]

The title compound was isolated during the purification of Example 155 step 2 (35 mg, 17%) as a white solid. ¹H NMR (CDCl₃) δ 7.38-7.27 (m, 1H), 6.80-6.58 (m, 2H), 5.08-4.92 (m, 2H), 4.78-4.50 (m, 2H), 4.08-3.91 (m, 2H), 2.94-2.82 (m, 3H), 2.75-2.58 (m, 3H), 1.80-1.63 (m, 2H), 1.48-1.26 (m, 2H), 0.85 (td, J=7.4, 1.3 Hz, 3H). HPLC (max plot) 94.0%, Rt 4.73 min. UPLC/MS: (MS+) 417.3 ([M+H]⁺).

Example 157

(2-butoxy-4-fluoro-phenyl)-(6-chloro-5-methyl-1H,3H-2,4,7a,8-tetraaza-cyclopenta[a]inden-2-yl)-methanone

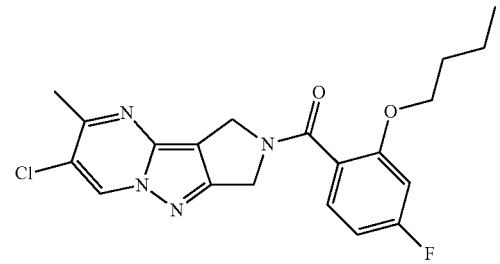 [SMILES: CCCCOc1cc(F)ccc1C(=O)N1Cc2nn3cc(Cl)c(C)nc3c2C1]

The title compound was isolated during the purification of Example 158 step 2 (40 mg, 23%) as a white solid. ¹H NMR (DMSO-d₆) δ 9.49 (d, J=5.6 Hz, 1H), 7.34 (ddd, J=8.4, 6.8, 3.9 Hz, 1H), 7.07 (m, 1H), 6.86 (td, J=8.4, 2.3 Hz, 1H), 4.79 (d, J=5.1 Hz, 2H), 4.51 (d, J=11.6 Hz, 2H), 4.07 (m, 2H), 2.60 (s, 1.5H), 2.54 (s, 1.5H), 1.66-1.51 (m, 2H), 1.34-1.18 (m, 2H), 0.76 (td, J=7.4, 4.8 Hz, 3H). HPLC (max plot) 98.7%, Rt 4.38 min. UPLC/MS: (MS+) 403.3 ([M+H]⁺).

Example 158

(6-chloro-5-methyl-1H,3H-2,4,7a,8-tetraaza-cyclopenta[a]inden-2-yl)-[4-fluoro-2-(2-methylamino-ethoxy)-phenyl]-methanone hydrochloride

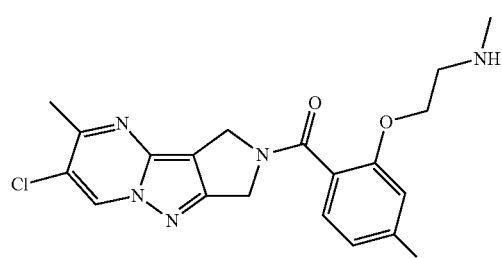

Step 1: {2-[2-(6-chloro-5-methyl-1H,3H-2,4,7a,8-tetraaza-cyclopenta[a]indene-2-carbonyl)-5-fluoro-phenoxy]-ethyl}-methyl-carbamic acid tert-butyl ester The title compound was prepared following procedure described in Method G starting from Intermediate Z7 and (2-hydroxy-ethyl)-methyl-carbamic acid tert-butyl ester (from intermediate B22 step 1). After work-up, purification by column chromatography (25% to 55% EA in heptane)

afforded the title compound (92 mg, 43%) as a pale yellow gum. HPLC (max plot) 94.5%, Rt 4.32 min. UPLC/MS: (MS+) 504.2 ([M+H]$^+$).

Step 2: (6-chloro-5-methyl-1H,3H-2,4,7a,8-tetraaza-cyclopenta[a]inden-2-yl)-[4-fluoro-2-(2-methylamino-ethoxy)-phenyl]-methanone hydrochloride A 4M solution of HCl in 1,4-dioxane (456 μL; 1.83 mmol; 10 eq.) was added to solution of {2-[2-(6-chloro-5-methyl-1H,3H-2,4,7a,8-tetraaza-cyclopenta[a]indene-2-carbonyl)-5-fluoro-phenoxy]-ethyl}-methyl-carbamic acid tert-butyl ester (92 mg; 0.18 mmol; 1 eq.) in DCM (2 mL) and the reaction mixture was stirred at room temperature for 30 minutes then concentrated in vacuo. Purification by mass directed preparative HPLC afforded the title compound (15 mg, 19%) as a yellow solid. $^1$H NMR (DMSO-d$_6$) δ 9.55-9.45 (d, J=5.0 Hz, 1H), 9.01-8.78 (s, 2H), 7.43 (ddd, J=8.4, 6.7, 4.5 Hz, 1H), 7.19 (dd, J=11.1, 2.3 Hz, 1H), 6.95 (td, J=8.5, 2.3 Hz, 1H), 4.82 (d, J=5.8 Hz, 2H), 4.58 (d, J=12.5 Hz, 2H), 4.36 (t, J=4.5 Hz, 2H), 3.26 (t, J=5.2 Hz, 2H), 2.60 (s, 1.5H), 2.57-2.51 (m, 4.5H). HPLC (max plot) 99.2%, Rt 2.48 min. UPLC/MS: (MS+) 404.3 ([M+H]$^+$).

Example 159

(6-chloro-5-methyl-1H,3H-2,4,7a,8-tetraaza-cyclopenta[a]inden-2-yl)-[2-(2-dimethylamino-ethoxy)-4-fluoro-phenyl]-methanone

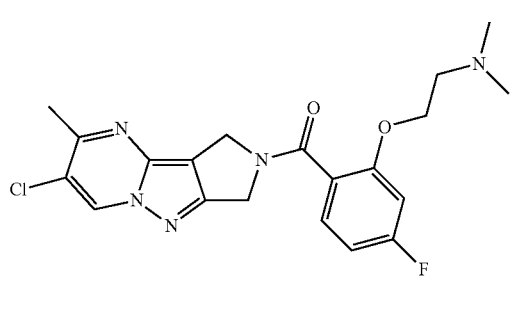 [SMILES: Cc1nc2c3c(nn2cc1Cl)CN(C(=O)c1ccc(F)cc1OCCN(C)C)C3]

(2-Chloro-ethyl)-dimethyl-amine hydrochloride (49 mg; 0.57 mmol; 1.2 eq.) was added to a suspension of Intermediate Z7 (100 mg; 0.29 mmol; 1 eq.) and K$_2$CO$_3$ (79 mg; 0.57 mmol; 2 eq.) in DMA (4 mL) was stirred at 60° C. for 16 hours. The mixture was diluted with EA, washed with water (2×), dried over magnesium sulfate and concentrated in vacuo. Purification by column chromatography (DCM to 2% MeOH in DCM) afforded the title compound (30 mg, 24%) as a yellow solid. $^1$H NMR (DMSO-d$_6$) δ 9.49 (d, J=2.3 Hz, 1H), 7.38-7.32 (m, 1H), 7.09 (dd, J=11.6 Hz, 2.4 Hz, 1H), 6.9-6.84 (m, 1H), 4.82-4.76 (m, 2H), 4.66-4.54 (m, 2H), 4.15 (t, J=5.3 Hz, 2H), 2.60 (s, 1H), 2.55 (s, 2H), 2.54-2.51 (m, 2H), 2.05 (s, 3H), 2.03 (s, 3H). HPLC (max plot) 98.7%, Rt 2.49 min. UPLC/MS: (MS+) 418.3 ([M+H]$^+$).

Example 160

(6-chloro-5-methyl-1H,3H-2,4,7a,8-tetraaza-cyclopenta[a]inden-2-yl)-[2-(1,1,2,2-tetrafluoro-ethoxy)-phenyl]-methanone

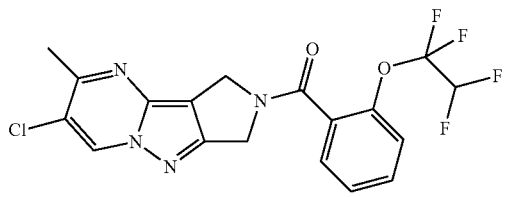 [SMILES: Cc1nc2c3c(nn2cc1Cl)CN(C(=O)c1ccccc1OC(F)(F)C(F)F)C3]

The title compound was prepared following procedure described in Method A starting from Intermediate A12 and 2-(1,1,2,2-tetrafluoro-ethoxy)-benzoic acid. After work-up, purification by column chromatography (50% EA in heptane to EA) afforded the title compound (230 mg, 75%) as a white solid. $^1$H NMR (DMSO-d$_6$) δ 9.50 (d, J=7.5 Hz, 1H), 7.66-7.59 (m, 2H), 7.53-7.44 (m, 2H), 6.92-6.54 (m, 1H), 4.85-4.79 (m, 2H), 4.57-4.48 (m, 2H), 2.61 (s, 2H), 2.54 (s, 1H). HPLC (max plot) 97.7%, Rt 4.04 min. UPLC/MS: (MS+) 429.2 ([M+H]$^+$).

Example 161

(6-chloro-5,7-dimethyl-1H,3H-2,4,7a,8-tetraaza-cyclopenta[a]inden-2-yl)-[2-(3-oxa-7,9-diaza-bicyclo[3.3.1]non-7-ylmethyl)-phenyl]-methanone dihydrochloride

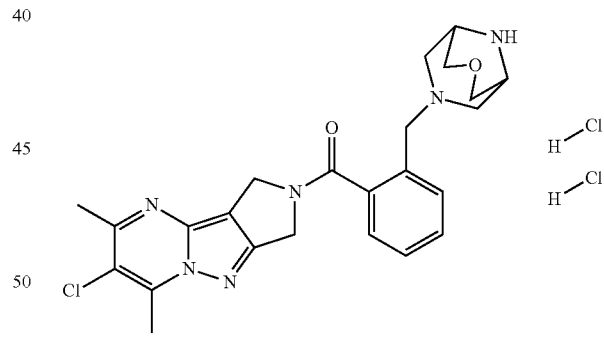

Step 1: 7-[2-(6-chloro-5,7-dimethyl-1H,3H-2,4,7a,8-tetraaza-cyclopenta[a]indene-2-carbonyl)-benzyl]-3-oxa-7,9-diaza-bicyclo[3.3.1]nonane-9-carboxylic acid 9H-fluoren-9-ylmethyl ester The title compound was prepared following procedure described in Method D starting from Intermediate Z3 and Intermediate D1. After purification by flash chromatography (silica, heptane/EtOAc), the title compound was obtained as a colorless glue (390 mg, 81%). $^1$H NMR (300 MHz, CDCl$_3$) δ 7.73 (d, J=7.7 Hz, 2H), 7.54-7.44 (m, 3H), 7.42-7.24 (m, 7H), 5.01-4.95 (m, 2H), 4.62-4.52 (m, 3H), 4.50-4.41 (m, 1H), 4.22-4.15 (m, 1H), 3.90 (br s, 1H), 3.67-3.35 (m, 7H), 2.94-

2.81 (m, 5H), 2.68 (s, 1H), 2.60 (s, 2H), 2.39-2.26 (m, 1H), 2.24-2.15 (m, 1H). HPLC (max plot) 98.6%, Rt 4.23 min. UPLC/MS: (MS+) 689.4 ([M+H]+).

Step 2: (6-chloro-5,7-dimethyl-1H,3H-2,4,7a,8-tetraaza-cyclopenta[a]inden-2-yl)-[2-(3-oxa-7,9-diaza-bicyclo[3.3.1]non-7-ylmethyl)-phenyl]-methanone dihydrochloride Piperidine (0.4 mL) was added to a solution of 7-[2-(6-chloro-5,7-dimethyl-1H,3H-2,4,7a,8-tetraaza-cyclopenta[a]indene-2-carbonyl)-benzyl]-3-oxa-7,9-diaza-bicyclo[3.3.1]nonane-9-carboxylic acid 9H-fluoren-9-ylmethyl ester (354 mg, 0.44 mmol) in DMF (4 mL). The resulting mixture was stirred at RT for 30 min, then diluted with water (20 mL). The precipitate was filtered off and washed with water (2×). After purification by flash chromatography (silica, DCM/EtOH/28% aqueous ammonia), the parent compound was dissolved in water (8 ml) and the solution was lyophilized to give the title compound as a yellow solid (170 mg, 72%). $^1$H NMR (300 MHz, DMSO-d$_6$) δ 10.92 (br s, 2H), 10.01 (br s, 1H), 7.95-7.78 (m, 2H), 7.72-7.60 (m, 2H), 5.01 (s, 1H), 4.99 (s, 1H), 4.85 (s, 1H), 4.80 (s, 1H), 4.46 (s, 2H), 4.19-4.04 (m, 4H), 3.97-3.70 (m, 6H), 2.86 (s, 1.5H), 2.82 (s, 1.5H), 2.63 (s, 1.5H), 2.57 (s, 1.5H). HPLC (max plot) 100%, Rt 2.26 min. UPLC/MS: (MS+) 467.3 ([M+H]+), (MS−) 465.4 ([M−H]−).

Example 162

(6-chloro-5,7-dimethyl-1H,3H-2,4,7a,8-tetraaza-cyclopenta[a]inden-2-yl)-[2-(3-trifluoromethyl-piperidin-4-yloxy)-phenyl]-methanone hydrochloride

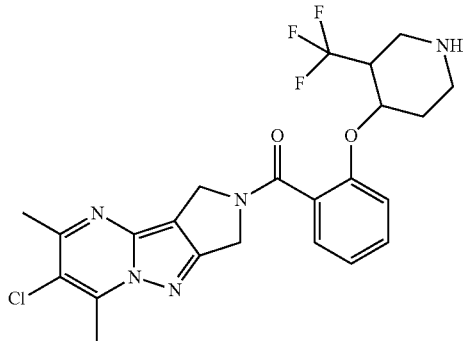 [SMILES: Cc1nc2c3c(nn2c(C)c1Cl)CN(C(=O)c1ccccc1OC1CCNCC1C(F)(F)F)C3]

Step 1: 4-[2-(6-chloro-5,7-dimethyl-1H,3H-2,4,7a,8-tetraaza-cyclopenta[a]indene-2-carbonyl)-phenoxy]-3-trifluoromethyl-piperidine-1-carboxylic acid tert-butyl ester The title compound was prepared following procedure described in Method A starting from Intermediate B23 and Intermediate A3. After work-up, purification by column chromatography (10% to 60% EA in heptane) afforded the title compound (116 mg, 88%) as a pale yellow solid. HPLC (max plot) 98.9%, Rt 5.05 min. UPLC/MS: (MS+) 594.4 ([M+H]+).

Step 2: (6-chloro-5,7-dimethyl-1H,3H-2,4,7a,8-tetraaza-cyclopenta[a]inden-2-yl)-[2-(3-trifluoromethyl-piperidin-4-yloxy)-phenyl]-methanone hydrochloride A 4M solution of HCl in 1,4-dioxane (4 mL; 16 mmol; 82 eq.) was added to a solution of 4-[2-(6-chloro-5,7-dimethyl-1H,3H-2,4,7a,8-tetraaza-cyclopenta[a]indene-2-carbonyl)-phenoxy]-3-trifluoromethyl-piperidine-1-carboxylic acid tert-butyl ester (116 mg; 0.20 mmol; 1 eq.) in 1,4-dioxane (2 mL) and the reaction mixture was stirred at room temperature for 16 hours then concentrated in vacuo. Crystallization from cold iPrOH afforded the title compound (65 mg, 62%) as a white solid. $^1$H NMR (DMSO-d$_6$) δ 9.14 (s, 2H), 7.48 (d, J=7.6 Hz, 1H), 7.44-7.34 (m, 1H), 7.30 (d, J=8.5 Hz, 1H), 7.15 (t, J=7.4 Hz, 1H), 5.23 (br s, 1H), 4.87 (d, J=6.3 Hz, 2H), 4.63-4.34 (m, 2H), 3.52-3.38 (m, 1H), 3.31-3.23 (m, 1H), 3.20-2.88 (m, 3H), 2.85 (s, 1.5H), 2.81 (s, 1.5H), 2.62 (s, 1.5H), 2.56 (s, 1.5H), 2.16-2.03 (m, 1H), 2.00-1.86 (m, 1H). HPLC (max plot) 96.5%, Rt 3.12 min. UPLC/MS: (MS+) 494.3 ([M+H]+).

Example 163

(6-chloro-7-methyl-1H,3H-2,4,7a,8-tetraaza-cyclopenta[a]inden-2-yl)-[2-(2-dimethylamino-ethoxy)-4-fluoro-phenyl]-methanone

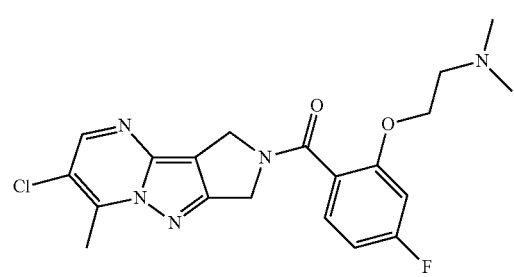 [SMILES: Cc1c(Cl)cnc2c3c(nn12)CN(C(=O)c1ccc(F)cc1OCCN(C)C)C3]

(2-Chloro-ethyl)-dimethyl-amine hydrochloride (41 mg; 0.29 mmol; 1.2 eq.) was added to a suspension of Intermediate Z8 (110 mg; 0.24 mmol; 1 eq.) and K$_2$CO$_3$ (66 mg; 0.48 mmol; 2 eq.) in DMA (4 mL) was stirred at 60° C. for 16 hours. The mixture was diluted with EA, washed with water (2×), dried over magnesium sulfate and concentrated in vacuo. Purification by mass directed preparative HPLC afforded the title compound (25 mg, 25%) as a beige solid. $^1$H NMR (DMSO-d$_6$) δ 8.58 (d, J=10.3 Hz, 1H), 7.39-7.33 (m, 1H), 7.10 (dd, J=11.6, 2.3 Hz, 1H), 6.87 (td, J=8.4, 2.3 Hz, 1H), 4.83 (d, J=5.9 Hz, 2H), 4.70-4.57 (m, 2H), 4.15 (t, J=5.4 Hz, 2H), 2.85 (s, 2H), 2.81 (s, 1H), 2.56-2.51 (m, 2H), 2.05 (s, 3H), 2.03 (s, 3H). HPLC (max plot) 94.2%, Rt 2.59 min. UPLC/MS: (MS+) 418.3 ([M+H]+).

Example 164

1-[2-(6-chloro-5,7-dimethyl-1H,3H-2,4,7a,8-tetraaza-cyclopenta[a]indene-2-carbonyl)-5-fluoro-phenoxy]-propan-2-one

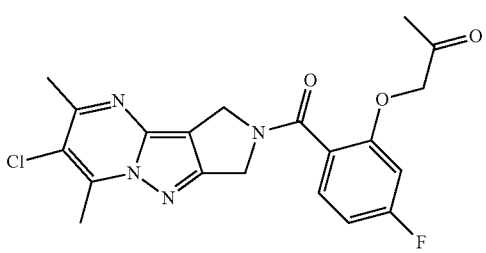 [SMILES: CC(=O)COc1cc(F)ccc1C(=O)N1Cc2nn3c(C)c(Cl)c(C)nc3c2C1]

A mixture of Intermediate Z2 (500 mg; 1.37 mmol; 1 eq.), K$_2$CO$_3$ (189 mg; 1.37 mmol; 1 eq.) and 1-chloro-propan-2-one (190 mg; 2.1 mmol; 1.5 eq.) in DMF (10 ML) was stirred at room temperature for 2 days. The suspension was diluted with EA, washed with water, dried over magnesium sulfate and concentrated in vacuo. Crystallization from hot EA afforded the title compound (330 mg, 58%) as a white solid. $^1$H NMR (DMSO-d$_6$) δ 7.35 (ddd, J=8.4, 6.8, 2.9 Hz, 1H), 6.97 (dd, J=11.6, 2.3 Hz, 1H), 6.85 (td, J=8.4, 2.2 Hz, 1H), 5.01 (d, J=6.4 Hz, 2H), 4.83 (d, J=9.0 Hz, 2H), 4.67 (d, J=22.3 Hz, 2H), 2.84 (s, 1.5H), 2.81 (s, 1.5H), 2.62 (s, 1.5H), 2.57 (s, 1.5H), 2.11 (d, J=2.9 Hz, 3H). HPLC (max plot) 98.0%, Rt 3.57 min. UPLC/MS: (MS+) 417.3 ([M+H]$^+$).

Example 165

{2-[2-(allyl-methyl-amino)-propoxy]-4-fluoro-phenyl}-(6-chloro-5,7-dimethyl-1H,3H-2,4,7a,8-tetraaza-cyclopenta[a]inden-2-yl)-methanone

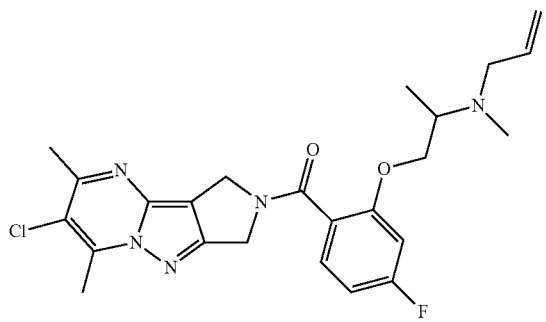 [SMILES: C=CCN(C)C(C)COc1cc(F)ccc1C(=O)N1Cc2nn3c(C)c(Cl)c(C)nc3c2C1]

A mixture of Example 164 (150 mg; 0.36 mmol; 1 eq.) allyl-methyl-amine (51 mg; 0.72 mmol; 2 eq.) and sodium triacetoxyborohydride (99 mg; 0.47 mmol; 1.3 eq.) in DCE (5 mL) was stirred at 70° C. for 2 hours. The suspension was diluted with EA, washed with water, dried over magnesium sulfate and concentrated in vacuo. Purification by column chromatography (EA to 12% MeOH in EA) afforded the title compound (95 mg, 56%) as a white solid. $^1$H NMR (DMSO-d$_6$) δ 7.45-7.29 (m, 1H), 7.17-7.02 (m, 1H), 6.87 (td, J=8.5, 2.4 Hz, 1H), 5.57-5.37 (m, 1H), 4.92 (dd, J=16.8, 5.8 Hz, 1H), 4.86-4.71 (m, 3H), 4.70-4.46 (m, 2H), 4.13-3.90 (m, 2H), 3.09-2.89 (m, 3H), 2.84 (s, 1.6H), 2.80 (s, 1.4H), 2.61 (s, 1.4H), 2.55 (s, 1.6H), 2.02 (d, J=4.9 Hz, 3H), 0.88 (dd, J=6.5, 1.9 Hz, 3H). HPLC (max plot) 94.9%, Rt 2.97 min. UPLC/MS: (MS+) 472.2 ([M+H]$^+$).

Example 166

(6-chloro-5,7-dimethyl-1H,3H-2,4,7a,8-tetraaza-cyclopenta[a]inden-2-yl)-[4-fluoro-2-(2-[1,2,4]triazol-4-yl-ethoxy)-phenyl]-methanone

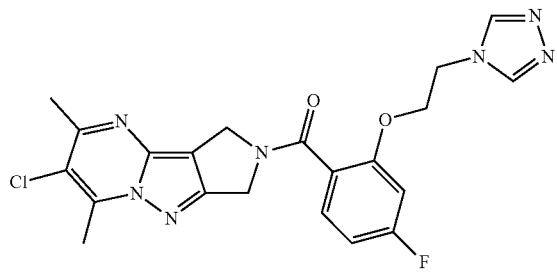 [SMILES: Cc1nc2c3c(nn2c(C)c1Cl)CN(C(=O)c1ccc(F)cc1OCCn1cnnc1)C3]

The title compound was prepared following procedure described in Method G starting from Intermediate Z2 and 2-[1,2,4]triazol-4-yl-ethanol. After work up, purification by column chromatography (30% MeOH in EA) followed by crystallization from ACN afforded the title compound (25 mg, 20%) as a white solid. $^1$H NMR (DMSO-d$_6$) δ 8.36 (s, 2H), 7.41-7.34 (m, 1H), 7.13-7.09 (m, 1H), 6.94-6.87 (m, 1H), 4.89-4.80 (m, 2H), 4.45-4.26 (m, 6H), 2.87 (s, 2H), 2.82 (s, 1H), 2.64 (s, 1H), 2.56 (s, 2H). HPLC (max plot) 99.4%, Rt 2.83 min. UPLC/MS: (MS+) 456.2 ([M+H]$^+$).

Example 167

(6-chloro-5,7-dimethyl-1H,3H-2,4,7a,8-tetraaza-cyclopenta[a]inden-2-yl)-[2-(2,6-diaza-spiro[3.3]hept-2-ylmethyl)-phenyl]-methanone

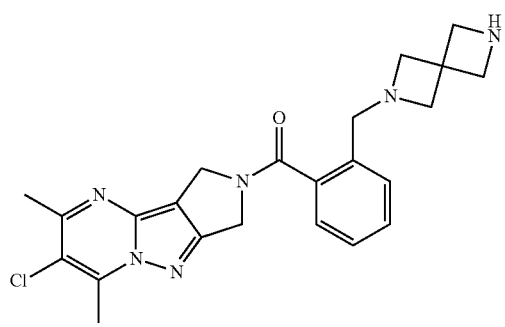 [SMILES: Cc1nc2c3c(nn2c(C)c1Cl)CN(C(=O)c1ccccc1CN1CC2(CNC2)C1)C3]

Step 1: 6-[2-(6-chloro-5,7-dimethyl-1H,3H-2,4,7a,8-tetraaza-cyclopenta[a]indene-2-carbonyl)-benzyl]-2,6-diaza-spiro[3.3]heptane-2-carboxylic acid tert-butyl ester The title compound was prepared following procedure described in Method D starting from Intermediate Z3 and 2-N-Boc-2,6-diazaspiro[3.3]heptanes hemioxalate (Shanghai SpeedChemical). After purification by flash chromatography (silica, EtOAc/THF), the title compound was obtained as a pale yellow foam (185 mg, 62%). $^1$H NMR (300 MHz, CDCl$_3$) δ 7.40-7.29 (m, 4H), 5.04-4.99 (m, 2H), 4.59-4.51 (m, 2H), 3.78-3.74 (m, 4H), 3.63 (s, 2H), 3.27-3.22 (m, 4H), 2.91 (s, 2H), 2.86 (s, 1H), 2.70 (s, 1H), 2.62 (s, 2H), 1.36 (s, 9H). HPLC (max plot) 86%, Rt 3.37 min. UPLC/MS: (MS+) 537.4 ([M+H]$^+$), (MS−) 535.5 ([M−H]$^-$).

Step 2: (6-chloro-5,7-dimethyl-1H,3H-2,4,7a,8-tetraaza-cyclopenta[a]inden-2-yl)-[2-(2,6-diaza-spiro[3.3]hept-2-ylmethyl)-phenyl]-methanone The title compound was prepared following procedure described in Method E starting from 6-[2-(6-chloro-5,7-dimethyl-1H,3H-2,4,7a,8-tetraaza-cyclopenta[a]indene-2-carbonyl)-benzyl]-2,6-diaza-spiro[3.3]heptane-2-carboxylic acid tert-butyl ester. After purification by flash chromatography (silica, DCM/EtOH/28% aqueous ammonia), the title compound was obtained as an off-white foam (62 mg, 47%). $^1$H NMR (300 MHz, CDCl$_3$) δ 7.39-7.27 (m, 4H), 5.03-4.97 (m, 2H), 4.58-4.51 (m, 2H), 3.61 (s, 2H), 3.58-3.51 (m, 4H), 3.28-3.15 (m, 4H), 2.91 (s, 2H), 2.84 (s, 1H), 2.69 (s, 1H), 2.61 (s, 2H). HPLC (max plot) 97.7%, Rt 2.26 min. UPLC/MS: (MS+) 437.2 ([M+H]$^+$).

Example 168

(6-chloro-5,7-dimethyl-1H,3H-2,4,7a,8-tetraaza-cyclopenta[a]inden-2-yl)-[4-fluoro-2-((1R,5S,7S)-9-methyl-3-oxa-9-aza-bicyclo[3.3.1]non-7-yloxy)-phenyl]-methanone

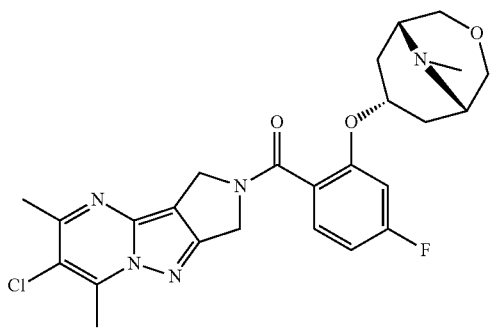 [SMILES: Cc1nc2c3c(nn2c(C)c1Cl)CN(C(=O)c1ccc(F)cc1O[C@H]1C[C@H]2COC[C@@H](C1)N2C)C3]

The title compound was prepared following procedure described in Method A starting from Intermediate B24 and Intermediate A3. After work up, purification by mass directed preparative HPLC afforded the title compound (185 mg, 41%) as an orange solid. $^1$H NMR (DMSO-$d_6$) δ 7.47-7.27 (m, 1H), 7.01-6.89 (m, 1H), 6.87-6.78 (m, 1H), 4.87-4.38 (m, 5H), 3.63-3.44 (m, 2H), 3.37-3.05 (m, 2H), 2.85-2.84 (m, 1.5H), 2.80 (s, 1.5H), 2.63-2.61 (m, 1.5H), 2.58-2.50 (m, 3.5H), 2.43-2.26 (m, 5H), 1.61-1.43 (m, 2H). HPLC (max plot) 100%, Rt 2.68 min. UPLC/MS: (MS+) 500.3 ([M+H]$^+$).

Example 169

(6-chloro-5,7-dimethyl-1H,3H-2,4,7a,8-tetraaza-cyclopenta[a]inden-2-yl)-[2-(2-dimethylamino-propoxy)-4-fluoro-phenyl]-methanone

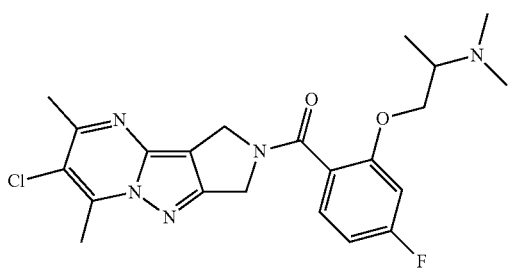 [SMILES: Cc1nc2c3c(nn2c(C)c1Cl)CN(C(=O)c1ccc(F)cc1OCC(C)N(C)C)C3]

A mixture of Example 164 (90 mg; 0.22 mmol; 1 eq.), a 2M solution of dimethylamine in THF and sodium triacetoxyborohydride (59 mg; 0.28 mmol; 1.3 eq.) in DCE (2 mL) was stirred at 50° C. for 1 hour whereupon triacetoxyborohydride (59 mg; 0.28 mmol; 1.3 eq.) was added. The resulting mixture was stirred at 70° C. for 3 hours then diluted with ethyl acetate. The solution was washed with 0.1M NaOH, dried over sodium sulfate and concentrated in vacuo. Purification by column chromatography (EA to 10 MeOH in EA) afforded the title compound (27 mg, 28%) as a white solid. $^1$H NMR (DMSO-$d_6$) δ 7.42-7.26 (m, 1H), 7.09 (d, J=11.5 Hz, 1H), 6.86 (t, J=8.2 Hz, 1H), 4.78 (d, J=7.9 Hz, 2H), 4.59 (d, J=15.0 Hz, 2H), 4.13-3.89 (m, 2H), 2.92-2.74 (m, 4H), 2.61 (s, 1.4H), 2.56 (s, 1.6H), 2.06 (s, 6H), 0.95-0.78 (m, 3H). HPLC (max plot) 99.9%, Rt 2.77 min. UPLC/MS: (MS+) 446.3 ([M+H]$^+$).

Example 170

(6-chloro-5,7-dimethyl-1H,3H-2,4,7a,8-tetraaza-cyclopenta[a]inden-2-yl)-[2-(3-trifluoromethyl-pyrrolidin-3-yloxy)-phenyl]-methanone

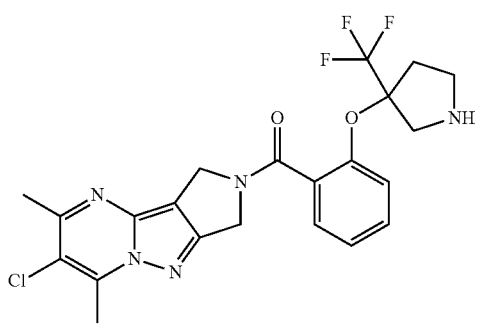 [SMILES: Cc1nc2c3c(nn2c(C)c1Cl)CN(C(=O)c1ccccc1OC1(C(F)(F)F)CCNC1)C3]

Step 1: 3-[2-(6-chloro-5,7-dimethyl-1H,3H-2,4,7a,8-tetraaza-cyclopenta[a]indene-2-carbonyl)-phenoxy]-3-trifluoromethyl-pyrrolidine-1-carboxylic acid tert-butyl ester The title compound was prepared following procedure described in Method A starting from Intermediate B25 and Intermediate A3. After work up, purification by column chromatography (DCM/EtOH/NH$_4$OH, 100/2.7/0.3) afforded the title compound (98 mg, 63%) as a pale yellow oil. HPLC (max plot) 87.0%, Rt 5.14 min. UPLC/MS: (MS+) 580.2 ([M+H]$^+$).

Step 2: (6-chloro-5,7-dimethyl-1H,3H-2,4,7a,8-tetraaza-cyclopenta[a]inden-2-yl)-[2-(3-trifluoromethyl-pyrrolidin-3-yloxy)-phenyl]-methanone A 4M solution of HCl in 1,4-dioxane (1.06 mL; 4.22 mmol; 25 eq.) was added to a solution of 3-[2-(6-chloro-5,7-dimethyl-1H,3H-2,4,7a,8-tetraaza-cyclopenta[a]indene-2-carbonyl)-phenoxy]-3-trifluoromethyl-pyrrolidine-1-carboxylic acid tert-butyl ester (98 mg; 0.17 mmol; 1 eq.) in 1,4-dioxane (10 mL) and the resulting mixture was stirred at room temperature for 20 hours then concentrated in vacuo. The residue was partitioned between DCM and sat. aq. NaHCO$_3$ and the aqueous layer was extracted with DCM. The combined organic phase was washed with brine, dried over magnesium sulfate and concentrated in vacuo. Purification by mass directed preparative HPLC afforded the title compound (15 mg, 25%) as a white solid. HPLC (max plot) 95.9%, Rt 3.23 min. UPLC/MS: (MS+) 480.3 ([M+H]+).

Example 171

(6-chloro-5,7-dimethyl-1H,3H-2,4,7a,8-tetraaza-cyclopenta[a]inden-2-yl)-[4-fluoro-2-(2-methylamino-propoxy)-phenyl]-methanone

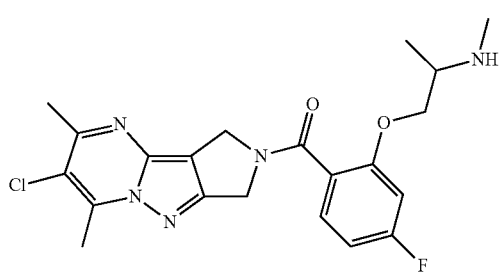 [SMILES: CNC(C)COc1cc(F)ccc1C(=O)N1Cc2nn3c(C)c(Cl)c(C)nc3c2C1]

A mixture of Pd(dba)$_2$ (5.2 mg; 0.01 mmol; 0.05 eq.) and 1,4-bis(diphenylphosphino)butane (3.8 mg; 0.01 mmol; 0.05 eq.) in THF (1 mL) was stirred for 10 minutes then added to a solution of {2-[2-(allyl-methyl-amino)-propoxy]-4-fluoro-phenyl}-(6-chloro-5,7-dimethyl-1H,3H-2,4,7a,8-tetraaza-cyclopenta[a]inden-2-yl)-methanone (85 mg; 0.18 mmol; 1 eq.) in THF (3 mL) followed by 2-mercapto-benzoic acid (31 mg; 0.20 mmol; 1.1 eq.) and the reaction mixture was stirred at 60° C. for 2 hours. The solution was diluted with EA, washed with 0.1M NaOH, dried over sodium sulfate and concentrated in vacuo. Purification by mass directed preparative HPLC afforded the title compound (10 mg, 13%) as a yellow solid. $^1$H NMR (DMSO-d$_6$) δ 8.25 (s, 1H), 7.39 (ddd, J=8.4, 6.8, 3.2 Hz, 1H), 7.11 (dd, J=11.4, 2.3 Hz, 1H), 6.99-6.80 (m, 1H), 4.84 (d, J=8.8 Hz, 2H), 4.55 (d, J=15.8 Hz, 2H), 4.02 (d, J=5.5 Hz, 2H), 2.97-2.86 (m, 1H), 2.84 (s, 1.5H), 2.81 (s, 1.5H), 2.62 (s, 1.5H), 2.56 (s, 1.5H), 2.25 (d, J=1.7 Hz, 3H), 0.96 (dd, J=6.5, 2.4 Hz, 3H). HPLC (max plot) 99.7%, Rt 2.82 min. UPLC/MS: (MS+) 432.3 ([M+H]+).

Example 172

(6-chloro-5,7-dimethyl-1H,3H-2,4,7a,8-tetraaza-cyclopenta[a]inden-2-yl)-[4-fluoro-2-(3,3,3-trifluoro-propoxy)-phenyl]-methanone

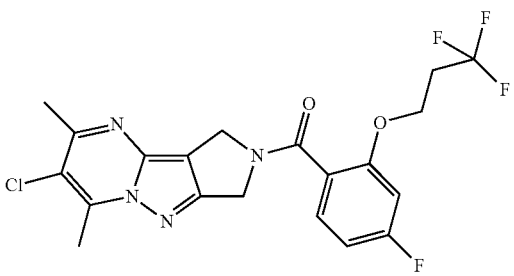 [SMILES: Cc1nc2c3c(nn2c(C)c1Cl)CN(C(=O)c1ccc(F)cc1OCCC(F)(F)F)C3]

The title compound was prepared following procedure described in Method G starting from Intermediate Z2 and 3,3,3-trifluoro-propan-1-ol. After work up, purification by column chromatography (50% EA in heptane to EA) followed by crystallization from ACN afforded the title compound (30 mg, 24%) as a white solid. $^1$H NMR (DMSO-d$_6$) δ 7.46-7.29 (m, 1H), 7.14 (d, J=11.2 Hz, 1H), 6.91 (dd, J=9.2, 6.8 Hz, 1H), 4.78 (d, J=7.1 Hz, 2H), 4.48 (d, J=14.2 Hz, 2H), 4.30 (t, J=5.8 Hz, 2H), 2.85 (s, 1.5H), 2.80 (s, 1.5H), 2.79-2.67 (m, 2H), 2.62 (s, 1.5H), 2.56 (s, 1.5H). HPLC (max plot) 92.9%, Rt 4.32 min. UPLC/MS: (MS+) 457.1 ([M+H]+).

Example 173

(6-chloro-5,7-dimethyl-1H,3H-2,4,7a,8-tetraaza-cyclopenta[a]inden-2-yl)-[2-(3-dimethylamino-propoxy)-4-fluoro-phenyl]-methanone

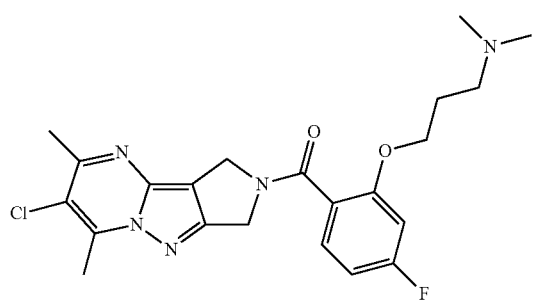 [SMILES: Cc1nc2c3c(nn2c(C)c1Cl)CN(C(=O)c1ccc(F)cc1OCCCN(C)C)C3]

The title compound was prepared following procedure described in Method G starting from Intermediate Z2 and 3-dimethylamino-propan-1-ol. After work up, purification by column chromatography (25% to 65% EA in heptane) afforded the title compound (10 mg, 8%) as a pale yellow solid. HPLC (max plot) 99.0%, Rt 2.83 min. UPLC/MS: (MS+) 446.3 ([M+H]+).

Example 174

{2-[2-(6-chloro-5,7-dimethyl-1H,3H-2,4,7a,8-tetraaza-cyclopenta[a]indene-2-carbonyl)-5-fluoro-phenoxy]-ethyl}-carbamic acid tert-butyl ester

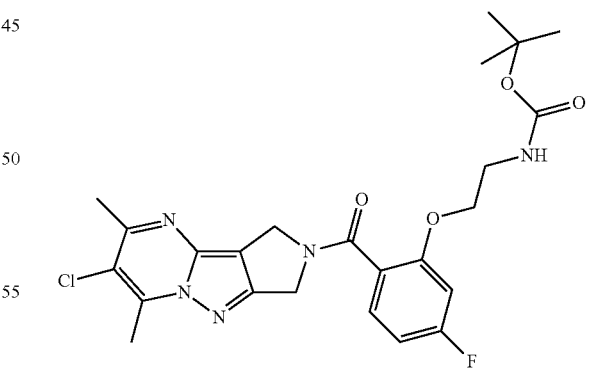

A mixture of Intermediate Z2 (250 mg; 0.69 mmol; 1 eq.), K$_2$CO$_3$ (114 mg; 0.82 mmol; 1.2 eq.) and (2-chloro-ethyl)-carbamic acid tert-butyl ester (Apollo Scientific) (246 mg; 1.37 mmol; 2 eq.) in DMF (5 mL) was stirred at 145° C. for 45 minutes (microwave heating) then diluted with EA. The solution was washed with sat. aq. NH$_4$Cl, dried over magnesium sulfate and concentrated in vacuo. Purification by column chromatography (40% EA in heptane to EA) afforded the title compound (240 mg, 69%) as a white solid. ¹H NMR (DMSO-d₆) δ 7.45-7.23 (m, 1H), 7.10 (dt, J=11.5, 2.0 Hz, 1H), 7.01-6.77 (m, 2H), 4.84 (d, J=9.0 Hz, 2H), 4.54 (d, J=14.4 Hz, 2H), 4.12-3.98 (m, 2H), 3.27-3.16 (m, 2H), 2.85 (s, 1.6H), 2.80 (s, 1.4H), 2.62 (s, 1.4H), 2.55 (s, 1.6H), 1.25-1.09 (m, 9H). HPLC (max plot) 98.9%, Rt 4.34 min. UPLC/MS: (MS+) 504.3 ([M+H]⁺).

Example 175

(6-chloro-5,7-dimethyl-1H,3H-2,4,7a,8-tetraaza-cyclopenta[a]inden-2-yl)-(2-piperidin-4-yl-phenyl)-methanone hydrochloride

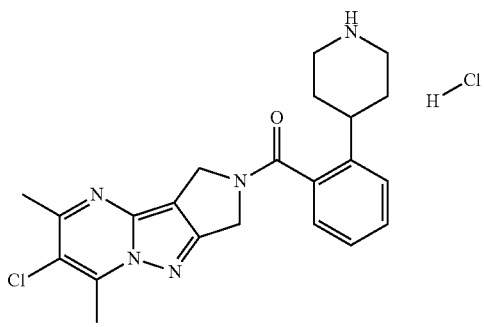

Step 1: 4-[2-(6-chloro-5,7-dimethyl-1H,3H-2,4,7a,8-tetraaza-cyclopenta[a]indene-2-carbonyl)-phenyl]-piperidine-1-carboxylic acid tert-butyl ester The title compound was prepared following procedure described in Method A starting from Intermediate A3 and 4-(2-carboxy-phenyl)-piperidine-1-carboxylic acid tert-butyl ester (AstaTech). After purification by flash chromatography (silica, heptane/EtOAc), the title compound was obtained as a colorless oil (361 mg, 73%). ¹H NMR (300 MHz, DMSO-d₆) δ 7.45-7.28 (m, 4H), 4.89 (s, 1H), 4.86 (s, 1H), 4.50 (s, 1H), 4.44 (s, 1H), 4.07-3.93 (m, 2H), 2.86-2.52 (m, 9H), 1.78-1.66 (m, 2H), 1.62-1.44 (m, 2H), 1.39 (s, 9H). HPLC (max plot) 99.5%, Rt 4.83 min. UPLC/MS: (MS+) 510.4 ([M+H]⁺), (MS−) 508.4 ([M−H]⁻).

Step 2: (6-chloro-5,7-dimethyl-1H,3H-2,4,7a,8-tetraaza-cyclopenta[a]inden-2-yl)-(2-piperidin-4-yl-phenyl)-methanone, hydrochloride salt The title compound was prepared following procedure described in Method E starting from 4-[2-(6-chloro-5,7-dimethyl-1H,3H-2,4,7a,8-tetraaza-cyclopenta[a]indene-2-carbonyl)-phenyl]-piperidine-1-carboxylic acid tert-butyl ester. After purification by flash chromatography (silica, DCM/EtOH/28% aqueous ammonia), the parent compound was dissolved in a 0.1N aqueous solution of HCl and the solution was lyophilized to give the title compound as a pale yellow powder (99 mg, 43%). ¹H NMR (300 MHz, DMSO-d₆) δ 8.98-8.72 (m, 2H), 7.54-7.44 (m, 1H), 7.44-7.31 (m, 3H), 4.91 (s, 1H), 4.88 (s, 1H), 4.51 (s, 1H), 4.45 (s, 1H), 3.35-3.22 (m, 2H), 3.03-2.76 (m, 6H), 2.63 (s, 1.5H), 2.55 (s, 1.5H), 2.04-1.81 (m, 4H). HPLC (max plot) 99.2%, Rt 2.70 min. UPLC/MS: (MS+) 410.3 ([M+H]⁺), (MS−) 408.3 ([M−H]⁻).

Example 176

1-[2-(6-chloro-5,7-dimethyl-1H,3H-2,4,7a,8-tetraaza-cyclopenta[a]indene-2-carbonyl)-phenyl]-ethanone

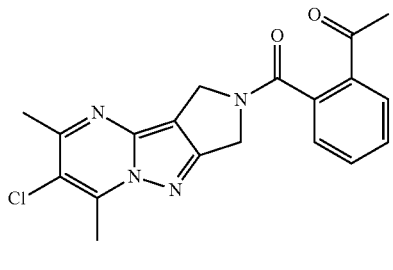 [SMILES: CC(=O)c1ccccc1C(=O)N1Cc2nn3c(C)c(Cl)c(C)nc3c2C1]

The title compound was prepared following procedure described in Method A starting from Intermediate A3 and 2-acetyl-benzoic acid. After purification by flash chromatography (silica, heptane/EtOAc) followed by a slurry in EtOAc, the title compound was obtained as a white powder (796 mg, 56%). ¹H NMR (300 MHz, DMSO-d₆) δ 8.08-8.03 (m, 1H), 7.75-7.68 (m, 1H), 7.67-7.59 (m, 1H), 7.53-7.47 (m, 1H), 4.84 (s, 1H), 4.81 (s, 1H), 4.42 (s, 1H), 4.36 (s, 1H), 2.84 (s, 1.5H), 2.79 (s, 1.5H), 2.62 (s, 1.5H), 2.57 (s, 3H), 2.53 (s, 1.5H). HPLC (max plot) 100%, Rt 3.17 min. UPLC/MS: (MS+) 369.3 ([M+H]⁺), (MS−) 367.3 ([M−H]⁻).

Example 177

[2-(2-amino-ethoxy)-4-fluoro-phenyl]-(6-chloro-5,7-dimethyl-1H,3H-2,4,7a,8-tetraaza-cyclopenta[a]inden-2-yl)-methanone hydrochloride

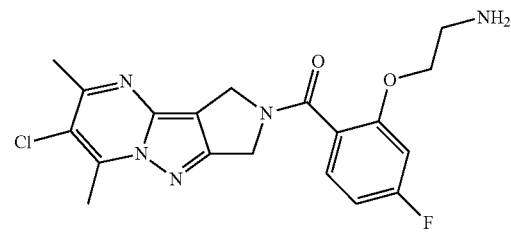 [SMILES: Cc1nc2c3c(nn2c(C)c1Cl)CN(C(=O)c1ccc(F)cc1OCCN)C3]

A 4M solution of HCl in 1,4-dioxane (1.67 mL; 6.7 mmol; 15 eq.) was added to a solution of Example 174 (225 mg; 0.45 mmol; 1 eq.) in DCM (10 mL) and the reaction mixture was stirred at room temperature for 15 minutes then concentrated in vacuo to afford the title compound (180 mg, 92%) as a yellow solid. ¹H NMR (DMSO-d₆) δ 7.92 (br s, 3H), 7.44 (ddd, J=8.4, 6.8, 4.3 Hz, 1H), 7.18 (dd, J=11.3, 2.4 Hz, 1H), 6.95 (td, J=8.4, 2.3 Hz, 1H), 4.85 (d, J=8.6 Hz, 2H), 4.59 (d, J=14.9 Hz, 2H), 4.32-4.26 (m, 2H), 3.15 (t, J=5.0 Hz, 2H), 2.86 (s, 1.6H), 2.82 (s, 1.4H), 2.62 (s, 1.4H), 2.56 (s, 1.6H). HPLC (max plot) 99.4%, Rt 2.69 min. UPLC/MS: (MS+) 404.3 ([M+H]⁺).

Example 178

N-{2-[2-(6-chloro-5,7-dimethyl-1H,3H-2,4,7a,8-tetraaza-cyclopenta[a]inden-2-carbonyl)-5-fluoro-phenoxy]-ethyl}-2,2,2-trifluoro-acetamide

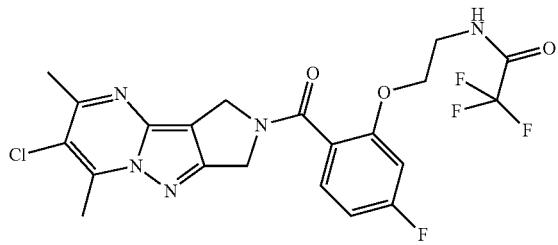 [SMILES: Cc1nc2c3c(nn2c(C)c1Cl)CN(C(=O)c1ccc(F)cc1OCCNC(=O)C(F)(F)F)C3]

Trifluoroacetic anhydride (31 μL; 0.22 mmol; 1.2 eq.) was added at 0° C. to a solution of Example 177 (80 mg; 0.18 mmol; 1 eq.) and DIEA (41 μL; 0.24 mmol; 1.3 eq.) in DCM (5 mL) and the reaction mixture was stirred at room temperature for 15 minutes whereupon trifluoroacetic anhydride (31 μL; 0.22 mmol; 1.2 eq.) and DIEA (41 μL; 0.24 mmol; 1.3 eq.) were added. The resulting mixture was stirred at room temperature for 20 minutes then concentrated in vacuo. Purification by column chromatography (40% EA in cyclohexane to EA) afforded the title compound (70 mg, 77%) as a white foam. ¹H NMR (DMSO-d₆) δ 9.45 (br s, 1H), 7.36 (ddd, J=8.4, 6.8, 3.9 Hz, 1H), 7.17-7.07 (m, 1H), 6.89 (td, J=8.5, 2.3 Hz, 1H), 4.77 (d, J=6.9 Hz, 2H), 4.51 (d, J=14.8 Hz, 2H), 4.23-4.13 (m, 2H), 3.57-3.46 (m, 2H), 2.85 (s, 1.6H), 2.81 (s, 1.4H), 2.62 (s, 1.4H), 2.55 (s, 1.6H). HPLC (max plot) 98.8%, Rt 3.94 min. UPLC/MS: (MS+) 500.3 ([M+H]⁺).

Example 179

(6-chloro-5,7-dimethyl-1H,3H-2,4,7a,8-tetraaza-cyclopenta[a]inden-2-yl)-{2-[(methyl-pyridin-2-ylmethyl-amino)-methyl]-phenyl}-methanone

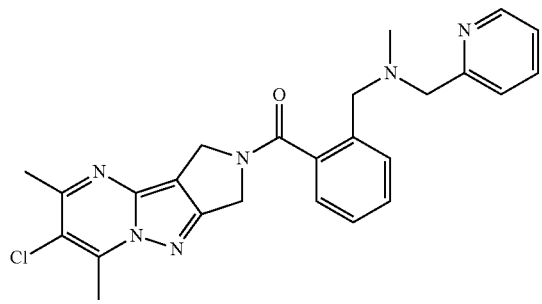 [SMILES: Cc1nc2c3c(nn2c(C)c1Cl)CN(C(=O)c1ccccc1CN(C)Cc1ccccn1)C3]

The title compound was prepared following procedure described in Method D starting from Intermediate Z3 and methyl-pyridin-2-ylmethyl-amine. After purification by flash chromatography (silica, DCM/EtOH/28% aqueous ammonia), the title compound was obtained as a white foam (138 mg, 63%). ¹H NMR (300 MHz, DMSO-d₆) δ 8.31-8.27 (m, 1H), 7.53-7.35 (m, 4H), 7.26-7.18 (m, 1H), 7.12-7.02 (m, 2H), 4.86 (s, 1H), 4.83 (s, 1H), 4.55 (s, 1H), 4.50 (s, 1H), 3.63 (br s, 2H), 3.56 (s, 2H), 2.87 (s, 1.5H), 2.81 (s, 1.5H), 2.64 (s, 1.5H), 2.54 (s, 1.5H), 2.01 (s, 3H). HPLC (max plot) 99.8%, Rt 2.93 min. UPLC/MS: (MS+) 461.3 ([M+H]⁺), (MS−) 459.3 ([M−H]⁻).

Example 180

(6-chloro-5,7-dimethyl-1H,3H-2,4,7a,8-tetraaza-cyclopenta[a]inden-2-yl)-[4-fluoro-2-(2-pyridazin-3-yl-ethoxy)-phenyl]-methanone

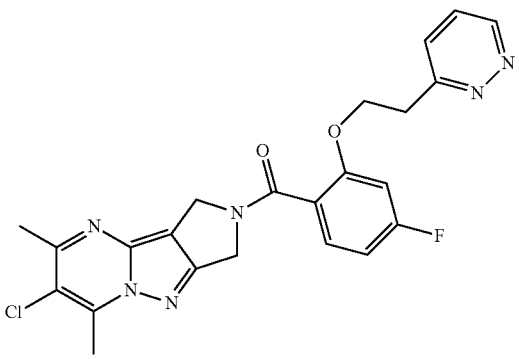 [SMILES: Cc1nc2c3c(nn2c(C)c1Cl)CN(C(=O)c1ccc(F)cc1OCCc1cccnn1)C3]

The title compound was prepared following procedure described in Method A starting from Intermediate A3 and Intermediate B26. After work up, purification by mass directed preparative HPLC afforded the title compound (6 mg, 7%) as a brown oil. ¹H NMR (DMSO-d₆) δ 8.79-8.67 (m, 1H), 7.39-7.24 (m, 2H), 7.12-6.97 (m, 1H), 6.82-6.68 (m, 2H), 4.97-4.89 (m, 2H), 4.55-4.43 (m, 2H), 4.39-4.29 (m, 2H), 3.40 (t, J=6.0 Hz, 2H), 2.94 (s, 2H), 2.89 (s, 1H), 2.72 (s, 1H), 2.64 (s, 2H). HPLC (max plot) 91.4%, Rt 2.98 min. UPLC/MS: (MS+) 467.3 ([M+H]⁺).

Example 181

M1 PAM Assay

M1-CHO cells are plated in culture medium (HAM's F12, P/S, 10% FCS) on the day before the experiment with 10 000 cells/well in a 384 well plate (3750 Corning White 384 w plate with lid). On the day of experiment, cells are washed with PBS and IPone buffer is added (glucose 5.5 mM, NaCl 146 mM, MgCl₂ 0.5 mM, HEPES 10 mM, LiCl 50 mM, CaCl₂ 1 mM, KCl 4.2 mM). Then diluted compounds (1% DMSO final concentration) are added together with EC₂₀ of acetylcholine and incubated with the cells for 1 hour at room temperature. The intracellular concentration of IP1 is then measured using the IP-One HTRF assay from Cisbio.

Activity range of the compounds of Formula (I) is the following:

| Ex | Structures | M1 PAM EC$_{50}$ (nM) |
|---|---|---|
| 1 | 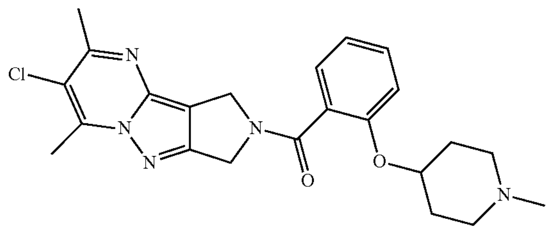 [SMILES: Cc1nc2c3c(nn2c(C)c1Cl)CN(C(=O)c1ccccc1OC1CCN(C)CC1)C3] | *** |
| 2 | 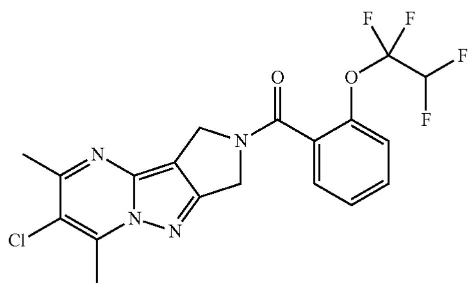 [SMILES: Cc1nc2c3c(nn2c(C)c1Cl)CN(C(=O)c1ccccc1OC(F)(F)C(F)F)C3] | *** |
| 3 | 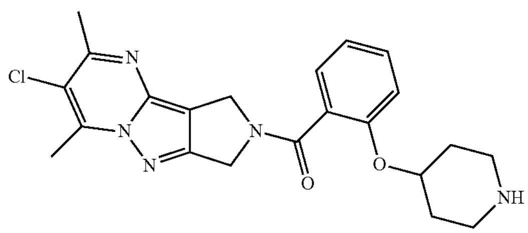 [SMILES: Cc1nc2c3c(nn2c(C)c1Cl)CN(C(=O)c1ccccc1OC1CCNCC1)C3] | *** |
| 4 | 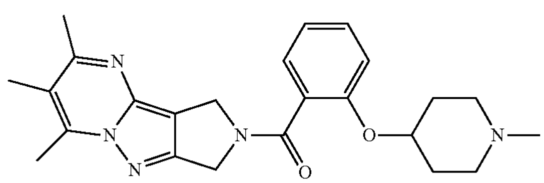 | ** |
| 5 | 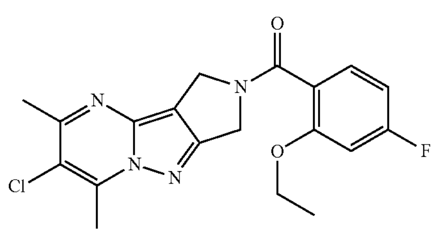 [SMILES: CCOc1cc(F)ccc1C(=O)N1Cc2nn3c(C)c(Cl)c(C)nc3c2C1] | ** |
| 6 | 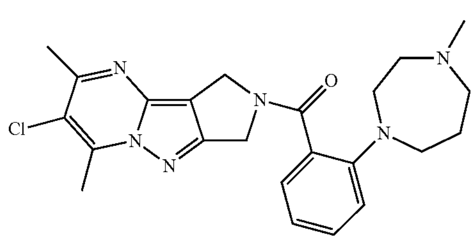 [SMILES: Cc1nc2c3c(nn2c(C)c1Cl)CN(C(=O)c1ccccc1N1CCCN(C)CC1)C3] | ** |

-continued

| Ex | Structures | M1 PAM EC$_{50}$ (nM) |
|---|---|---|
| 7 | 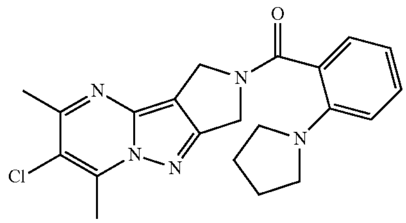 [SMILES: Cc1nc2c3c(nn2c(C)c1Cl)CN(C(=O)c1ccccc1N1CCCC1)C3] | ** |
| 8 | 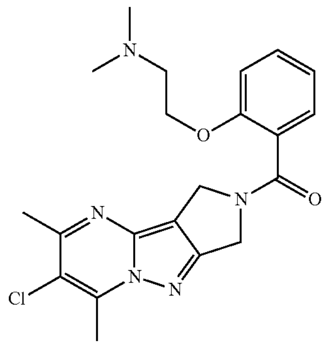 [SMILES: Cc1nc2c3c(nn2c(C)c1Cl)CN(C(=O)c1ccccc1OCCN(C)C)C3] | ** |
| 9 | 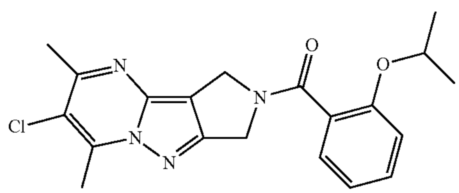 [SMILES: Cc1nc2c3c(nn2c(C)c1Cl)CN(C(=O)c1ccccc1OC(C)C)C3] | ** |
| 10 | 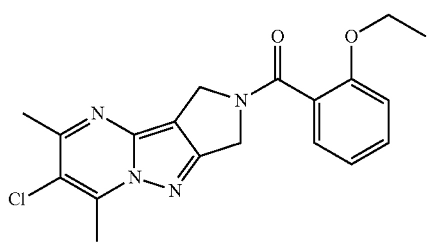 [SMILES: CCOc1ccccc1C(=O)N1Cc2nn3c(C)c(Cl)c(C)nc3c2C1] | ** |
| 11 | 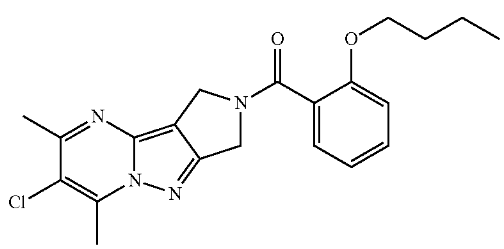 [SMILES: CCCCOc1ccccc1C(=O)N1Cc2nn3c(C)c(Cl)c(C)nc3c2C1] | ** |
| 12 | 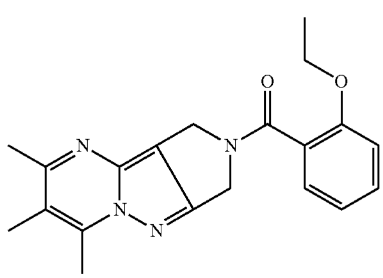 [SMILES: CCOc1ccccc1C(=O)N1Cc2nn3c(C)c(C)c(C)nc3c2C1] | ** |

-continued

| Ex | Structures | M1 PAM EC$_{50}$ (nM) |
|---|---|---|
| 13 | 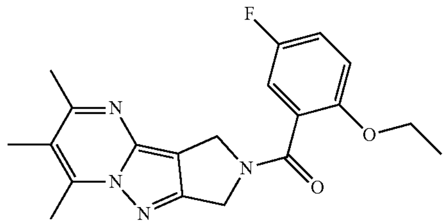 [SMILES: CCOc1ccc(F)cc1C(=O)N1Cc2nn3c(C)c(C)c(C)nc3c2C1] | ** |
| 14 | 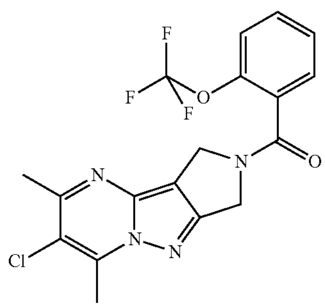 [SMILES: Cc1nc2c3c(nn2c(C)c1Cl)CN(C(=O)c1ccccc1OC(F)(F)F)C3] | ** |
| 15 | 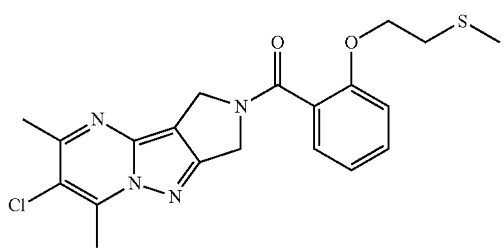 | ** |
| 16 | 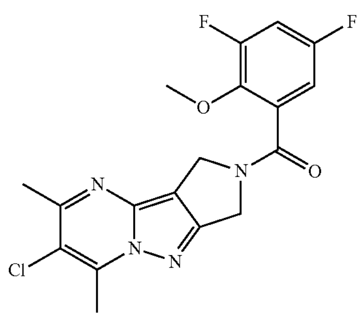 [SMILES: COc1c(F)cc(F)cc1C(=O)N1Cc2nn3c(C)c(Cl)c(C)nc3c2C1] | ** |
| 17 | 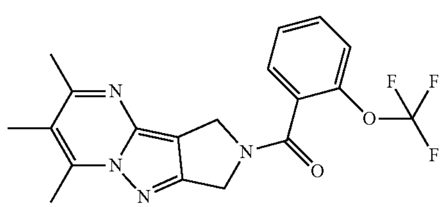 [SMILES: Cc1nc2c3c(nn2c(C)c1C)CN(C(=O)c1ccccc1OC(F)(F)F)C3] | ** |
| 18 | 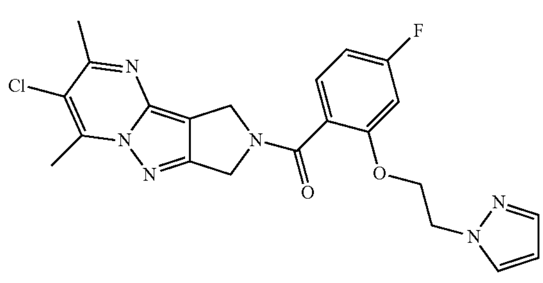 [SMILES: Cc1nc2c3c(nn2c(C)c1Cl)CN(C(=O)c1ccc(F)cc1OCCn1cccn1)C3] | ** |

| Ex | Structures | M1 PAM EC$_{50}$ (nM) |
|---|---|---|
| 19 | 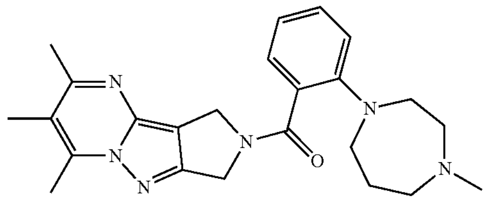 | ** |
| 20 | 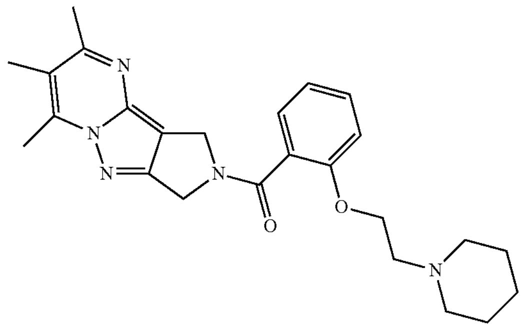 [SMILES: Cc1nc2c3c(nn2c(C)c1C)CN(C(=O)c1ccccc1OCCN1CCCCC1)C3] | ** |
| 21 | 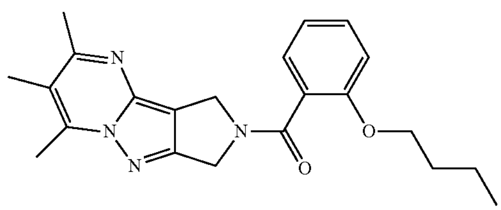 [SMILES: CCCCOc1ccccc1C(=O)N1Cc2nn3c(C)c(C)c(C)nc3c2C1] | ** |
| 22 | 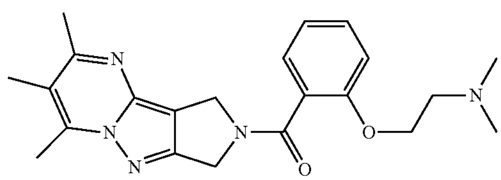 | ** |
| 23 | 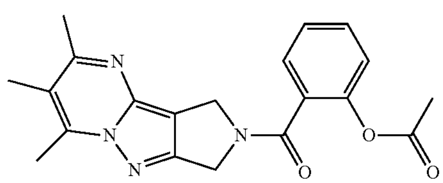 [SMILES: CC(=O)Oc1ccccc1C(=O)N1Cc2nn3c(C)c(C)c(C)nc3c2C1] | ** |
| 24 | 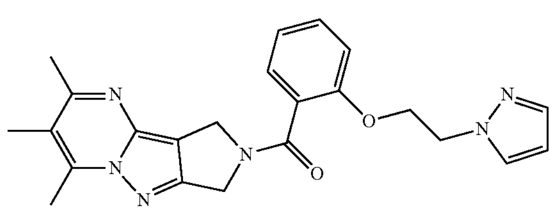 [SMILES: Cc1nc2c3c(nn2c(C)c1C)CN(C(=O)c1ccccc1OCCn1cccn1)C3] | ** |
| 25 | 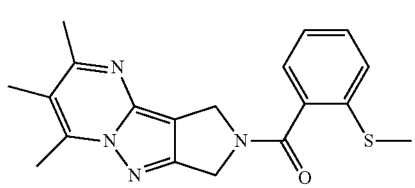 | ** |

| Ex | Structures | M1 PAM EC$_{50}$ (nM) |
|---|---|---|
| 26 | 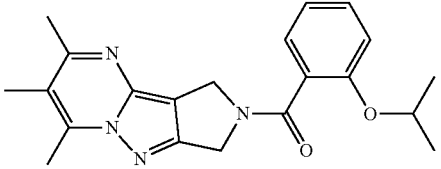 [SMILES: Cc1nc2c3c(nn2c(C)c1C)CN(C(=O)c1ccccc1OC(C)C)C3] | ** |
| 27 | 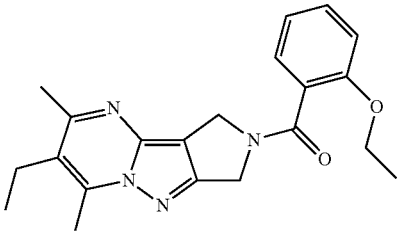 [SMILES: CCOc1ccccc1C(=O)N1Cc2nn3c(C)c(CC)c(C)nc3c2C1] | * |
| 28 | 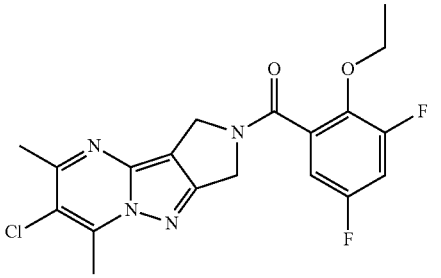 [SMILES: CCOc1c(F)cc(F)cc1C(=O)N1Cc2nn3c(C)c(Cl)c(C)nc3c2C1] | * |
| 29 | 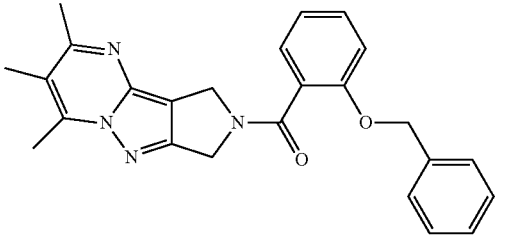 [SMILES: Cc1nc2c3c(nn2c(C)c1C)CN(C(=O)c1ccccc1OCc1ccccc1)C3] | * |
| 30 | 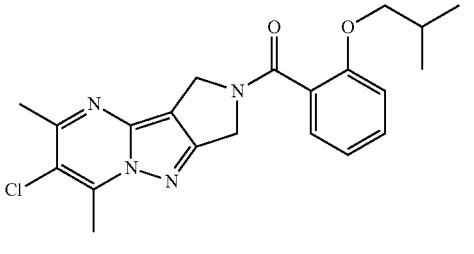 [SMILES: Cc1nc2c3c(nn2c(C)c1Cl)CN(C(=O)c1ccccc1OCC(C)C)C3] | * |
| 31 | 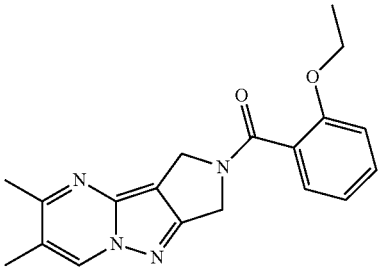 [SMILES: CCOc1ccccc1C(=O)N1Cc2nn3cc(C)c(C)nc3c2C1] | * |

| Ex | Structures | M1 PAM EC$_{50}$ (nM) |
|---|---|---|
| 32 | 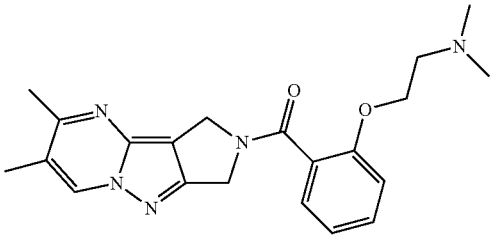 | * |
| 33 | 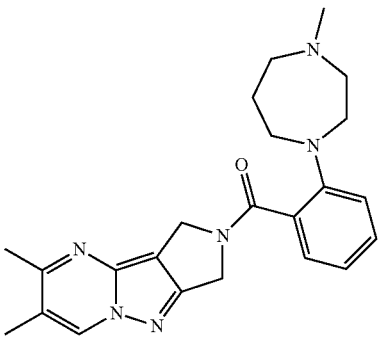 [SMILES: Cc1cn2nc3c(c2nc1C)CN(C(=O)c1ccccc1N1CCCN(C)CC1)C3] | * |
| 34 | 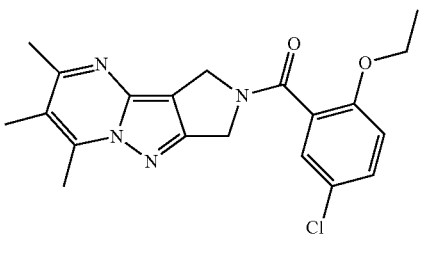 [SMILES: CCOc1ccc(Cl)cc1C(=O)N1Cc2nn3c(C)c(C)c(C)nc3c2C1] | * |
| 35 | 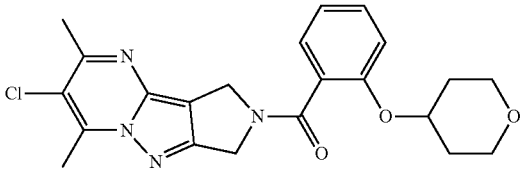 [SMILES: Cc1nc2c3c(nn2c(C)c1Cl)CN(C(=O)c1ccccc1OC1CCOCC1)C3] | * |
| 36 | 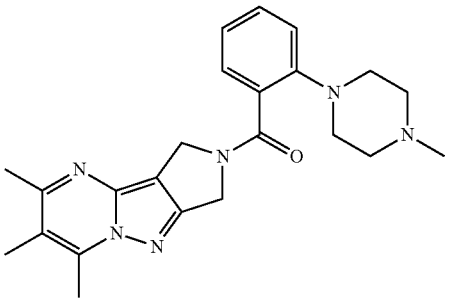 | * |
| 37 | 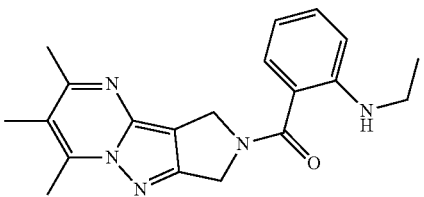 [SMILES: CCNc1ccccc1C(=O)N1Cc2nn3c(C)c(C)c(C)nc3c2C1] | * |

-continued
| Ex | Structures | M1 PAM EC$_{50}$ (nM) |
|---|---|---|
| 38 | 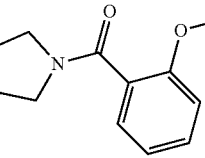 | * |
| 39 | 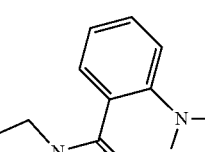 | * |
| 40 | 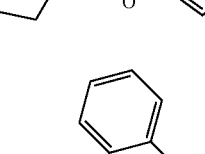 | * |
| 41 | 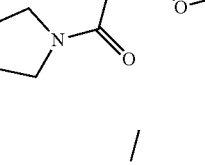 | * |
| 42 | 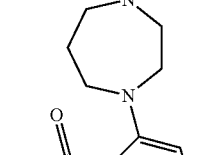 | * |
| 43 | 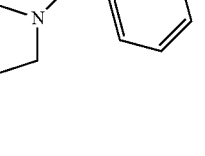 | * |

US 9,403,835 B2

223
224

-continued

| Ex | Structures | M1 PAM EC$_{50}$ (nM) |
|---|---|---|
| 44 | 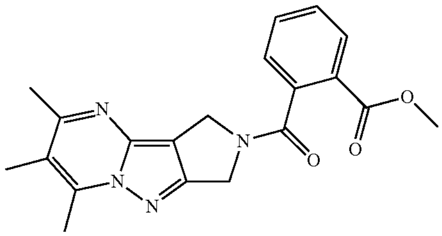 | * |
| 45 | 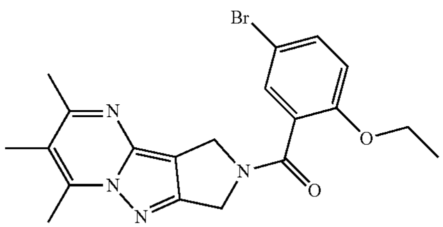 [SMILES: CCOc1ccc(Br)cc1C(=O)N1Cc2nn3c(C)c(C)c(C)nc3c2C1] | * |
| 46 | 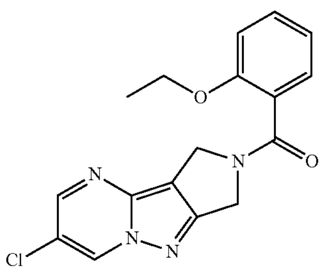 [SMILES: CCOc1ccccc1C(=O)N1Cc2nn3cc(Cl)cnc3c2C1] | * |
| 47 | 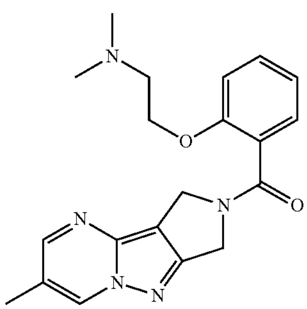 [SMILES: Cc1cnc2c3c(nn2c1)CN(C(=O)c1ccccc1OCCN(C)C)C3] | * |
| 48 | 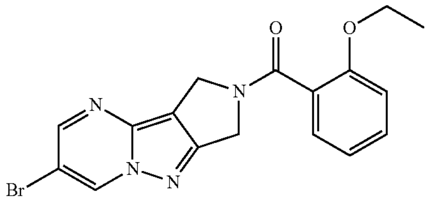 [SMILES: CCOc1ccccc1C(=O)N1Cc2nn3cc(Br)cnc3c2C1] | * |
| 49 | 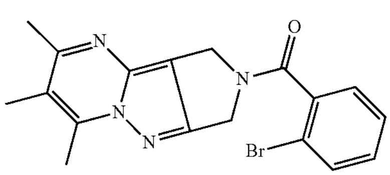 [SMILES: Cc1nc2c3c(nn2c(C)c1C)CN(C(=O)c1ccccc1Br)C3] | * |

* 1 to 2 µM
** 0.2 to 1 µM
*** below 0.2 µM

Example 182

Preparation of a Pharmaceutical Formulations

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:
1. A compound of Formula (I)

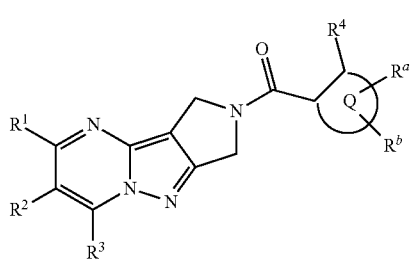

wherein
$R^1$, $R^2$, $R^3$ are each independently H, linear or branched $C_1$-$C_6$-alkyl, linear or branched $C_1$-$C_6$-alkoxy, Hal, or hydroxyl;
$R^a$, $R^b$ are each independently H, Hal, hydroxy or A;
Q denotes a 6-membered aromatic group or a 5-6-membered heteroaromatic group having 1 to 4 heteroatoms independently selected from N, O and S;
$R^4$ denotes G, OG, SG, OCHF$_2$, OCF$_2$CHF$_2$, NR$^5$G, —COOG, or OCOG;
each $R^5$ is independently H or a linear or branched alkyl having 1 to 6 carbon atoms;
each G is independently —CH$_3$, —CF$_3$, —CH$_2$-A, Het, Cyc, Ar, —CH$_2$-Het, —CH$_2$-Cyc, —CH$_2$—Ar, Hal, or hydroxy;
each Hal is independently F, Cl, Br or I;
each A is independently a linear or branched carbon chain having 1 to 6 carbon atoms, wherein 1 to 3 non adjacent —CH$_2$-groups may be independently from each other substituted by a group selected from O, NR$^5$, S, SO, SO$_2$, CO, and wherein 1 to 5 hydrogen atoms may be independently from each other substituted by Het, Cyc, Ar, or Hal;
each Het is independently a saturated, unsaturated or aromatic ring, each of which is monocyclic, bicyclic, or fused-bicyclic, and having 3- to 8-members and containing 1 to 4 heteroatoms independently selected from N, NR$^5$, O, S, CO, SO or SO$_2$, each of which may be substituted by 1 to 3 substituents independently selected from A, Hal, OH and Het$^1$;
Het$^1$ denotes a 4, 5 or 6 membered carbocyclic ring wherein 1 or 2 carbon atom are replaced by Oxygen atoms;
each Ar is independently a 6-membered carbocyclic aromatic ring or a fused or non fused byclic aromatic ring, and optionally substituted by 1 to 3 substituents independently selected from A or Hal;
each Cyc is independently a saturated or unsaturated carbocyclic ring having from 3 to 8 carbon atoms and optionally substituted by 1 to 3 substituents independently selected from A or Hal;
and/or pharmaceutically acceptable derivatives, tautomers, salts, and stereoisomers thereof.

2. The compound of claim 1 wherein
Q is a phenyl ring;
$R^a$, $R^b$ are each independently H, Hal, Hydroxy, or a linear or branched alkyl group having 1 to 6 carbon atoms and wherein 1 to 3 hydrogen atoms may be replaced by Hal; and
$R^4$ is G or OG.

3. The compound of claim 1, wherein

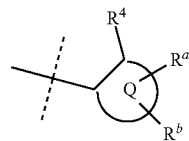

is selected from:

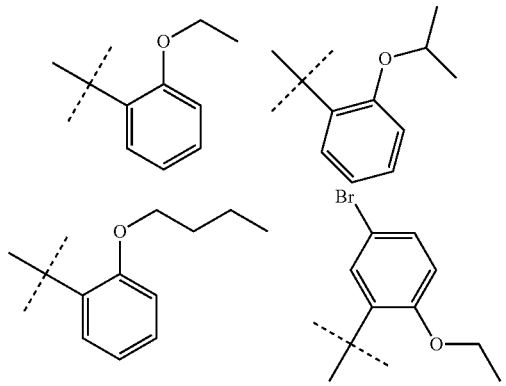

227
-continued
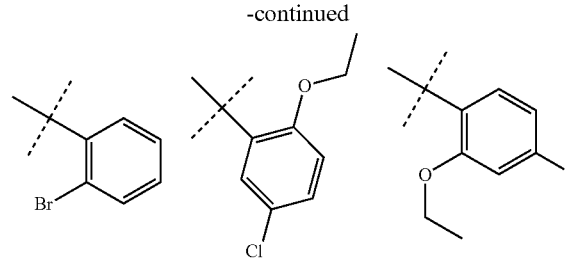
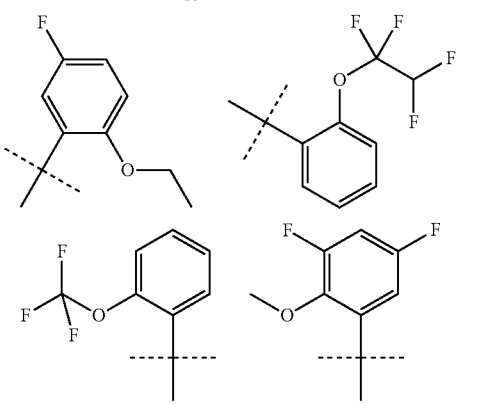
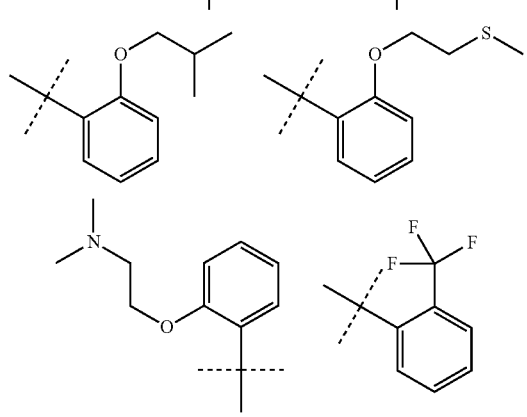
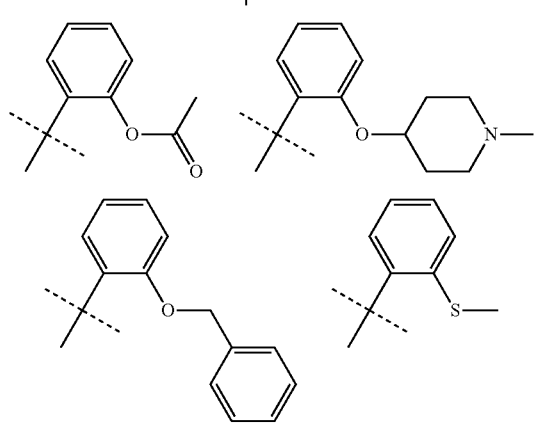
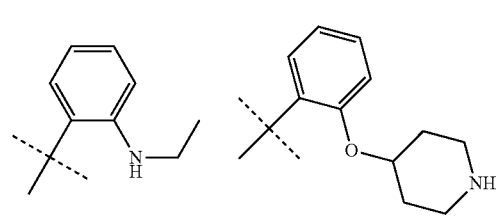
228
-continued
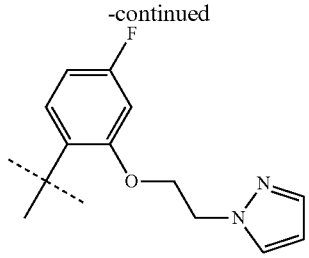
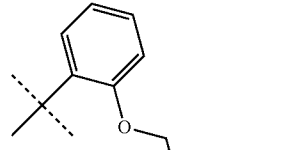
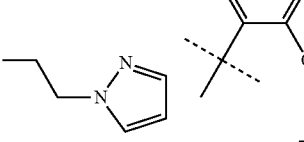
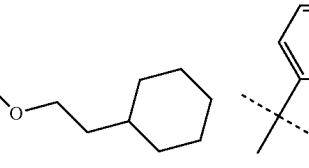
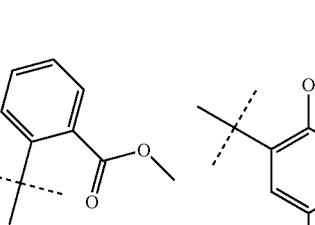
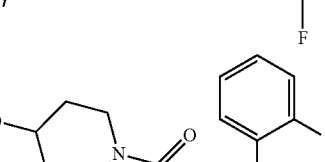
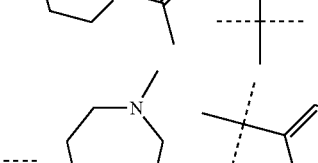
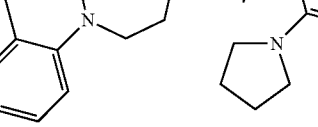
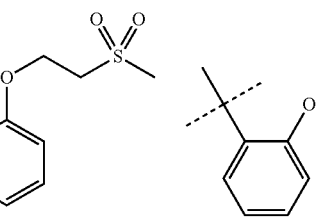

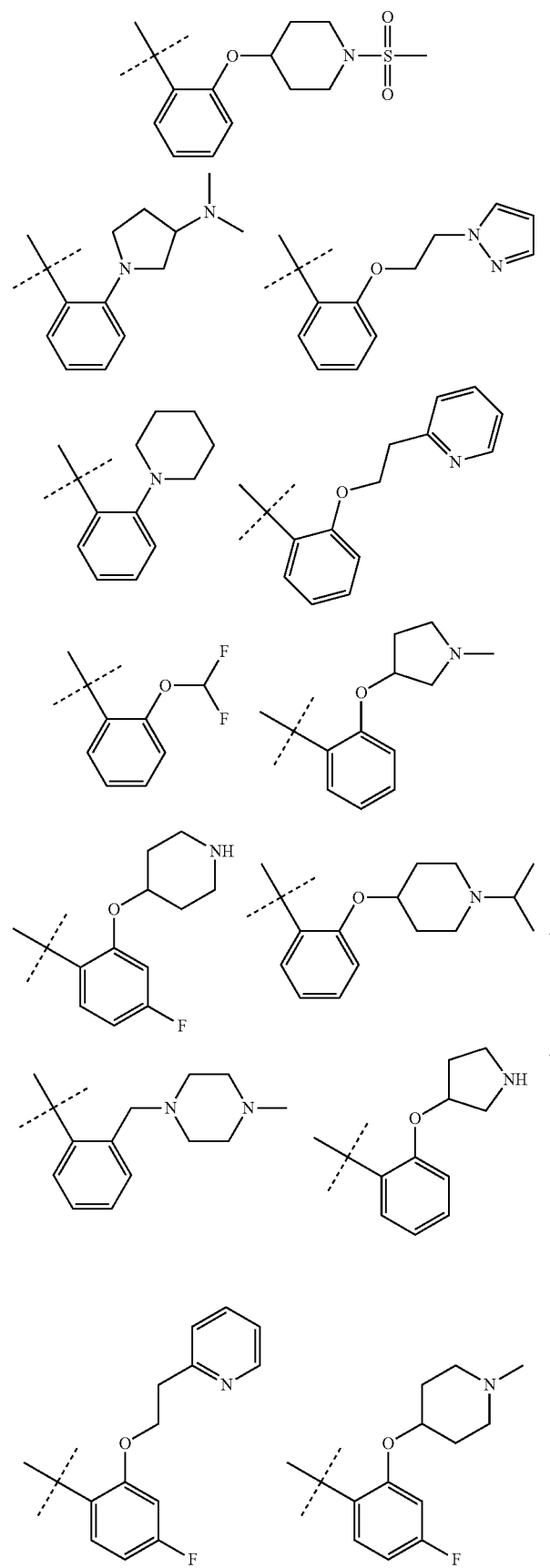
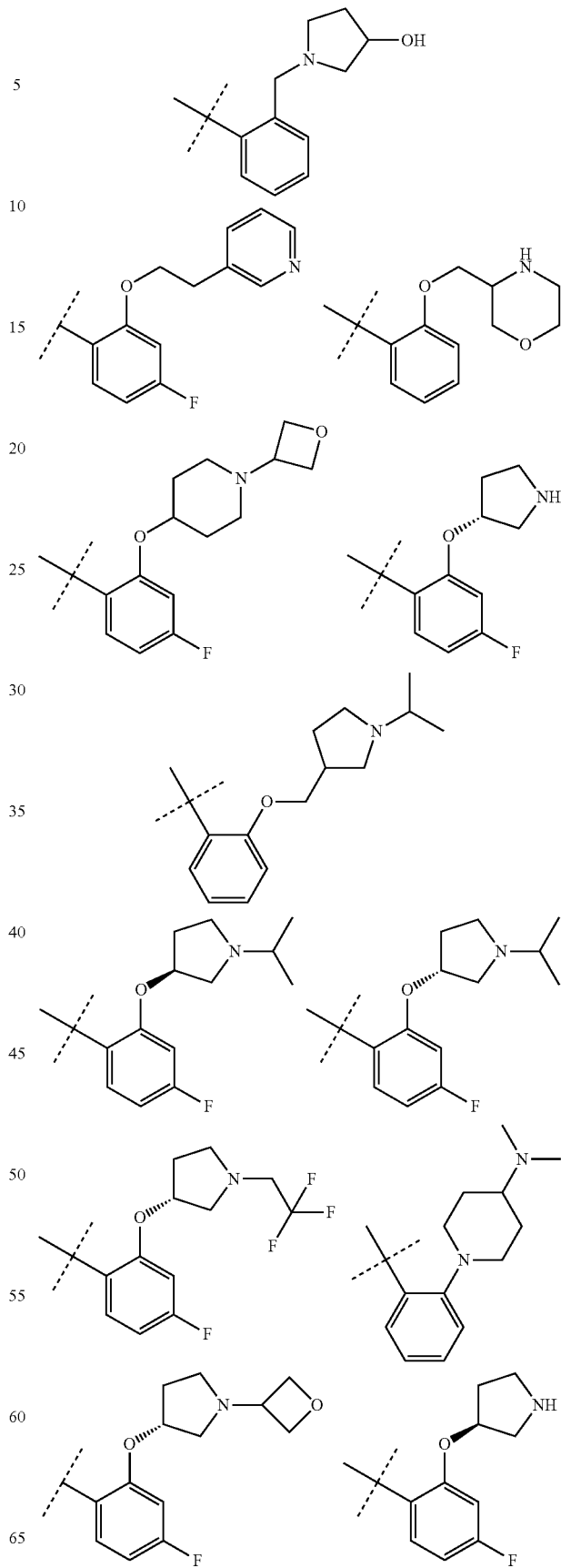

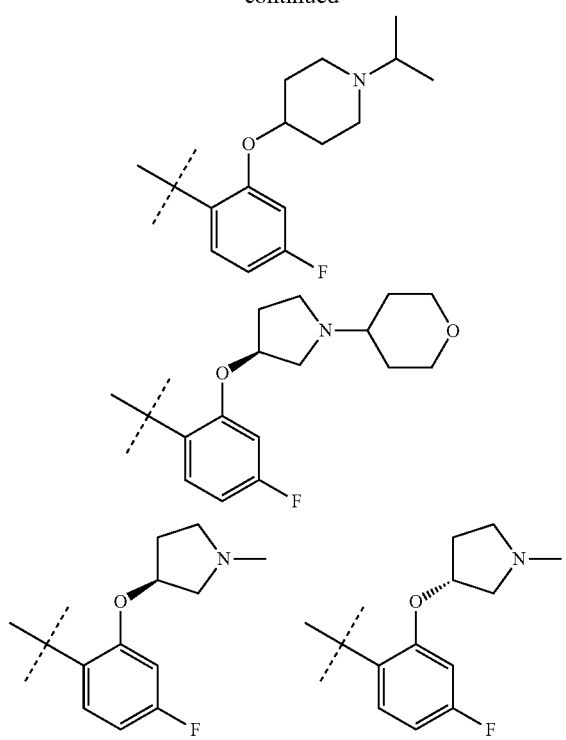
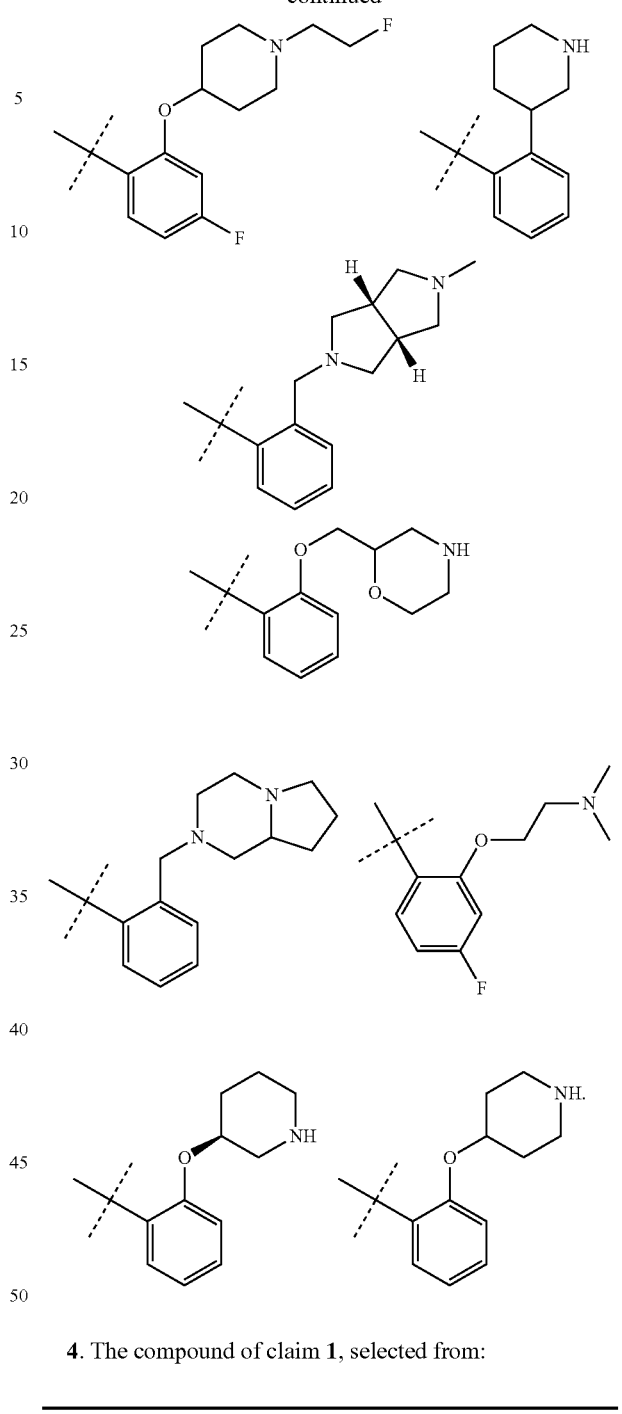
4. The compound of claim 1, selected from:
| Ex | Structures |
|---|---|
| 1 | 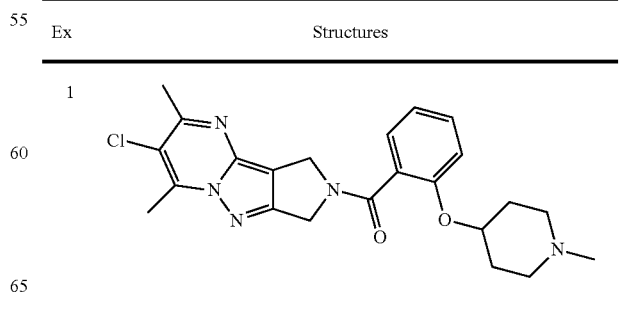 |

233
-continued
| Ex | Structures |
|---|---|
| 2 | 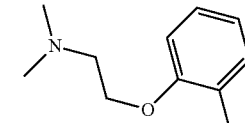 |
| 3 | 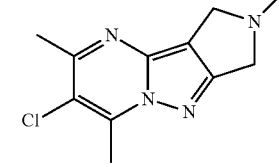 |
| 4 | 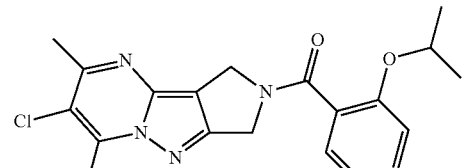 |
| 5 | 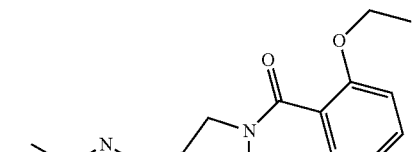 |
| 6 | 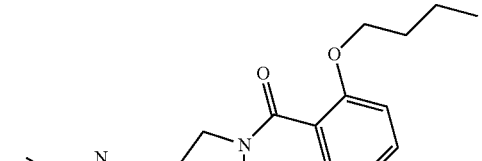 |
| 7 | 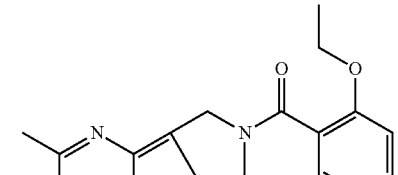 |
234
-continued
| Ex | Structures |
|---|---|
| 8 | 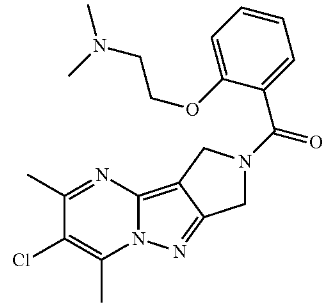 [SMILES: Cc1nc2c3c(nn2c(C)c1Cl)CN(C(=O)c1ccccc1OCCN(C)C)C3] |
| 9 | 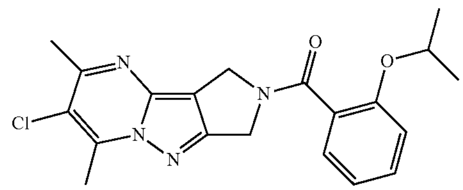 [SMILES: Cc1nc2c3c(nn2c(C)c1Cl)CN(C(=O)c1ccccc1OC(C)C)C3] |
| 10 | 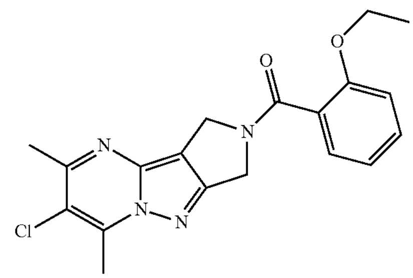 [SMILES: CCOc1ccccc1C(=O)N1Cc2nn3c(C)c(Cl)c(C)nc3c2C1] |
| 11 | 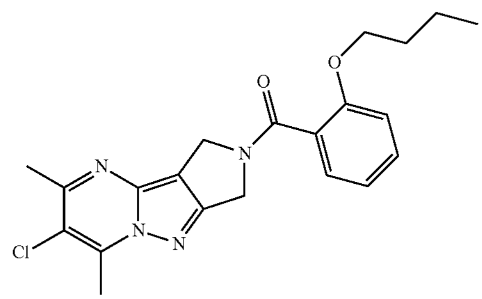 [SMILES: CCCCOc1ccccc1C(=O)N1Cc2nn3c(C)c(Cl)c(C)nc3c2C1] |
| 12 | 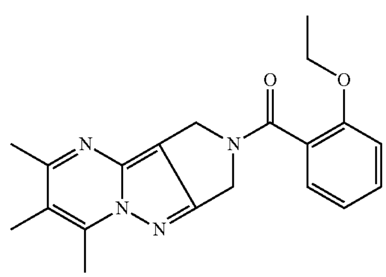 [SMILES: CCOc1ccccc1C(=O)N1Cc2nn3c(C)c(C)c(C)nc3c2C1] |
| 13 | 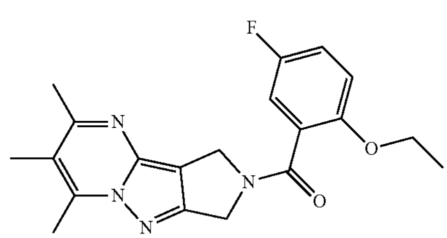 [SMILES: CCOc1ccc(F)cc1C(=O)N1Cc2nn3c(C)c(C)c(C)nc3c2C1] |
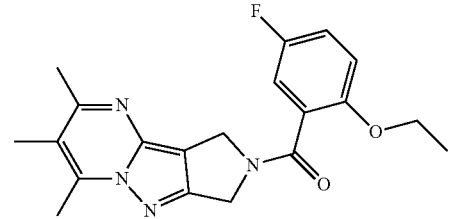

-continued

| Ex | Structures |
|---|---|
| 14 | 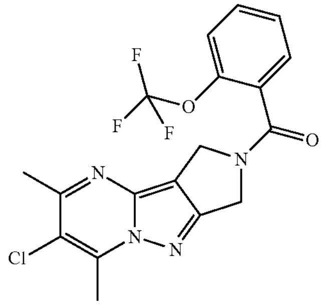 [SMILES: Cc1nc2c3c(nn2c(C)c1Cl)CN(C(=O)c1ccccc1OC(F)(F)F)C3] |
| 15 | 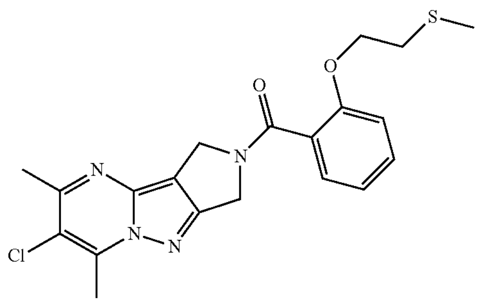 |
| 16 | 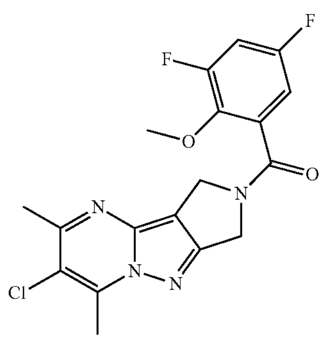 [SMILES: COc1c(F)cc(F)cc1C(=O)N1Cc2nn3c(C)c(Cl)c(C)nc3c2C1] |
| 17 | 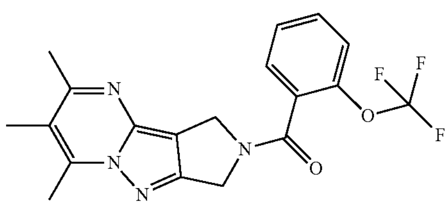 [SMILES: Cc1nc2c3c(nn2c(C)c1C)CN(C(=O)c1ccccc1OC(F)(F)F)C3] |
| 18 | 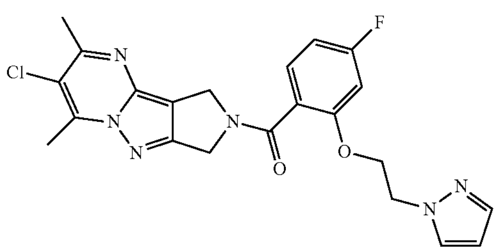 [SMILES: Cc1nc2c3c(nn2c(C)c1Cl)CN(C(=O)c1ccc(F)cc1OCCn1cccn1)C3] |
| 19 | 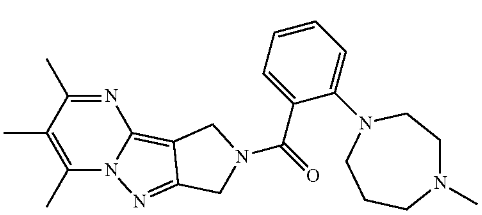 |

-continued

| Ex | Structures |
|---|---|
| 20 | |
| 21 | |
| 22 | |
| 23 | |
| 24 | |
| 25 | |
| 26 | |

| Ex | Structures |
|---|---|
| 27 | 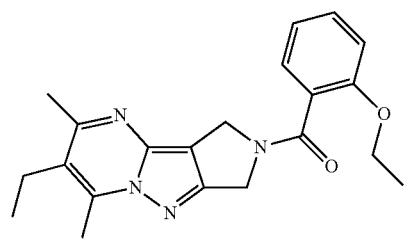 [SMILES: CCOc1ccccc1C(=O)N1Cc2nn3c(C)c(CC)c(C)nc3c2C1] |
| 28 | 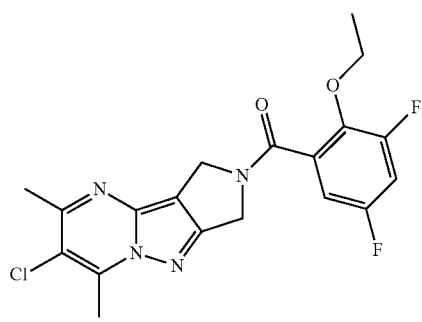 [SMILES: CCOc1c(F)cc(F)cc1C(=O)N1Cc2nn3c(C)c(Cl)c(C)nc3c2C1] |
| 29 | 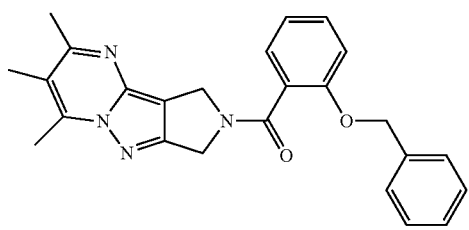 [SMILES: Cc1nc2c3c(nn2c(C)c1C)CN(C(=O)c1ccccc1OCc1ccccc1)C3] |
| 30 | 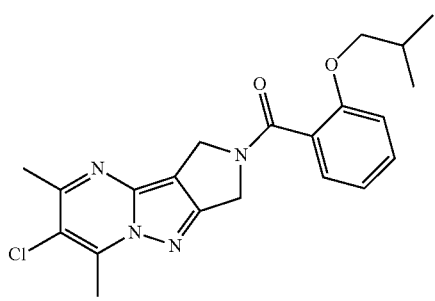 [SMILES: Cc1nc2c3c(nn2c(C)c1Cl)CN(C(=O)c1ccccc1OCC(C)C)C3] |
| 31 | 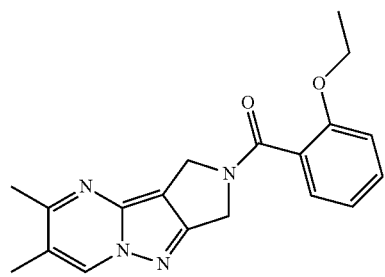 [SMILES: CCOc1ccccc1C(=O)N1Cc2nn3cc(C)c(C)nc3c2C1] |
| Ex | Structures |
|---|---|
| 32 | 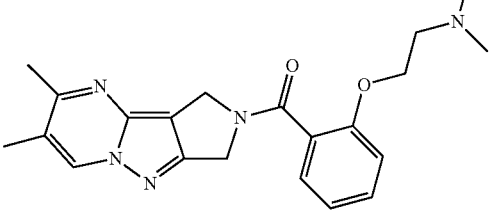 |
| 33 | 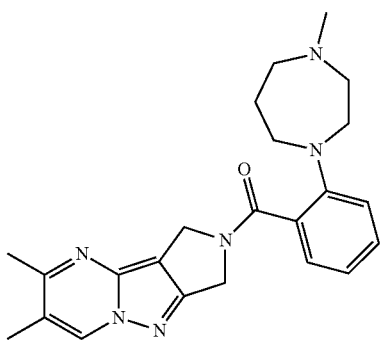 [SMILES: Cc1cn2nc3c(c2nc1C)CN(C(=O)c1ccccc1N1CCCN(C)CC1)C3] |
| 34 | 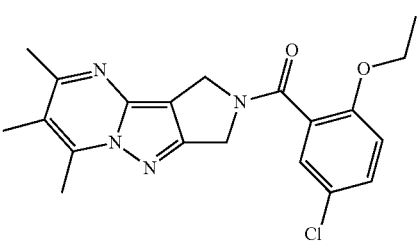 [SMILES: CCOc1ccc(Cl)cc1C(=O)N1Cc2nn3c(C)c(C)c(C)nc3c2C1] |
| 35 | 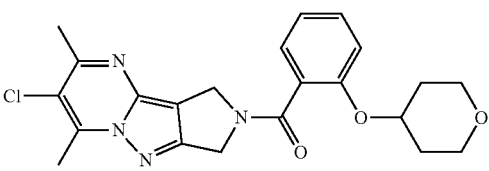 [SMILES: Cc1nc2c3c(nn2c(C)c1Cl)CN(C(=O)c1ccccc1OC1CCOCC1)C3] |
| 36 | 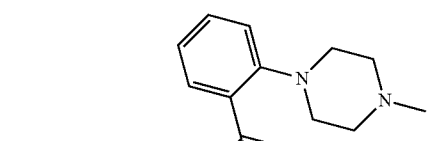 |
| 37 | 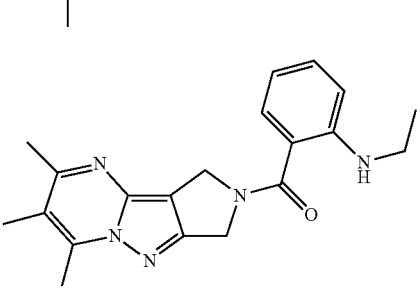 |

| Ex | Structures |
|---|---|
| 38 | 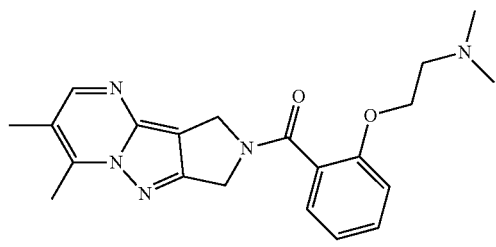 |
| 39 | 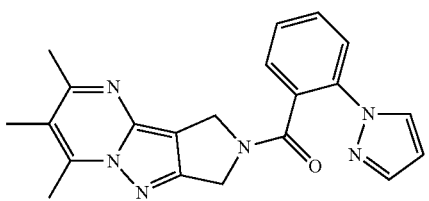 [SMILES: Cc1nc2c3c(nn2c(C)c1C)CN(C(=O)c1ccccc1-n1cccn1)C3] |
| 40 | 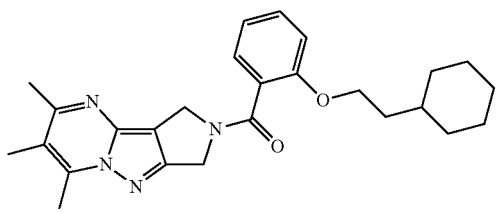 [SMILES: Cc1nc2c3c(nn2c(C)c1C)CN(C(=O)c1ccccc1OCCC1CCCCC1)C3] |
| 41 | 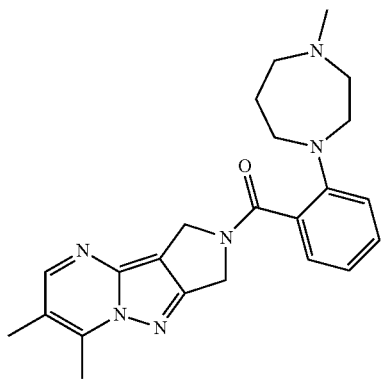 [SMILES: Cc1cnc2c3c(nn2c1C)CN(C(=O)c1ccccc1N1CCCN(C)CC1)C3] |
| 42 | 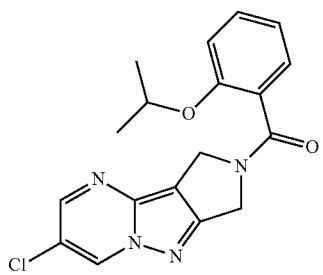 [SMILES: CC(C)Oc1ccccc1C(=O)N1Cc2nn3cc(Cl)cnc3c2C1] |
| 43 | 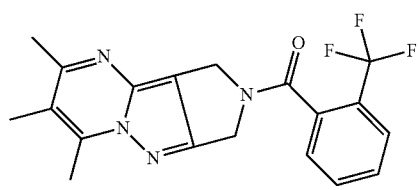 [SMILES: Cc1nc2c3c(nn2c(C)c1C)CN(C(=O)c1ccccc1C(F)(F)F)C3] |
| Ex | Structures |
|---|---|
| 44 | 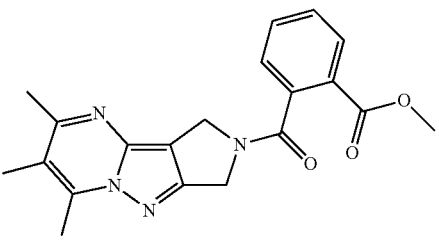 |
| 45 | 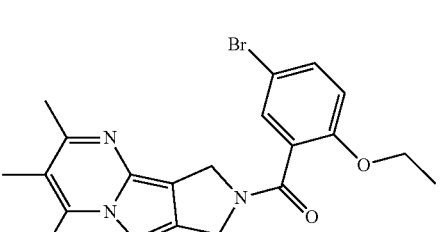 |
| 46 | 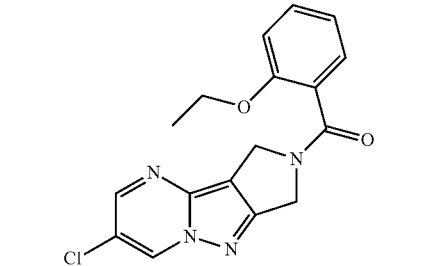 [SMILES: CCOc1ccccc1C(=O)N1Cc2nn3cc(Cl)cnc3c2C1] |
| 47 | 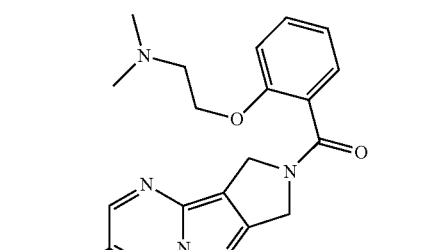 |
| 48 | 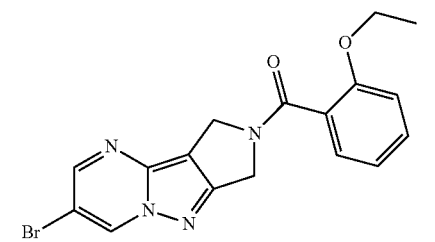 [SMILES: CCOc1ccccc1C(=O)N1Cc2nn3cc(Br)cnc3c2C1] |
| 49 | 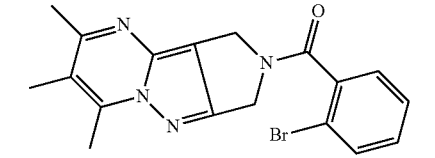 [SMILES: Cc1nc2c3c(nn2c(C)c1C)CN(C(=O)c1ccccc1Br)C3] |

| Ex | Structures |
|---|---|
| 50 | 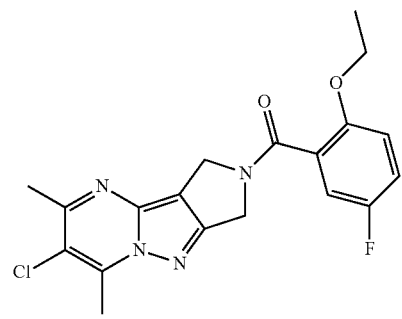 [SMILES: CCOc1ccc(F)cc1C(=O)N1Cc2nn3c(C)c(Cl)c(C)nc3c2C1] |
| 51 | 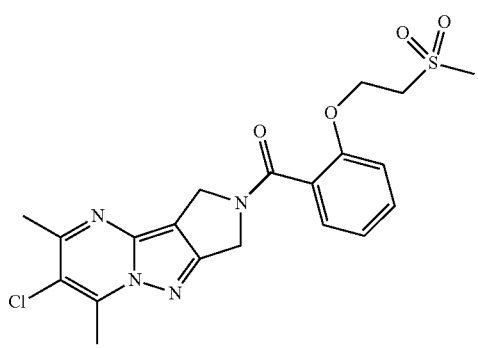 [SMILES: Cc1nc2c3c(nn2c(C)c1Cl)CN(C(=O)c1ccccc1OCCS(C)(=O)=O)C3] |
| 52 | 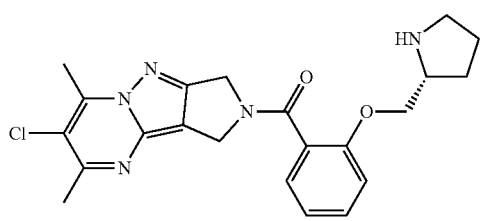 [SMILES: Cc1nc2c3c(nn2c(C)c1Cl)CN(C(=O)c1ccccc1OC[C@H]1CCCN1)C3] |
| 53 | 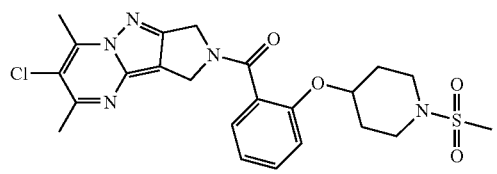 [SMILES: Cc1nc2c3c(nn2c(C)c1Cl)CN(C(=O)c1ccccc1OC1CCN(S(C)(=O)=O)CC1)C3] |
| 54 | 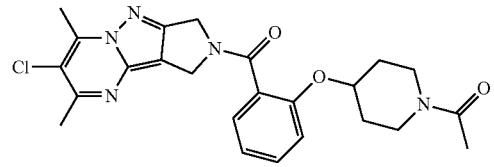 [SMILES: CC(=O)N1CCC(Oc2ccccc2C(=O)N2Cc3nn4c(C)c(Cl)c(C)nc4c3C2)CC1] |
| 55 | 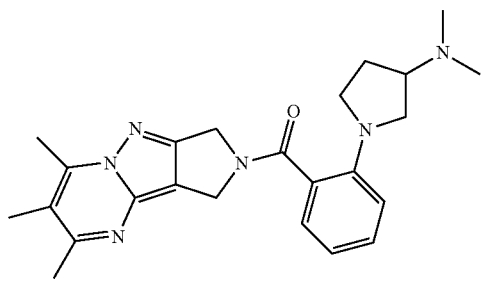 |
| Ex | Structures |
|---|---|
| 56 | 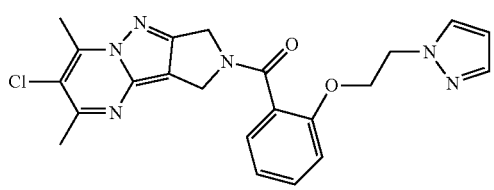 [SMILES: Cc1nc2c3c(nn2c(C)c1Cl)CN(C(=O)c1ccccc1OCCn1cccn1)C3] |
| 57 | 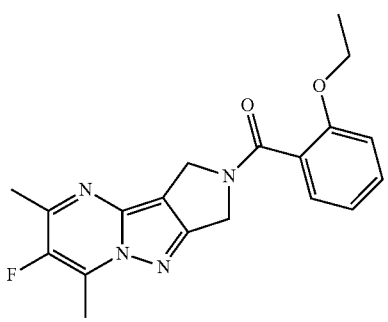 [SMILES: CCOc1ccccc1C(=O)N1Cc2nn3c(C)c(F)c(C)nc3c2C1] |
| 58 | 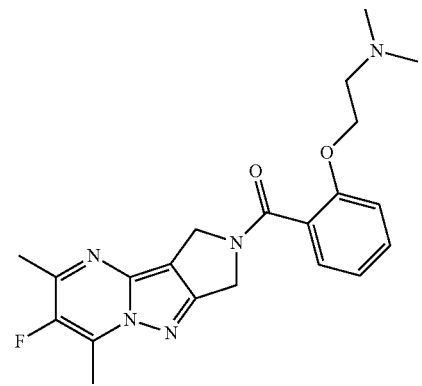 |
| 59 | 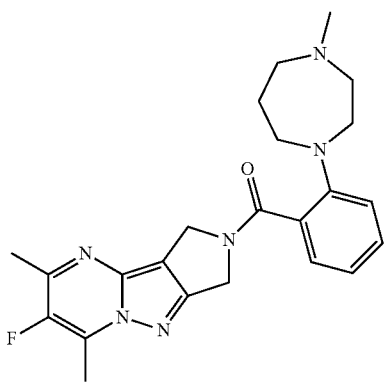 [SMILES: Cc1nc2c3c(nn2c(C)c1F)CN(C(=O)c1ccccc1N1CCCN(C)CC1)C3] |

| Ex | Structures |
|---|---|
| 60 | 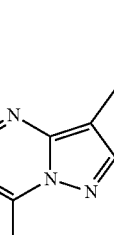 |
| 62 | 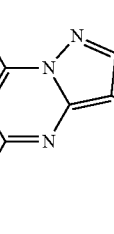 |
| 63 | 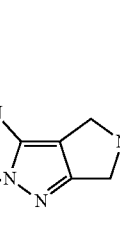 |
| 64 |  |
| 65 | 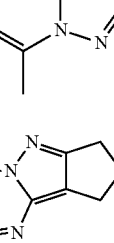 |
| 66 | 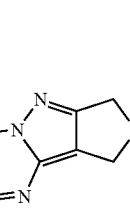 |
| Ex | Structures |
|---|---|
| 67 | |
| 68 | |
| 69 | |
| 70 | |

| Ex | Structures |
|---|---|
| 71 | |
| 72 | |
| 73 | |
| 74 | |
| 75 | 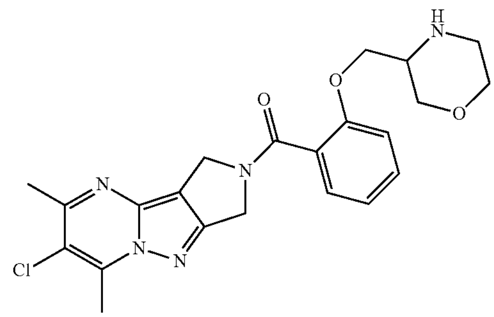 [SMILES: Cc1nc2c3c(nn2c(C)c1Cl)CN(C(=O)c1ccccc1OCC1COCCN1)C3] |
| 76 | 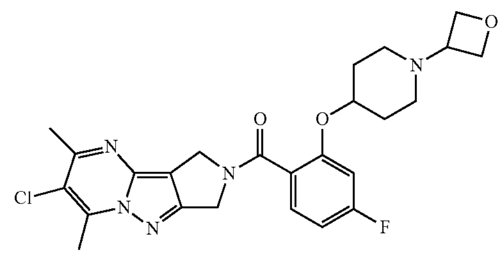 [SMILES: Cc1nc2c3c(nn2c(C)c1Cl)CN(C(=O)c1ccc(F)cc1OC1CCN(C2COC2)CC1)C3] |
| 77 | 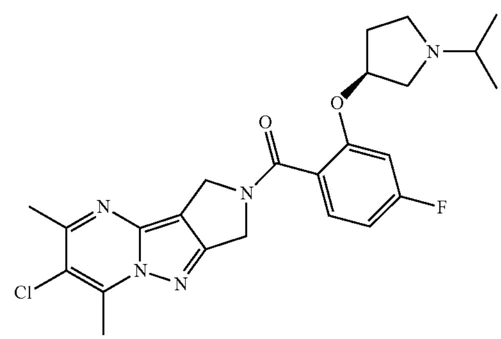 [SMILES: Cc1nc2c3c(nn2c(C)c1Cl)CN(C(=O)c1ccc(F)cc1O[C@H]1CCN(C(C)C)C1)C3] |
| 78 | 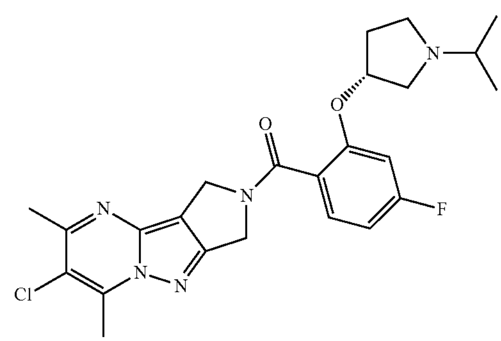 [SMILES: Cc1nc2c3c(nn2c(C)c1Cl)CN(C(=O)c1ccc(F)cc1O[C@@H]1CCN(C(C)C)C1)C3] |
| 79 | 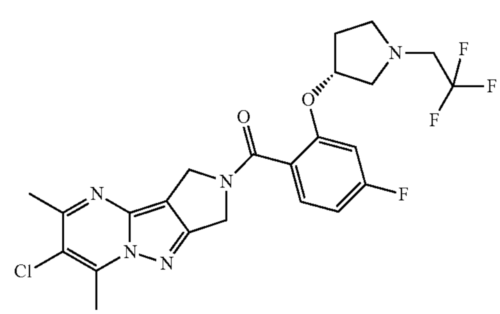 [SMILES: Cc1nc2c3c(nn2c(C)c1Cl)CN(C(=O)c1ccc(F)cc1O[C@@H]1CCN(CC(F)(F)F)C1)C3] |

-continued

| Ex | Structures |
|---|---|
| 80 | 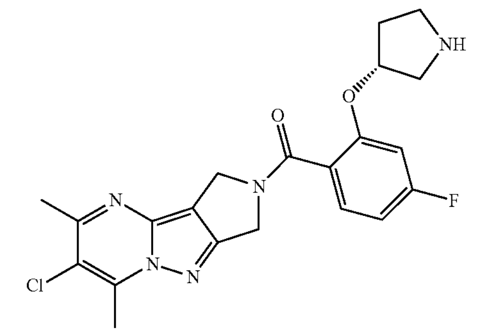 [SMILES: Cc1nc2c3c(nn2c(C)c1Cl)CN(C(=O)c1ccc(F)cc1O[C@@H]1CCNC1)C3] |
| 81 | 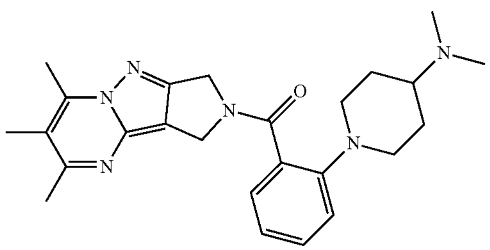 |
| 82 | 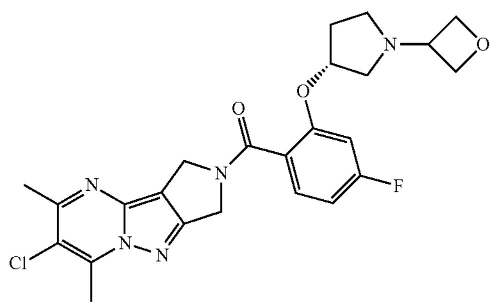 [SMILES: Cc1nc2c3c(nn2c(C)c1Cl)CN(C(=O)c1ccc(F)cc1O[C@@H]1CCN(C2COC2)C1)C3] |
| 83 | 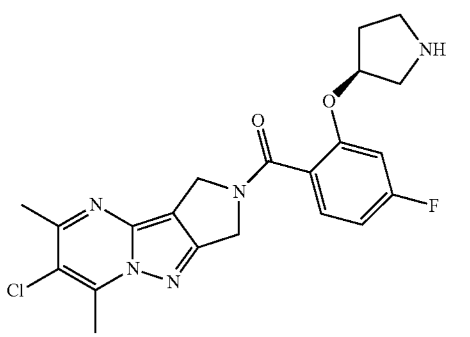 [SMILES: Cc1nc2c3c(nn2c(C)c1Cl)CN(C(=O)c1ccc(F)cc1O[C@H]1CCNC1)C3] |
| 84 | 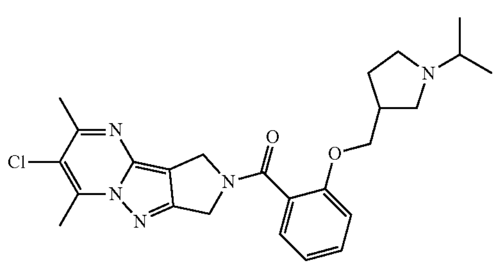 [SMILES: Cc1nc2c3c(nn2c(C)c1Cl)CN(C(=O)c1ccccc1OCC1CCN(C(C)C)C1)C3] |

-continued

| Ex | Structures |
|---|---|
| 85 | 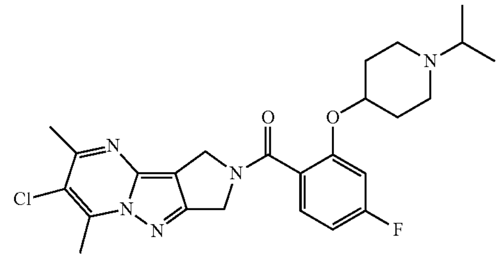 [SMILES: Cc1nc2c3c(nn2c(C)c1Cl)CN(C(=O)c1ccc(F)cc1OC1CCN(C(C)C)CC1)C3] |
| 86 | 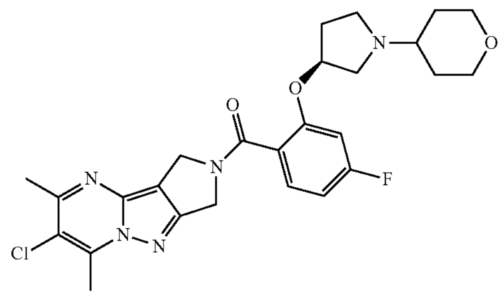 [SMILES: Cc1nc2c3c(nn2c(C)c1Cl)CN(C(=O)c1ccc(F)cc1O[C@H]1CCN(C2CCOCC2)C1)C3] |
| 87 | 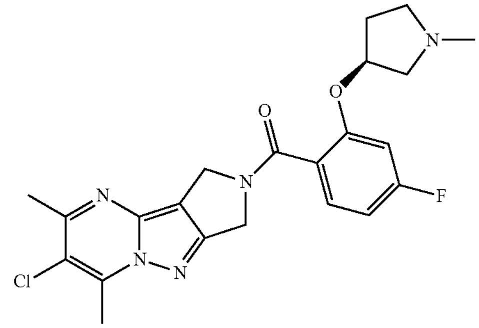 |
| 88 | 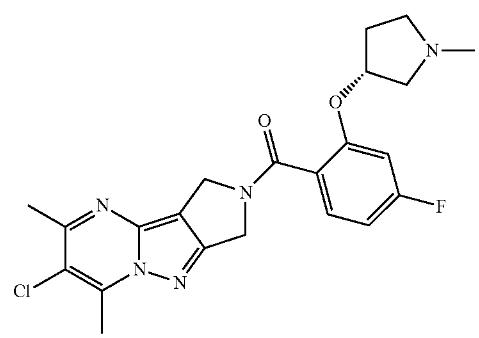 |
| 89 | 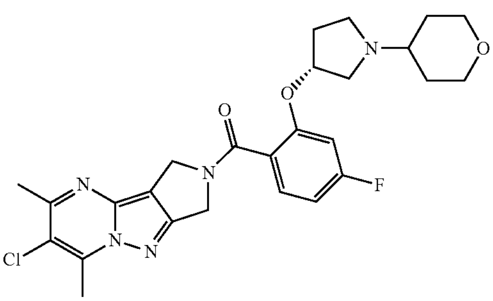 [SMILES: Cc1nc2c3c(nn2c(C)c1Cl)CN(C(=O)c1ccc(F)cc1O[C@@H]1CCN(C2CCOCC2)C1)C3] |

-continued
| Ex | Structures |
|---|---|
| 90 | 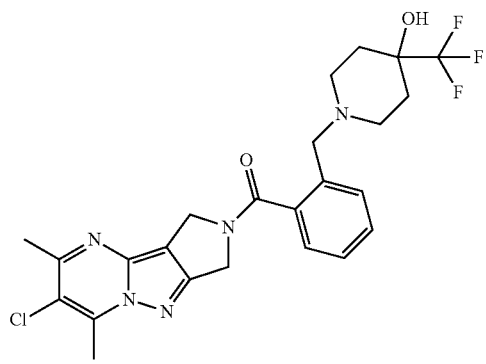 [SMILES: Cc1nc2c3c(nn2c(C)c1Cl)CN(C(=O)c1ccccc1CN1CCC(O)(C(F)(F)F)CC1)C3] |
| 91 | 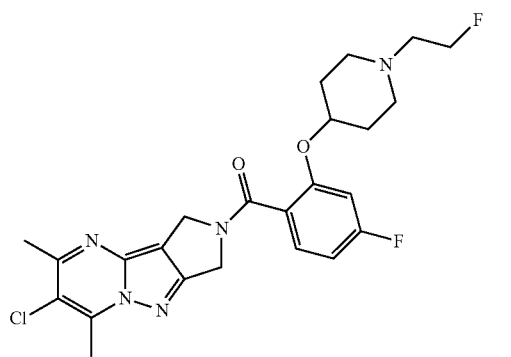 [SMILES: Cc1nc2c3c(nn2c(C)c1Cl)CN(C(=O)c1ccc(F)cc1OC1CCN(CCF)CC1)C3] |
| 92 | 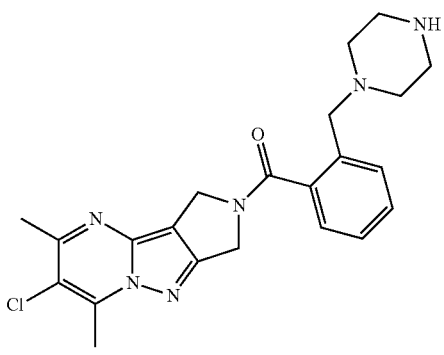 [SMILES: Cc1nc2c3c(nn2c(C)c1Cl)CN(C(=O)c1ccccc1CN1CCNCC1)C3] |
| 93 | 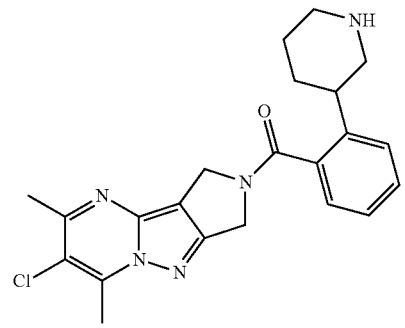 [SMILES: Cc1nc2c3c(nn2c(C)c1Cl)CN(C(=O)c1ccccc1C1CCCNC1)C3] |
-continued
| Ex | Structures |
|---|---|
| 94 | 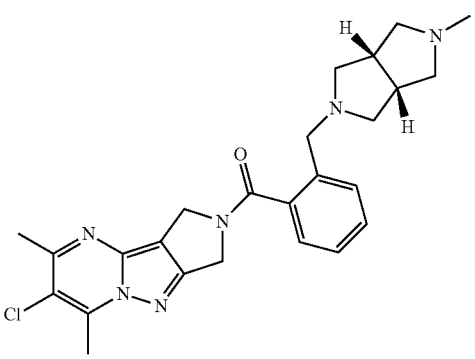 |
| 95 | 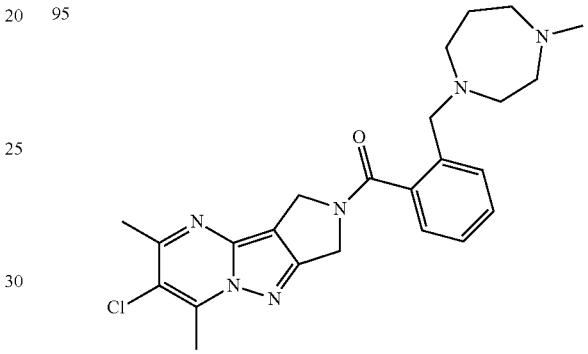 |
| 96 | 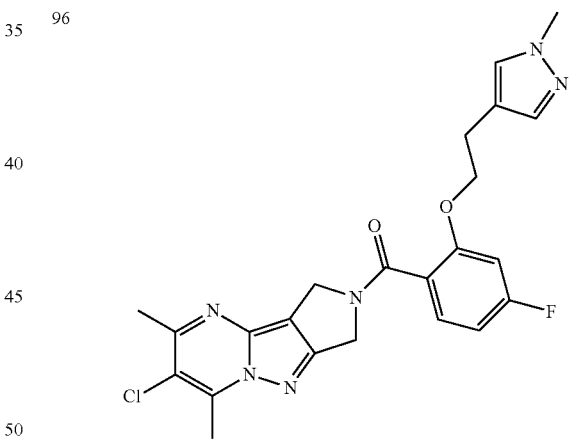 |
| 97 | 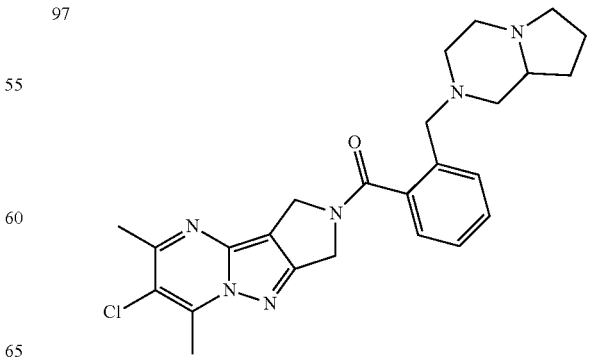 |

| Ex | Structures |
|---|---|
| 98 | 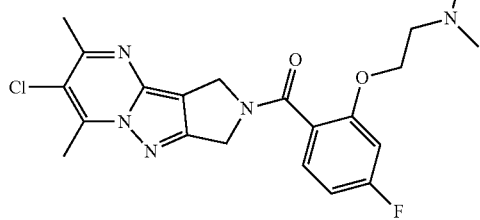 |
| 99 | 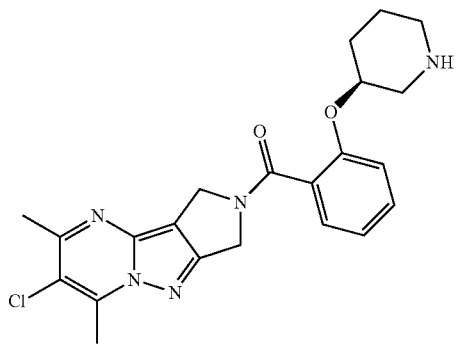 [SMILES: Cc1nc2c3c(nn2c(C)c1Cl)CN(C(=O)c1ccccc1O[C@H]1CCCNC1)C3] |
| 100 | 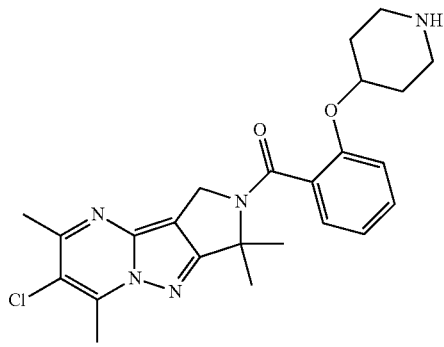 [SMILES: Cc1nc2c3c(nn2c(C)c1Cl)C(C)(C)N(C(=O)c1ccccc1OC1CCNCC1)C3] |
| 101 | 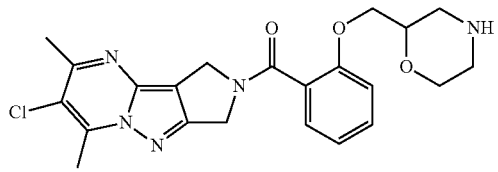 |
| 102 | 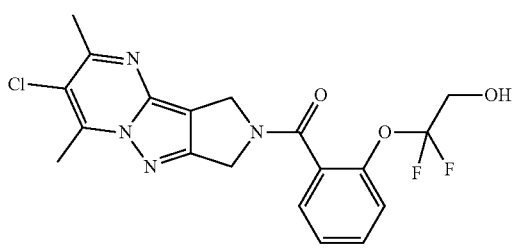 [SMILES: Cc1nc2c3c(nn2c(C)c1Cl)CN(C(=O)c1ccccc1OC(F)(F)CO)C3] |
| Ex | Structures |
|---|---|
| 103 | 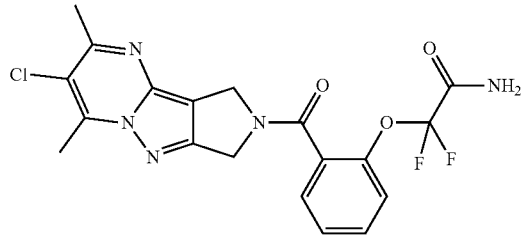 [SMILES: Cc1nc2c3c(nn2c(C)c1Cl)CN(C(=O)c1ccccc1OC(F)(F)C(N)=O)C3] |
| 104 | 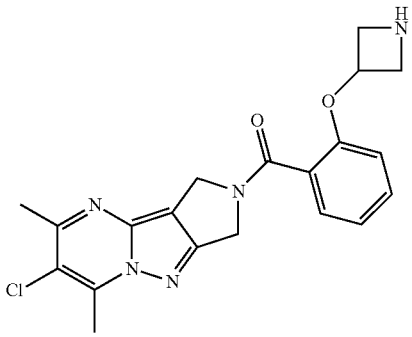 [SMILES: Cc1nc2c3c(nn2c(C)c1Cl)CN(C(=O)c1ccccc1OC1CNC1)C3] |
| 105 | 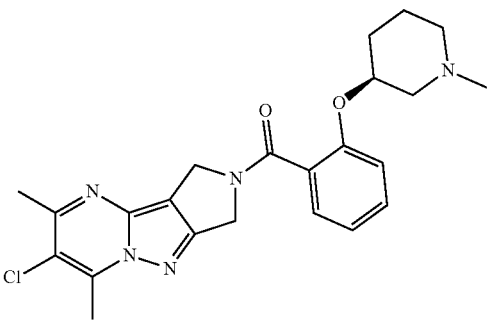 |
| 106 | 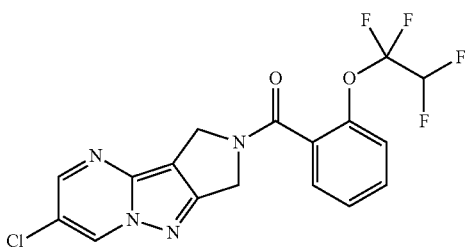 [SMILES: O=C(c1ccccc1OC(F)(F)C(F)F)N1Cc2nn3cc(Cl)cnc3c2C1] |
| 107 | 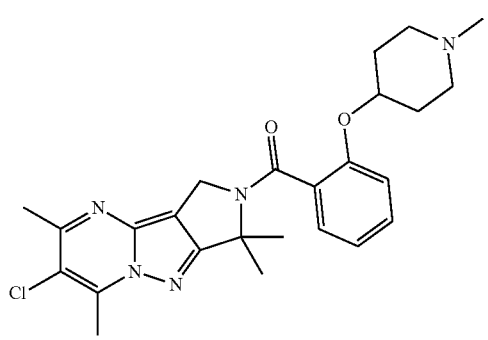 [SMILES: Cc1nc2c3c(nn2c(C)c1Cl)C(C)(C)N(C(=O)c1ccccc1OC1CCN(C)CC1)C3] |

-continued
| Ex | Structures |
|---|---|
| 108 | 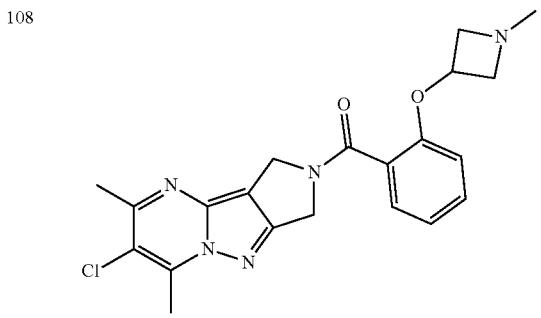 |
| 109 | 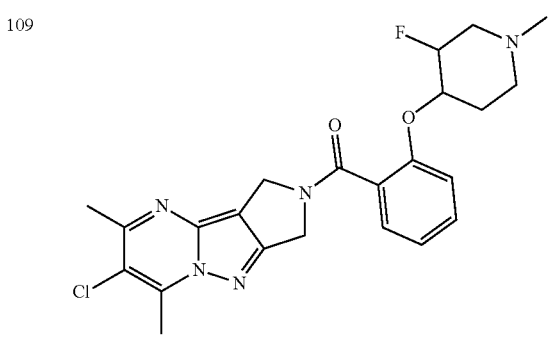 |
| 110 | 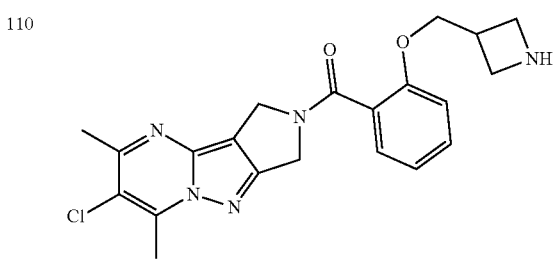 |
| 111 | 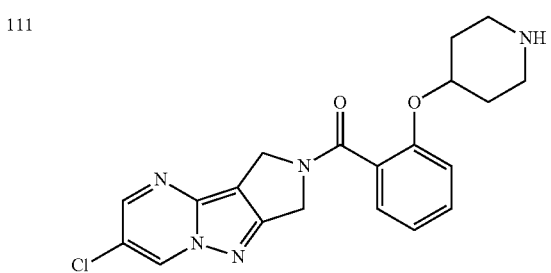 |
| 112 | 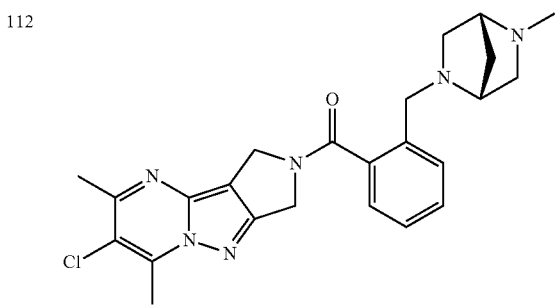 |
-continued
| Ex | Structures |
|---|---|
| 113 | 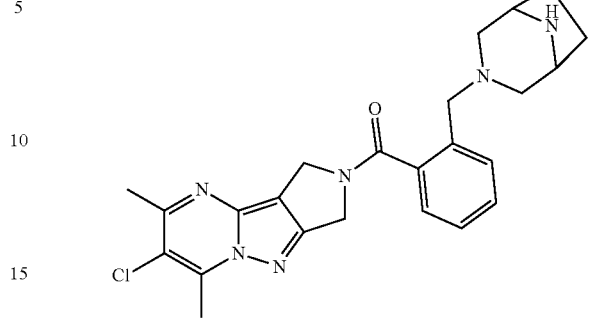 |
| 114 | 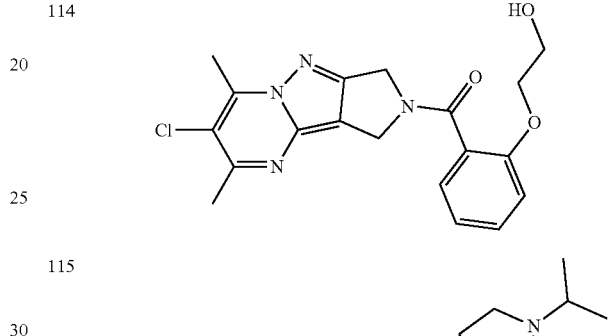 |
| 115 | 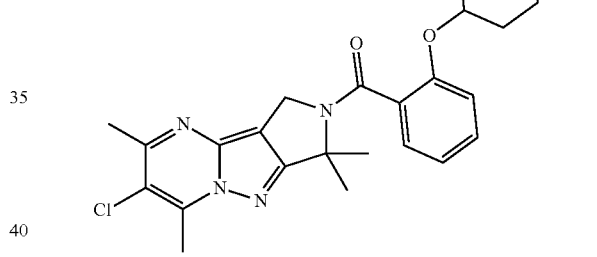 |
| 116 | 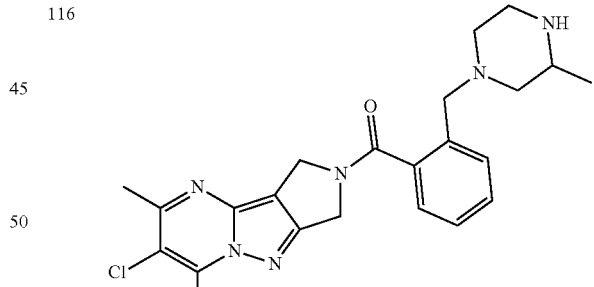 |
| 117 | 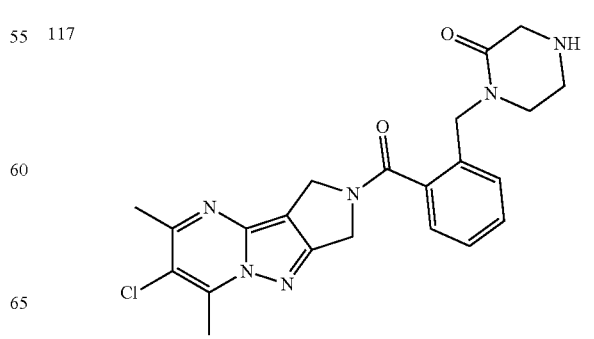 |

| Ex | Structures |
|---|---|
| 118 | 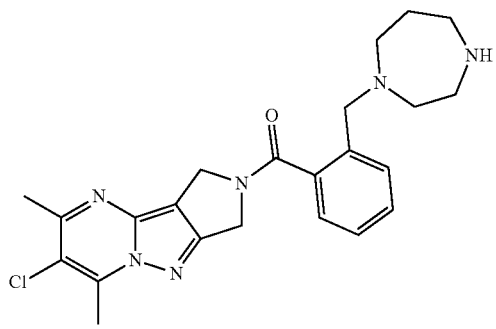 [SMILES: Cc1nc2c3c(nn2c(C)c1Cl)CN(C(=O)c1ccccc1CN1CCCNCC1)C3] |
| 119 | 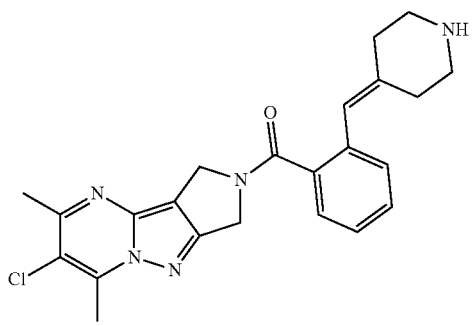 [SMILES: Cc1nc2c3c(nn2c(C)c1Cl)CN(C(=O)c1ccccc1C=C1CCNCC1)C3] |
| 120 | 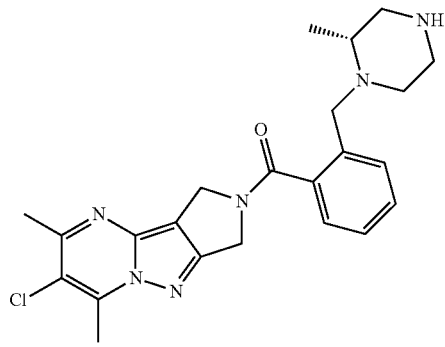 [SMILES: Cc1nc2c3c(nn2c(C)c1Cl)CN(C(=O)c1ccccc1CN1CCNC[C@H]1C)C3] |
| 121 | 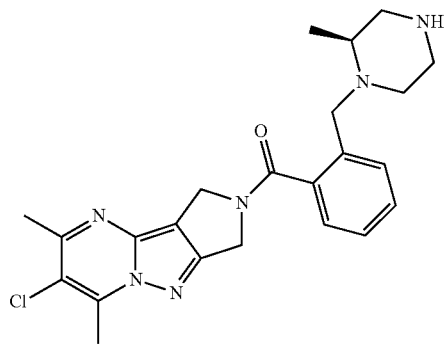 [SMILES: Cc1nc2c3c(nn2c(C)c1Cl)CN(C(=O)c1ccccc1CN1CCNC[C@@H]1C)C3] |
| 122 | 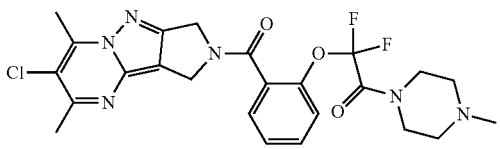 [SMILES: Cc1nc2c3c(nn2c(C)c1Cl)CN(C(=O)c1ccccc1OC(F)(F)C(=O)N1CCN(C)CC1)C3] |
| Ex | Structures |
|---|---|
| 123 | 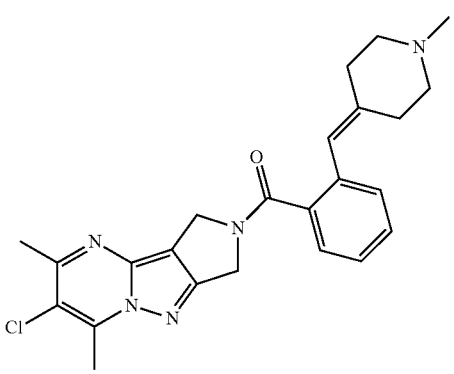 [SMILES: Cc1nc2c3c(nn2c(C)c1Cl)CN(C(=O)c1ccccc1C=C1CCN(C)CC1)C3] |
| 124 | 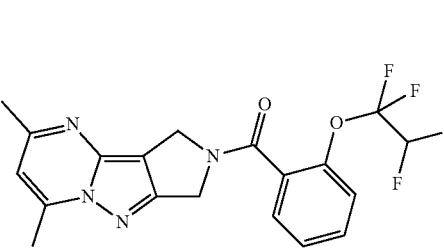 |
| 125 | 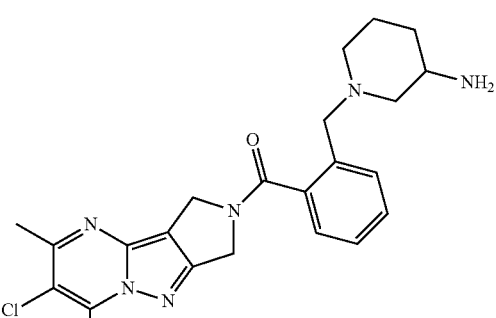 |
| 126 | 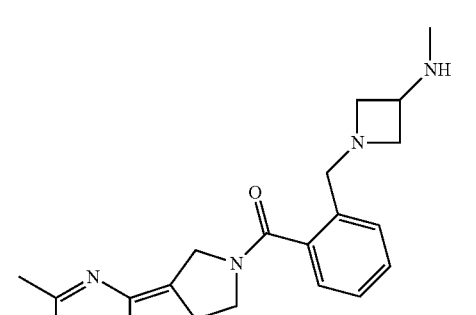 |

| Ex | Structures |
|---|---|
| 127 | 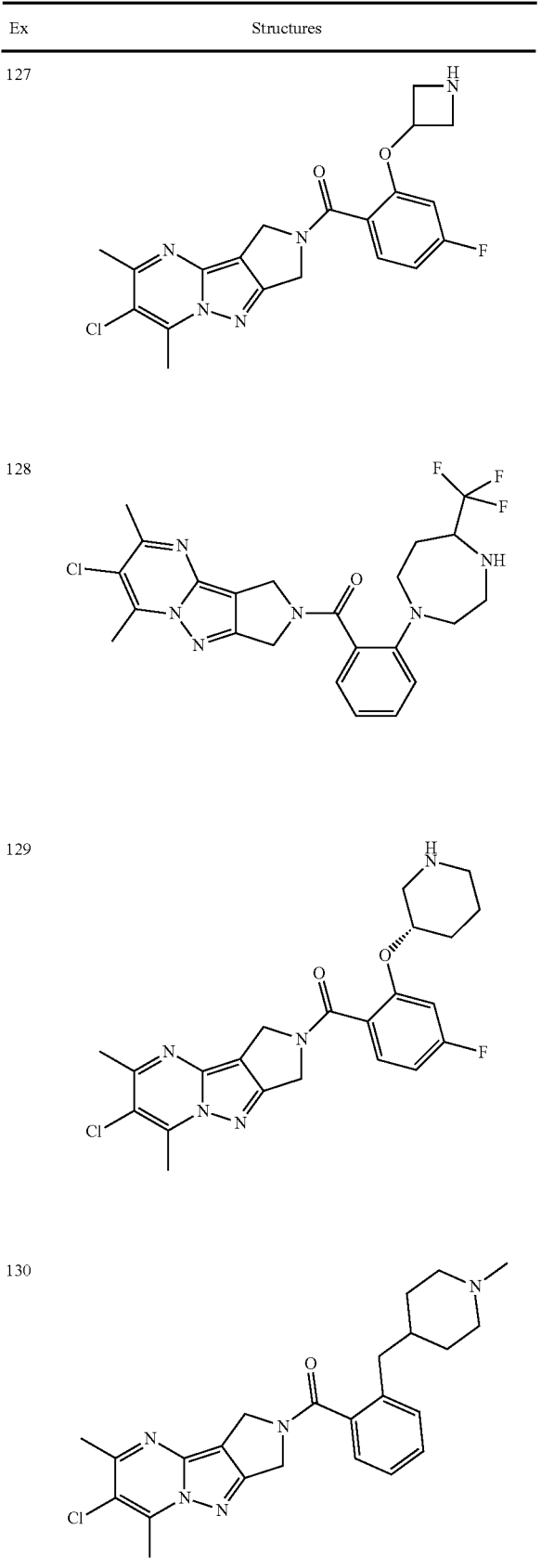 |
| 128 | |
| 129 | |
| 130 | |
| Ex | Structures |
|---|---|
| 131 | 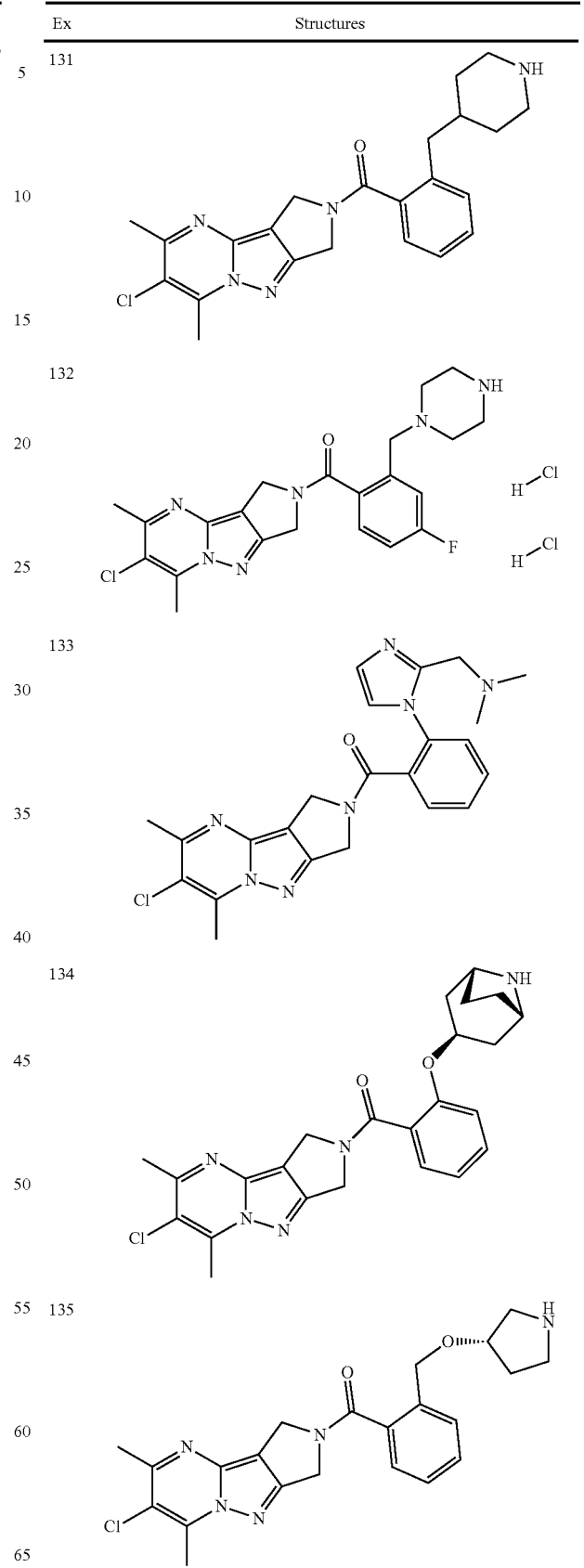 |
| 132 | |
| 133 | |
| 134 | |
| 135 | |

-continued
| Ex | Structures |
|---|---|
| 136 | 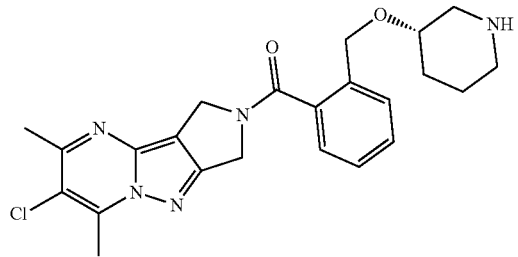 [SMILES: Cc1nc2c3c(nn2c(C)c1Cl)CN(C(=O)c1ccccc1CO[C@H]1CCCNC1)C3] |
| 138 | 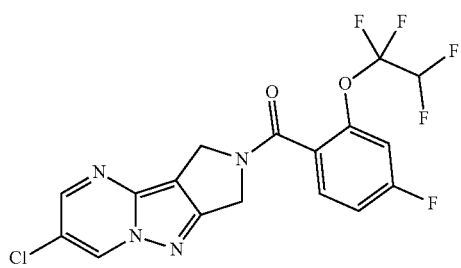 [SMILES: O=C(c1ccc(F)cc1OC(F)(F)C(F)F)N1Cc2nn3cc(Cl)cnc3c2C1] |
| 139 | 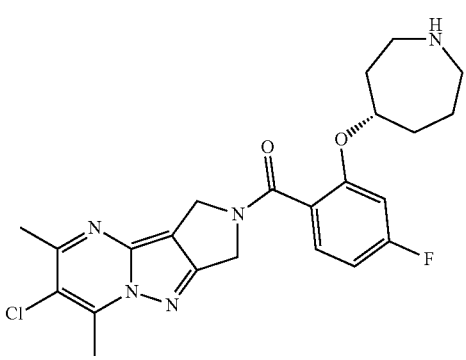 [SMILES: Cc1nc2c3c(nn2c(C)c1Cl)CN(C(=O)c1ccc(F)cc1O[C@H]1CCCNCC1)C3] |
| 140 | 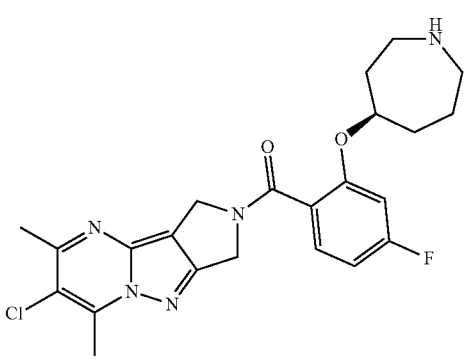 [SMILES: Cc1nc2c3c(nn2c(C)c1Cl)CN(C(=O)c1ccc(F)cc1O[C@@H]1CCCNCC1)C3] |
| 141 | 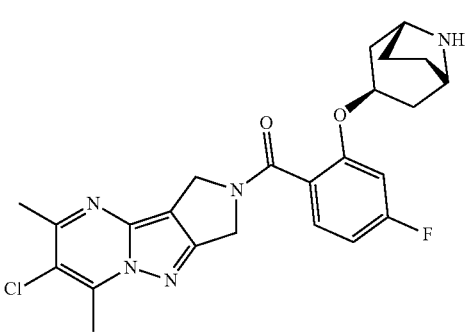 |
-continued
| Ex | Structures |
|---|---|
| 142 | 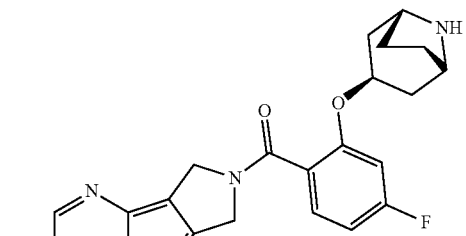 |
| 143 | 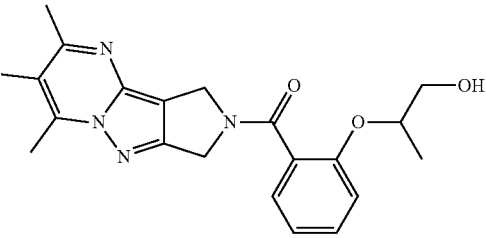 |
| 144 | 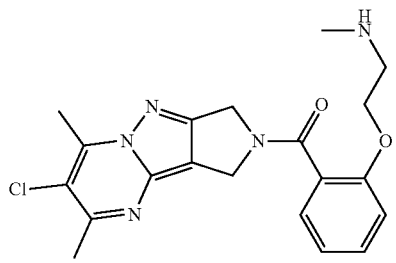 [SMILES: CNCCOc1ccccc1C(=O)N1Cc2nn3c(C)c(Cl)c(C)nc3c2C1] |
| 145 | 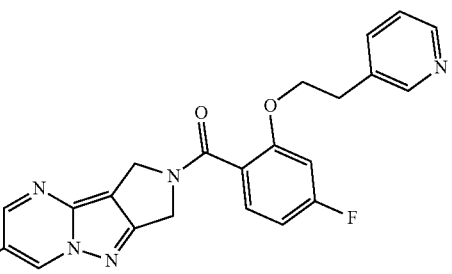 |
| 146 | 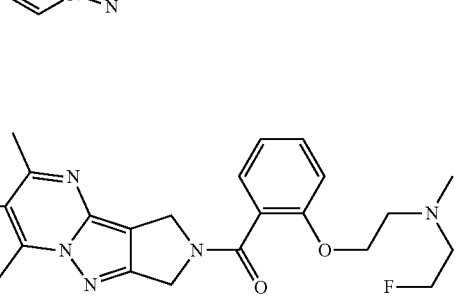 |

261
-continued

| Ex | Structures |
|---|---|
| 147 | 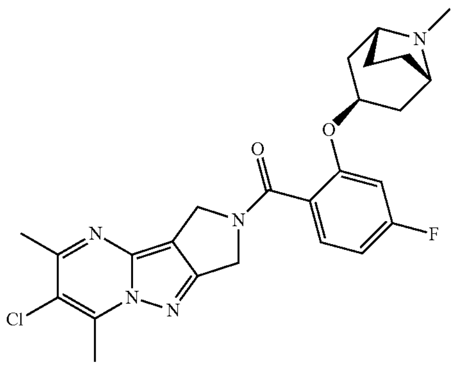 [SMILES: Cc1nc2c3c(nn2c(C)c1Cl)CN(C(=O)c1ccc(F)cc1O[C@H]1C[C@H]2CC[C@@H](C1)N2C)C3] |
| 148 | 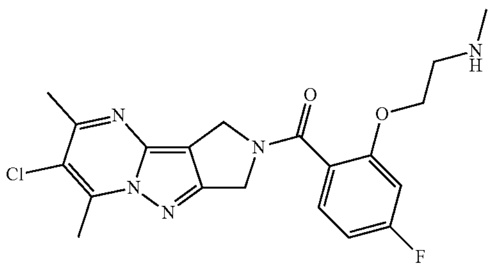 [SMILES: CNCCOc1cc(F)ccc1C(=O)N1Cc2nn3c(C)c(Cl)c(C)nc3c2C1] |
| 149 | 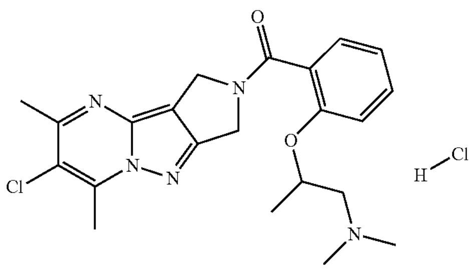 [SMILES: Cc1nc2c3c(nn2c(C)c1Cl)CN(C(=O)c1ccccc1OC(C)CN(C)C)C3 ; Cl] |
| 150 | 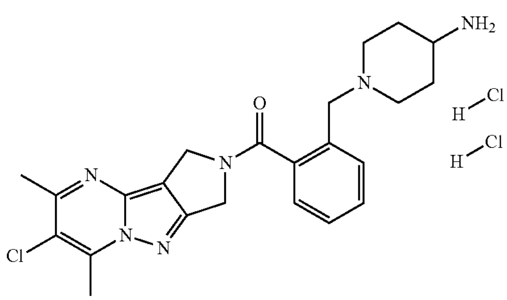 |
| 151 | 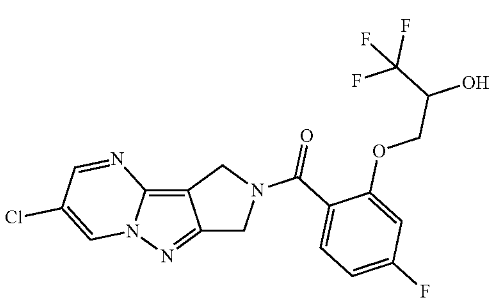 [SMILES: O=C(c1ccc(F)cc1OCC(O)C(F)(F)F)N1Cc2nn3cc(Cl)cnc3c2C1] |

262
-continued

| Ex | Structures |
|---|---|
| 152 | 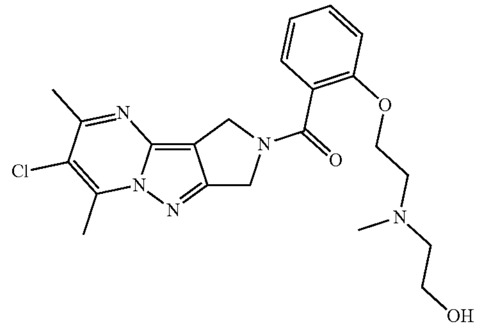 [SMILES: Cc1nc2c3c(nn2c(C)c1Cl)CN(C(=O)c1ccccc1OCCN(C)CCO)C3] |
| 153 | 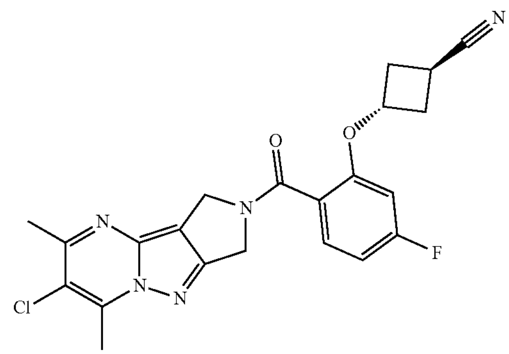 [SMILES: Cc1nc2c3c(nn2c(C)c1Cl)CN(C(=O)c1ccc(F)cc1O[C@H]1C[C@H](C#N)C1)C3] |
| 154 | 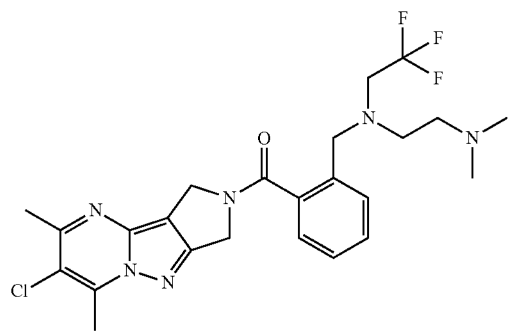 |
| 155 | 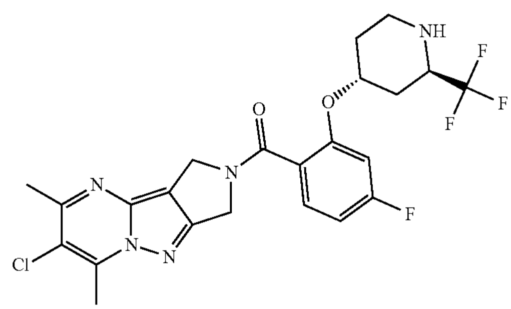 [SMILES: Cc1nc2c3c(nn2c(C)c1Cl)CN(C(=O)c1ccc(F)cc1O[C@@H]1CCN[C@@H](C(F)(F)F)C1)C3] |
| 156 | 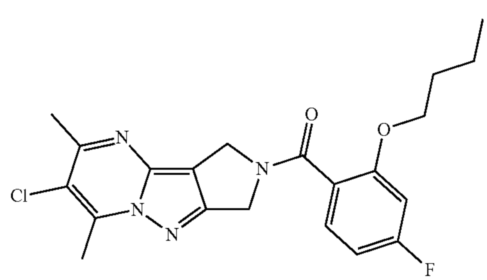 [SMILES: CCCCOc1cc(F)ccc1C(=O)N1Cc2nn3c(C)c(Cl)c(C)nc3c2C1] |

| Ex | Structures |
|---|---|
| 157 | 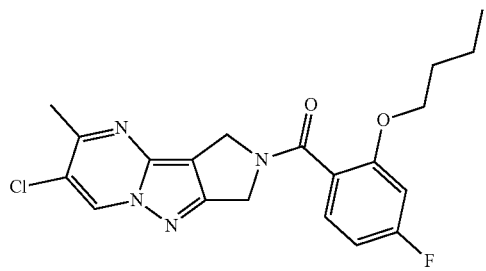 |
| 158 | 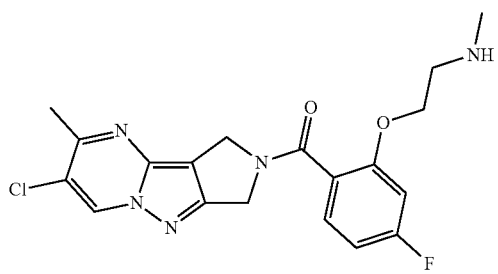 [SMILES: CNCCOc1cc(F)ccc1C(=O)N1Cc2nn3cc(Cl)c(C)nc3c2C1] |
| 159 | 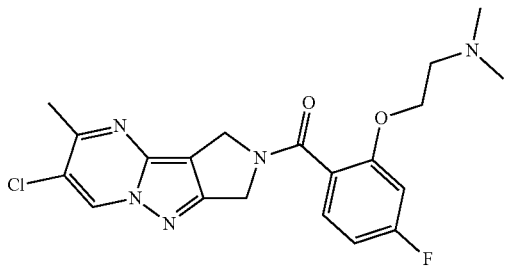 [SMILES: Cc1nc2c3c(nn2cc1Cl)CN(C(=O)c1ccc(F)cc1OCCN(C)C)C3] |
| 160 | 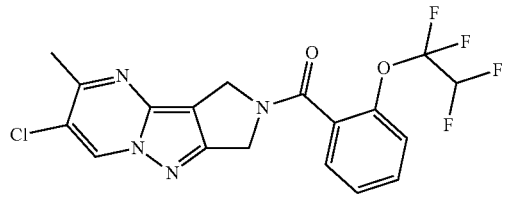 [SMILES: Cc1nc2c3c(nn2cc1Cl)CN(C(=O)c1ccccc1OC(F)(F)C(F)F)C3] |
| 161 | 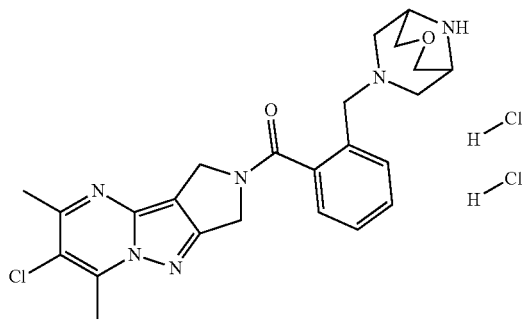 |
| Ex | Structures |
|---|---|
| 162 | 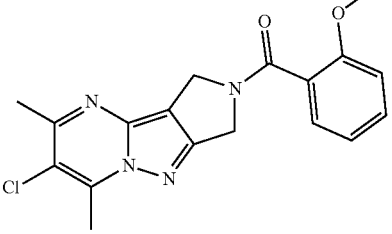 |
| 163 | 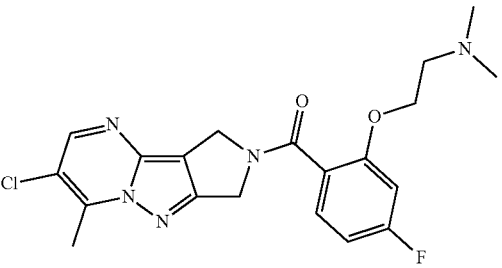 [SMILES: Cc1c(Cl)cnc2c3c(nn12)CN(C(=O)c1ccc(F)cc1OCCN(C)C)C3] |
| 164 | 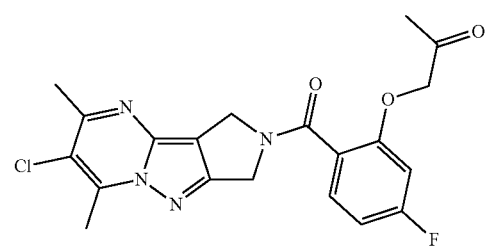 [SMILES: CC(=O)COc1cc(F)ccc1C(=O)N1Cc2nn3c(C)c(Cl)c(C)nc3c2C1] |
| 165 | 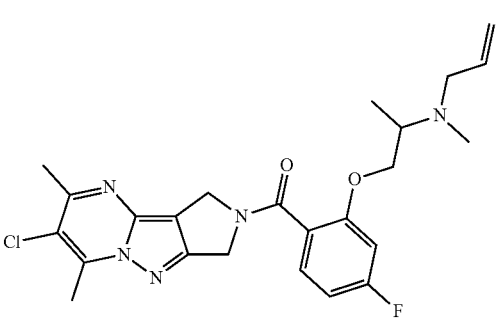 [SMILES: C=CCN(C)C(C)COc1cc(F)ccc1C(=O)N1Cc2nn3c(C)c(Cl)c(C)nc3c2C1] |
| 166 | 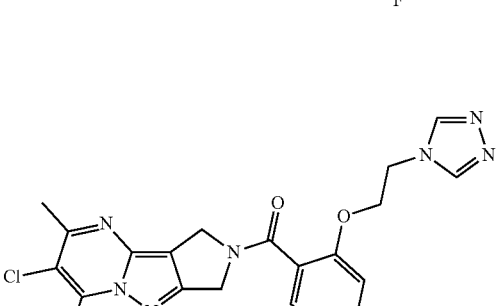 |

| Ex | Structures |
|---|---|
| 167 | 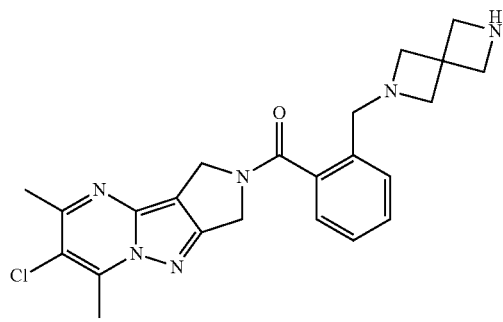 [SMILES: Cc1nc2c3c(nn2c(C)c1Cl)CN(C(=O)c1ccccc1CN1CC2(CNC2)C1)C3] |
| 168 | 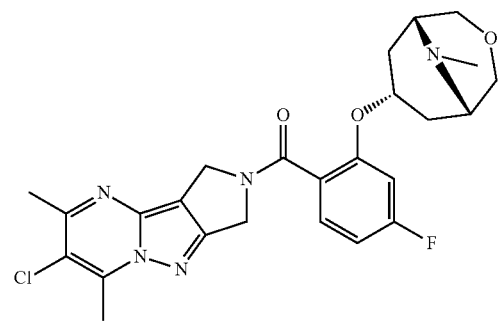 [SMILES: Cc1nc2c3c(nn2c(C)c1Cl)CN(C(=O)c1ccc(F)cc1O[C@H]1C[C@H]2COC[C@@H](C1)N2C)C3] |
| 169 | 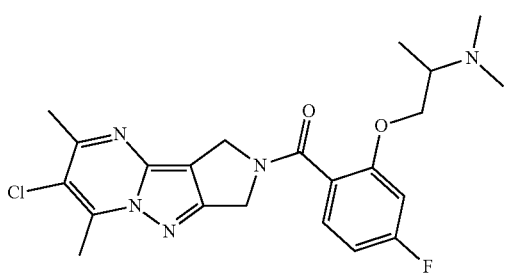 [SMILES: Cc1nc2c3c(nn2c(C)c1Cl)CN(C(=O)c1ccc(F)cc1OCC(C)N(C)C)C3] |
| 170 | 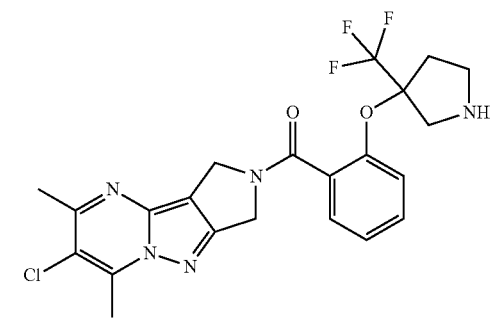 [SMILES: Cc1nc2c3c(nn2c(C)c1Cl)CN(C(=O)c1ccccc1OC1(C(F)(F)F)CCNC1)C3] |
| 171 | 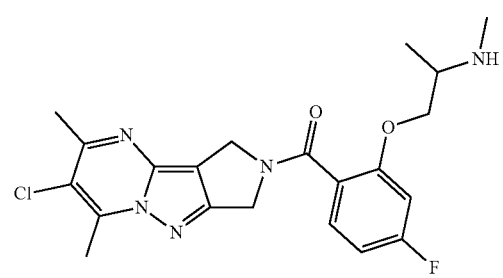 [SMILES: CNC(C)COc1cc(F)ccc1C(=O)N1Cc2nn3c(C)c(Cl)c(C)nc3c2C1] |
| Ex | Structures |
|---|---|
| 172 | 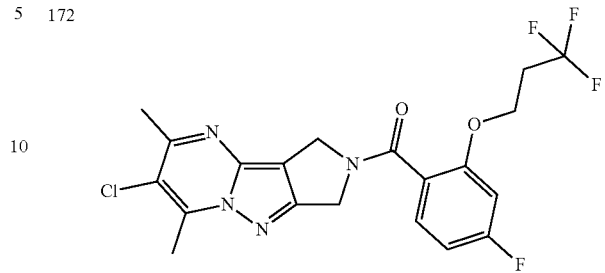 |
| 173 | 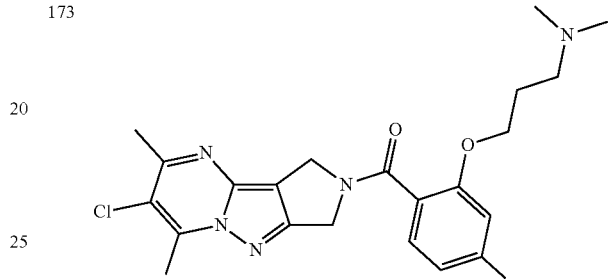 |
| 174 | 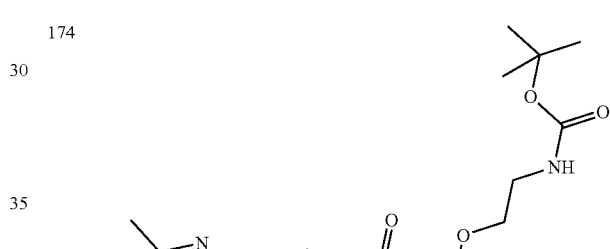 |
| 175 | 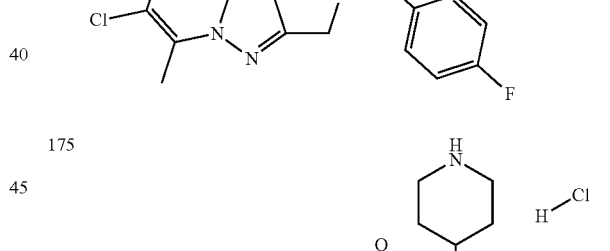 |
| 176 | 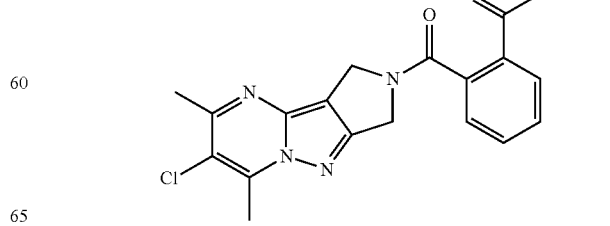 |

-continued

| Ex | Structures |
|---|---|
| 177 | 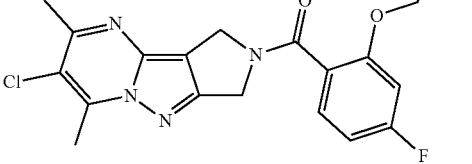 |
| 178 | 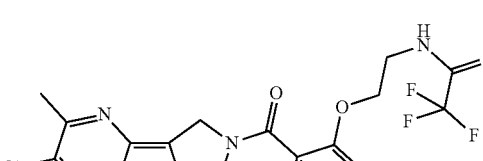 |
| 179 | 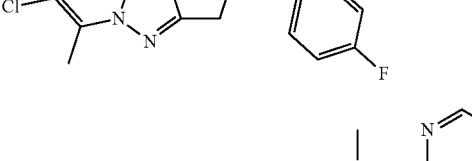 |
| 180 | 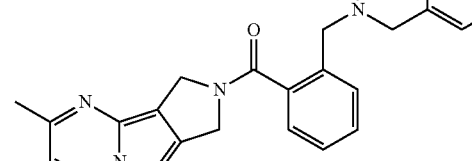 |

5. A pharmaceutical composition comprising at least one compound of claim 1 and/or pharmaceutically acceptable derivatives, tautomers, salts, and stereoisomers thereof, including mixtures thereof in all ratios, and optionally excipients and/or adjuvants.

6. A pharmaceutical composition comprising at least one compound of claim 1 and/or pharmaceutically acceptable derivatives, tautomers, salts, and stereoisomers thereof, including mixtures thereof in all ratios, and at least one further active ingredient.

7. A kit consisting of separate packs of
(a) an effective amount of a compound of claim 1 and/or pharmaceutically acceptable derivatives, tautomers, salts, and stereoisomers thereof, including mixtures thereof in all ratios,
and
(b) an effective amount of a further medicament active ingredient.

8. A method for the treatment of a M1 associated disorder or central nervous system disorder, comprising administering a compound of claim 1, and pharmaceutically acceptable derivatives, salts, tautomers, and stereoisomers thereof, including mixtures thereof in all ratios.

9. The method of claim 8, wherein the M1 associated disorder is a central nervous system disorder.

10. The method of claim 8, wherein the central nervous system disorder is Alzheimer's disease, Parkinson disease, schizophrenia, movement disorders and memory disorders, chronic and neuropathic pain, sleep disorders, or epilepsy.

11. A process to manufacture the compounds of claim 1, comprising the step of reacting a compound of Formula (A)

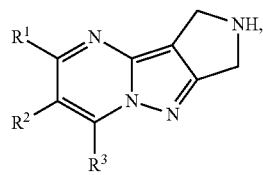

(A)

wherein $R^1$, $R^2$, $R^3$ are as defined in claim 1, with a compound of Formula (B)

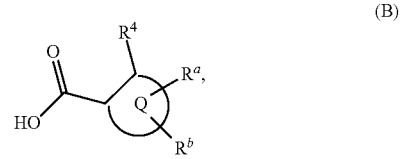

(B)

wherein $R^4$, $R^a$ and $R^b$ are as defined in claim 1, in the presence of a coupling agent.

12. The process according to claim 11 wherein the coupling agent is selected from EDC, HATU, DCC, and DIC.

13. The compound of claim 1, wherein $R^1$ and $R^3$ are a linear or branched 01-06-alkyl.

14. The compound of claim 1, wherein $R^2$ is halogen.

15. The compound of claim 14, wherein $R^2$ is Cl.

16. The compound of claim 1, wherein $R^4$ is G or OG.

17. The compound of claim 16, wherein G is —$CH_2$-A.

18. The compound of claim 17, wherein A is a linear or branched carbon chain having 1 to 6 carbon atoms, wherein 1 —$CH_2$— group may be substituted by $NR^5$.

19. The compound of claim 1, of formula (I'):

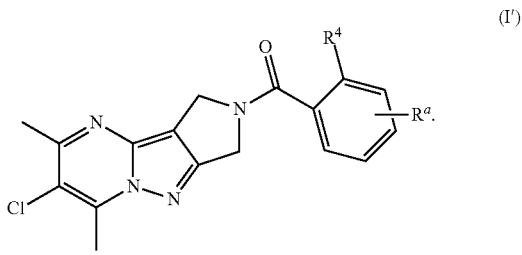

(I')

* * * * *